US011360104B2

(12) United States Patent
Galagan et al.

(10) Patent No.: US 11,360,104 B2
(45) Date of Patent: Jun. 14, 2022

(54) MICROBIAL-BASED BIOSENSORS

(71) Applicants: TRUSTEES OF BOSTON UNIVERSITY, Boston, MA (US); L'UNIVERSITÉ DE BORDEAUX, Bordeaux (FR); L'INSTITUT POLYTECHNIQUE DE BORDEAUX, Talence (FR); CENTRE NATIONAL DE LA RECHERCHE SCIENTIFIQUE, Paris (FR)

(72) Inventors: James Galagan, Needham, MA (US); Allison Dennis, Auburndale, MA (US); Catherine Klapperich, Brookline, MA (US); Mark Grinstaff, Brookline, MA (US); Thuy Nguyen, Brighton, MA (US); R. Baer, Boston, MA (US); Uros Kuzmanovic, Boston, MA (US); Marjon Zamani, Allston, MA (US); Mingfu Chen, Boston, MA (US); Margaret Chern, Brookline, MA (US); Chloe Grazon, Boston, MA (US)

(73) Assignees: TRUSTEES OF BOSTON UNIVERSITY, Boston, MA (US); L'UNIVERSITÉ DE BORDEAUX, Bordeaux (FR); L'INSTITUT POLYTECHNIQUE DE BORDEAUX, Talence (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 74 days.

(21) Appl. No.: 16/209,678

(22) Filed: Dec. 4, 2018

(65) Prior Publication Data

US 2019/0195894 A1 Jun. 27, 2019

Related U.S. Application Data

(60) Provisional application No. 62/594,209, filed on Dec. 4, 2017.

(51) Int. Cl.
| | |
|---|---|
| *G01N 33/74* | (2006.01) |
| *C07K 14/245* | (2006.01) |
| *G01N 33/566* | (2006.01) |
| *G01N 33/542* | (2006.01) |
| *C07K 14/195* | (2006.01) |
| *C12N 9/00* | (2006.01) |
| *C07K 14/34* | (2006.01) |
| *C12N 9/22* | (2006.01) |

(52) U.S. Cl.
CPC ........... *G01N 33/74* (2013.01); *C07K 14/195* (2013.01); *C07K 14/245* (2013.01); *C07K 14/34* (2013.01); *C12N 9/22* (2013.01); *C12N 9/93* (2013.01); *G01N 33/542* (2013.01); *G01N 33/566* (2013.01); *C07K 2319/20* (2013.01); *C07K 2319/21* (2013.01); *C07K 2319/60* (2013.01)

(58) Field of Classification Search
None
See application file for complete search history.

(56) References Cited

U.S. PATENT DOCUMENTS

| | | | |
|---|---|---|---|
| 9,895,692 B2 | 2/2018 | Battrell et al. | |
| 2002/0028457 A1 | 3/2002 | Empedocules et al. | |
| 2002/0127623 A1 | 9/2002 | Minshull et al. | |
| 2004/0259096 A1 | 12/2004 | Allen et al. | |
| 2008/0087843 A1 | 4/2008 | Medintz et al. | |
| 2010/0075361 A1 | 3/2010 | Mattoussi et al. | |
| 2010/0256918 A1 | 10/2010 | Chen et al. | |
| 2013/0140518 A1 | 6/2013 | Jain et al. | |
| 2014/0294873 A1* | 10/2014 | Ghosh | G01N 33/6872 424/184.1 |
| 2015/0346097 A1 | 12/2015 | Battrell et al. | |
| 2020/0078781 A1 | 3/2020 | Beckley | |

FOREIGN PATENT DOCUMENTS

| | | |
|---|---|---|
| JP | 2016161420 A | 9/2016 |
| WO | 2006037226 A1 | 4/2006 |

OTHER PUBLICATIONS

Li et al (Chemical Communications, Jan. 2017, vol. 53, pp. 99-102).*
Moore et al (Molecular Endocrinology, 2010, vol. 24 (4), pp. 683-695).*
Boeneman et al. "Quantum Dots and Flourescent Protein FRET-Based Biosensors" Adv Exp Med Biol Epublished vol. 733 63-74 (2012).
Chou et al. "Forster Resonance Energy Transfer between Quantum Dot Donors and Quantum Dot Acceptors" Sensors 15(6); 13288-13325 (2015).
Alhadrami et al., "High affinity truncated DNA aptamers for the development of fluorescence based progesterone biosensors." Analytical biochemistry 525 (2017): 78-84.
ALON "Network motifs: theory and experimental approaches." Nature Reviews Genetics 8.6 (2007): 450-461.
Alvarez et al., "Emerging trends in micro-and nanoscale technologies in medicine: From basic discoveries to translation." ACS nano 11.6 (2017): 5195-5214.
Bergstrand et al., "Delineation of steroid-degrading microorganisms through comparative genomic analysis." MBio 7.2(2016) e00166-16.
Bolintineanu et al., "Investigation of changes in tetracycline repressor binding upon mutations in the tetracycline operator." Journal of Chemical & Engineering Data 59.10 (2014): 3167-3176.

(Continued)

*Primary Examiner* — Nancy J Leith
(74) *Attorney, Agent, or Firm* — Nixon Peabody LLP; Ronald I. Eisenstein; Susanna C. Benn

(57) ABSTRACT

Described herein are methods, compositions and processes related to a microbial-based biosensor system for the detection of small molecules and analytes based on an analyte-responsive transcription factor-DNA binding mechanism with either a ratiometric fluorescent output through Förster resonance energy transfer (FRET) or a redox sensor output for the quantification of the target analyte with high sensitivity.

29 Claims, 77 Drawing Sheets
(66 of 77 Drawing Sheet(s) Filed in Color)

Specification includes a Sequence Listing.

(56) References Cited

OTHER PUBLICATIONS

Bowring et al., "Mutagenesis of Clostridium acetobutylicum." Journal of applied bacteriology 58.6 (1985): 577-584.
Chern et al., "Shell thickness effects on quantum dot brightness and energy transfer." Nanoscale 9.42 (2017) 16446-16458.
Clapp et al., "Capping of CdSe—ZnS quantum dots with DHLA and subsequent conjugation with proteins." Nature protocols 1.3 (2006): 1258-1266.
Constantinides "Steroid transformation at high substrate concentrations using immobilized Corynebacterium simplex cells." Biotechnology and bioengineering 22.1 (1980): 119-136.
Damassa et al., "*Mycoplasma auris* sp. nov., *Mycoplasma cottewii* sp. nov., and *Mycoplasma yeatsii* sp. nov., new sterol-requiring mollicutes from the external ear canals of goats." International Journal of Systematic Bacteriology 44.3 (1994): 479-484.
Dennis et al., "Quantum dot—fluorescent protein pairs as novel fluorescence resonance energy transfer probes." Nano Letters 8.5 (2008): 1439-1445.
Dennis et al., "Surface ligand effects on metal-affinity coordination to quantum dots: Implications for nanoprobe self-assembly." Bioconjugate chemistry 21.7 (2010): 1160-1170.
Diaz-Gonzalez et al., "Recent advances in electrochemical enzyme immunoassays." Electroanalysis 17.21 (2005): 1901-1918.
Du et al., "Colorimetric aptasensor for progesterone detection based on surfactant-induced aggregation of gold nanoparticles." Analytical biochemistry 514 (2016): 2-7.
Eglen et al.," The Use of AlphaScreen Technology in HTS: Current Status" Current Chemical Genomics 1 (2008) 2-10.
Fahrbach et al., "*Steroidobacter denitrificans* gen. nov., sp. nov., a steroidal hormone-degrading gammaproteobacterium." International Journal of Systematic and Evolutionary Microbiology 58.9 (2008): 2215-2223.
Feng et al., A general strategy to construct small molecule biosensors in eukaryotes. Elife 4 (2015): e10606.
French et al., "Synthetic biology and the art of biosensor design." The science and applications of synthetic and systems biology: Workshop summary. Washington DC: National Academies Press (2011): 178-201.
Fujii et al., "*Novosphingobium tardaugens* sp. nov., an oestradiol-degrading bacterium isolated from activated sludge of a sewage treatment plant in Tokyo." International Journal of Systematic and Evolutionary Microbiology 53.1 (2003) 47-52.
Galagan"Genomic insights into tuberculosis." Nature Reviews Genetics 15.5 (2014): 307-320.
Galagen et al., "ChIP-Seq and the complexity of bacterial transcriptional regulation." Current Topics in Microbiology and Immunology (2013): 43-68.
Gao et al., "Photogenerated excitons in plain core CdSe nanocrystals with unity radiative decay in single channel: the affects of surface and ligands" Journal of the American Chemical Society 137.12 (2015): 4230-4235.
Garcia et al., "Catabolism and biotechnological applications of cholesterol degrading bacteria." Microbial biotechnology 5.6 (2012): 679-699.
Garcia-Fernandez et al., "Deciphering the transcriptional regulation of cholesterol catabolic pathway in mycobacteria: identification of the inducer of KstR repressor." Journal of Biological Chemistry 289.25 (2014) 17576-17588.
Ghosh et al., "New insights into the complexities of shell growth and the strong influence of particle volume in nonblinking "giant" core/shell nanocrystal quantum dots." Journal of the American Chemical Society 134.23 (2012) 9634-9643.
Hildebrandt et al., "Energy transfer with semiconductor quantum dot bioconjugates: a versatile platform for biosensing, energy harvesting, and other developing applications." Chemical reviews 117.2 (2017): 536-711.
Holstein et al., "Statistical method for determining and comparing limits of detection of bioassays." Analytical chemistry 87.19 (2015): 9795-9801.
Jaini et al., "Transcription factor binding site mapping using ChIP-Seq." Microbiology Spectrum 2.2 (2014): 161-181.
Kamionka et al., "Two mutations in the tetracycline repressor change the inducer anhydrotetracycline to a corepressor." Nucleic acids research 32.2 (2004): 842-847.
Kashtan et al., "Topological generalizations of network motifs." Physical Review E 70.3 (2004): 031909.
Kendall et al., "Cholesterol utilization in mycobacteria is controlled by two TetR-type transcriptional regulators: kstR and kstR2." Microbiology 156.Pt5 (2010): 1362-1371.
Kendall et al., "What a dinner party! Mechanisms and functions of interkingdom signaling in host-pathogen associations." MBio 7.2 (2016): e01748-15.
Lee et al., "Small molecule-based ratiometric fluorescence probes for cations, anions, and biomolecules." Chemical Society Reviews 44.13 (2015): 4185-4191.
Leung et al., "Development of an aptamer-based sensing platform for metal ions, proteins, and small molecules through terminal deoxynucleotidyl transferase induced G-quadruplex formation." ACS applied materials & interfaces 7.43 (2015): 24046-24052.
Li et al., "Large-scale synthesis of nearly monodisperse CdSe/CdS core/shell nanocrystals using air-stable reagents via successive ion layer adsorption and reaction." Journal of the American Chemical Society 125.41 (2003): 12567-12575.
Li et al., "A platform for the development of novel biosensors by configuring allosteric transcription factor recognition with amplified luminescent proximity homogeneous assays." Chemical communications 53.1 (2017): 99-102.
Libis et al., "Sensing new chemicals with bacterial transcription factors." Current opinion in microbiology 33 (2016): 105-112.
Liu et al. "Exciton energy transfer-based fluorescent sensing through aptamer-programmed self-assembly of quantum dots." Analytical chemistry 85.22 (2013): 11121-11128.
Lopez-Fernandez et al. "Whole-genome comparative analysis of virulence genes unveils similarities and differences between endophytes and other symbiotic bacteria" Front Microbiol. 6 (2015): Article 419.
McCormick et al., "Biosynthesis of the tetracyclines. IX. 4-Amino dedimethylaminoanhydrodemethylchlortetracycline from a mutant of Streptomyces aureofaciens." Journal of the American Chemical Society 90.8 (1968): 2201-2202.
McGuire et al., "Comparative analysis of Mycobacterium and related Actinomycetes yields insight into the evolution of Mycobacterium tuberculosis pathogenesis." BMC genomics 13.1 (2012): Article 120.
Medintz et al. "Quantum dot bioconjugates for imaging, labelling and sensing." Nature materials 4.6 (2005): 435-446.
Neuman et al. "Microbial endocrinology: the interplay between the microbiota and the endocrine system." FEMS microbiology reviews 39.4 (2015): 509-521.
Oh et al., "Simple and sensitive progesterone detection in human serum using a CdSe/ZnS quantum dot-based direct binding assay." Analytical biochemistry 483 (2015): 54-61.
Pardee et al., "Paper-based synthetic gene networks." Cell 159.4 (2014): 940-954.
Pons et al., "Solution-phase single quantum dot fluorescence resonance energy transfer." Journal of the American Chemical Society 128.47 (2006): 15324-15331.
Posthuma-Trumpie et al., "Perspectives for on-site monitoring of progesterone." Trends in biotechnology 27.11 (2009): 652-660.
Rosenfeld et al, "Negative autoregulation speeds the response times of transcription networks." Journal of molecular biology 323.5 (2002): 785-793.
Fernandez-Lopez et al., "Transcription factor-based biosensors enlightened by the analyte." Frontiers in microbiology 6 (2015): Article 648.
Saenger et al., "The tetracycline repressor—a paradigm for a biological switch." Angewandte Chemie International Edition 39.12 (2000): 2042-2052.
Sebaugh et al., "Defining the linear portion of a sigmoid-shaped curve: bend points." Pharmaceutical Statistics 2.3 (2003): 167-174.

(56) References Cited

OTHER PUBLICATIONS

Shaner et al., "Improved monomeric red, orange and yellow fluorescent proteins derived from *Discosoma* sp. red fluorescent protein." Nature biotechnology 22.12 (2004): 1567-1572.

Susumu et al., "Multifunctional compact zwitterionic ligands for preparing robust biocompatible semiconductor quantum dots and gold nanoparticles." Journal of the American Chemical Society 133.24 (2011): 9480-9496.

Trapiella-Alfonso et al., "Development of a quantum dot-based fluorescent immunoassay for progesterone determination in bovine milk." Biosensors and Bioelectronics 26.12 (2011): 4753-4759.

Uhia et al., "Characterization of the KstR-dependent promoter of the gene for the first step of the cholesterol degradative pathway in Mycobacterium smegmatis." Microbiology 157.9 (2011): 2670-2680.

Wang et al., "Photoligation of an amphiphilic polymer with mixed coordination provides compact and reactive quantum dots." Journal of the American Chemical Society 137.16 (2015): 5438-5451.

Williamson et al., "*Mycoplasma somnilux* sp. nov., *Mycoplasma luminosum* sp. nov., and *Mycoplasma lucivorax* sp. nov., new sterol-requiring mollicutes from firefly beetles (*Coleoptera: Lampyridae*)." International Journal of Systematic and Evolutionary Microbiology 40.2 (1990): 160-164.

Yu et al., "Microbial degradation of steroidal estrogens." Chemosphere 91.9 (2013): 1225-1235.

Yu et al., "Water-soluble quantum dots for biomedical applications." Biochemical and biophysical research communications 348.3 (2006): 781-786.

Zhang et al., "Quantum dot enabled molecular sensing and diagnostics." Theranostics 2.7 (2012): 631-654.

\* cited by examiner

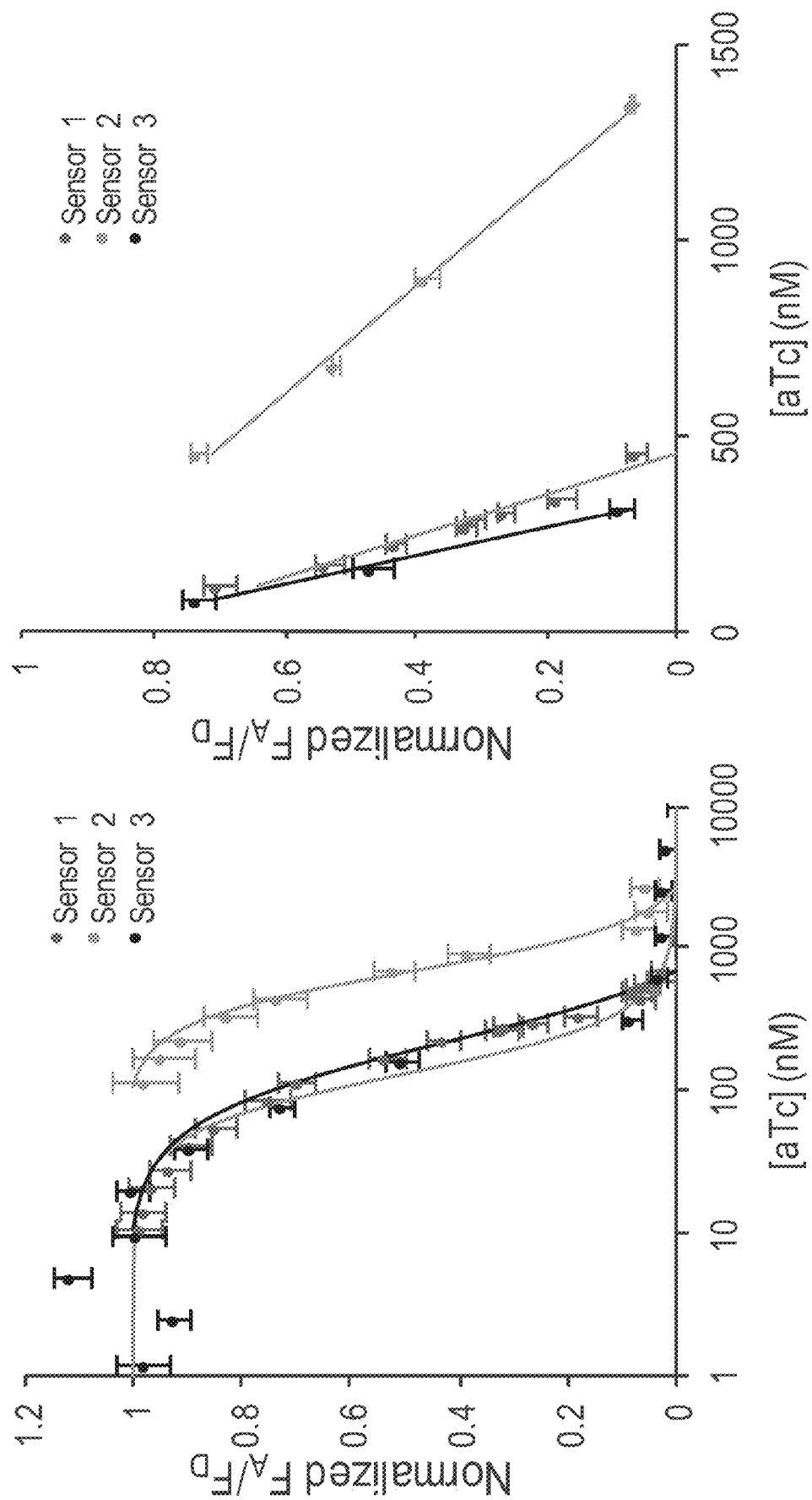

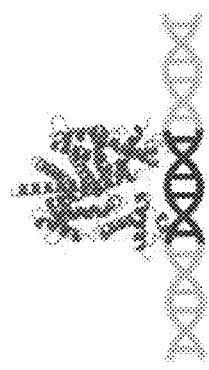
FIG. 7A
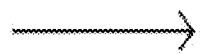
FIG. 7B
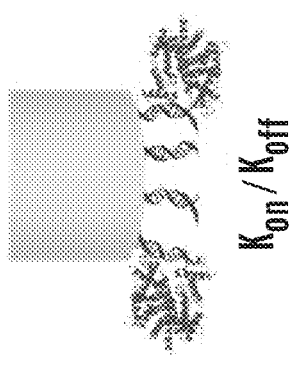
FIG. 7C
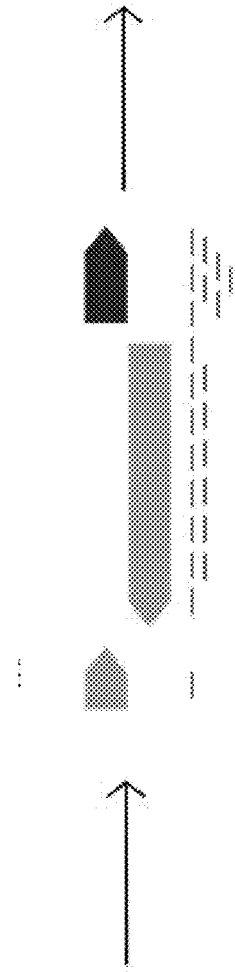
FIG. 7D
FIG. 7E
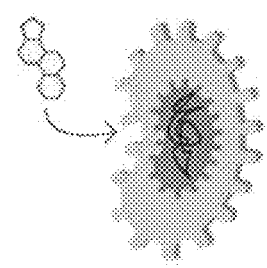
FIG. 7F DNA sequences
| | | | | | | | | |
|---|---|---|---|---|---|---|---|---|
| strong | GCCT | AAC | TAG | CCG | TTC | GGC | TAG | TT | ATTC |
| int. | GCCT | AAC | TAG | CCG | TTC | GGC | AAG | TA | ATTC |
| weak | GCCT | AAC | TAG | CCG | TTC | TGT | TAG | TT | ATTC |
| scbd | TGTG | CGT | GTC | CCT | CGC | TCG | GTT | TC | ACGA |

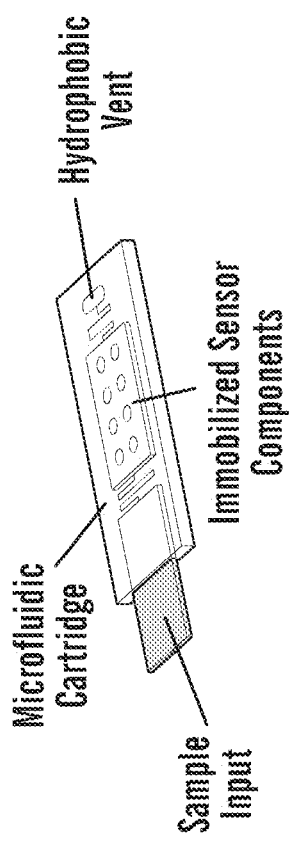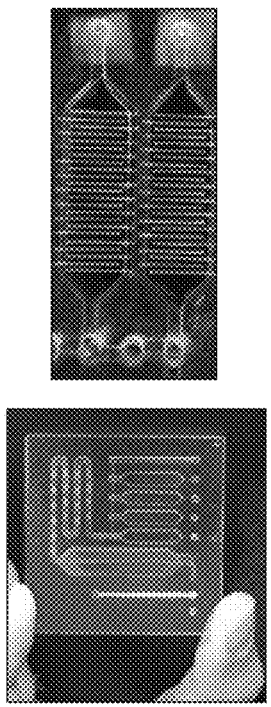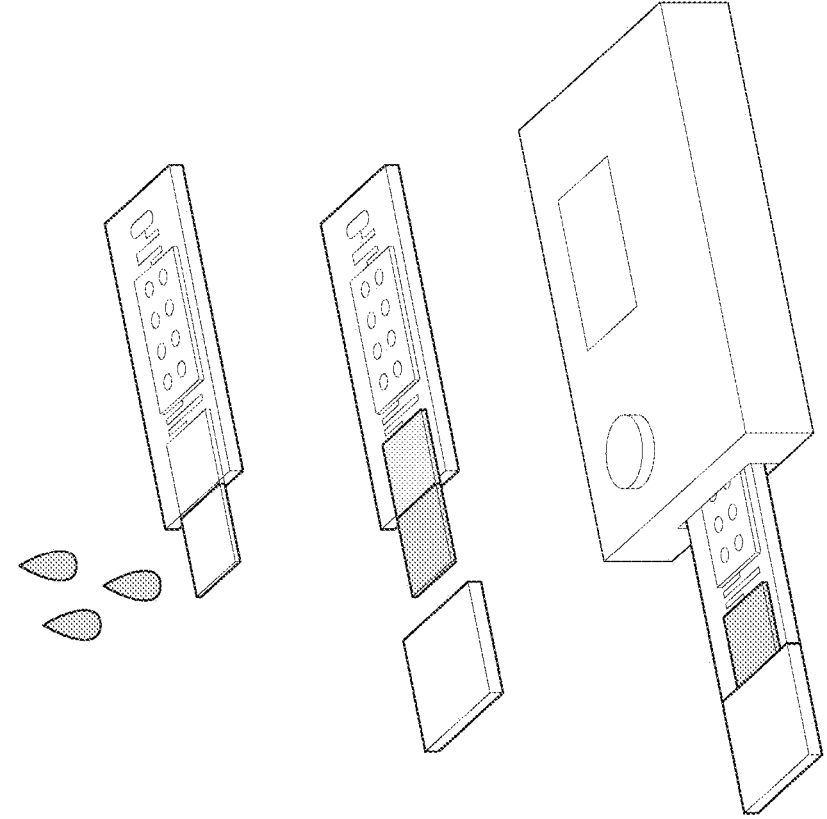
FIG. 12B
FIG. 12C
FIG. 12A

Steroid skeleton
(Carbons 18 and above can be absent)

(PRG)
Progesterone
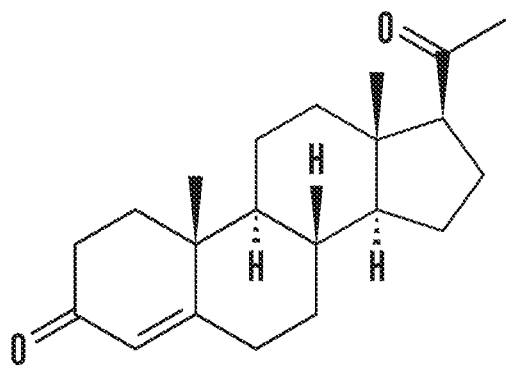
$C_{21}H_{30}O_2$
$M$: 314.46 g/mol
(CRT)
Hydrocortisone
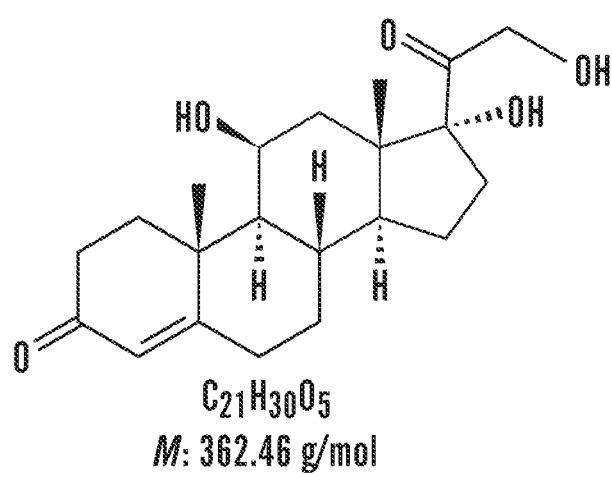
$C_{21}H_{30}O_5$
$M$: 362.46 g/mol
(ESD)
17β-Estradiol
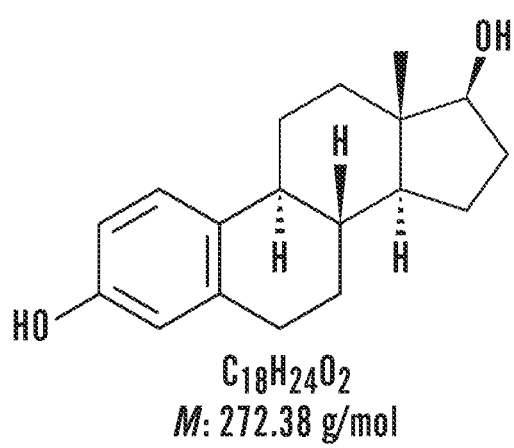
$C_{18}H_{24}O_2$
$M$: 272.38 g/mol
*FIG. 14 (cont.)*

(ALD)
Aldosterone
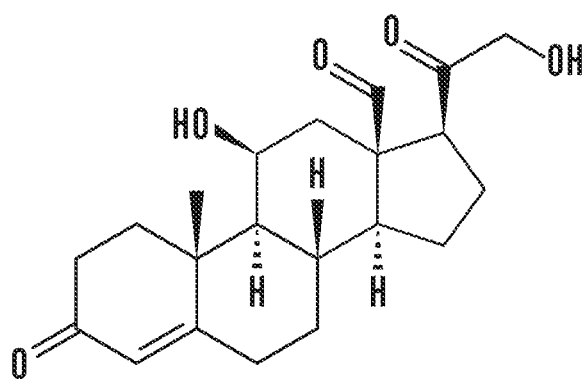
$C_{21}H_{28}O_5$
M: 360.44 g/mol
(TST)
Testosterone
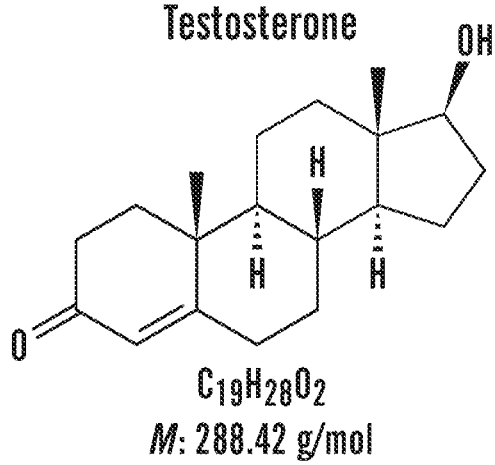
$C_{19}H_{28}O_2$
M: 288.42 g/mol
(ESN)
Estrone
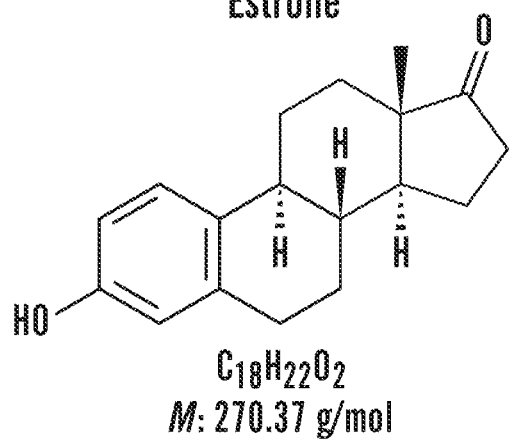
$C_{18}H_{22}O_2$
M: 270.37 g/mol
*FIG. 14 (cont.)*

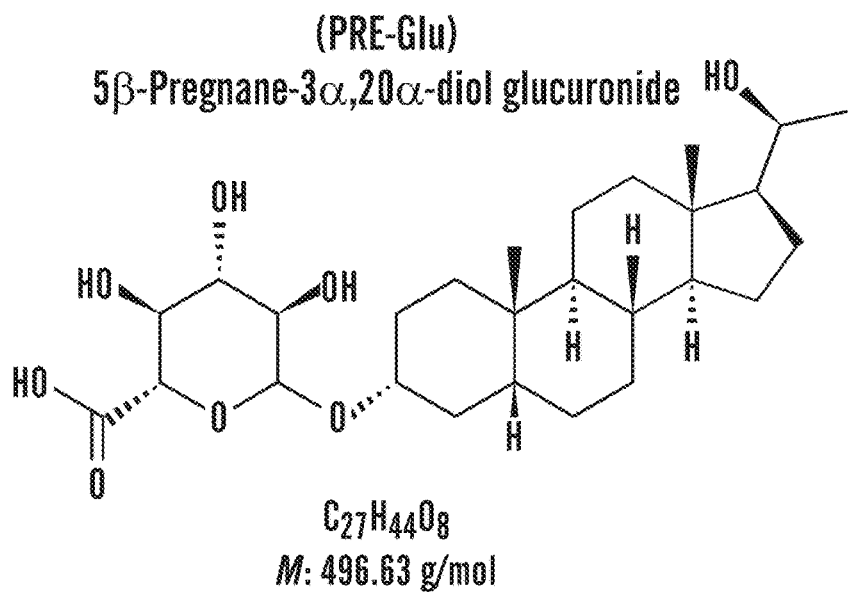
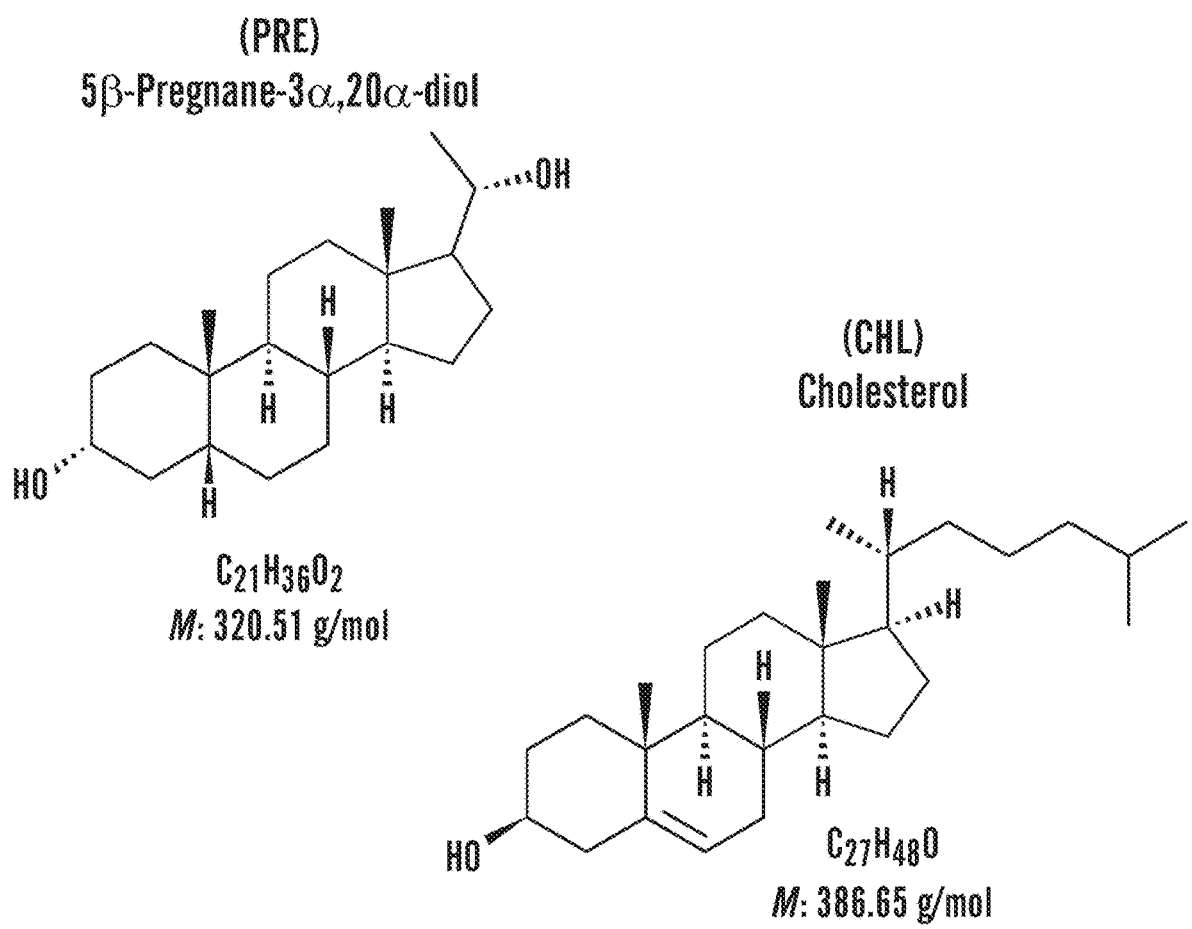
FIG. 14 (cont.)

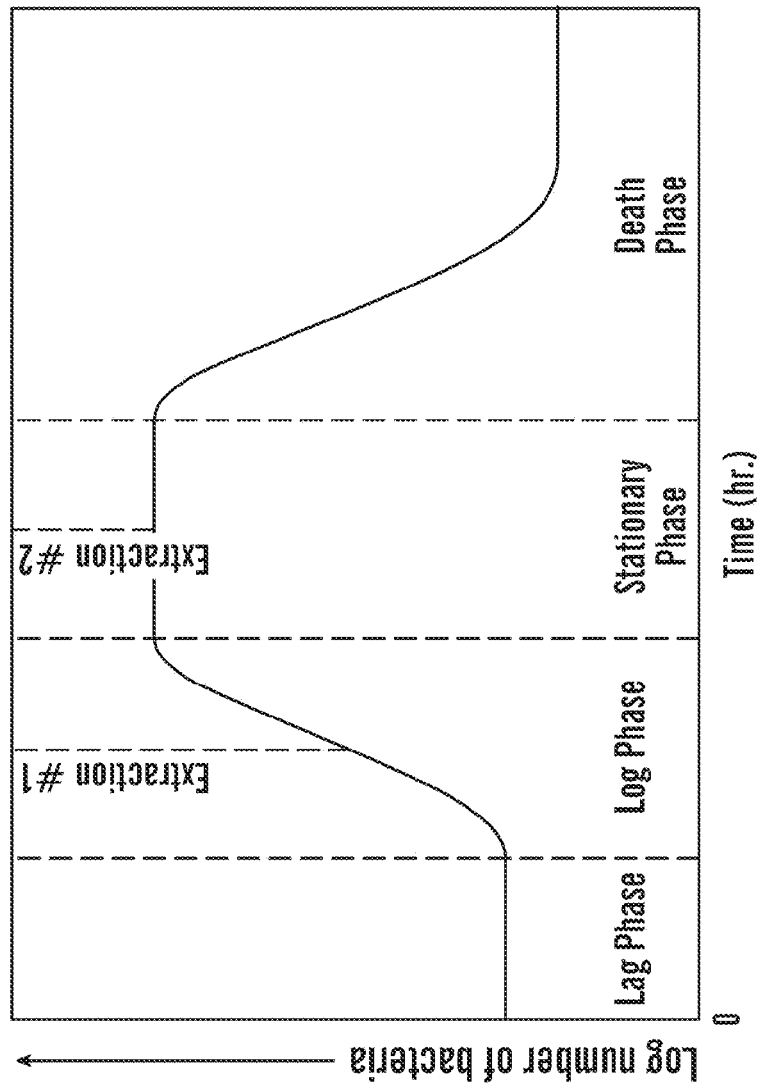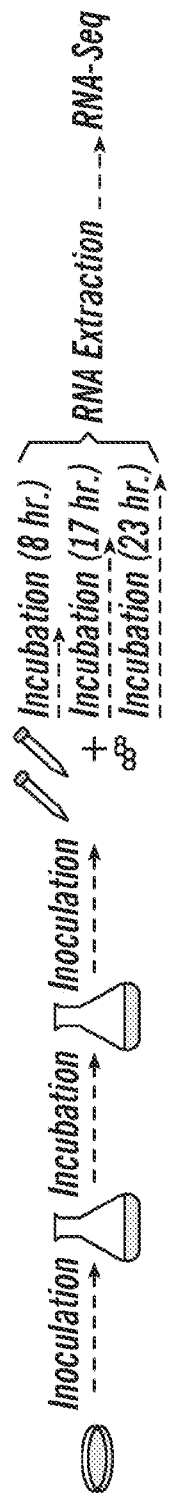
FIG. 15A
FIG. 15B

```
            cov     pid    1                                                                              . 80
1 PinR     100.0%  100.0%    MSSTAERIRPGRSGILAAATRLFATHGVSGTSLQQIADATGITKAAVVHHFPTKEEVVAVLAPALEAIQGIVRTAGAHE
2 PinR-CHis 100.0% 95.9%    MSSTAERIRPGRSGILAAATRLFATHGVSGTSLQQIADATGITKAAVVHHFPTKEEVVAVLAPALEAIQGIVRTAGAHE cov     pid   81                                                                              . 160
1 PinR     100.0%  100.0%   DPRAATEAAIIGLADQAVTHRQRWAVLLQDAAVEEYVRNNPDHDELFTRLRLILLTGPDPTPGTRLQVSLFLSGLLGPAQD
2 PinR-CHis 100.0% 95.9%    DPRAATEAAIIGLADQAVTHRQRWAVLLQDAAVEEYVRNNPDHDELFTRLRLILLTGPDPTPGTRLQVSLFLSGLLGPAQD cov     pid  161                                   ] 197
1 PinR     100.0%  100.0%   PSCADIDDDALRAGIVRAGRRLLLADDDA-----------
2 PinR-CHis 100.0% 95.9%    PSCADIDDDALRAGIVRAGRRLLLADDDDAGSHHHHHH
```

FIG. 29A

```
            cov     pid    1                                                                              . 80
1 PinR          100.0% 100.0%  MSSTAERIRPGRSGILAAATRLFATHGVSGTSLQQIADATGITKAAVVHHFPTKEEVVAVLAPALEAIQGIVRTAGAHE
2 PinR-CHis     100.0% 95.9%   MSSTAERIRPGRSGILAAATRLFATHGVSGTSLQQIADATGITKAAVVHHFPTKEEVVAVLAPALEAIQGIVRTAGAHE
3 PinR-CHis_A65V_Q70H 100.0% 94.9% MSSTAERIRPGRSGILAAATRLFATHGVSGTSLQQIADATGITKAAVVHHFPTKEEVVAVLAPVLEAHGIVRTAGAHE cov     pid   81                                                                              . 160
1 PinR          100.0% 100.0%  DPRAATEAAIIGLADQAVTHRQRWAVLLQDAAVEEYVRNNPDHDELFTRLRLILLTGPDPTPGTRLQVSLFLSGLLGPAQD
2 PinR-CHis     100.0% 95.9%   DPRAATEAAIIGLADQAVTHRQRWAVLLQDAAVEEYVRNNPDHDELFTRLRLILLTGPDPTPGTRLQVSLFLSGLLGPAQD
3 PinR-CHis_A65V_Q70H 100.0% 94.9% DPRAATEAAIIGLADQAVTHRQRWAVLLQDAAVEEYVRNNPDHDELFTRLRLILLTGPDPTPGTRLQVSLFLSGLLGPAQD cov     pid  161                                   ] 197
1 PinR          100.0% 100.0%  PSCADIDDDALRAGIVRAGRRLLLADDDA-----------
2 PinR-CHis     100.0% 95.9%   PSCADIDDDALRAGIVRAGRRLLLADDDDAGSHHHHHH
3 PinR-CHis_A65V_Q70H 100.0% 94.9% PSCADIDDDALRAGIVRAGRRLLLADDDDAGSHHHHHH
```

FIG. 29B

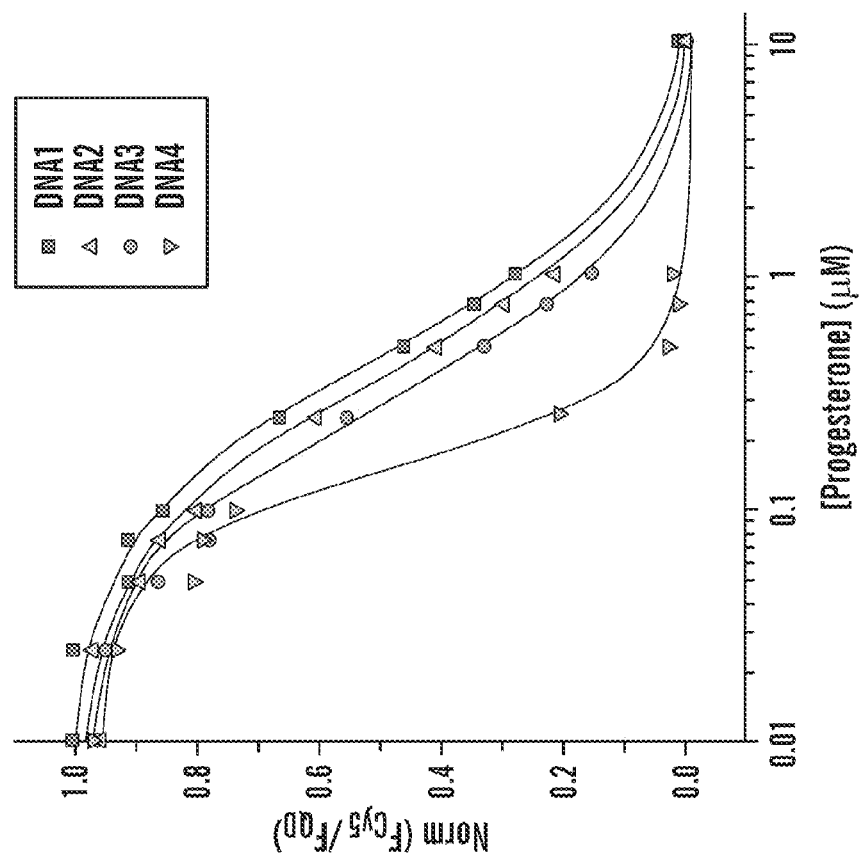
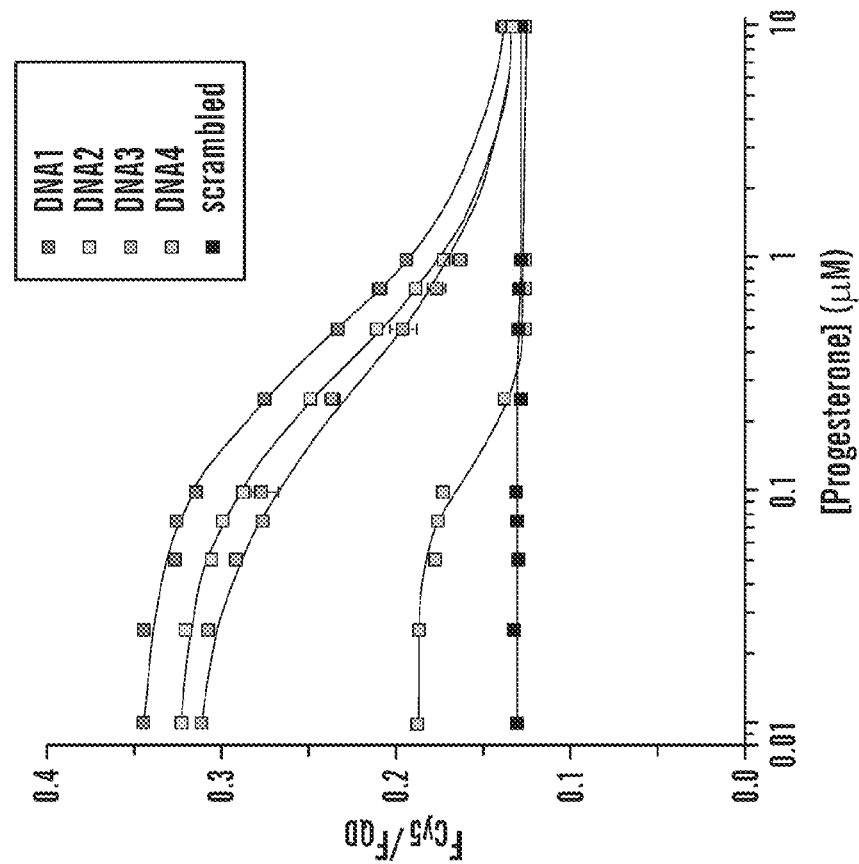
FIG. 38B
FIG. 38A

SEQUENCE LISTING

```
<160> NUMBER OF SEQ ID NOS: 38

<210> SEQ ID NO 1
<211> LENGTH: 189
<212> TYPE: PRT
<213> ORGANISM: Pimelobacter simplex

<400> SEQUENCE: 1

Met Ser Ser Thr Ala Glu Arg Ile Arg Pro Gly Arg Ser Gly Ile Leu
1               5                   10                  15

Ala Ala Ala Thr Arg Leu Phe Ala Thr His Gly Val Ser Gly Thr Ser
            20                  25                  30

Leu Gln Gln Ile Ala Asp Ala Thr Gly Ile Thr Lys Ala Ala Val Tyr
        35                  40                  45

His His Phe Pro Thr Lys Glu Glu Val Val Ala Val Leu Ala Pro
    50                  55                  60

Ala Leu Glu Ala Ile Gln Gly Ile Val Arg Thr Ala Gly Ala His Glu
65                  70                  75                  80

Asp Pro Arg Ala Ala Thr Glu Ala Ala Ile Ile Gly Leu Ala Asp Gln
            85                  90                  95

Ala Val Thr His Arg Gln Arg Trp Ala Val Leu Leu Gln Asp Ala Ala
            100                 105                 110

Val Glu Glu Tyr Val Arg Asn Asn Pro Asp His Asp Glu Leu Phe Thr
        115                 120                 125

Arg Leu Arg Leu Leu Leu Thr Gly Pro Asp Pro Thr Pro Gly Thr Arg
    130                 135                 140

Leu Gln Val Ser Leu Phe Leu Ser Gly Leu Leu Gly Pro Ala Gln Asp
145                 150                 155                 160

Pro Ser Cys Ala Asp Ile Asp Asp Ala Leu Arg Ala Gly Ile Val
                165                 170                 175

Arg Ala Gly Arg Arg Leu Leu Leu Ala Asp Asp Asp Ala
            180                 185

<210> SEQ ID NO 2
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ser Ser Thr Ala Glu Arg Ile Arg Pro Gly Arg Ser Gly Ile Leu
1               5                   10                  15

Ala Ala Ala Thr Arg Leu Phe Ala Thr His Gly Val Ser Gly Thr Ser
            20                  25                  30

Leu Gln Gln Ile Ala Asp Ala Thr Gly Ile Thr Lys Ala Ala Val Tyr
        35                  40                  45

His His Phe Pro Thr Lys Glu Glu Val Val Ala Val Leu Ala Pro
    50                  55                  60
```

```
Ala Leu Glu Ala Ile Gln Gly Ile Val Arg Thr Ala Gly Ala His Glu
 65                  70                  75                  80

Asp Pro Arg Ala Ala Thr Glu Ala Ala Ile Ile Gly Leu Ala Asp Gln
                 85                  90                  95

Ala Val Thr His Arg Gln Arg Trp Ala Val Leu Leu Gln Asp Ala Ala
            100                 105                 110

Val Glu Glu Tyr Val Arg Asn Asn Pro Asp His Asp Glu Leu Phe Thr
        115                 120                 125

Arg Leu Arg Leu Leu Leu Thr Gly Pro Asp Pro Thr Pro Gly Thr Arg
    130                 135                 140

Leu Gln Val Ser Leu Phe Leu Ser Gly Leu Leu Gly Pro Ala Gln Asp
145                 150                 155                 160

Pro Ser Cys Ala Asp Ile Asp Asp Ala Leu Arg Ala Gly Ile Val
                165                 170                 175

Arg Ala Gly Arg Arg Leu Leu Leu Ala Asp Asp Ala Gly Ser His
            180                 185                 190

His His His His His
        195

<210> SEQ ID NO 3
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ser Ser Thr Ala Glu Arg Ile Arg Pro Gly Arg Ser Gly Ile Leu
  1               5                  10                  15

Ala Ala Ala Thr Arg Leu Phe Ala Thr His Gly Val Ser Gly Thr Ser
                 20                  25                  30

Leu Gln Gln Ile Ala Asp Ala Thr Gly Ile Thr Lys Ala Ala Val Tyr
             35                  40                  45

His His Phe Pro Thr Lys Glu Glu Val Val Ala Val Leu Ala Pro
 50                  55                  60

Val Leu Glu Ala Ile His Gly Ile Val Arg Thr Ala Gly Ala His Glu
 65                  70                  75                  80

Asp Pro Arg Ala Ala Thr Glu Ala Ala Ile Ile Gly Leu Ala Asp Gln
                 85                  90                  95

Ala Val Thr His Arg Gln Arg Trp Ala Val Leu Leu Gln Asp Ala Ala
            100                 105                 110

Val Glu Glu Tyr Val Arg Asn Asn Pro Asp His Asp Glu Leu Phe Thr
        115                 120                 125

Arg Leu Arg Leu Leu Leu Thr Gly Pro Asp Pro Thr Pro Gly Thr Arg
    130                 135                 140

Leu Gln Val Ser Leu Phe Leu Ser Gly Leu Leu Gly Pro Ala Gln Asp
145                 150                 155                 160

Pro Ser Cys Ala Asp Ile Asp Asp Ala Leu Arg Ala Gly Ile Val
                165                 170                 175

Arg Ala Gly Arg Arg Leu Leu Leu Ala Asp Asp Ala Gly Ser His
            180                 185                 190

His His His His His
        195
```

<210> SEQ ID NO 4
<211> LENGTH: 567
<212> TYPE: DNA
<213> ORGANISM: Pimelobacter simplex

<400> SEQUENCE: 4

```
atgagcagca ccgccgaacg catccgcccg ggccgcagcg gcatcctcgc cgccgcgacc    60
cggctcttcg ccacgcacgg cgtctccggc acctcgctgc agcagatcgc ggacgccacc   120
gggatcacca aggccgccgt ctaccaccac ttccccacca aggaggaggt cgtcgtcgcc   180
gtcctggcgc ccgcgctcga ggcgatccag ggcatcgtcc gcaccgccgg cgcccacgag   240
gacccgcggg ccgcgaccga ggccgccatc atcggcctcg ccgaccaggc cgtcacccac   300
cgccagcgct gggccgtgct cctccaggac gccgccgtcg aggagtacgt ccgcaacaac   360
cccgaccacg acgagctctt cacccggctg cgcctgctcc tcaccggccc ggatcccacc   420
ccgggcaccc ggctccaggt ctccctcttc ctctccggcc tgctcgggcc cgcgcaggac   480
cccagctgcg ccgacatcga cgacgacgcg ctgcgcgcgg catcgtccg ggccggacgc    540
cggctcctgc tggccgacga cgacgcc                                      567
```

<210> SEQ ID NO 5
<211> LENGTH: 591
<212> TYPE: DNA
<213> ORGANISM: Artificial Sequence
<220> FEATURE:
<223> OTHER INFORMATION: Description of Artificial Sequence: Synthetic
        polynucleotide

<400> SEQUENCE: 5

```
atgtcgtcaa cggctgaacg catccgtcct ggacgttctg ggattcttgc tgcagcaacg    60
cgcttattcg caacccacgg cgtaagcgga acctcactgc agcaaattgc agacgcaacg   120
ggtatcacta aggcggcggt atatcaccat ttccctacaa aggaagaagt tgtagtggcc   180
gtgttagcac ctgcgttaga ggccattcaa ggtattgtgc gcacagccgg agcgcatgag   240
gacccacgtg cagcaacaga ggccgccatt attggattag cggatcaggc ggttactcac   300
cgtcaacgct gggcggtact gttgcaagac gctgccgtcg aagagtatgt tcgcaataac   360
ccagatcacg atgagctttt cacacgttta cgcctgttat tgacgggtcc agacccaaca   420
ccaggcactc gtttacaagt gtcgttgttc ttgtcgggat tgctgggtcc agctcaagat   480
ccgtcatgtg ctgacatcga tgacgacgcc cttcgtgccg gatcgtccg tgccggacgt    540
cgtttattac ttgcggacga cgacgccggg tcacatcatc accaccatca c           591
```

<210> SEQ ID NO 6
<211> LENGTH: 591
<212> TYPE: DNA
<213> ORGANISM: Artificial Sequence
<220> FEATURE:
<223> OTHER INFORMATION: Description of Artificial Sequence: Synthetic
        polynucleotide

<400> SEQUENCE: 6

```
atgtcgtcaa cggctgaacg catccgtcct ggacgttctg ggattcttgc tgcagcaacg    60
cgcttattcg caacccacgg cgtaagcgga acctcactgc agcaaattgc agacgcaacg   120
ggtatcacta aggcggcggt atatcaccat ttccctacaa aggaagaagt tgtagtggcc   180
gtgttagcac ctgtgttaga ggccattcat ggtattgtgc gcacagccgg agcgcatgag   240
gacccacgtg cagcaacaga ggccgccatt attggattag cggatcaggc ggttactcac   300
```

```
cgtcaacgct gggcggtact gttgcaagac gctgccgtcg aagagtatgt tcgcaataac    360
ccagatcacg atgagctttt cacacgttta cgcctgttat tgacgggtcc agacccaaca    420
ccaggcactc gtttacaagt gtcgttgttc ttgtcgggat tgctgggtcc agctcaagat    480
ccgtcatgtg ctgacatcga tgacgacgcc cttcgtgccg ggatcgtccg tgccggacgt    540
cgtttattac ttgcggacga cgacgccggg tcacatcatc accaccatca c             591
```

<210> SEQ ID NO 7
<211> LENGTH: 47
<212> TYPE: PRT
<213> ORGANISM: Pimelobacter simplex

<400> SEQUENCE: 7

```
Ile Leu Ala Ala Ala Thr Arg Leu Phe Ala Thr His Gly Val Ser Gly
1               5                   10                  15

Thr Ser Leu Gln Gln Ile Ala Asp Ala Thr Gly Ile Thr Lys Ala Ala
            20                  25                  30

Val Tyr His His Phe Pro Thr Lys Glu Glu Val Val Val Ala Val
        35                  40                  45
```

<210> SEQ ID NO 8
<211> LENGTH: 141
<212> TYPE: DNA
<213> ORGANISM: Pimelobacter simplex

<400> SEQUENCE: 8

```
atcctcgccg ccgcgacccg gctcttcgcc acgcacggcg tctccggcac ctcgctgcag    60
cagatcgcgg acgccaccgg gatcaccaag gccgccgtct accaccactt ccccaccaag   120
gaggaggtcg tcgtcgccgt c                                             141
```

<210> SEQ ID NO 9
<211> LENGTH: 384
<212> TYPE: DNA
<213> ORGANISM: Pimelobacter simplex

<400> SEQUENCE: 9

```
ctggcgcccg cgctcgaggc gatccagggc atcgtccgca ccgccggcgc ccacgaggac    60
ccgcgggccg cgaccgaggc cgccatcatc ggcctcgccg accaggccgt cacccaccgc   120
cagcgctggg ccgtgctcct ccaggacgcc gccgtcgagg agtacgtccg caacaacccc   180
gaccacgacg agctcttcac ccggctgcgc ctgctcctca ccggcccgga tcccacccg    240 ggcaccggc tccaggtctc cctcttcctc tccggcctgc tcgggcccgc gcaggacccc    300
agctgcgccg acatcgacga cgacgcgctg cgcgcgggca tcgtccgggc cggacgccgg    360
ctcctgctgg ccgacgacga cgcc                                          384
```

<210> SEQ ID NO 10
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
attcttgctg cagcaacgcg cttattcgca acccacggcg taagcggaac ctcactgcag    60
caaattgcag acgcaacggg tatcactaag gcggcggtat atcaccattt ccctacaaag   120
gaagaagttg tagtggccgt g                                             141
```

<210> SEQ ID NO 11
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
ttagcacctg cgttagaggc cattcaaggt attgtgcgca cagccggagc gcatgaggac      60
ccacgtgcag caacagaggc cgccattatt ggattagcgg atcaggcggt tactcaccgt     120
caacgctggg cggtactgtt gcaagacgct gccgtcgaag agtatgttcg caataaccca     180
gatcacgatg agcttttcac acgtttacgc ctgttattga cgggtccaga cccaacacca     240
ggcactcgtt tacaagtgtc gttgttcttg tcgggattgc tgggtccagc tcaagatccg     300
tcatgtgctg acatcgatga cgacgcccct cgtgccggga tcgtccgtgc cggacgtcgt     360
ttattacttg cggacgacga cgccgggtca catcatcacc accatcac               408

<210> SEQ ID NO 12
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
ttagcacctg tgttagaggc cattcatggt attgtgcgca cagccggagc gcatgaggac      60
ccacgtgcag caacagaggc cgccattatt ggattagcgg atcaggcggt tactcaccgt     120
caacgctggg cggtactgtt gcaagacgct gccgtcgaag agtatgttcg caataaccca     180
gatcacgatg agcttttcac acgtttacgc ctgttattga cgggtccaga cccaacacca     240
ggcactcgtt tacaagtgtc gttgttcttg tcgggattgc tgggtccagc tcaagatccg     300
tcatgtgctg acatcgatga cgacgcccct cgtgccggga tcgtccgtgc cggacgtcgt     360
ttattacttg cggacgacga cgccgggtca catcatcacc accatcac               408

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aactagccgt tcggcaagta                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aactagccgt tcggctagtt                                                   20

<210> SEQ ID NO 15

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aactagccgt tctgttagtt                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tacttaacga taggtaagta                                                   20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gactagccga tcggctagtt                                                   20

<210> SEQ ID NO 18
<211> LENGTH: 128
<212> TYPE: PRT
<213> ORGANISM: Pimelobacter simplex

<400> SEQUENCE: 18

Leu Ala Pro Ala Leu Glu Ala Ile Gln Gly Ile Val Arg Thr Ala Gly
1               5                   10                  15

Ala His Glu Asp Pro Arg Ala Ala Thr Glu Ala Ala Ile Ile Gly Leu
            20                  25                  30

Ala Asp Gln Ala Val Thr His Arg Gln Arg Trp Ala Val Leu Leu Gln
        35                  40                  45

Asp Ala Ala Val Glu Glu Tyr Val Arg Asn Asn Pro Asp His Asp Glu
    50                  55                  60

Leu Phe Thr Arg Leu Arg Leu Leu Thr Gly Pro Asp Pro Thr Pro
65                  70                  75                  80

Gly Thr Arg Leu Gln Val Ser Leu Phe Leu Ser Gly Leu Leu Gly Pro
                85                  90                  95

Ala Gln Asp Pro Ser Cys Ala Asp Ile Asp Asp Ala Leu Arg Ala
            100                 105                 110

Gly Ile Val Arg Ala Gly Arg Arg Leu Leu Ala Asp Asp Ala
        115                 120                 125

<210> SEQ ID NO 19
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19
```

```
Leu Ala Pro Ala Leu Glu Ala Ile Gln Gly Ile Val Arg Thr Ala Gly
1               5                   10                  15

Ala His Glu Asp Pro Arg Ala Ala Thr Glu Ala Ala Ile Ile Gly Leu
                20                  25                  30

Ala Asp Gln Ala Val Thr His Arg Gln Arg Trp Ala Val Leu Leu Gln
            35                  40                  45

Asp Ala Ala Val Glu Glu Tyr Val Arg Asn Asn Pro Asp His Asp Glu
        50                  55                  60

Leu Phe Thr Arg Leu Arg Leu Leu Leu Thr Gly Pro Asp Pro Thr Pro
65                  70                  75                  80

Gly Thr Arg Leu Gln Val Ser Leu Phe Leu Ser Gly Leu Leu Gly Pro
                85                  90                  95

Ala Gln Asp Pro Ser Cys Ala Asp Ile Asp Asp Ala Leu Arg Ala
                100                 105                 110

Gly Ile Val Arg Ala Gly Arg Arg Leu Leu Leu Ala Asp Asp Ala
            115                 120                 125

<210> SEQ ID NO 20
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Leu Ala Pro Val Leu Glu Ala Ile His Gly Ile Val Arg Thr Ala Gly
1               5                   10                  15

Ala His Glu Asp Pro Arg Ala Ala Thr Glu Ala Ala Ile Ile Gly Leu
                20                  25                  30

Ala Asp Gln Ala Val Thr His Arg Gln Arg Trp Ala Val Leu Leu Gln
            35                  40                  45

Asp Ala Ala Val Glu Glu Tyr Val Arg Asn Asn Pro Asp His Asp Glu
        50                  55                  60

Leu Phe Thr Arg Leu Arg Leu Leu Leu Thr Gly Pro Asp Pro Thr Pro
65                  70                  75                  80

Gly Thr Arg Leu Gln Val Ser Leu Phe Leu Ser Gly Leu Leu Gly Pro
                85                  90                  95

Ala Gln Asp Pro Ser Cys Ala Asp Ile Asp Asp Ala Leu Arg Ala
                100                 105                 110

Gly Ile Val Arg Ala Gly Arg Arg Leu Leu Leu Ala Asp Asp Ala
            115                 120                 125

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgtgcgtgtc cctcgctcgg tttcacga                                      28

<210> SEQ ID NO 22
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 22

Gly Ser His His His His His His
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcctaactag ccgttcggct agttattc                                       28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gaataactag ccgaacggct agttaggc                                       28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcctaactag ccgatcggct agtcattc                                       28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaatgactag ccgatcggct agttaggc                                       28

<210> SEQ ID NO 28
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 28
gcctaactag ccgttcggca agtaattc                                              28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gaattacttg ccgaacggct agttaggc                                              28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ccttaactag ccgttctgtt agttattc                                              28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gaataactaa cagaacggct agttaagg                                              28

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgtgcgtgtc cctcgctcgg tttcaga                                               27

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tcgtgaaacc gagcgaggga cacgcaca                                              28

<210> SEQ ID NO 34
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 34
gtcatccctc tcattgatag agatactg                                          28

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cagtatctct atcaatgata gggatgac                                          28

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tcgtgaaacc gagcgaggga cacgcaca                                          28

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aggtcgcggc ctaactagcc gttcggctag ttattctaga ccgca                       45

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcctaactag ccgttctgtt agttattc                                          28
```

MICROBIAL-BASED BIOSENSORS

CROSS-REFERENCE TO RELATED APPLICATIONS

This application claims benefit under 35 U.S.C. § 119(e) of U.S. Provisional Application No. 62/594,209 filed Dec. 4, 2017, the contents of which are incorporated herein by reference in their entirety.

GOVERNMENT SUPPORT

This invention was made with government support under Contract No. W911NF-16-C-0044 awarded by the Army Research Office. The government has certain rights in the invention.

SEQUENCE LISTING

The instant application contains a Sequence Listing which has been submitted electronically in ASCII format and is hereby incorporated by reference in its entirety. Said ASCII copy, created on Jan. 16, 2019, is named 701586-090900US-PT_SL.txt and is 20,510 bytes in size.

TECHNICAL FIELD

The technology described herein relates to a microbial-based biosensor system for the detection of small molecules based on an analyte-responsive transcription factor-DNA binding mechanism for the quantification of a target analyte with high sensitivity.

BACKGROUND

Label-free sensing of small molecules and analytes is of critical importance to biomedical research, point of care diagnostics, and environmental sensing, among other applications. Label-free sensors directly detect small molecules and analytes in samples without the need for additional sample preparation (i.e., sample purification or analyte labeling), enabling high-throughput measurements on native samples. Typical approaches to label-free biosensing utilize aptamers or antibodies as molecularly specific recognition elements. The use of monoclonal antibodies is ubiquitous in many aspects of biomedical research and clinical treatment, but has drawbacks in the cost and effort required for development and production and the challenges related to developing antibodies for small molecules. Aptamers refer to nucleic acid-based affinity probes that have been developed for protein targets and small molecules. Aptamers are considered to be more effective than antibodies at recognizing small molecule targets. However, the identification of aptamer sequences through SELEX (systematic evolution of ligands by exponential enrichment), is even more technically challenging for small molecule targets. Most critically, both antibodies and aptamers provide a specific binding element, but no inherent transduction mechanism, i.e., there is no change to the aptamer or antibody upon target binding that can be harnessed for signal output other than the binding itself.

Detection and quantification of hormones levels are central to fertility planning and assisted reproductive technologies; one million women in the U.S. suffer from infertility and another 7.5 million women suffer from decreased fertility. Quantitative measures of hormone levels are also critical to the diagnosis, management, and treatment of endocrine disorders and hormone imbalances that affect up to 20% of the population. Consequently, advanced hormone biosensors that enable improved sensitivity, selectivity, and greater target diversity are critically needed to meet these health challenges. Such hormone biosensors will capitalize on current improvements in microfluidic, electronic, and computational technologies that are moving clinical assays to the point-of-care and wearable sensors. Real-time continuous monitoring of hormones levels would enable fundamentally new approaches to fertility planning and the management of endocrine disorders. A critical limiting factor is the lack of adequate hormone biosensors and the limitations of existing antibody- and aptamer-based approaches.

There is a need in the art for improved methods of detecting small molecules, including hormones. Bacteria have evolved over 3 billion years to detect and respond to virtually all classes of stimuli relevant to our own biology, including steroid hormones. Steroid utilizing bacteria have been isolated from diverse sources including activated sludge from wastewater, soil, composts, aquifers, sea waters, and the human microbiome. However, using components from the human microbiome for real-time, quick sensitive and reliable assay detection, and in a cell-free assays has not been established.

SUMMARY

The technology described herein relates generally to a microbial-based biosensor system for the detection of small molecules and analytes based on an analyte-responsive transcription factor-DNA binding mechanism with either a fluorescent output through Förster resonance energy transfer (FRET) or a redox sensor output for the quantification of a target analyte with high sensitivity. Accordingly, as described herein are compositions, methods and processes to identify and isolate bacterial allosteric Transcription factors (aTFs) that recognize a target analyte and to develop these aTFs into in vitro biosensors that can be used in a range of assays and devices. Transcription factors are regulatory proteins that contain a DNA-binding domain as well as a ligand-binding domain that is able to recognize small molecules with high specificity and selectivity. In the presence of a target small molecule, TF affinity for its DNA binding sequence is modulated, facilitating the repressor or derepressor regulation of downstream gene expression. Described herein is an analyte-responsive transcription factor-DNA binding mechanism with either a ratiometric fluorescent output through Förster resonance energy transfer (FRET) or a redox sensor output for the quantification of the target analyte with high sensitivity.

For example, the inventors have utilized and modified microbial allosteric transcription factors (aTFs), which are a mechanism by which bacteria sense stimuli, into a biosensor that can be used in a real-time, sensitive and cell free assay for analyte detection, including analyte quantification, in a sample.

By way of an illustrative example only, a microbial-based biosensor described herein comprises an allosteric transcription factor that is conjugated to a quantum dot (QD), where the transcription factor can, in the presence of an analyte, bind to a binding site on a nucleic acid probe, where the nucleic acid probe comprises at least one florescent dye, such that when the analyte binds to the transcription factor, it induces a conformational change to allow the transcription factor to bind to the nucleic acid probe, bringing the QD and the fluorescent dye in to close proximity, such that Fluorescence Resonance Energy Transfer (FRET) occurs, and is detected by an optical sensor as disclosed herein. Accordingly, in such embodiments, in the presence of an analyte, binding between the aTF and the nucleic acid prone occurs, and thus, the microbial biosensor serves as an ON-biosensor (e.g., see FIG. 10).

In alternative embodiments, and by way of an illustrative example only, a microbial biosensor comprises an allosteric transcription factor that is conjugated to a quantum dot (QD), where the transcription factor in the absence of an analyte binds to a binding site on a nucleic acid probe, where the probe comprises at least one fluorescent dye, such that in the absence of the analyte, the QD and the fluorescent dye are close proximity and FRET occurs. When the analyte is present, it binds to the transcription factor and induces a conformational change in the transcription factor to decrease its affinity for the binding site on the nucleic acid probe such that the probe dissociates from the transcription factor, therefore, the QD and the fluorescent dyes are no longer in close proximity to enable FRET to occur, and therefore a decrease or absence of FRET is detected by an optical sensor. Accordingly, in such embodiments, in the presence of an analyte, binding between the aTF and the nucleic acid probe does not occur, and the microbial biosensor serves as an OFF-biosensor (e.g., see, FIGS. 1 and 9A).

As described herein, FRET is one output system for determining the presence of the analyte. However, as described herein, in alternative embodiments, the output system is the transfer of electrons between electroactive molecules attached to the allosteric transcription factor and/or the nucleic acid probe, where the flow of electrons when the transcription factor and nucleic acid probe are bound can be detected using a semi-conductor device.

Moreover, as described herein, the affinity of the transcription factor for the analyte can be modified to increase the sensitivity of the biosensor, for example, the affinity for the analyte can be increased or decreased. Additionally, the affinity of the transcription factor for the nucleic acid probe can be modified to increase the sensitivity of the biosensor. For example, where the biosensor is an ON-biosensor, the affinity for the aTF for the binding site on the nucleic acid probe could be increased, such that binding is rapid when the analyte is present. Alternatively, in some embodiments, where the biosensor is an OFF-biosensor, the affinity for the aTF for the binding site on the nucleic acid probe could be decreased, such that dissociation of the aTF from the nucleic acid probe is rapid in the presence of the analyte.

The biosensors described herein a modular system. For example, the aTF comprise an analyte binding domain, also referred to as a "ligand binding domain" or LBD, and a DNA binding domain (DBD) which has an affinity for a specific target nucleic acid sequence, referred to herein as a "transcription factor binding domain" or "TFBD" in the nucleic acid probe. It is envisioned that any DBD and TFBD pair known to an ordinary skilled artisan can be used, provided that their affinity for binding to each other is modified (i.e., increased in an ON-biosensor, or decreased on an OFF-biosensor) when an analyte binds to the LBD of the aTF.

Similarly, as discussed above, while a fluorescent output is one method for detecting the presence of analytes, other detection system can be used, as disclosed herein. Additionally, while in some embodiments, aTF is conjugated to a QD and the nucleic acid probe is conjugated to a fluorescent dye, it is envisioned modifications can be made, for example, aTF can be conjugated to one or more fluorescent dyes and the nucleic acid probe can be conjugated to a QD, or alternatively, both the aTF and the nucleic acid probe are conjugated to QDs, or both the aTF and the nucleic acid probe are conjugated to different fluorescence dyes. Such modifications are easily determined by one of ordinary skill in the art, and can be assessed using the methods and assays described herein and in the Examples.

Accordingly, in some embodiments of these aspects and all such aspects described herein, is a composition comprising: A composition comprising: an allosteric transcription factor conjugated to one or more first fluorescent molecules of a Fluorescence Resonance Energy Transfer (FRET) pair, the allosteric transcription factor comprising one or more ligand binding domains (LBDs) and one or more DNA binding domains (DBDs), a nucleic acid probe conjugated to one or more second fluorescent molecules of the FRET pair, the nucleic acid probe having a sequence comprising one or more transcription factor binding domains (TFBDs) that is specific to the DBD of the transcription factor, wherein when an analyte binds to the allosteric transcription factor, the affinity of the DBD for the TFBD is altered, wherein in the presence of an analyte at least one of the following occurs: the DNA binding domain (DBD) binds to the TFBD, the first fluorescent reporter and the second fluorescent reporter of the FRET pair emits a fluorescent signal; or the DNA binding domain (DBD) does not bind to the TFBD, and the first fluorescent reporter and the second fluorescent reporter of the FRET pair does not emit a fluorescent signal.

In some embodiments of these aspects and all such aspects described herein, first fluorescent molecule comprises a FRET acceptor, and the second fluorescent reporter each comprises a FRET donor.

In some embodiments of these aspects and all such aspects described herein, the first fluorescent molecule comprises a FRET donor, and the second fluorescent reporter each comprises a FRET acceptor.

In some embodiments of these aspects and all such aspects described herein, the fluorescent molecule is selected from the group consisting of a quantum dot, a fluorescent dye, a fluorescent protein, and combinations thereof.

In some embodiments of these aspects and all such aspects described herein, the composition comprises an allosteric transcription factor conjugated to one or more electroactive molecules, the allosteric transcription factor comprising one or more ligand binding domains (LBDs) and one or more DNA binding domains (DBDs), a nucleic acid probe attached to a conducting surface, the nucleic acid probe having a sequence comprising one or more transcription factor binding domains (TFBDs) that is specific to the DBD of the transcription factor, wherein when an analyte binds to the allosteric transcription factor, the affinity of the DBD for the TFBD is altered, wherein in the presence of an analyte at least one of the following occurs: the DNA binding domain (DBD) binds to the TFBD, the electroactive molecule alters the flow of electrons to the conductive surface, and is detected by an increase in current in the surface; or the DNA binding domain (DBD) binds to the TFBD, the electroactive molecule alters the flow of electrons to the conductive surface, and is detected by an increase in current in the surface.

In some embodiments of these aspects and all such aspects described herein, the ligand binding domain (LBD) that binds to an analyte of interest.

In some embodiments of these aspects and all such aspects described herein, the analyte of interest is selected from any of a small molecule, toxin, neurotransmitter, immunomodulator, metabolite, hormone.

In some embodiments of these aspects and all such aspects described herein, the hormone is selected from any of the group of: progesterone, estradiol, estrone, estriol, progesterone, testosterone, aldosterone, prednisolone, androstadienone, cortisol, cholesterol.

In some embodiments of these aspects and all such aspects described herein, the DNA binding domain (DBD) has been modified to increase or decrease its affinity for binding to the TFBD.

the TFBD has been modified to increase or decrease its affinity for binding to the DBD.

In some embodiments of these aspects and all such aspects described herein, the allosteric transcription factor undergoes a confirmation change upon binding of the ligand to the LBD, thereby allowing the DBD to bind to the transcription factor binding domain.

In some embodiments of these aspects and all such aspects described herein, the allosteric transcription factor undergoes a confirmation change upon binding of the ligand to the LBD, thereby allowing the DBD to bind to the transcription factor binding domain.

In some embodiments of these aspects and all such aspects described herein, the allosteric transcription factor is a microbial transcription factor.

In some embodiments of these aspects and all such aspects described herein, is a process for detecting an analyte in a sample, comprising; contacting the sample with an allosteric transcription factor conjugated to a first quantum dot of a FRET pair, the allosteric transcription factor comprising a ligand binding domain (LBD) and a DNA binding domain (DBD), a nucleic acid probe conjugated to a second quantum dot of the FRET pair, the nucleic acid probe having a sequence comprising a transcription factor binding domain (TFBD) that is specific to the DBD of the transcription factor, measuring the QD photoluminescence of the sample, wherein a change in fluorescence in the sample indicates the presence of at least one analyte in the sample.

Other aspects of the technology described herein relate to biosensors, hormone biosensors, microbial biosensors as disclosed herein and their methods of use of detecting an analyte (e.g., hormone or other analyte) in a sample. Other aspects disclosed herein relate to biosensors for point of care (POC) diagnostics and can be measured on POC devices that can electronically communicate with mobile devices and smart devices (e.g., tablets, smartwatches and smartphones etc.). Other aspects of the technology disclosed herein relate to systems and methods comprising contacting a biosensor as disclosed herein with an analyte and detecting an output signal (e.g., presence or absence of FRET or a change in current) in the presence of the analyte. In some embodiments, the detecting the output signal is on a POC device and optionally uses consumable cartridges and/or cassettes.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

This application file contains at least one drawing executed in color. Copies of this patent application publication with color drawings will be provided by the Office upon request and payment of the necessary fee. The present teachings described herein be more fully understood from the following description of various illustrative embodiments, when read together with the accompanying drawings. It should be understood that the drawings described below are for illustration purposes only and are not intended to limit the scope of the present teachings in any way.

FIG. 1A shows the binding of the TF to a specific DNA sequence brings the donor and acceptor fluorophores into close proximity, enabling FRET. Upon binding of a derepressor analyte, the affinity of the TF for the DNA binding sequence is significantly reduced, resulting in unbinding of the TF-DNA complex. In the presence of the analyte, TF-DNA binding is low and energy transfer to the acceptor is minimal; thus, donor emission intensity is higher, and acceptor emission intensity is lower. Schematic not to scale. FIG. 1B shows spectra for the absorbance (dashed lines) and emission (solid lines) of the donor (tdTomato and QD) and acceptor (Cy5).

FIG. 2A shows sensor 1: tdTomato-TetRc+Cy5-DNA; FIG. 2B shows sensor 2: QD1-TetRc+Cy5-DNA and FIG. 2C shows Sensor 3: QD2-TetRd+Cy5-DNA. The data depicted by a red dotted line use the target binding sequence of TetO, while the scrambled sequence, depicted by a black dash line acts as a non-binding control for collisional quenching and non-specific binding. The red dotted line is a fit of the specific binding to a modified Hill equation, while the black dash line shows the linear fit that is typical of Stern-Vollmer collisional quenching. Data are mean+/− standard deviation for n=3.

FIG. 3A shows sensor 1: tdTomato-TetRc+Cy5-DNA; FIG. 3B shows sensor 2: QD1-TetRc+Cy5-DNA, and FIG. 3C shows sensor 3: QD2-TetRd+Cy5-DNA titrated with anhydrotetracycline (aTc). At higher concentrations of aTc, binding of the TF and DNA is disrupted, reducing FRET, thereby increasing donor emission and reducing acceptor emission. Spectra are background subtracted to eliminate the effects of direct acceptor excitation. FIG. 3D-3F show the ratio of acceptor fluorescence intensity to donor fluorescence intensity as a function of aTc concentration. FIG. 3D shows the ratio of acceptor fluorescence intensity to donor fluorescence intensity as a function of aTc concentration for sensor 1. FIG. 3E shows the ratio of acceptor fluorescence intensity to donor fluorescence intensity as a function of aTc concentration for sensor 2 and FIG. 3F shows the ratio of acceptor fluorescence intensity to donor fluorescence intensity as a function of aTc concentration for sensor 3. Sensor 1 was prepared with a 1:1:3 ratio of tdTomato:TF:DNA, while sensors 2 and 3 were prepared with a 1:4:18 ratio of QD:TF:DNA. tdTomato (200 nM) and QD (50 nM) concentrations were selected to keep TF concentration constant at 200 nM. Data are mean±standard deviation for n=3.

FIGS. 4A-4B show the normalized ratio of acceptor and donor fluorescence intensity ($F_A/F_D$). The c50 (analyte concentration that yields 50% signal aka the effective concentration, or EC50) is 205 nM, 682 nM, and 117 nM for sensors 1, 2, and 3, respectively. FIG. 4B shows the normalized linear ranges of sensor outputs.

FIG. 5A shows the Peak fitting results from Origin Pro of sensor 1. Sensor 1 was fitted with a sum of an asymmetric sigmodal and an exponential modified Gaussian. FIG. 5B shows the Peak fitting results from Origin Pro of sensor 2. Sensor 2 was fitted with a sum of two exponentially modified Gaussians.

FIG. 6A shows representative spectral data for sensor 1: tdTomato-TetRc+Cy5-DNA, FIG. 6B shows representative spectral data for sensor 2: QD1-TetRc+Cy5-DNA, and FIG. 6C shows representative spectral data for sensor 3: sensor 3: QD2-TetRd+Cy5-DNA titrated with anhydrotetracycline (aTc).

FIGS. 7A-7F show a schematic of the development and implementation of ratiometric sensors based on aTF-DNA binding. FIG. 7A shows a schematic of the growth of microbial cells in the presence and absence of the target small molecule (e.g., hormone). FIG. 7B shows a schematic of the analysis of a comprehensive RNA sequencing (RNA-seq) data. Islands of genes up- or down-regulated in response to the analyte are identified using this method and the aTF responsible for regulation of these genes is determined, cloned, and recombinantly expressed. FIG. 7C shows a schematic of a specific DNA binding sequence for the aTF that is confirmed using in vitro chromatin immunoprecipitation sequencing (ChIP-Seq), and FIG. 7D shows a schematic of the binding affinities quantified using bilayer interferometry (BLI). FIG. 7E shows a schematic of Fluorescence resonance energy transfer (FRET)-based sensors generated using semiconductor quantum dots (QDs) as a donor fluorophore with histidine-tagged TFs self-assembled to their surface. Dye-labeled DNA oligomers act as FRET acceptors that bind to the TF with different affinities depending on the presence or absence of the effector analyte. FIG. 7F shows a schematic of a sensor that is used to measure analyte concentrations in physiological solutions like milk or urine in either a plate reader or our benchtop device engineered to yield sensitive sensor output measurements from inexpensive off-the-shelf optical components.

FIG. 8A shows that *P. simplex* possesses a steroid responsive genome island (srgi) and shows a whole genome view of the upregulation of *P. simplex* genes with progesterone (PRG) exposure against a solvent control (CNTL). FIG. 8B shows a zoomed in view of the srgi (genes 5313-5333) and reveal steroid specific enzymes and two TFs. Zoomed in view of the rightmost TF in the srgi, a TetR Family TF. Putative TetR family TF binding site upstream of its own gene.

FIG. 8B discloses SEQ ID NO: 37. FIG. 8C shows a whole genome view of the upregulation of *P. simplex* genes with aldosterone (ALD), hydrocortisone (CRT), 17β-estradiol (ESL), estrone (ESE), and testosterone (TST) exposure vs a control. In all of the gene plots, individual genes are depicted by triangles; genes exhibiting greater than 1-fold log change in their expression frequency are colored green. Genes identified in accession tags as steroid enzymes are green with a blue edge, while those labeled as TFs are depicted in red.

FIG. 9A shows a schematic that shows that the excited QDs (donor) is able to emit fluorescence and transfer energy via FRET to the DNA-Cy5 (acceptor). FIG. 9B shows that there was a significant decrease of the fluorescence of Cy5 (FA), and an increase of the fluorescence of QDs (FD) when the PRG concentration varies from 0 to 10 uM. FIG. 9C shows the DNA sequences of nucleic acid probes containing TFBDs with different affinities varying from weak to strong. In order to homogenize the fluorescent signals in between batches and different sensor variations, $F_A/F_D$ was normalized to give the signal output. FIG. 9C discloses SEQ ID NOS 24, 28 38 and 21, respectively. FIG. 9D shows the signal output plotted against PRG concentration to give a dose-response curve. FIG. 9E shows the sensor output plotted against PRG concentration. FIG. 9F shows the sensor output plotted against PRG concentration. FIG. 9G shows the crosscreactivity of the TF when exposed to different hormones. FIG. 9H shows the sensor output. FIGS. 9I-9K show the reversibility of the sensor 3 after exposure to PRG and dialysis on a 10k membrane. After the first round of dialysis, sensor 3 recovered the original signal output.

FIGS. 12A-12B show a schematic flow of the microfluidic chip and reader. FIG. 12A shows that body fluids such as urine, sweat or saliva can be introduced to the wicking pad. The wicking pad cover keeps the chip and reader clean. Finally, the chip is introduced into the reader where quantitative measures of sensor activity are made and reported. FIG. 12B shows a schematic of the microfluidic chip. Sensor components are spotted inside of the transparent plastic reaction chamber and dried in place. Sensor components are rehydrated upon contact with the urine sample. The hydrophobic vent ensures that air can escape during filling, while a precise volume of sample fluid is taken into the reaction chamber. FIG. 12C shows images of a similar PMMA chips, showing chamber architecture (left) and a hydrophobic vent structure (right).

FIG. 13A shows tips that are baselined by dipping in 1× binding buffer for 60 seconds, then are loaded with DNA by dipping into buffer containing 250 nM biotinylated oligo. Binding is allowed to proceed for 50 to 90 seconds, and is terminated before binding curves plateau and the tip becomes saturated. A second baseline step of 60 seconds is done to ensure DNA:tip stability. PinR association assayed by dipping the tip in varying concentrations of PinR (150 nM for all hormone dissociation curves) until equilibrium is reached. Hormone-induced dissociation is assayed by dipping PinR:DNA:tip complex into buffer containing varying concentrations of hormone or ethanol control. FIG. 13B shows Time 0-normalized dissociation curves collected as in FIG. 13A showing PinR:WT-DNA dissociation induced by 5 μM of various hormones. Side panel shows the fraction of complex dissociated at 30 seconds. Asterisks indicate a p value≤a Bonferroni-corrected alpha of 0.05. FIG. 13C shows Progesterone-induced dissociation of PinR:WT-DNA at varying concentrations. Side panel shows fraction complex dissociated at 5 seconds.

FIGS. 15A-15B show the growth of *P. simplex* with respect to the starting inoculation density, solvent toxicity and the addition of steroids. A starting OD of 0.0005 produced an optimal growth curve with a clear lag phase, linear log phase, and steady stationary phase.

As shown in FIG. 16, *P. simplex* was grown in the presence of 700 μM testosterone, 21.88 μM progesterone, 87.50 estrone, 21.88 μM 17β-estradiol, 21.88 μM hydrocortisone, or 175.00 μM aldosterone.

FIG. 17A shows a schematic of aTF-TF Protein FRET.

FIG. 17B shows a schematic of a conformational change TF-FRET Mechanism.

FIGS. 20A and 20B show graphs of sensor outputs in the presence of changing ratios of QD/TF and QD/DNA. FIG. 20C shows a graph of the $IC_{50}$ in the presence of changing ratios of TF/QD.

FIG. 26A shows the sensor outputs ($F_A/F_D$) from sensor 1. FIG. 26B shows the sensor outputs ($F_A/F_D$) from sensor 2 and FIG. 26C shows the sensor outputs ($F_A/F_D$) from sensor 13.

FIG. 27A shows the sensor output, FIG. 27B shows the $F_A/F_D$ ratio at [PRG]=25 nM.

FIGS. 28A-E show the evolution of the sensor output after cycles of three adds (+) of PRG to the sensor and two dialysis cycles (−). Each panel corresponds to a specific concentration of PRG added (0, 25, 75, 100 and 10,000 nM).

FIGS. 29A-29B show the sequence alignments of the identified aTF PinR. FIG. 29A discloses SEQ ID NOS 1-2 and FIG. 29B discloses SEQ ID NOS 1-3, all respectively, in order of appearance.

FIG. 30 shows a method to screen for transcription factors (TFs) that bind a hormone of interest. The method is based on the differential regulation of sterol utilization genes and TFs on exposure to sterols. Initial hits are identified using RNA-Seq, cloned, and validated in vitro using a multiple methods including BLI.

FIG. 31A shows the gene expression screening identified a novel progesterone responsive TF (gene d) (Triangles: genes ordered by genomic position Y axis: fold change expression in response to progesterone exposure relative to control). FIG. 31B show the in vitro responsiveness of TF to progesterone. Y axis is probe tip thickness. (i) probe, (ii-iii) probe+DNA, (iv) probe+DNA+TF, (v) probe+DNA+TF+hormone. Insert: change in binding in (v) for each hormone relative to progesterone. All hormones at 6.5 uM. FIG. 31C shows the response of QD-FRET sensor based on the identified TF verified using BLI (Bio-Layer Interferometry).

FIG. 34A shows the distance between donor and acceptor. FIG. 34B shows an initial model of our system predicts that altering KDNA increases sensitivity.

FIG. 35A shows that the excitation light at 400 nm is preferentially absorbed by the ZnSe of the donor QD; energy is efficiently transferred to an InP/ZnS acceptor QD, if the donor and acceptor are in close proximity. Ratiometric analysis of the two emission peaks provides internal calibration of the system. FIG. 35B shows the absorbance (dotted lines) and emission spectra (solid lines) of donor InP/ZnSe (green) and acceptor InP/ZnS (orange). Even with relatively thin-shelled ZnSe donors, the absorbance of the donor QD at 400 nm is significantly higher than that of the ZnS-shelled acceptor. The emission peak of the donor overlaps completely with the 1S excitation peak of the acceptor (inset), facilitating efficient energy transfer. FIG. 35C Shell-thickness dependent ratio of InP/ZnSe to InP/ZnS absorption cross-section at 400 nm. The donor dot absorbs light several orders of magnitude more efficiently than the acceptor dot while still maintaining an overall dot diameter below 12 nm (2 nm diameter core+5 nm thick shell). This facilitates the preferential excitation of the donor InP/ZnSe QD.

FIG. 37A shows fluorescence emissions when no progesterone is present in the media ($\lambda$exc=400 nm) and fit of the QD-TF (donor) and DNA-Cy5 (acceptor) emission spectra with a Gaussian curve. Right. FIG. 37B shows the evolution of the QDs (left, yellow) and Cy5 (right, salmon) fluorescence emission as a function of the progesterone concentration in the media. Example is for [QD]=25 nM, QD/TF/DNA=1/4/18, DNA1. By adding progesterone to the media, the fluorescence emission of the QDs (donor) increase while the fluorescence emission of the Cy5 (acceptor) decrease. This is due to the Fluorescence energy transfer (FRET) occurring between the QDs-TF and the DNA-Cy5: when the DNA-Cy5 unbind the QD-TF, the Cy5 is too far from the QDs surface to be able to receive energy from the QDs. As such, no fluorescence is emitted anymore from the Cy5.

FIGS. 38A-38B show fluorescent emission signals of Cy5 and QD as a function of the progesterone concentration. FIG. 38A shows the evolution of the ratio of the fluorescence emission signal of Cy5 and QDs as a function of the progesterone concentration ($\lambda$exc=400 nm). FIG. 38B shows the normalization of the ratio of Cy5 and QDs between the value of [Progesterone]=0 nM and [Progesterone]=10 uM. The experiments have been performed in triplicate using five different oligonucleotides sequences with final [QD]=25 nM and QD/TF/DNA=1/4/18.

FIG. 39A shows the evolution of the ratio of the fluorescence emission signal of Cy5 and QDs as a function of the progesterone concentration ($\lambda$exc=400 nm). FIG. 39B shows the normalization of the ratio of Cy5 and QDs between the value of [Progesterone]=0 nM and [Progesterone]=10 uM. The experiments have been performed in triplicate using DNA sequence DNA3 and different ratio of QD/TF/keeping the ratio QD/DNA=2, with a final [QD]=25 nM.

FIG. 40A shows the evolution of the ratio of the fluorescence emission signal of Cy5 and QDs as a function of the progesterone concentration ($\lambda$exc=400 nm). FIG. 40B shows the normalization of the ratio of Cy5 and QDs between the value of [Progesterone]=0 nM and [Progesterone]=10 uM. The experiments have been performed in triplicate using DNA sequence DNA3 and different ratio of QD/TF/keeping the ratio QD/DNA=8, with a final [QD]=25 nM.

FIG. 41A shows the evolution of the ratio of the fluorescence emission signal of Cy5 and QDs as a function of the progesterone concentration ($\lambda$exc=400 nm). FIG. 41B shows normalization of the ratio of Cy5 and QDs between the value of [Progesterone]=0 nM and [Progesterone]=10 uM. The experiments have been performed in triplicate using DNA sequence DNA3 and different ratio of QD/TF/keeping the ratio QD/DNA=18, with a final [QD]=25 nM.

FIG. 42A shows the evolution of the ratio of the fluorescence emission signal of Cy5 and QDs as a function of the progesterone concentration ($\lambda$exc=400 nm). FIG. 42B shows normalization of the ratio of Cy5 and QDs between the value of [Progesterone]=0 nM and [Progesterone]=10 uM. The experiments have been performed in triplicate using DNA sequence DNA3 and different ratio of QD/TF/keeping the ratio QD/DNA=18, with a final [QD]=25 nM.

FIG. 43A shows a tetR-tdTomato as the FRET donor and the OligoCy5 as the FRET acceptor. In the presence of aTc, tetR-tdTomato will unbind the OligoCy5 and tetR-tdTomato emission will recover. FIG. 43B shows the spectral data of OligoCy5 (acceptor) titration to TetR-tdTomato (donor) to determine the optimal ratio of acceptor to donor to yield the highest FRET efficiency. No analyte has been added. FIG. 43C shows the spectral data of a scrambled OligoCy5 (acceptor) titration to TetR-tdTomato (donor) to determine the background signal due to direct acceptor excitation and collisional quenching. No analyte has been added. tetR-tdTomato=200 nM; OligoCy5=0-1.8 uM (TetO binding sequence for sensor; scrambled sequence for negative control); Legend shows Molar Acceptor Ratio (Number of OligoCy5 molecules per tetR-tdTomato). FIG. 43D shows the Relative tetR-tdTomato emission vs. Number of oligoCy5 molecules per TetR-tdTomato. FIG. 43E shows the Ratio of acceptor emission intensity to donor emission intensity as a function of the number of oligoCy5 molecules per TetR-tdTomato donors. These two graphs show the difference between our sensor (blue) and negative control (orange). The lowest number of acceptor molecules with the largest difference between the signal and noise (difference between blue and orange) is the concentration ratio that we want to work with moving forward. For the final sensor, a ratio of 3 oligo-dye acceptors per TF-fluorescent protein donors was used. Fda=Donor emission intensity in the presence of acceptor; Fd=Donor emission intensity in the absence of acceptor; Relative Donor Emission=Fda/Fd; FRET efficiency=1−Fda/Fd; Fa=Acceptor emission intensity in the presence of the donor; [tetR-tdTomato]=200 nM; Oligo-Cy5(tetO+/−):tetR-tdT=0-9. FIGS. 43F-43G show spectral data analyzed by looking at the ratio of the two peaks as a function of analyte concentration. The signal for the negative control (scrambled oligo) does not change with analyte concentration, while the functional sensor signal does: the ratio Fa/Fd decreases as the aTc concentration increases, indicating less TF-oligo binding and increased donor emission. FIG. 43H shows a schematic of a biosensor using QD-tetR conjugate as the FRET donor and the OligoCy5 as the FRET acceptor. In the presence of aTc, fewer oligonucleotides will be bound by the QD-tetR conjugate and QD emission will recover.

FIG. 44A shows a schematic of the biosensor system. FIG. 44B shows the relative QD-TF emission vs. number of oligoCy5 molecules per QD (with an average of 4 TFs bound to each QD). FIG. 44C shows the ratio of acceptor emission intensity to donor emission intensity as a function of the number of oligoCy5 molecules per QD donors (with an average of 4 TFs bound to each QD). These two graphs show the difference between our sensor (blue) and negative control (orange). The lowest number of acceptor molecules with the largest difference between the signal and noise (difference between blue and orange) is the concentration ratio that we want to work with moving forward. The sensor tested moving forward comprised a 1:4:6 ratio of QD:TF:oligo-dye. Fda=Donor emission intensity in the presence of acceptor; Fd=Donor emission intensity in the absence of acceptor; Relative Donor Emission=Fda/Fd; FRET efficiency=1−Fda/Fd; Fa=Acceptor emission intensity in the presence of the donor; [QD]=50 nM; Oligo-Cy5:QD=0-48. FIG. 44D shows a spectrum using a ratio of 1:4:6 QD:TF:oligo, the small molecule analyte (progesterone) is titrated to the sensor to see the change in spectral response. When the TF is bound to the QD and the oligo is bound to the TF, which is more likely in the absence of the analyte (red line), the donor emission intensity is decreased and the acceptor emission intensity is increased (energy transfer from the QD to the dye on the oligo). The presence of the analyte decreases the affinity of the TF for the oligo, so binding is less likely; as a result, the donor emission intensity is increased and the acceptor emission intensity decreased. FIG. 44E shows a spectrum analyzed by looking at the ratio of the two peaks as a function of analyte concentration. The signal for the negative control (scrambled oligo) does not change with analyte concentration, while the functional sensor signal does: the ratio Fa/Fd decreases as the progesterone concentration increases, indicating less TF-oligo binding and increased donor emission. This same sensor was tested with estradiol (estrogen) as well to test for cross-reactivity. Estradiol concentration had no impact on the sensor binding/unbinding. The shaded areas indicate the region that is 3 standard deviations (3sigma) from either the positive or negative control—our valid sensing region is between these shaded areas.

FIG. 45A shows the result of screening the bacterium *P. simplex* to identify sterol responsive genes. FIG. 45B shows the result results of screening of the bacterium *P. simplex* zoomed into one genomic region with a cluster of sterol responsive genes. The number in parentheses corresponds to the position on the x-axis of the figure. Red are transcription factors (potential biosensors for our application). Bolded blue are enzymes that are likely associated with steroid degradation that could serve as enzymatic biosensors. The gene that is pointed to by the arrows (Gene 5330) is the genetic part that we isolated to develop a sensor.

FIG. 46A shows a schematic for the biosensor system. FIG. 46B shows a schematic of the progesterone biosensor sensor: without hormone, a FRET signal is emitted between the QD and the DNA-fluorophore; adding hormone induces a decrease in FRET signal. FIG. 46C shows the validation of the biosensor. Different concentrations of either progesterone or estradiol were added and FRET was measured at each concentration. A difference in FRET output is shown in the presence of progesterone.

Definitions

Figure 1A:
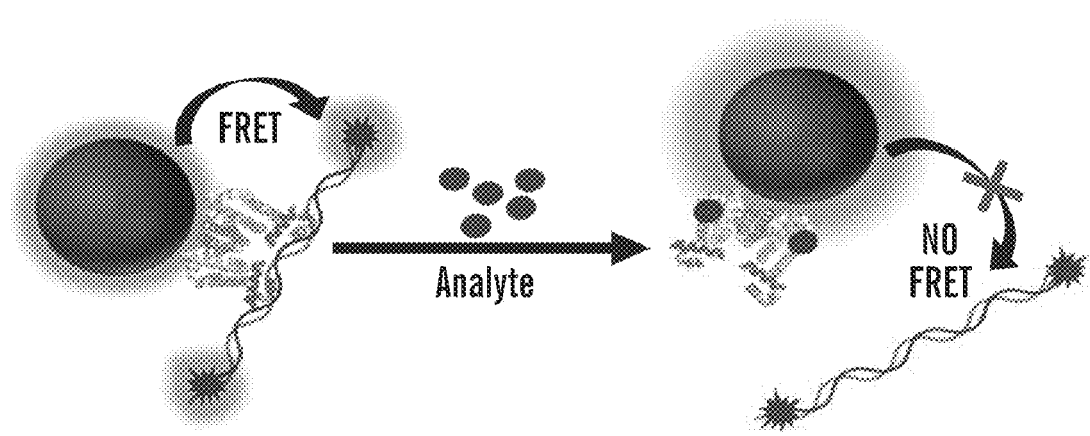
FIGS. 1A-1B show a schematic of the Quantum Dot (QD)-based Förster resonance energy transfer (FRET) sensor system using TF-DNA binding mechanism.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

The following terms are used in the description herein and the appended claims:

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even±0.1% of the specified amount.

Also as used herein, "and/or" refers to and encompasses any and all possible combinations of one or more of the associated listed items, as well as the lack of combinations when interpreted in the alternative ("or").

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed (e.g., by negative proviso). For example, in particular embodiments the amino acid is not A, G or I; is not A; is not G or V; etc. as if each such possible disclaimer is expressly set forth herein.

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

As used herein, the term "biological sample" refers to a sample obtained from a subject. The sample may be from a subject who has been treated with a drug, or may be from an untreated or drug naïve subject. Exemplary samples include, but are not limited to serum, plasma, cell lysate, milk, saliva, vitrous fluid, and other secretions, synovial fluid, peritoneal cavity fluid, lacrimal fluid, and tissue homogenate. In some embodiments, the sample is a bodily fluid, including sweat, blood, cerebrospinal fluid (CSF), plasma, whole blood, serum, semen, synovial fluid, saliva, vaginal lubrication, breast milk, amniotic fluid, urine, human feces, phlegm tears, saliva, lymph, peritoneal intracellular fluid, or an original tissue from fetuses, newborn babies, children, teenagers, adults or animals. Moreover, the sample can be in various forms including but not limited to a liquid, frozen, chilled, lyophilized sample. The sample may be subjected to additional purification or treatment steps prior to and/or following the affinity purification step herein.

As used herein, the term "allosteric" refers to a thermodynamic phenomenon in which the binding of a small molecule (or a posttranslational modification event) alters the affinity with which a protein binds to a second molecule. In the classical two-state Monod-Wyman-Changeux model the structural basis for this functional behavior is attributed to the ability of the allosteric protein to adopt two alternative conformations. The allosteric effector, by virtue of its preference for one versus the other structure, drives the system toward one or the other conformation. Allosteric effector binding, either the small molecule or the DNA, simply limits the conformations that are energetically available to the protein.

As used herein, the term "allosteric transcription factor (aTFs)" refers to proteins that undergo a conformational change upon binding of a small molecule thereby altering their affinity for a DNA sequence. aTFs encompass several large families of proteins that provide environmental response in bacteria. The alteration of transcriptional activity is a direct consequence of the ability of the small molecule to elicit a change in the affinity of the transcription factor for its target regulatory site on DNA. Allosteric control of TFs enables organisms to respond to changes in environmental and metabolic conditions. Eukaryotic and prokaryotic TFs sense the availability of a broad range of small molecules including hormones, metal ions, metabolites, and drugs with the final biological outcome of altering transcriptional activity of specific genes. Allosteric mechanisms of several well-characterized TFs, including the *Escherichia coli* tryptophan, and biotin repressors, and the *Escherichia coli* catabolite repressor protein, involve ligand-induced folding. In each of these proteins the small molecule acts as a corepressor and its binding promotes DNA binding by promoting folding. Presumably the loss of flexibility accompanying effector binding freezes out conformations that are not productive for binding and/or lowers the entropic penalty for binding. An examples for allosteric mechanism of a transcription factor is the tetracycline repressor (TetR). Binding of the small ligand, tetracycline, alters the folding properties of the repressor protein. The TetR senses intracellular tetracycline concentration. Antibiotic binding to TetR leads to a decrease in affinity of the protein for DNA that allows transcription of the genes that code for TetA, a membrane protein that exports the tetracyline out of the bacterial cell before it can attack its target, the ribosome, and TetR itself. The TetR senses intracellular tetracycline concentration. Tetracycline binding to TetR leads to a decrease in affinity of the protein for DNA that allows transcription of the genes that code for TetA, a membrane protein that exports the tetracyline out of the bacterial cell before it can attack its target, the ribosome, and TetR itself. The repressor protein is a homodimer in which each monomer is composed of a tetracycline binding/dimerization domain and a helix-turn-helix DNA binding domain (Saenger W. et al., 2000).

As used herein, a "ligand binding domain (LBD)" refers to a domain responsible for the bindings including small molecules and hormones. LBDs have been shown to be involved in hormone binding, homo- and/or heterodimerization, formation of heat-shock protein complexes and transcriptional activation and repression.

As used herein, the term "DNA binding domain (DBD)" refers to an independently folded protein domain that contains at least one structural motif that recognizes double- or single-stranded DNA. A DBD can recognize a specific DNA sequence (a recognition sequence) or have a general affinity to DNA. Some DNA-binding domains may also include nucleic acids in their folded structure. Examples for DBDs include the helix-turn-helix motif, the zinc finger domain, the basic leucine zipper (bZIP) domain, the winged helix (WH) domain, the winged helix-turn-helix (wHTH) domain, the High Mobility Group box (HMG)-box domains, White-Opaque Regulator 3 domains and oligonucleotide/oligosaccharide folding domains. The helix-turn-helix motif is commonly found in repressor proteins and is about 20 amino acids long. The zinc finger domain is generally between 23 and 28 amino acids long and is stabilized by coordinating zinc ions with regularly spaced zinc-coordinating residues (either histidines or cysteines).

As used, herein, a "transcription factor binding domain (TFBD)" refers to a transcription factor that contains an independently folded protein domain that contains at least one structural motif that recognizes double- or single-stranded DNA.

As used herein, the term "DNA-binding proteins" refers to proteins that bind to single- or double-stranded DNA, generally in the major groove if the binding is sequence-specific—as with transcription factors that regulate expression of genes, and nucleases that cleave DNA between nucleotides. DNA-binding proteins can also bind DNA non-specifically, such as polymerases and histones.

As used herein, the term "affinity" refers to the strength of the binding interaction between a single biomolecule (e.g. between an allosteric Transcription Factor and its Transcription Factor binding domain) to its ligand/binding partner (e.g. small molecule, hormone, drug or inhibitor).

As used herein, a "nucleic acid probe" refers to an oligomer or polymer of ribonucleic acid (RNA) or deoxyribonucleic acid (DNA) or mimetics thereof. This term includes nucleic acid composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

As used herein, a "nucleoside" is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

As used herein, the term "analyte" refers to any compound, or chemical species is a substance or chemical constituent that is of interest in an analytical procedure. Non-limiting examples of analytes detected by the bioswitch as described herein can be selected from any of non-limiting examples of analytes that can be detected by the current invention include Thyroid-stimulating hormone (TSH), Follicle-stimulating hormone (FSH), Luteinizing hormone (LH), Prolactin (PRL), Growth hormone (GH), Adrenocorticotropic hormone (ACTH), Vasopressin, Oxytocin, Thyrotropin-releasing hormone (TRH), Gonadotropin-releasing hormone (GnRH), Growth hormone-releasing hormone (GHRH), Corticotropin-releasing hormone (CRH), Somatostatin, Calcitonin, Parathyroid hormone (PTH), FGF-23 (phosphatonin), Osteocalcin, Erythropoietin (EPO), Human chorionic gonadotropin (HCG), Insulin, Glucagon, Somatostatin, Amylin, Atrial-natriuretic peptide (ANP), Gastrin, Secretin, Cholecystokinin (CCK), Fibroblast Growth Factor 19 (FGF19), Incretins, Somatostatin, Neuropeptide Y, Ghrelin, PYY3-36, Insulin-like growth factor-1 (IGF-1), Angiotensinogen, Thrombopoietin, Hepcidin, Betatrophin, Leptin, Retinol Binding Protein 4, Adiponectin, Irisin. Non-limiting examples of steroid hormones that can be detected by the current invention include progesterone, aldosterone, testosterone, estradiol, and Cortisol. Additional examples of hormones that can be measured according to the current invention are well known to a person of ordinary skill in the art and such embodiments are within the purview of the current invention.

As used herein, the term "small molecule" refers to low molecular weight molecules (<900 daltons) that include lipids, monosaccharides, second messengers, other natural products and metabolites, as well as drugs and other xenobiotics. They are distinct from macromolecules such as proteins. A small molecule is able to enter cells easily because it has a low molecular weight. Once inside the cells, it can affect other molecules, such as proteins. This is different from drugs that have a large molecular weight, such as monoclonal antibodies, which are not able to get inside cells very easily.

As used herein, the term "conjugate" or "conjugation" refers to the attachment of two or more entities to form one entity. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art.

As used herein, the term "ligand" refers to a substance that forms a complex with a biomolecule to serve a biological purpose. In protein-ligand binding, the ligand is usually a molecule, which produces a signal by binding to a site on a target protein. The binding typically results in a change of conformational isomerism (conformation) of the target protein. In DNA-ligand binding studies, the ligand can be a small molecule, ion, or protein, which binds to the DNA double helix. The relationship between ligand and binding partner is a function of charge, hydrophobicity, and molecular structure. The instance of binding occurs over an infinitesimal range of time and space, so the rate constant is usually a very small number.

As used herein, the term "Progesterone" refers to endogenous steroid and progestogen sex hormone involved in the menstrual cycle, pregnancy, and embryogenesis of humans and other species. Progesterone is also a crucial metabolic intermediate in the production of other endogenous steroids, including the sex hormones and the corticosteroids, and plays an important role in brain function as a neurosteroid.

As used herein, "immobilized" refers to the binding of the TF or nucleic acid probe to a support or matrix. The support or matrix on which the enzymes or nucleic acid probes are immobilized to allows the exchange of medium containing substrate or effector or inhibitor molecules. In some embodiments, the nucleic acid probes are immobilized on, or within a solid support. As a non-limiting example, the nucleic acids can be immobilized on the solid surface by the 5' end of said oligonucleotides. In some embodiments, the solid surface is selected from a group of materials comprising silicon, metal, and glass. In some embodiments, the solid support comprises oligonucleotides at assigned positions defined by x and y coordinates.

As used herein, the term "binding" refers to an association between proteins or nucleotides that occurs through intermolecular forces, such as ionic bonds, hydrogen bonds and Van der Waals forces. The association of docking is actually reversible through dissociation. Measurably irreversible covalent bonding between a ligand and target molecule is atypical in biological systems. Ligand binding to a receptor protein or to an allosteric transcription factor can alter the conformation by affecting the three-dimensional shape orientation. The conformation of a receptor protein or allosteric transcription factor composes the functional state. Ligands include small molecules, hormones, inhibitors, activators, and neurotransmitters.

As used herein, the term "fluorescent molecule" refers to a fluorescent chemical compound that can reemit light upon light excitation. Fluorescent molecules typically contain several combined aromatic groups, or planar or cyclic molecules with several 7E bonds. Current fluorescence imaging probes typically consist of single conventional fluorophore (e.g., organic dyes, fluorescent proteins), fluorescent proteins (e.g., GFP) and semiconductor quantum dots (Q-dots). Single fluorophores are usually not stable and have limited brightness for imaging. Similar to dyes, the fluorescent proteins tend to exhibit excited state interactions which can lead to stochastic blinking, quenching and photobleaching. Fluorescent molecules are known in the art and include florescent proteins (e.g. CAP, WFP, BFP, and other GFP derivatives). Other suitable fluorescent molecules are known in the art and commercially available from, for example, Molecular Probes (Eugene, Oreg.). These include, e.g., donor/acceptor (i.e., first and second signaling moieties) molecules such as: fluorescein isothiocyanate (FITC)/tetramethylrhodamine isothiocyanate (TRITC), FITC/Texas Red™ Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X (ROX), FITC/tetramethylrhodamine (TAMRA), and others. In addition to the organic fluorophores already mentioned, various types of nonorganic fluorescent labels are known in the art and are commercially available from, for example, Quantum Dot Corporation, Inc. Hayward Calif.). These include, e.g., donor/acceptor (i.e., first and second signaling moieties) semiconductor nanocrystals (i.e., 'quantum dots') whose absorption and emission spectra can be precisely controlled through the selection of nanoparticle material, size, and composition.

As used herein, the term "semiconductor quantum dots" refers to fluorophores for multi-photon excitation. It has been shown that that quantum dots are unique donor fluorophores for FRET where multiple acceptor dyes can be positioned around the quantum dot (QD) to substantially enhance the overall rate of FRET between QD and proximal dyes.

As used herein, resonance energy transfer (FRET) refers to FRET is a distance-dependent interaction between the electronic excited states of two fluorescent molecules in which excitation is transferred from an excited donor molecule to an acceptor molecule without emission of a photon. The absorption spectrum of the acceptor must overlap the fluorescence emission spectrum of the donor. FRET, between donor and acceptor, occurs over distances that typically span a distance of at least 1 Å, or of at least 5 Å or of at least 10 Å, or of at least 20 Å, or of at least 30 Å, or of at least 40 Å, or of at least 50 Å, or of at least 60 Å, or of at least 70 Å, or of at least 80 Å, or at least 90 Å, or 100 Å. As used herein, the term "biosensor" refers to an analytical device that combines the biological recognition element with a signal transducer to convert the response with analytes into a measurable signal which is proportional to the concentration of the analytes.

As used herein, the term "microbial biosensor" refers to an analytical device which integrates microorganisms with a physical transducer to generate a measurable signal proportional to the concentration of analytes.

As used herein, the term "electroactive molecule" relates to any molecule that is able to undergo an electrochemical reaction. Upon which one or more electrons are either added to or removed from the molecule, converting it into a different oxidative state. For example, 1,4-Benzoquinone is an electroactive molecule that can be converted to hydroquinone upon the reduction of the molecule with an addition of two electrons and two protons according to a specific embodiment.

As used herein, the term "device" refers to an electrically addressable unit that performs some task, such as switching, storing a single bit of information, or sensing a particular molecule or class of molecules according to an embodiment of the present invention. Depending upon the embodiment, other examples of definitions also exist.

As used herein, the term "circuit" refers to a group of devices, each of which are designed to carry out similar tasks according to a specific embodiment. For example, a transistor is a switching device. A multiplier is a logic circuit constructed from many transistors, which is a circuit. As another example, a nanowire is a chemical sensing device. An array of nanowires each coated with a different molecular probe, constitutes a sensor circuit designed to sense many different molecular targets according to a specific embodiment. Depending upon the embodiment, other examples of definitions also exist.

The term "percent (%) amino acid sequence identity" or "% sequence identity to amino acids" with respect to a particular SEQ ID NO is defined as the percentage of amino acid residues in a candidate sequence that are identical with the amino acid residues in the comparative sequence identified by the SEQ ID NO, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., Methods in Enzymology 266, 460-480 (1996); available at world-wide web address: blast.wustUedu/blast/README.html). WU-BLAST-2 uses several search parameters, most of which are set to the default values. The adjustable parameters are set with the following values; overlap span=1, overlap fraction=0.125, world threshold (T)=11. HSP score (S) and HSP S2 parameters are dynamic values and are established by the program itself, depending upon the composition of the particular sequence, however, the minimum values may be adjusted and are set as indicated above.

As used herein, the term "integrated circuit" refers to a group of circuits, each design to carry out different specific tasks, but operating together to perform some larger function. For example, a multiplier circuit can retrieve two numbers from a memory circuit, multiply them together, and store them back into the memory circuit. Depending upon the embodiment, other examples of definitions also exist.

DETAILED DESCRIPTION

The technology described herein relates generally to an in vitro label-free biosensor system for the detection of small molecules and analytes based on bacterial allosteric TFs (aTFs) and nucleic acid probes conjugated to fluorescent molecules (e.g., quantum dots and dyes) or electroactive molecules. Also described herein are compositions, methods and processes to identify and isolate bacterial TFs that specifically recognize a target analyte and to develop these TFs into in vitro biosensors that can be used in a range of assays and devices, and in a cell-free system. In the presence of a target small molecule or a target analyte, TF affinity for its DNA binding sequence is modulated, facilitating the repressor or derepressor regulation of downstream gene expression. Described herein, is a microbial biosensor system with either a fluorescent output through Förster resonance energy transfer (FRET) or a redox sensor output for the quantification of the target analyte with high sensitivity.

I. Microbial Biosensors—in General:

Microbial biosensors refer to an analytical device which integrates microorganisms with a physical transducer to generate a measurable signal proportional to the concentration of analytes. The label-free sensing of small molecule analytes is of critical importance to biomedical research, point of care diagnostics, and environmental sensing, among other applications. Connected devices that monitor human biology in real-time represent the next frontier in biosensors. Monitoring hormones is of significant interest as hormones play critical roles in multiple physiological processes including stress adaptation, blood pressure control, reproductive rhythms, and body odor. However, the real-time monitoring of hormones is challenging from a biology, chemistry, and engineering perspective, glucose detection being the one notable success. Using natural sensing elements from microbial species e.g. native biomolecules that have evolved sensor and modulator capabilities provides the opportunity to utilize a detection platform that is distinct from the typical antibody- or aptamer-based strategies. Described herein, is an analyte-responsive transcription factor-DNA microbial biosensor with either a ratiometric fluorescent output through Förster resonance energy transfer (FRET) or a redox sensor output for the quantification of the target analyte with high sensitivity.

IA. Biosensor ON or Biosensor OFF systems: In general, the biosensor can be an ON-biosensor or an OFF-biosensor as described herein. For example, referring to FIGS. 1 and 9A, in some embodiments a microbial biosensor can turn OFF a signal in the presence of an analyte (i.e., be an OFF-biosensor). In such an embodiment, the biosensor comprises an allosteric transcription factor that is conjugated to a first reporter molecule (e.g., quantum dot (QD)), where the transcription factor binds to a binding site on a nucleic acid probe only when the analyte is not presence (i.e., the absence of the analyte), such that in the absence of the analyte, the QD and the fluorescent dye are close proximity and FRET occurs, and when the analyte is present, it binds to the transcription factor and induces a conformational change to decrease the aTF's affinity for the binding site on the nucleic acid probe such that the probe dissociates from the transcription factor, resulting in the QD and the fluorescent dyes no longer being in close proximity to enable FRET to occur, and therefore a decrease or absence of FRET is detected by an optical sensor. Accordingly, in such embodiments, in the presence of an analyte, binding between the aTF and the nucleic acid probe does not occur, and the microbial biosensor serves as an OFF-switch.

Figure 10:
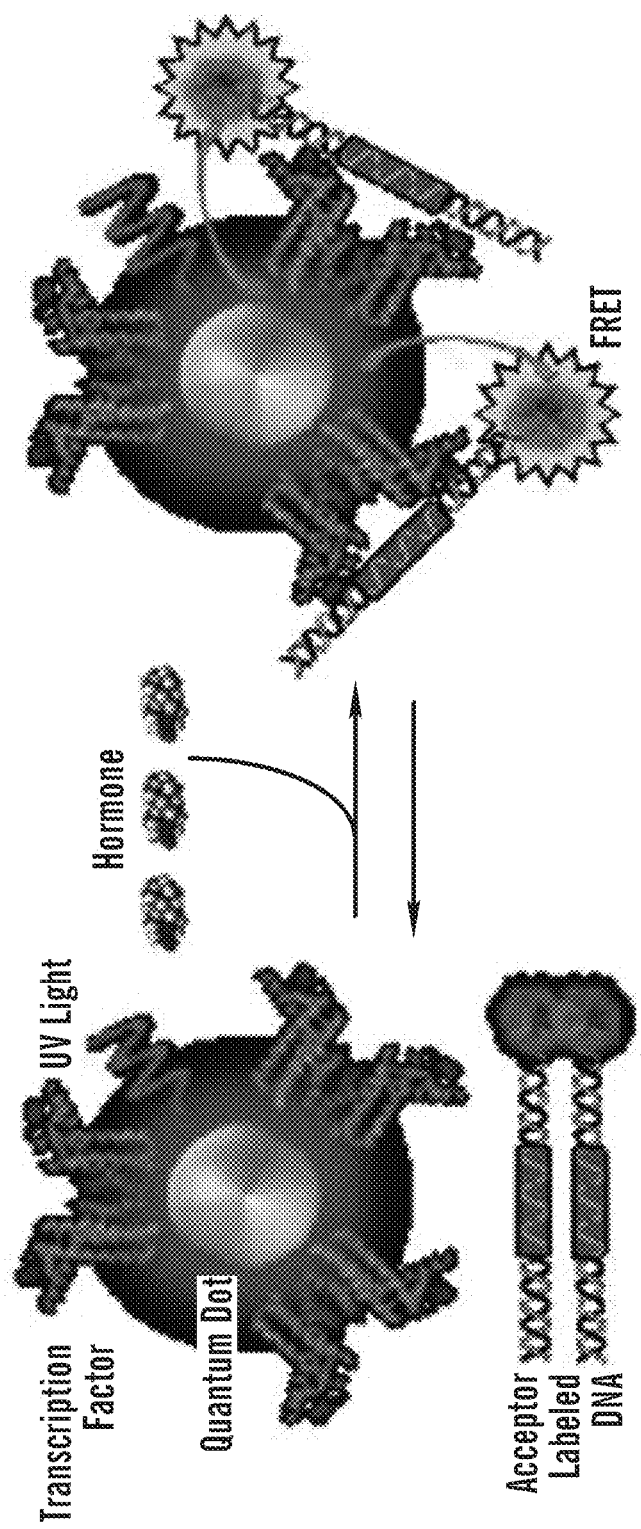
FIG. 10 shows a schematic of the Quantum Dot-FRET (QD-FRET) strategy for transducing hormone binding to a quantitative signal. TFs are conjugated to QDs and a DNA probe with the TF binding site is conjugated to a FRET acceptor. TF-hormone binding alters TF-DNA binding resulting in changes in FRET that can be used to quantify hormone concentration.

In another embodiment, referring to FIG. 10, a microbial-based biosensor described herein can turn on a signal on the presence of an analyte (i.e., is an ON-biosensor). In such an embodiment, the biosensor comprises an allosteric transcription factor that is conjugated to a reporter molecule (e.g., a quantum dot (QD)), where the transcription factor in the absence of the analyte cannot bind the nucleic acid probe. In the presence of an analyte, the sTF undergoes a conformational change such that it can now bind to a binding site on a nucleic acid probe, bringing the reporter molecule on the aTF (e.g., QD) and the reporter molecule on the probe (e.g., fluorescent dye) in to close proximity, such that FRET occurs, and is detected by an optical sensor as disclosed herein.

Figure 17A:
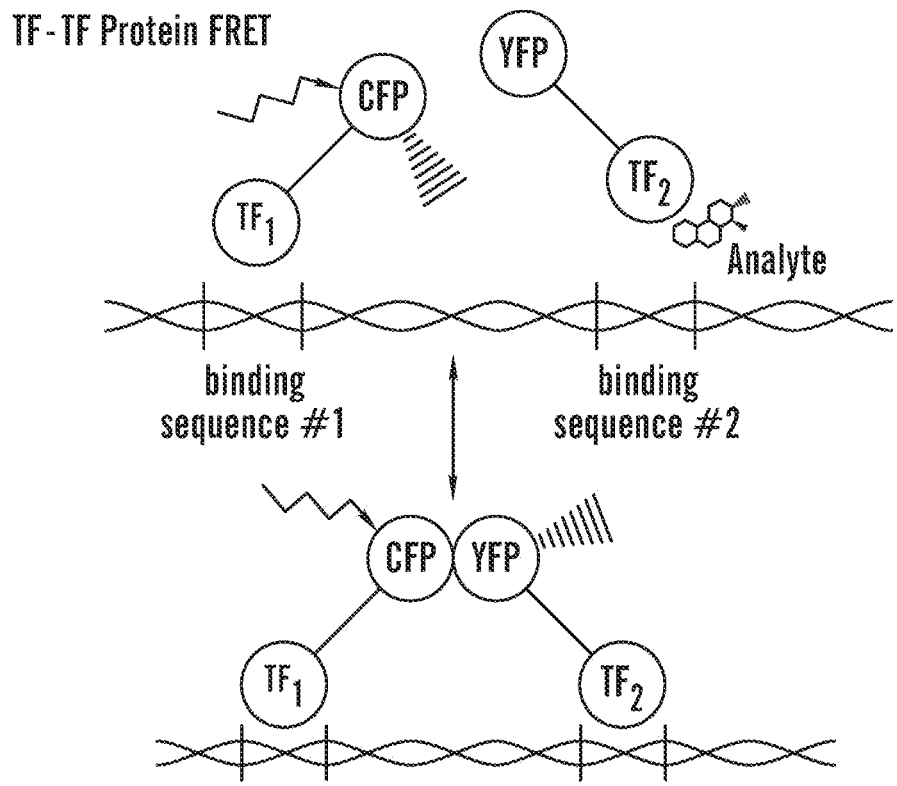
FIGS. 17A-17B shows a schematic of TF-TF Protein FRET and a schematic of a conformational change TF-FRET Mechanism.

IB. TF-TF Protein FRET Biosensor System:

In another embodiment, a TF-TF Protein FRET biosensor system is used for the quantification of the target analyte with high sensitivity (e.g., see FIG. 17A). In such an embodiment, a TF-TF Protein FRET biosensor system comprises a nucleic acid probe comprising at least two TFBD sequences for two TFs. Referring to FIG. 17A as an exemplary embodiment, the nucleic acid probe comprises a first TFBD for a first TF conjugated to a fluorescent molecule (e.g. CFP) (a TF1-CFP conjugate), and a second TFBD for a second TF, e.g. TF2 conjugated to a fluorescent molecule (e.g. YFP) (aTF2-YFP conjugate). The TFBD1 and TFBD2 are configured so that when TF1 and TF2 bind to their cognate TFBD1 and TFBD2 nucleic acid sequences, FRET occurs between the two fluorescent molecules (e.g., CFP and YFP) attached to TF1 and TF2. In the presence of an analyte (e.g. progesterone), one of the TFs would decrease its affinity for its cognate TFBD and FRET would no longer occur. TF-TF Protein FRET can be measured by a change in a ratiometric FRET signal.

Conformational Change TF-FRET biosensor system

Figure 17B:
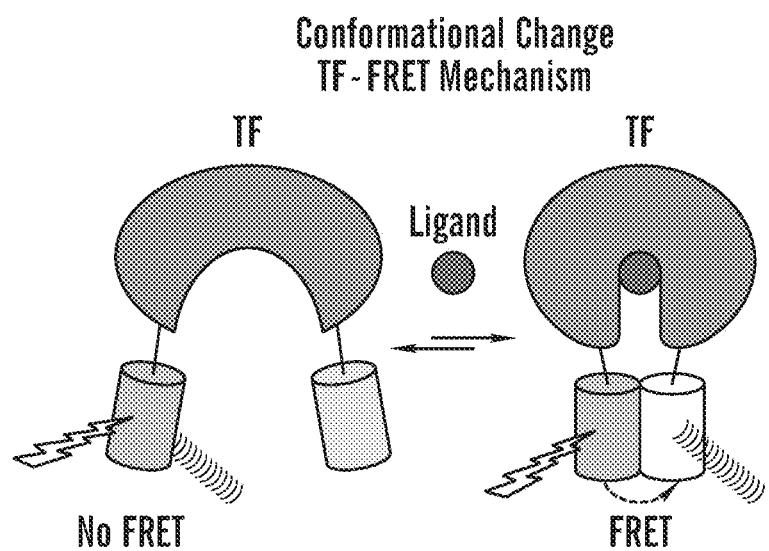
Figure 18:
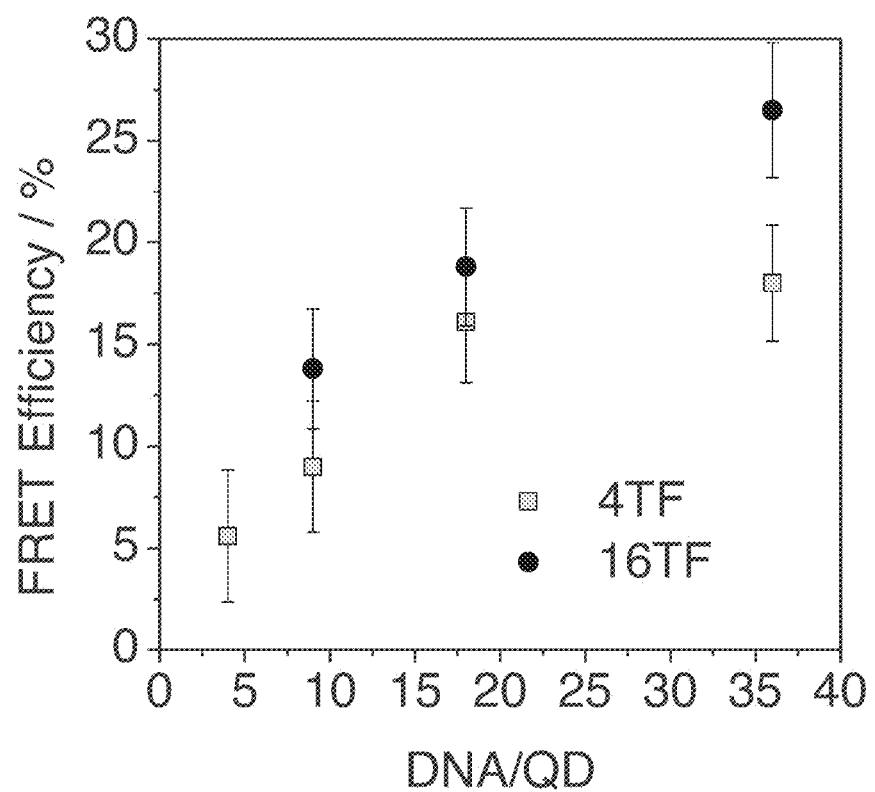
FIG. 18 shows the FRET efficiency using weak TBD binding.
Figure 19:
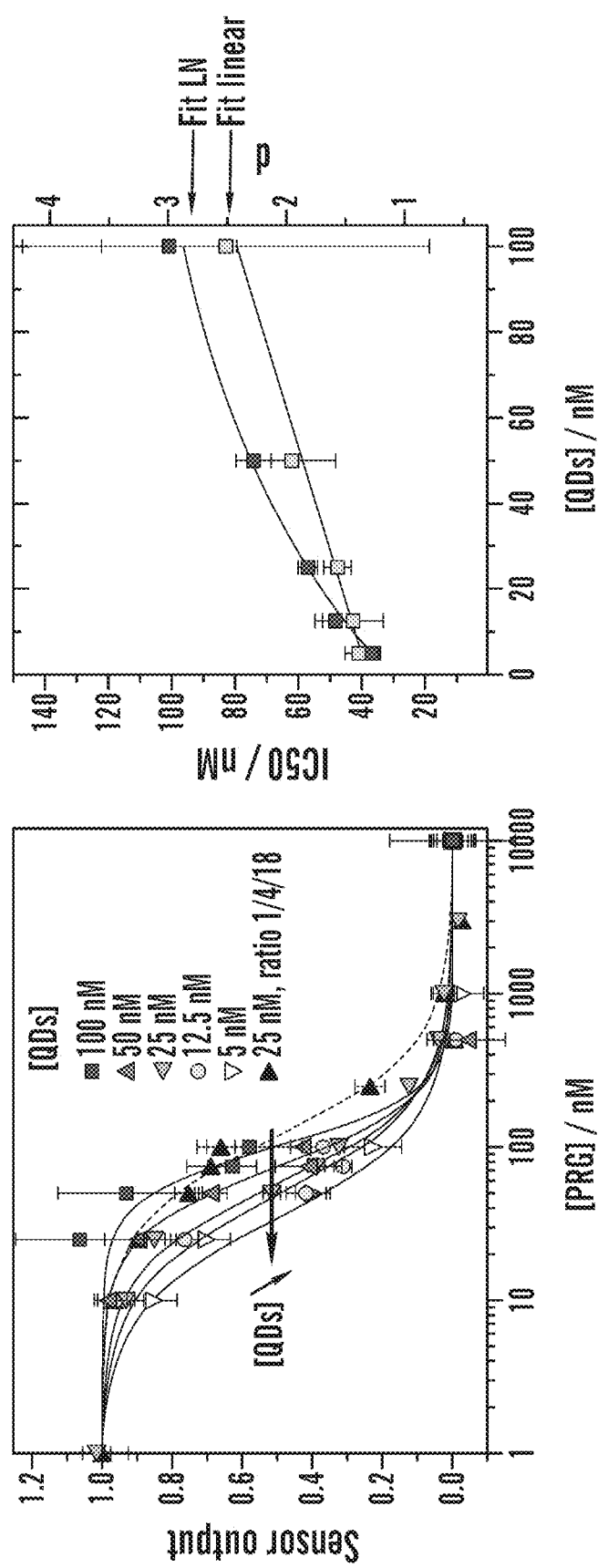
FIG. 19 shows the FRET efficiency using different sensor concentrations.
Figures 20A, 20B, 20C:
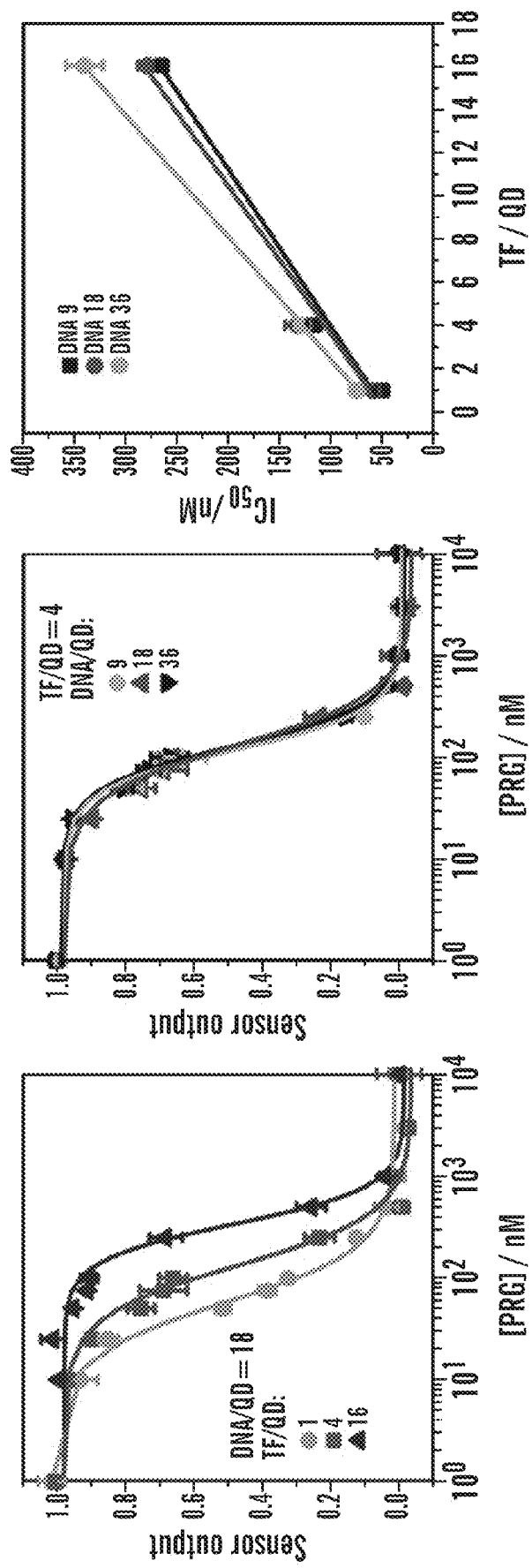
FIGS. 20A-20C show how changing the ratios of QD/TF and QD/DNA affects the sensitivity and slope of the sensor output signal.
Figure 21B:
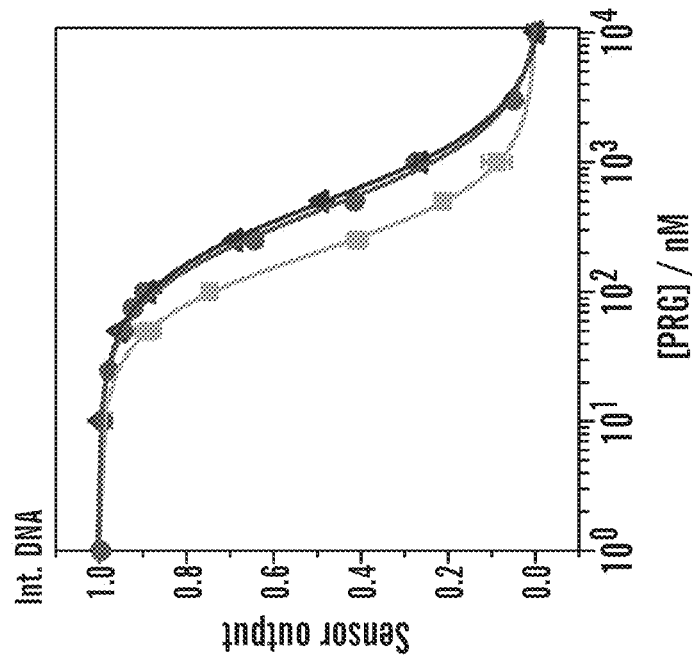
FIGS. 21A-21B show the sensor output signals using stronger TFBDs in the presence of PRG.
Figure 21A:
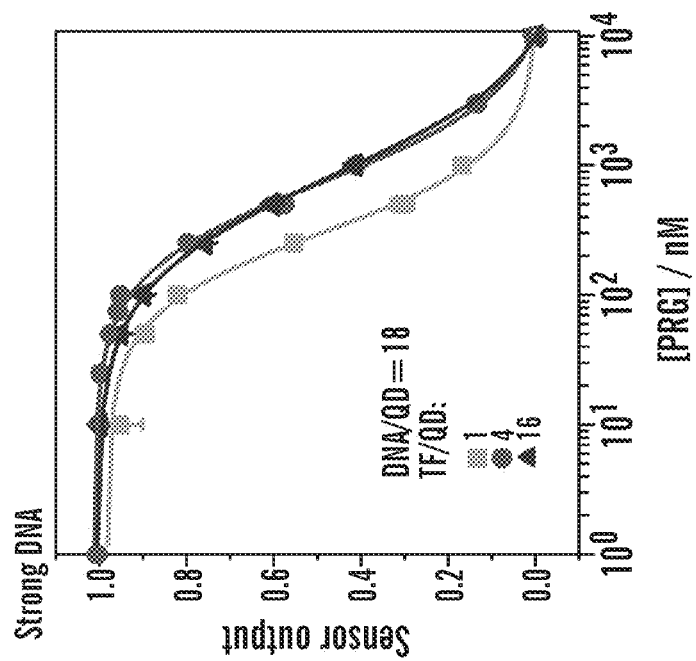
Figure 22:
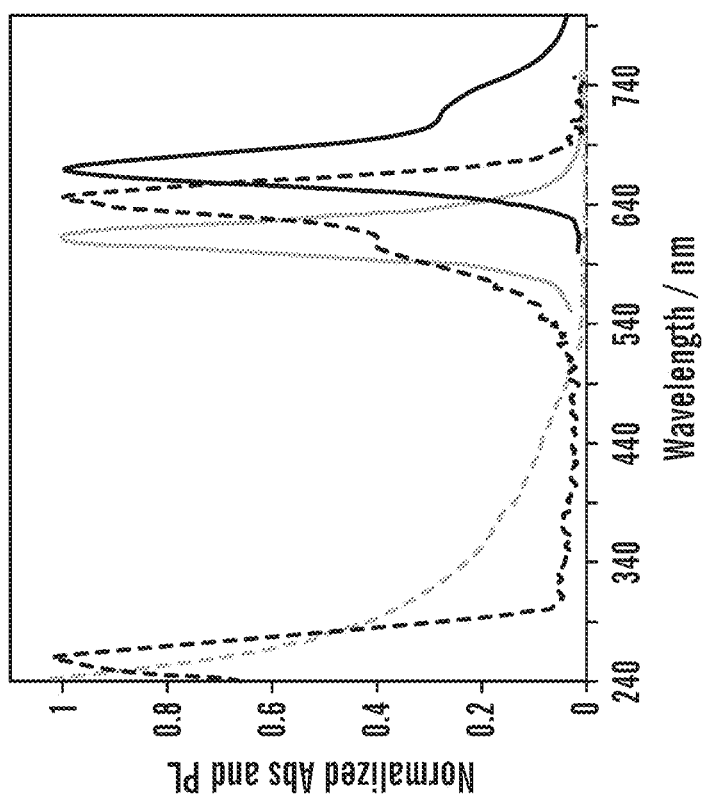
FIG. 22 shows the Absorption (dashed) and fluorescent emission (plain) of QDs (yellow, $\lambda exc=400$ nm) and DNA-Cy5 (salmon, $\lambda exc=540$ nm) in HEPES 1×, pH 7.6.
Figure 23B:
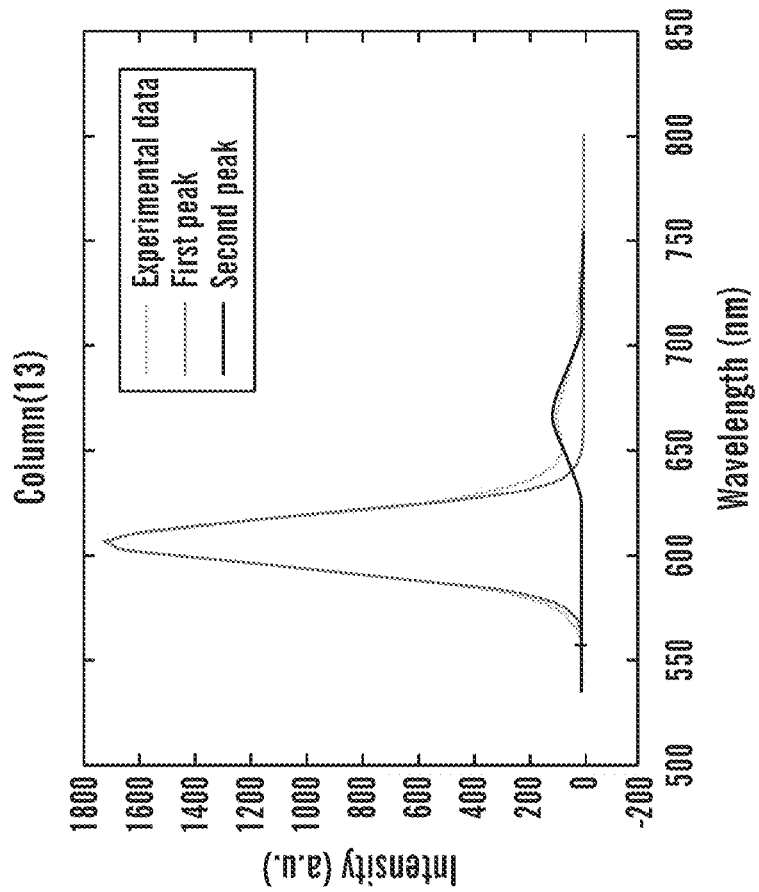
FIGS. 23A-23B show the Fluorescent emission spectra of sensor 1.
Figure 23A:
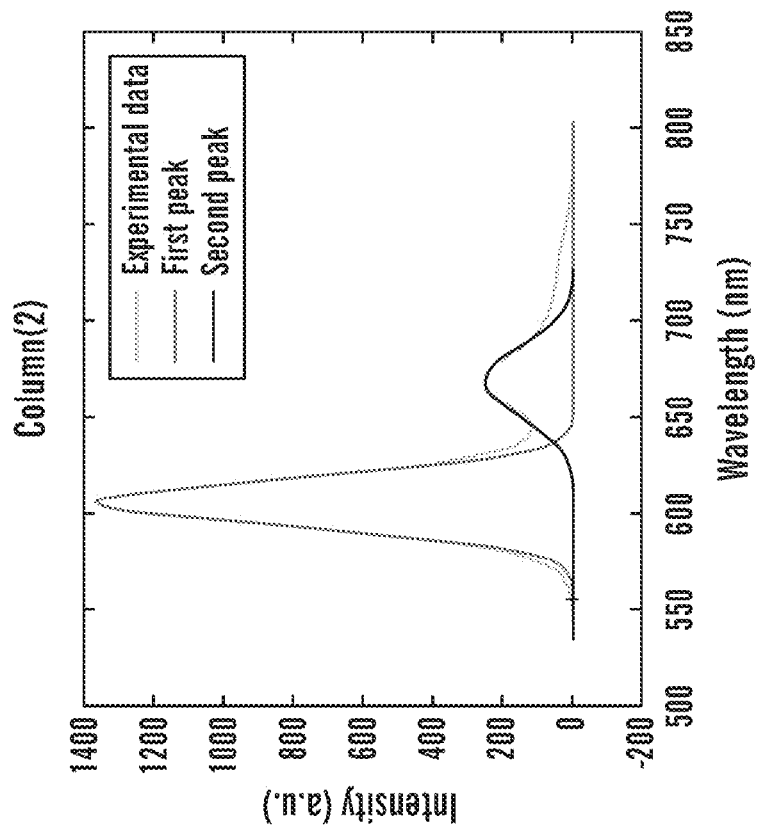
Figure 24:
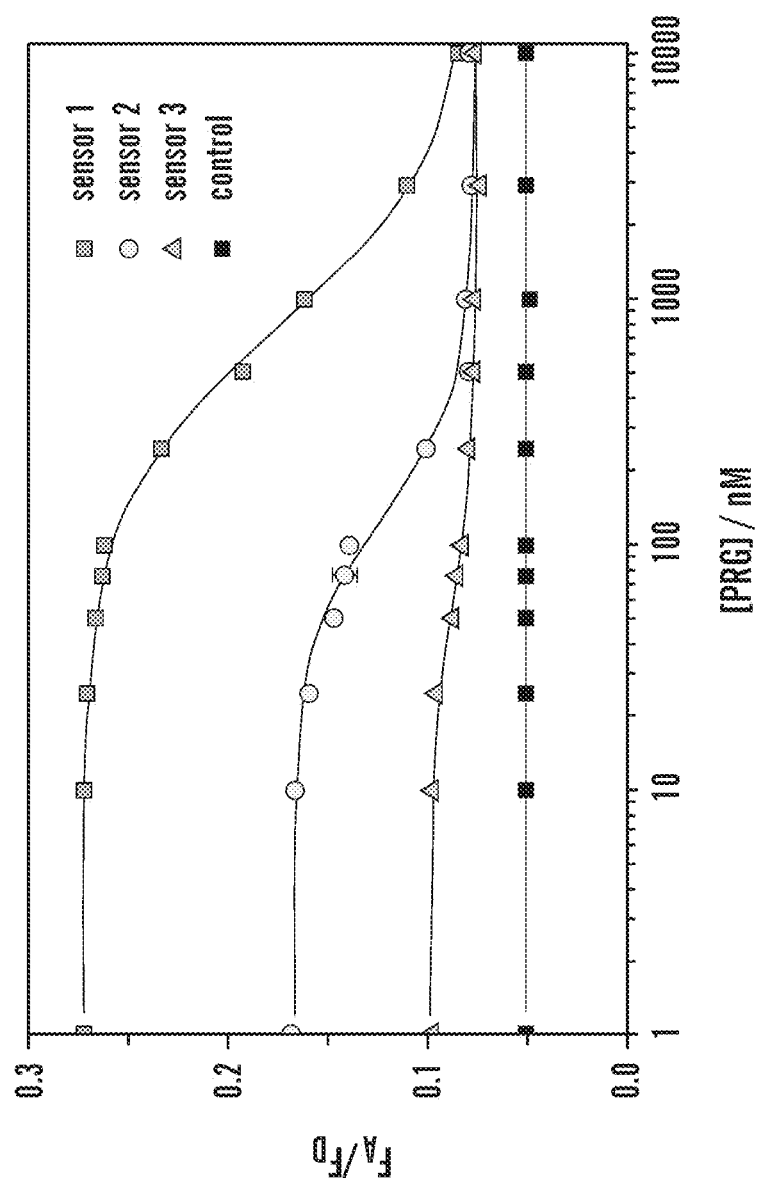
FIG. 24 shows dose-response curves for 3 sensors recorded in HEPES 1×, after addition of Progesterone from 0 to 10 uM. Sensor 1 (DNA1, QD/TF/DNA=1/4/18), sensor 2 (DNA 2, QD/TF/DNA=1/4/18), sensor 3 (DNA 2, QD/TF/DNA=1/1/18). Control is performed using the scrambled DNA (QD/TF/DNA=1/4/18).
Figure 25:
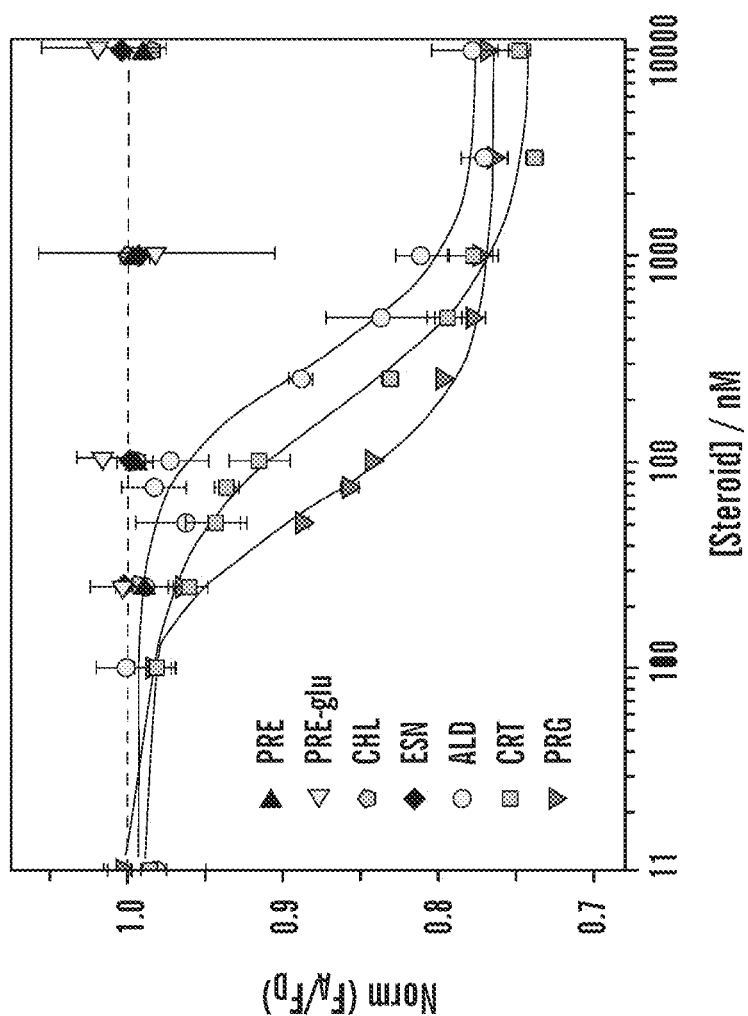
FIG. 25 shows the normalized fluorescent dose-response curve of the sensor in presence of 7 different steroids, in HEPES 1×.
Figure 26A:
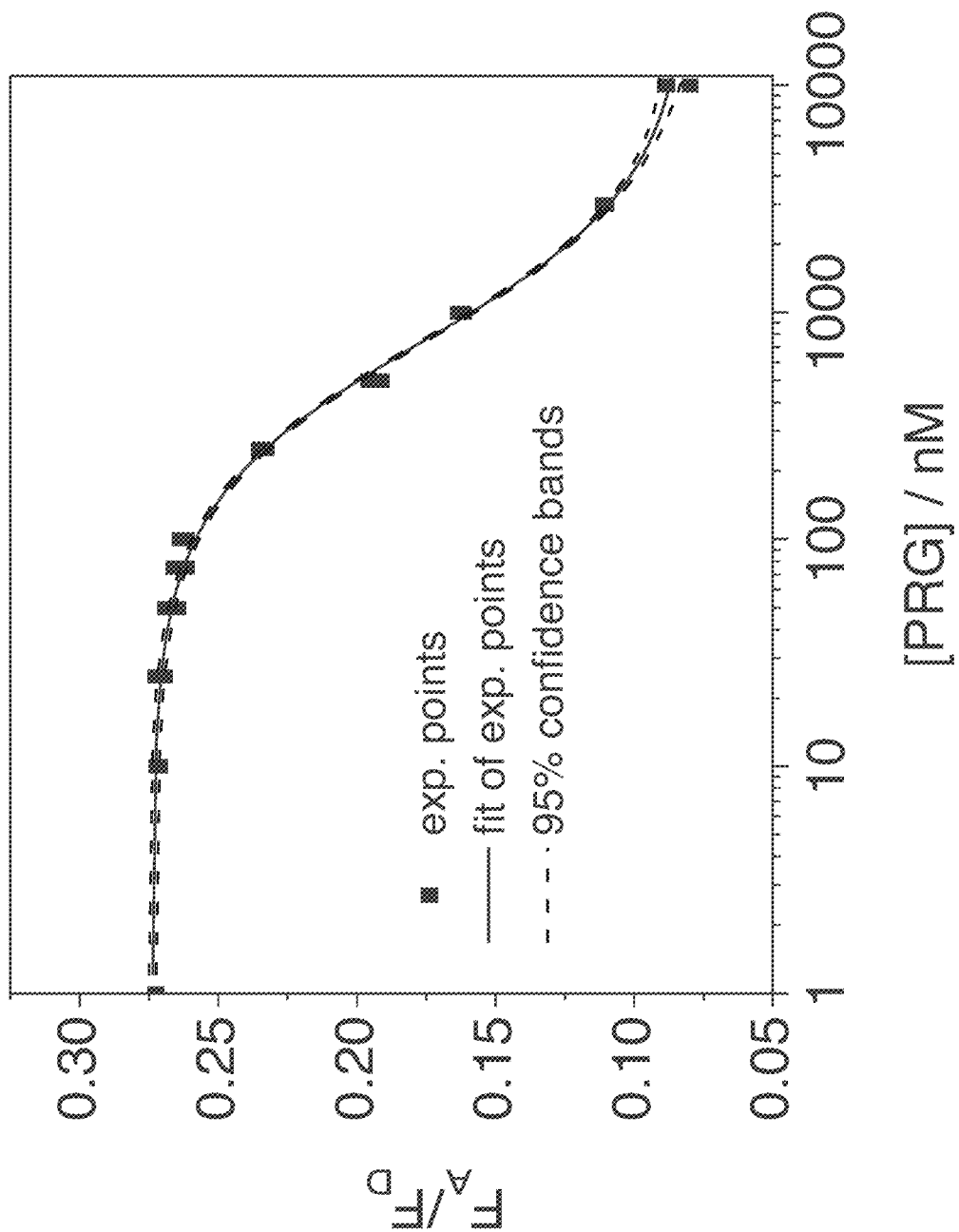
FIGS. 26A-26C show the sensor outputs ($F_A/F_D$) from sensor 1, 2 and 3.
Figure 26B:
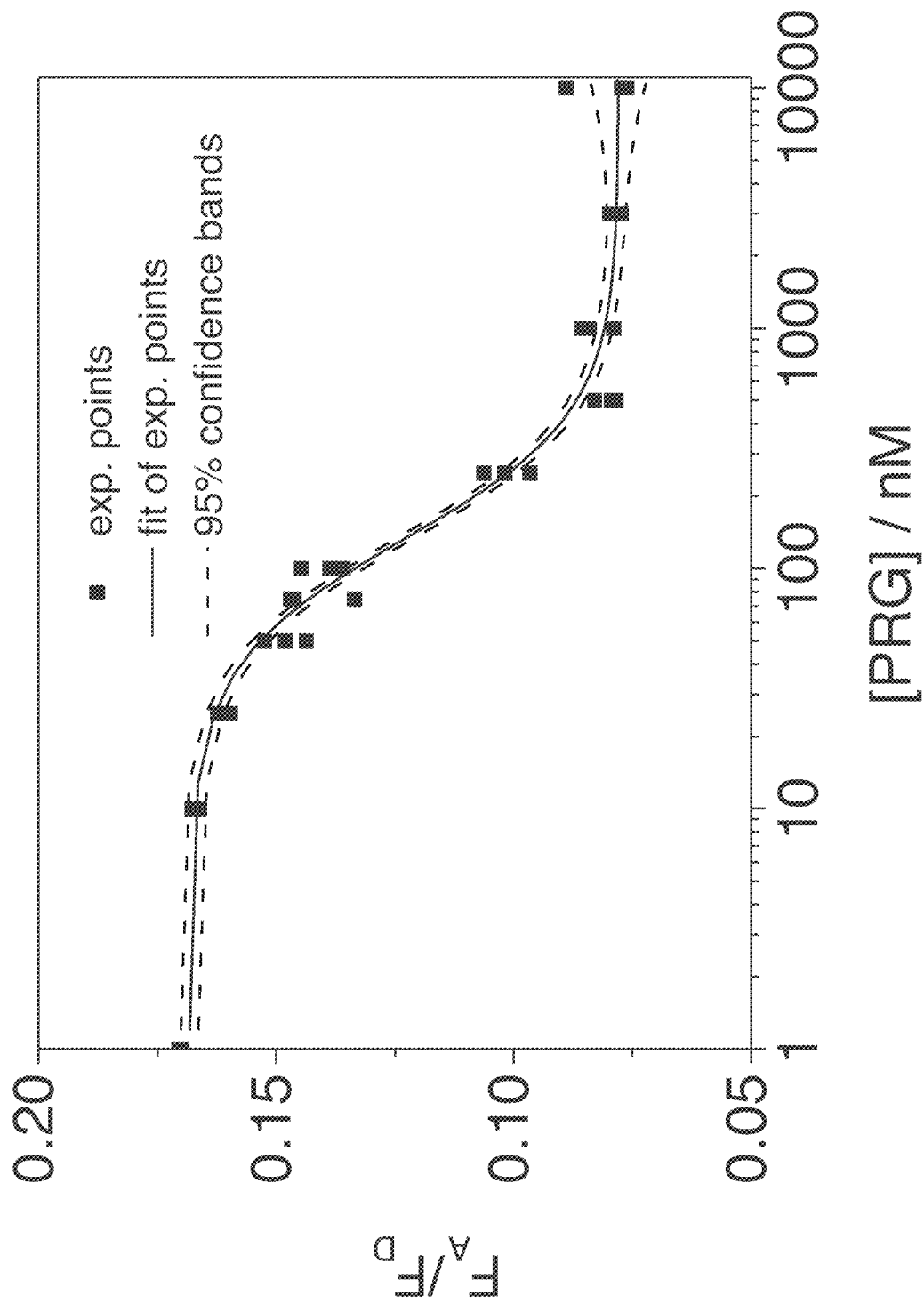
Figure 26C:
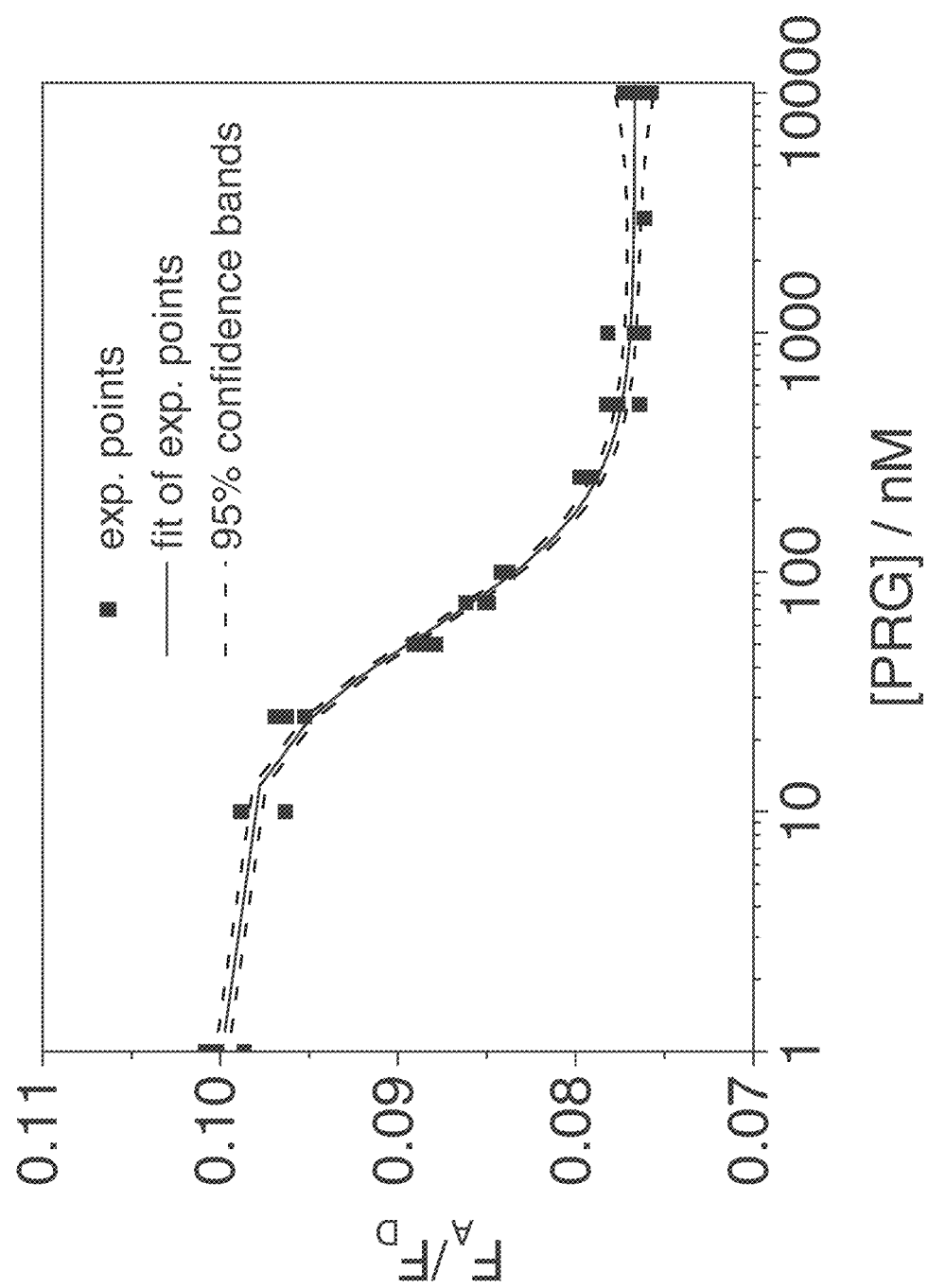
Figure 27B:
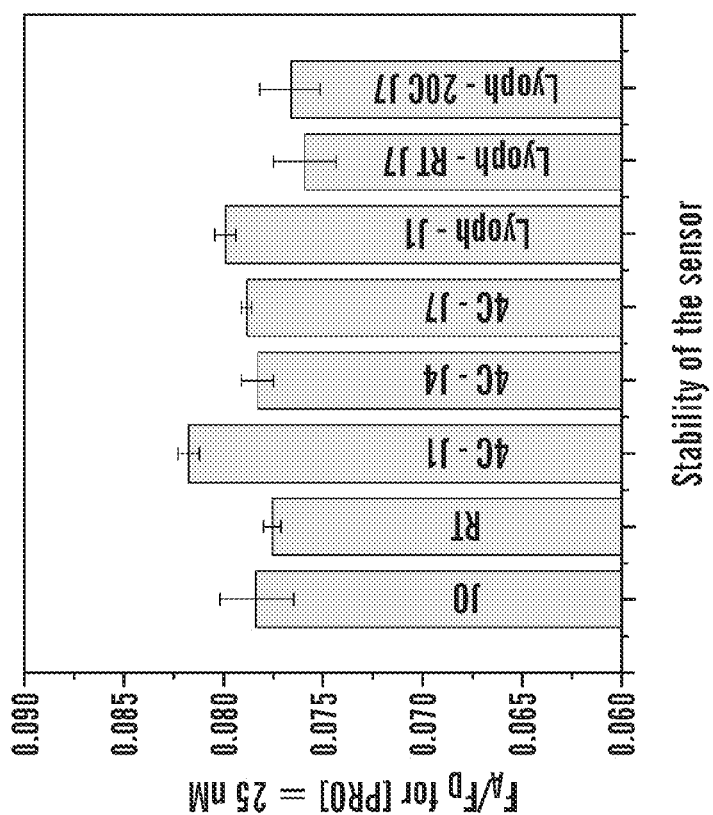
FIGS. 27A-27B show the stability of the sensor under different storage conditions in the dark: room temperature (RT), in a fridge (4C) or lyophilized and stored in a freezer (−20° C.) or at RT.
Figure 27A:
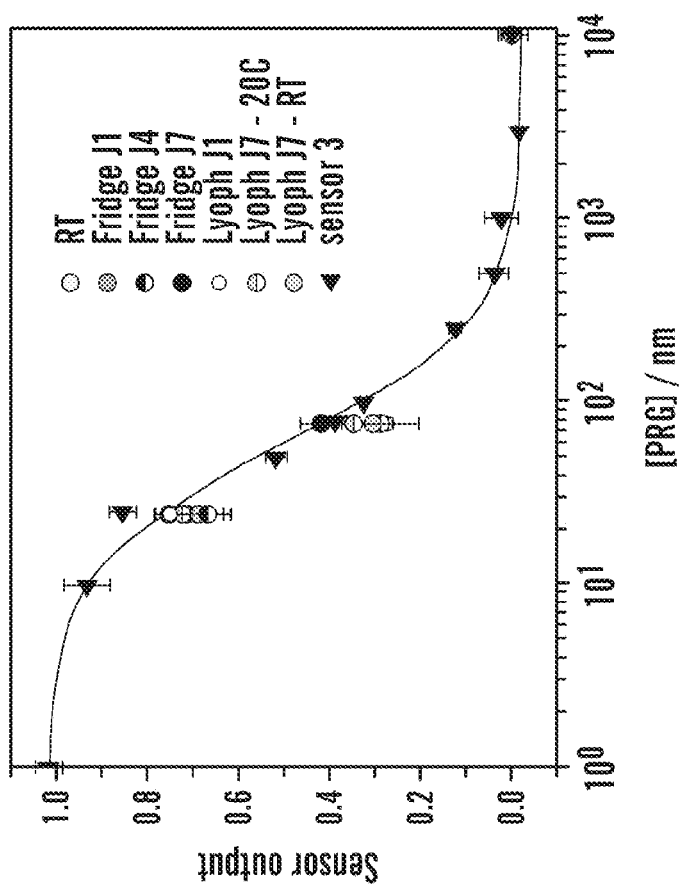
Figure 28A:
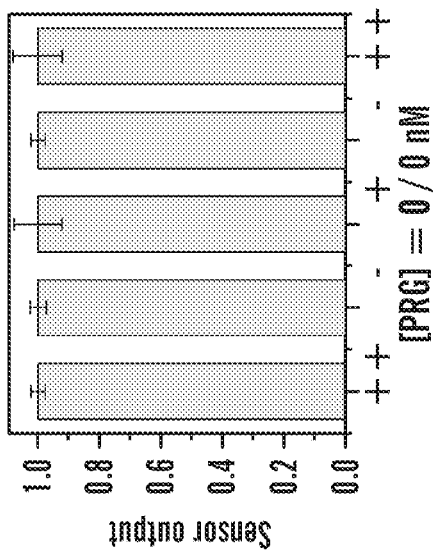
FIGS. 28A-28E show the reversibility of the sensor.
Figure 28B:
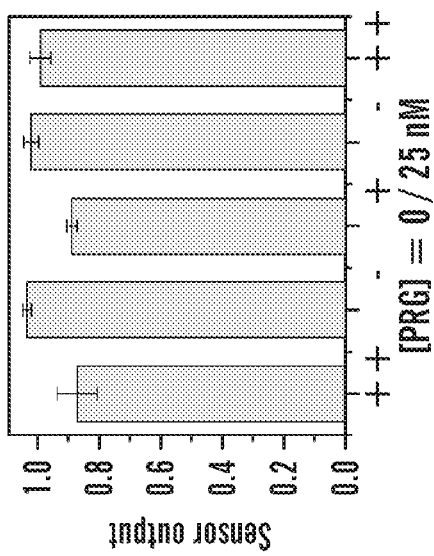
Figure 28C:
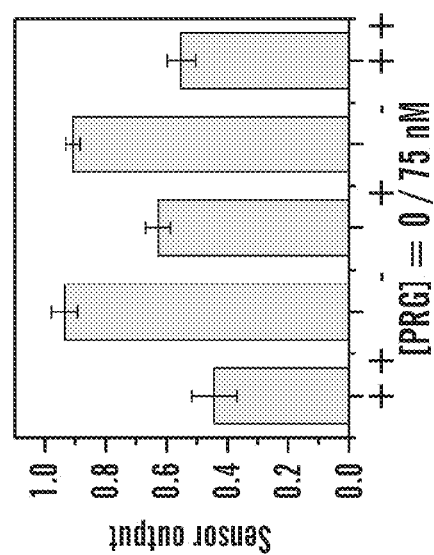
Figure 28E:
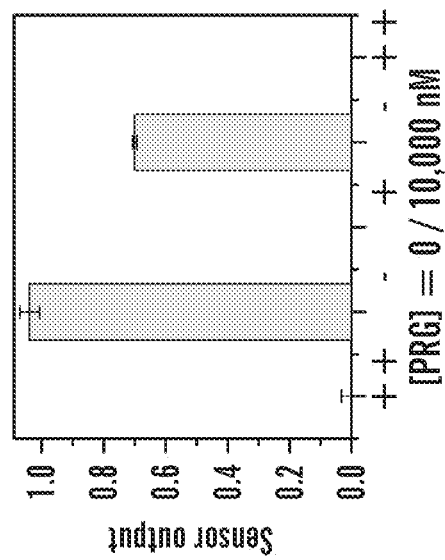
Figure 28D:
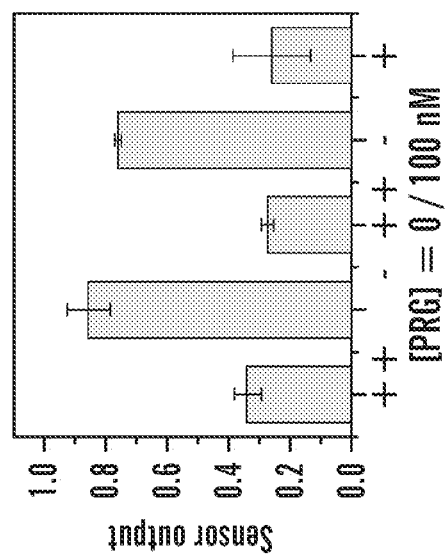
Figure 30:
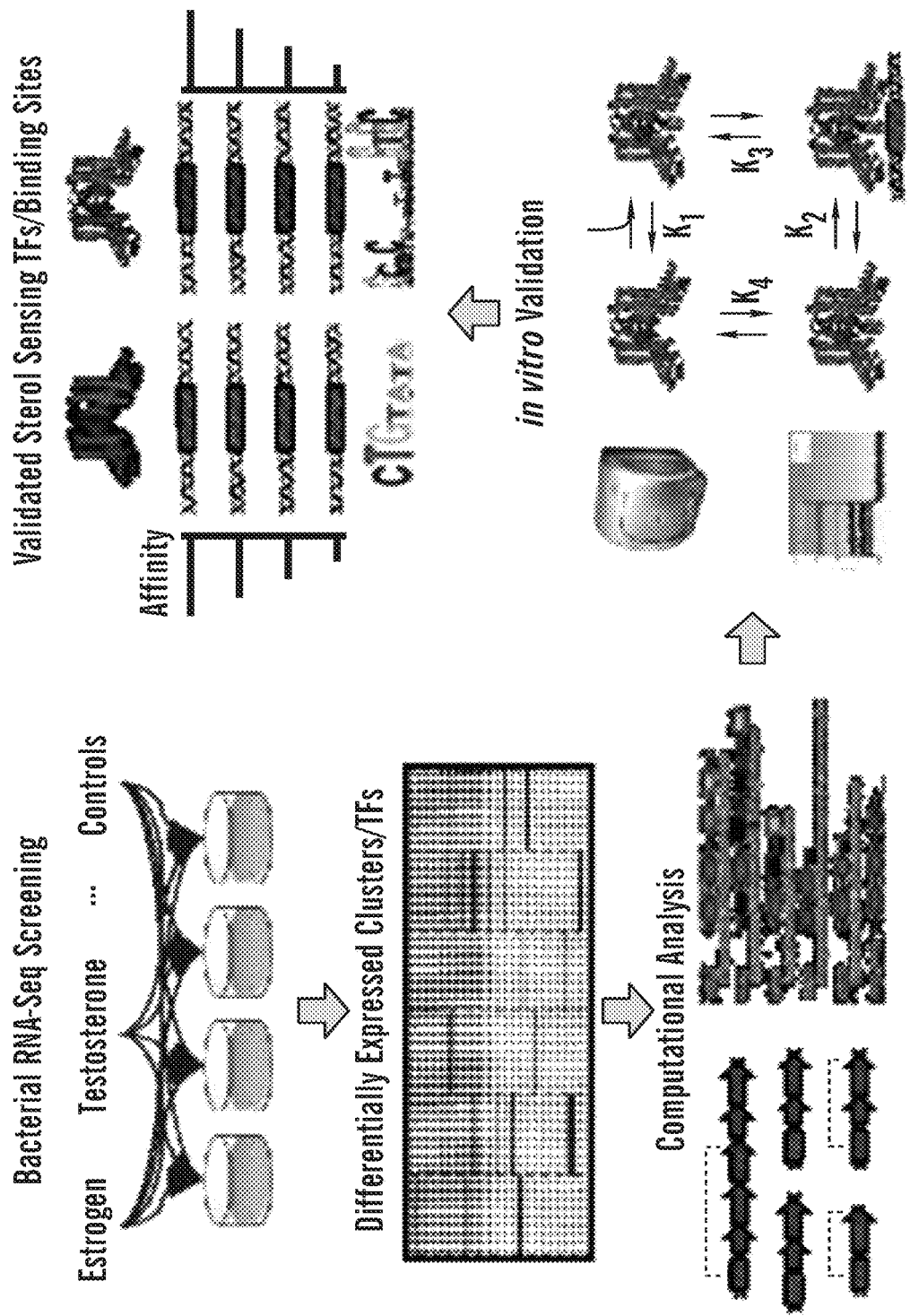
FIG. 30 shows a schematic of the approach.
Figure 31A:
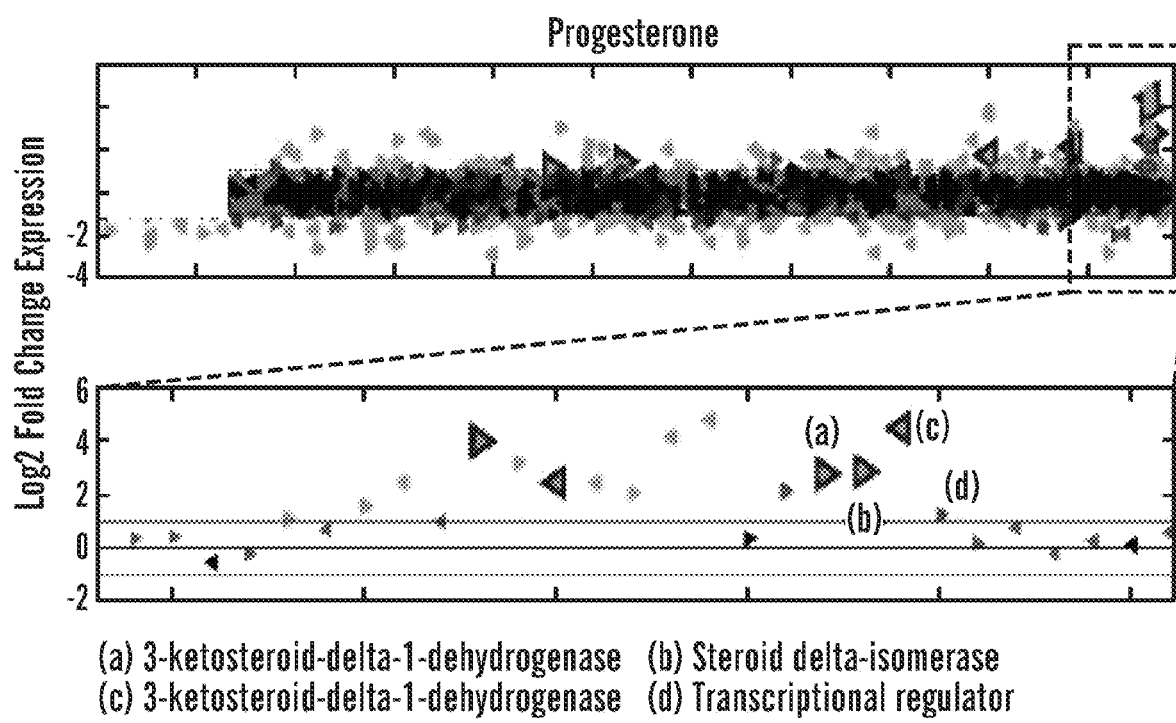
FIGS. 31A-31C shows the discovery, development, and validation of novel progesterone biosensor.
Figure 31B:
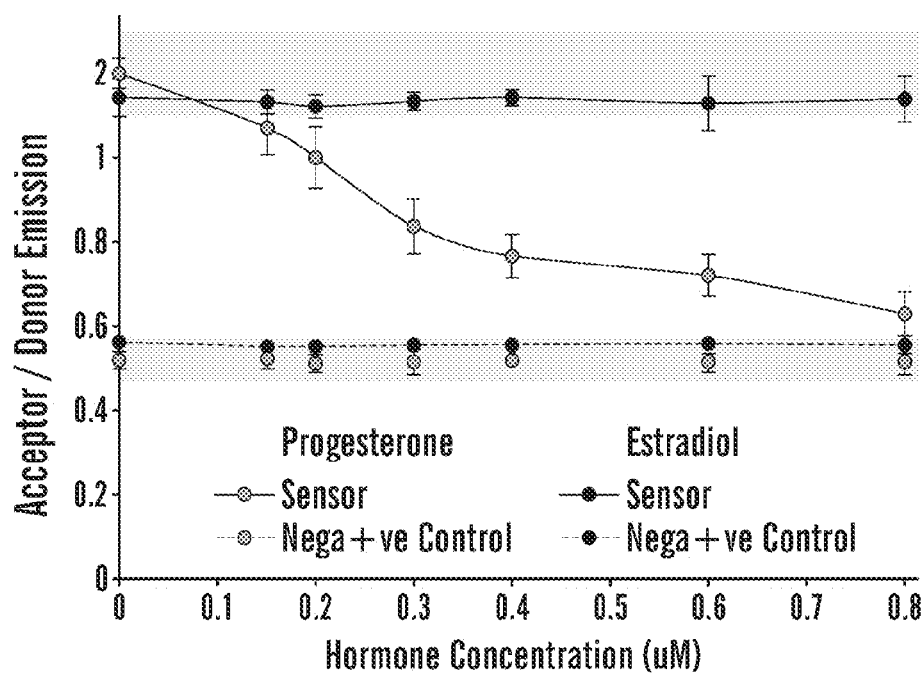
Figure 31C:
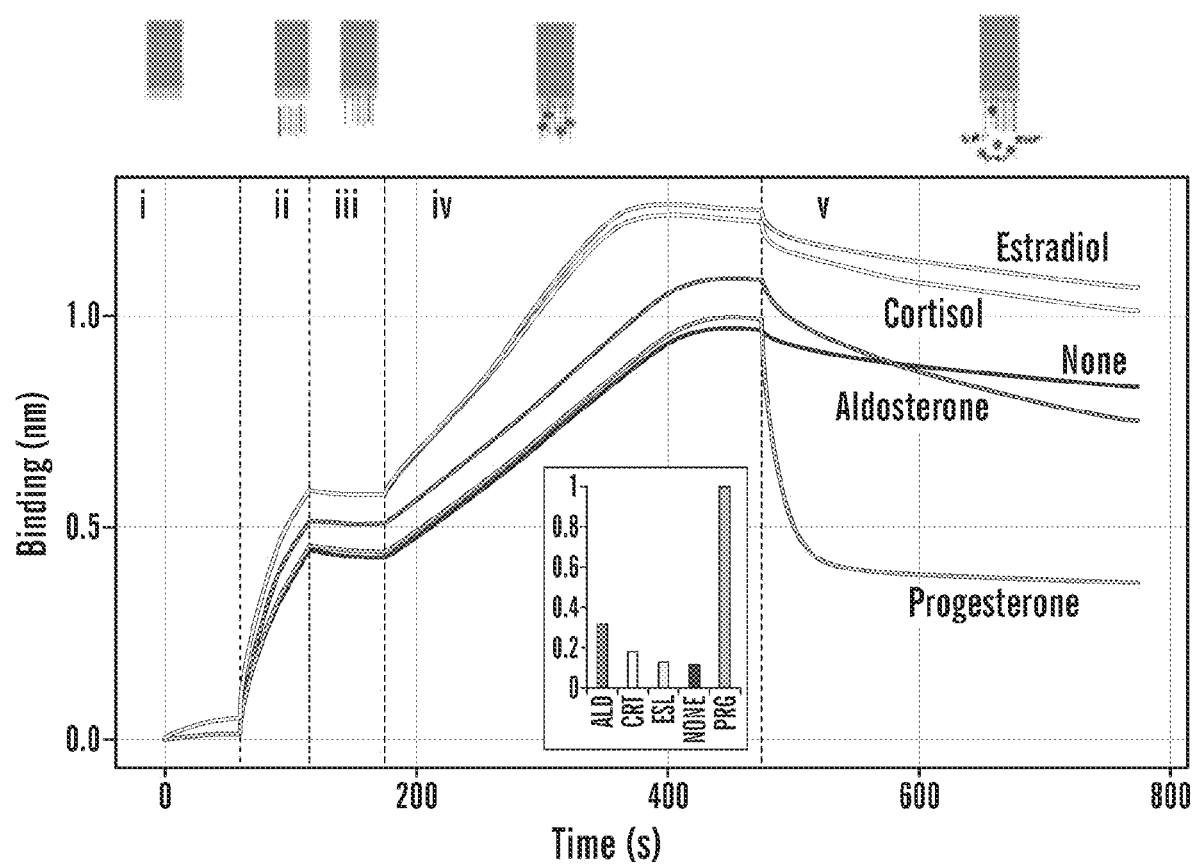
Figure 32:
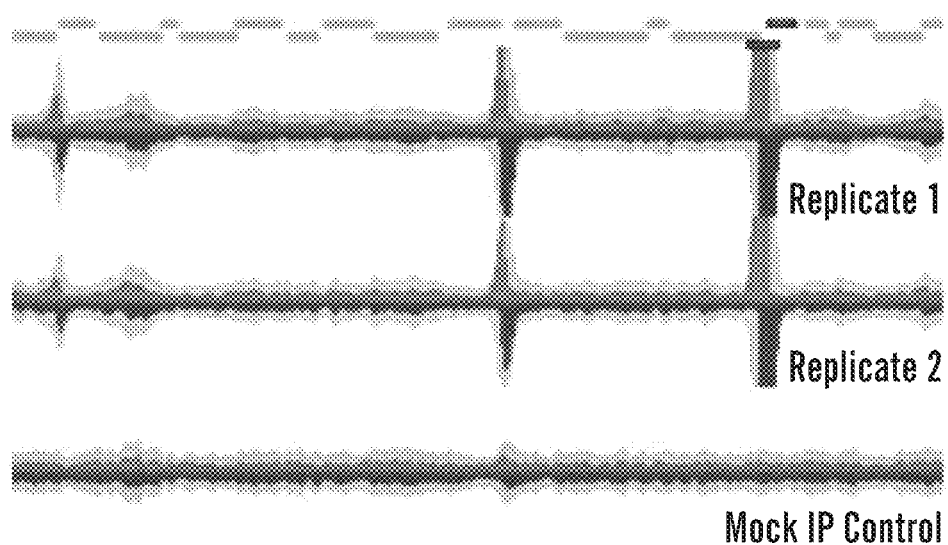
FIG. 32 shows in vitro ChIP-Seq of the *P. simplex* progesterone sensing TF. Plot displays enrichment in the region of the *P. simplex* genome containing the TF (cyan=genes, red gene=progesterone TF). Forward and reverse coverage is shown in green upwards and blue downwards histograms. Yellow envelope indicates total coverage. Three regions of significant enrichment are evident in the experimental replicates with the expected spatial shift between forward and reverse coverage for TF binding. One (red line, not to scale) corresponds to the autobinding region used for development of the progesterone optical sensor
Figure 33:
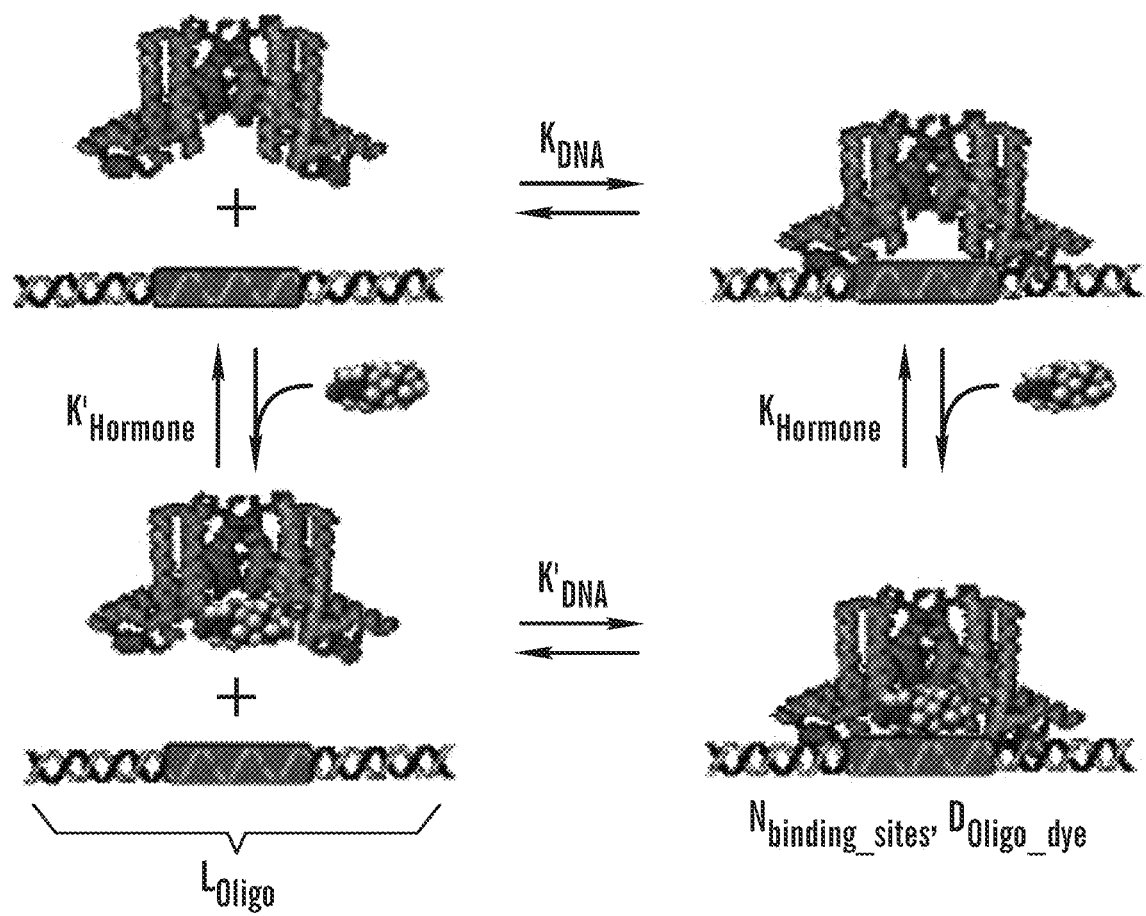
FIG. 33 shows a schematic of the binding of the aTF to oligo that can be described by a Michaelis-Menton model with several tuneable parameters.
Figure 34A:
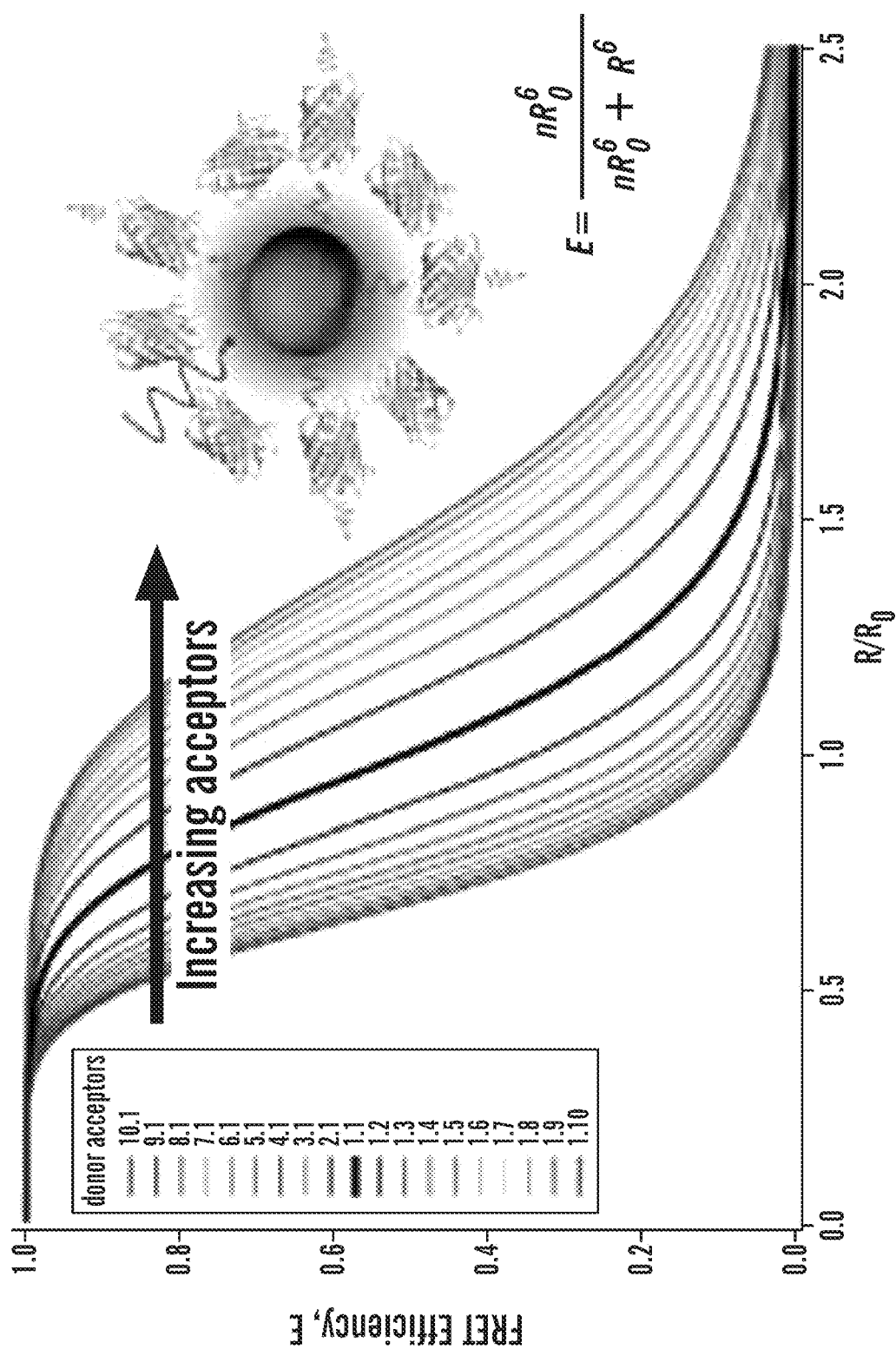
FIGS. 34A-34B show the relationship between FRET efficiency.
Figure 34B:
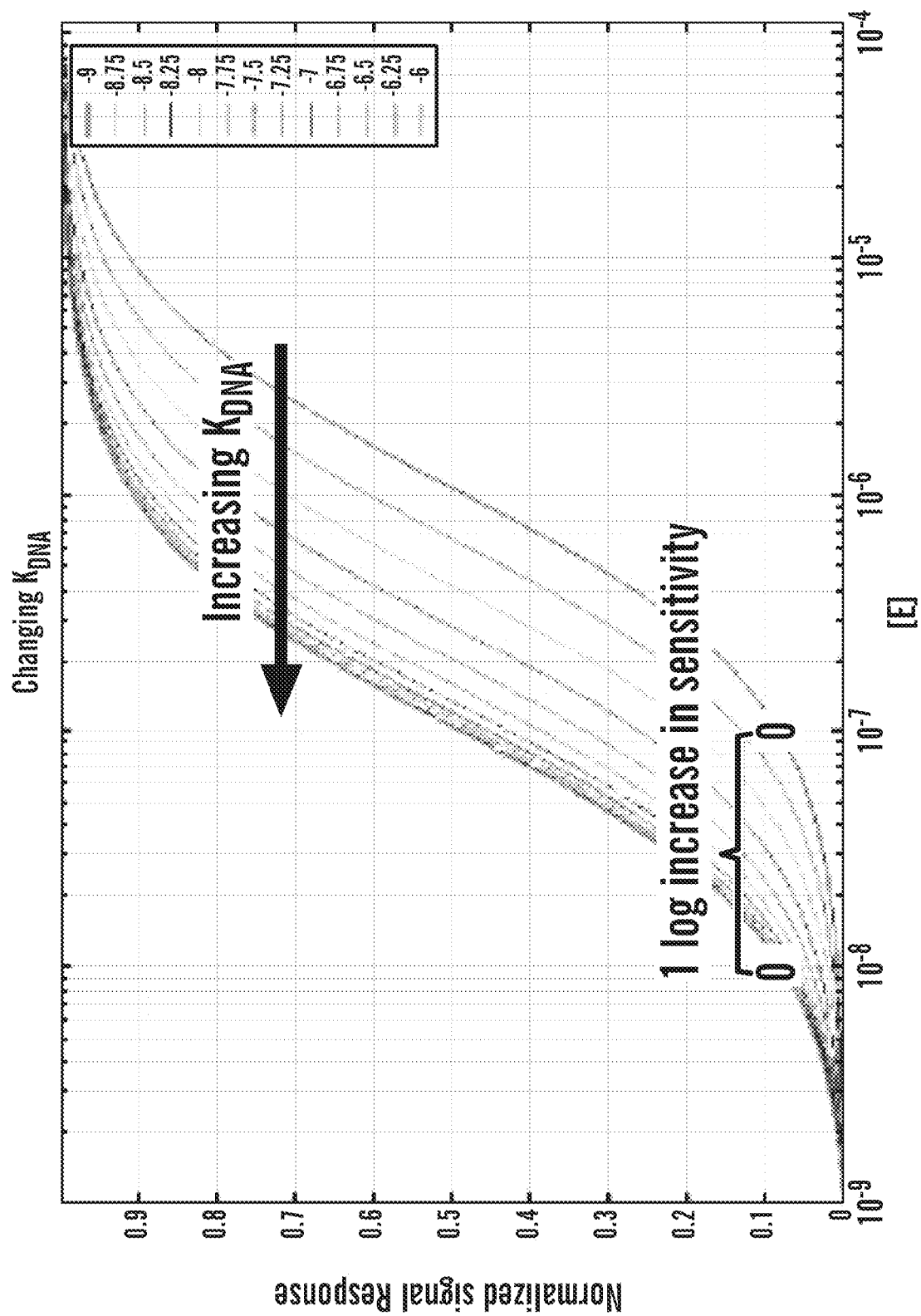
Figure 35A:
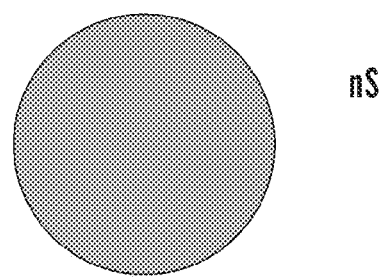
FIGS. 35A-35C show a schematic of the QD-QD FRET biosensor system.
Figure 35B:
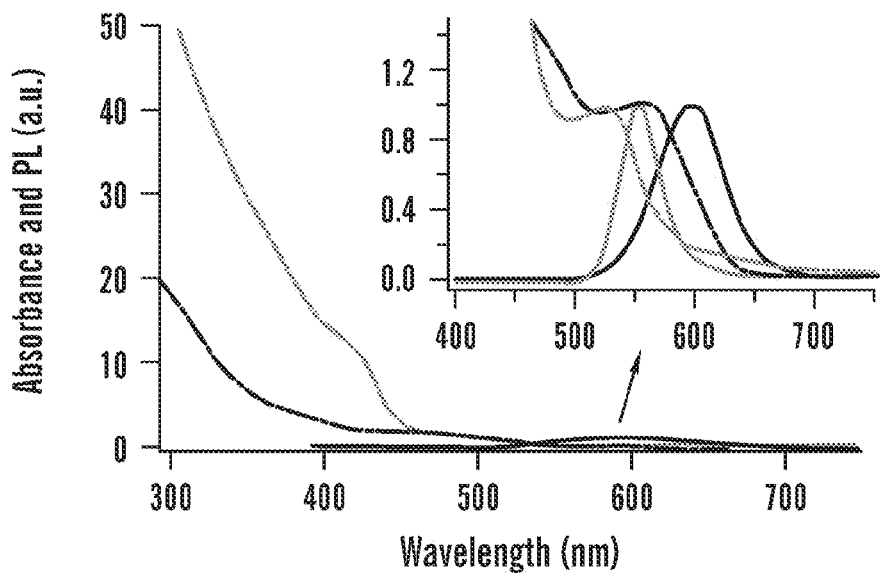
Figure 35C:
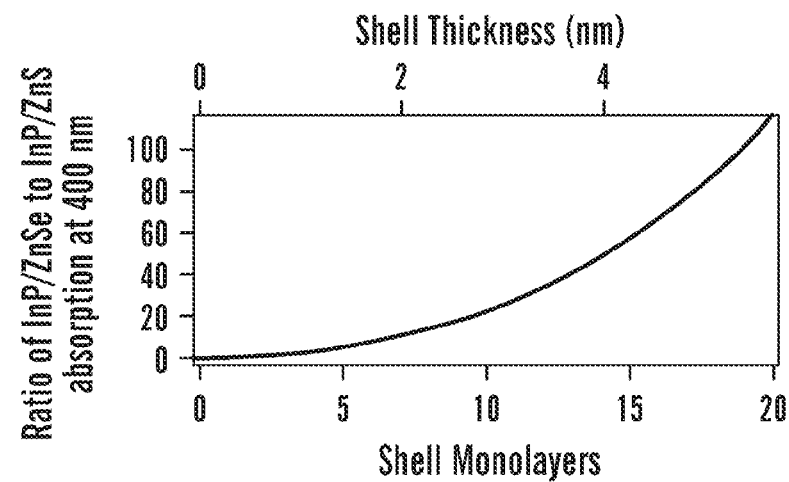
Figure 36:
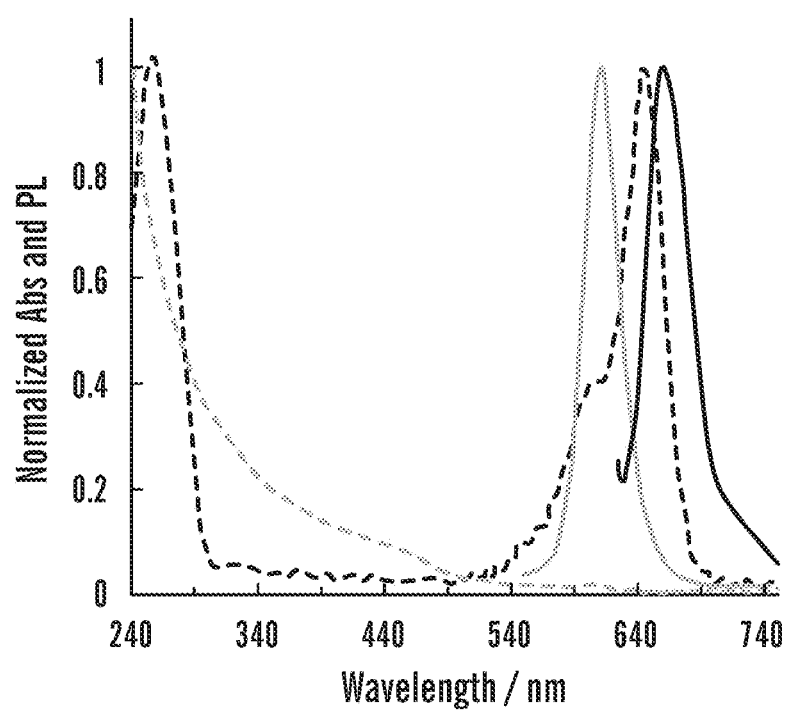
FIG. 36 shows the absorption (dashed) and fluorescence emission (plain) spectra of QDs-TF-Donor (yellow) and DNA-Cy5—acceptor (salmon) in HEPES 1×.
Figures 37A, 37B:
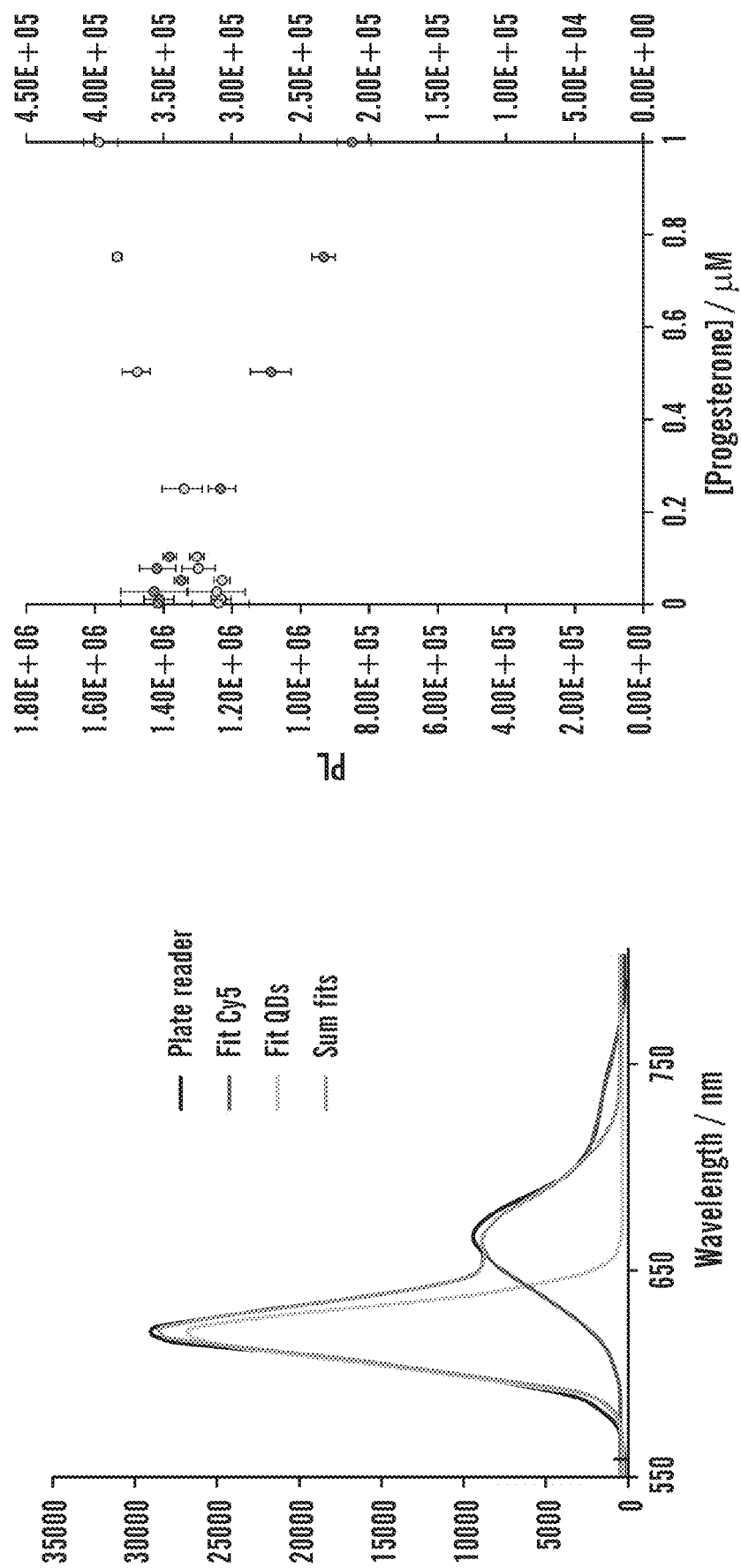
FIGS. 37A-37B show fluorescence emissions of the sensor.
Figures 39A, 39B:
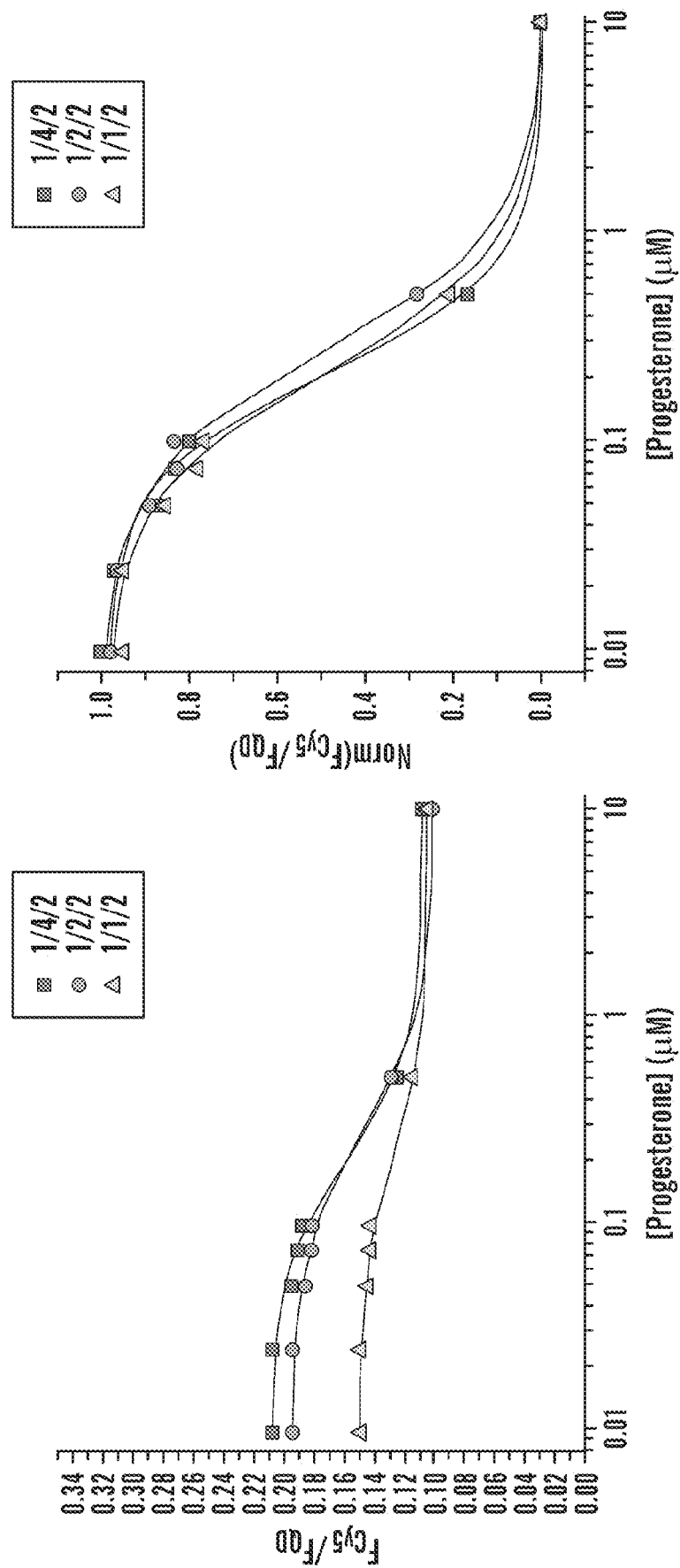
FIGS. 39A-39B show the ratio of the fluorescence emission signal of Cy5 and QDs as a function of the progesterone concentration.
Figure 40B:
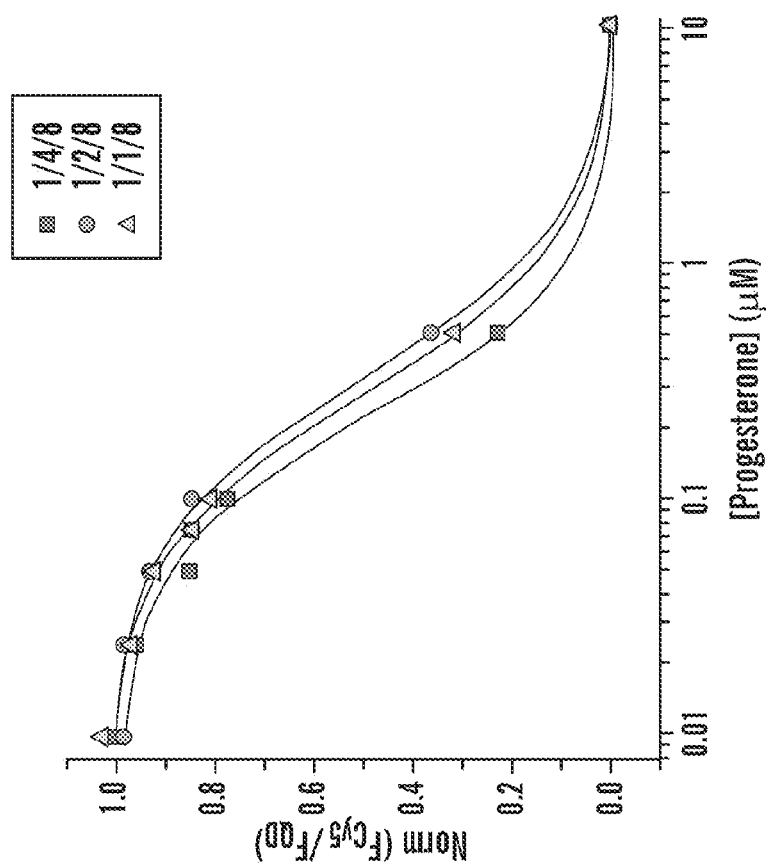
FIGS. 40A-40B show the ratio of the fluorescence emission signal of Cy5 and QDs.
Figure 40A:
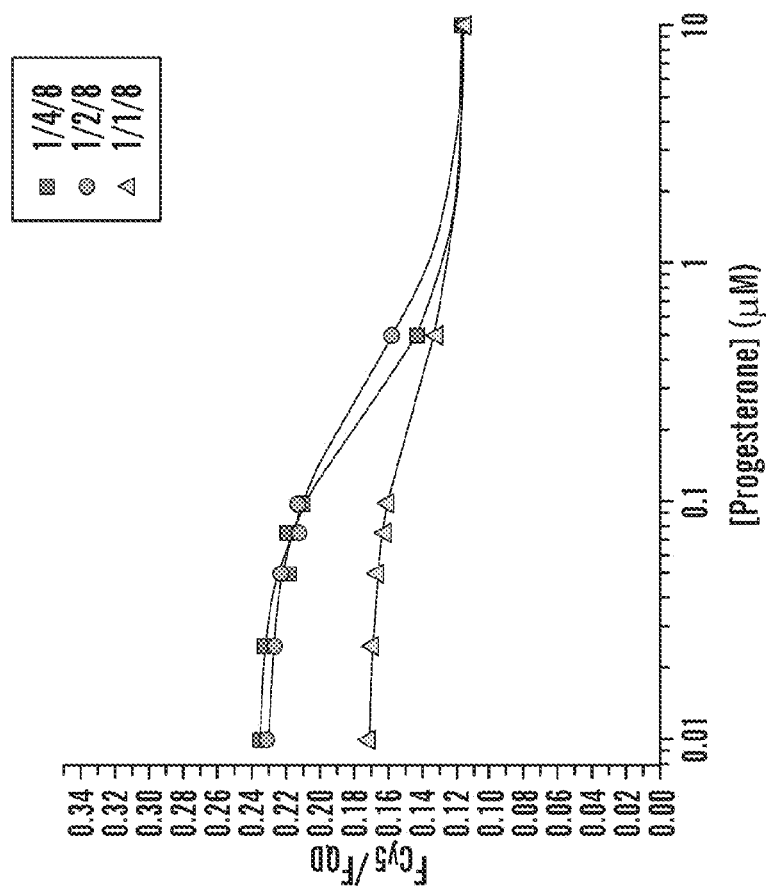
Figure 41B:
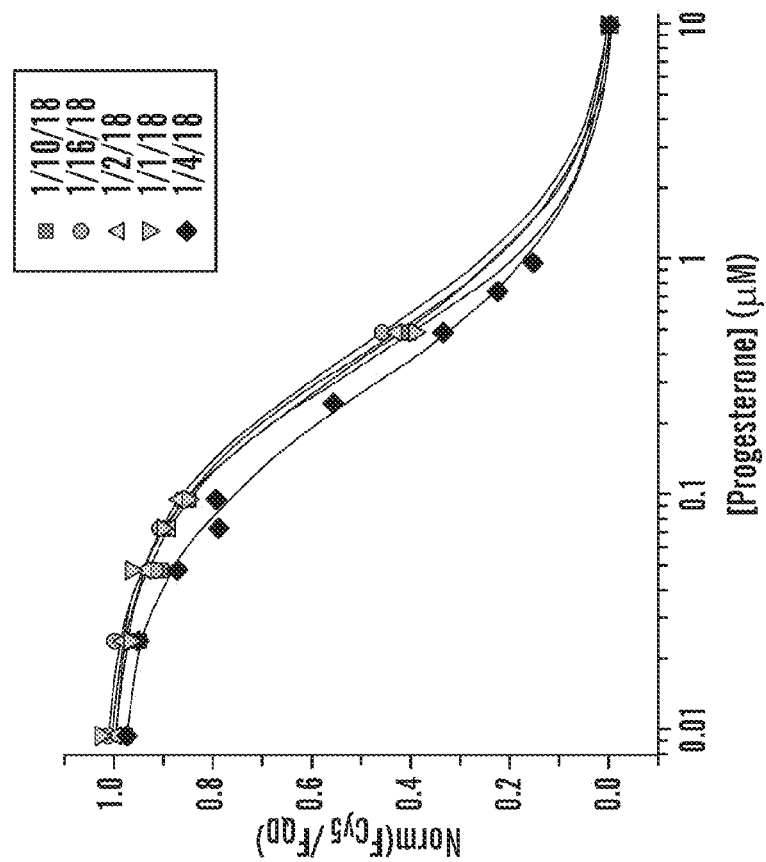
FIGS. 41A-41B show the ratio of the fluorescence emission signal of Cy5 and QDs.
Figure 41A:
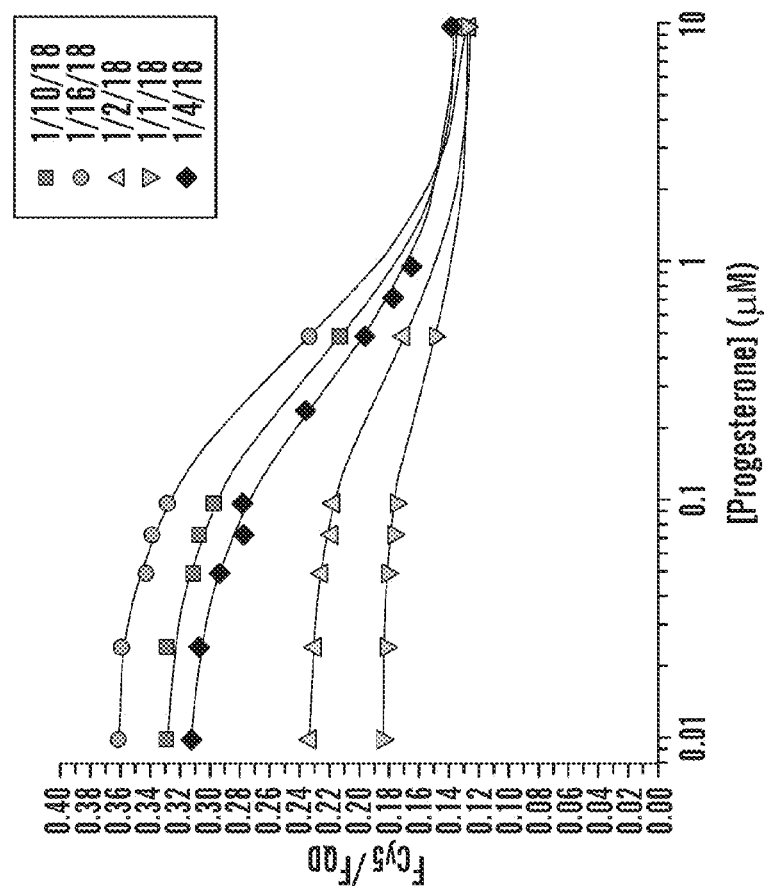
Figure 42B:
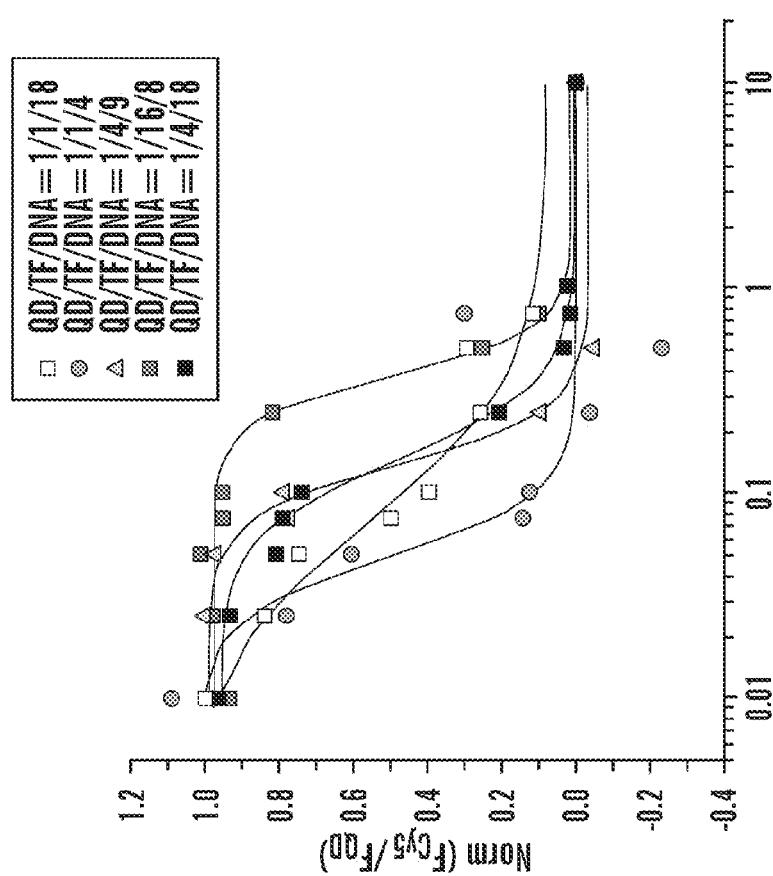
FIGS. 42A-42B show the ratio of the fluorescence emission signal of Cy5 and QDs.
Figure 42A:
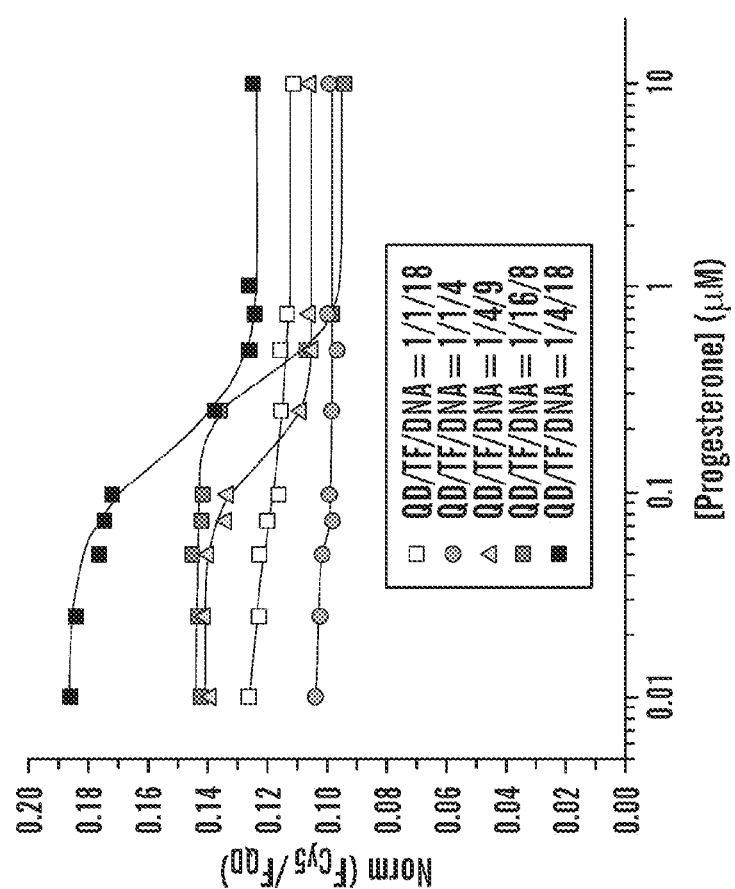
Figure 43A:
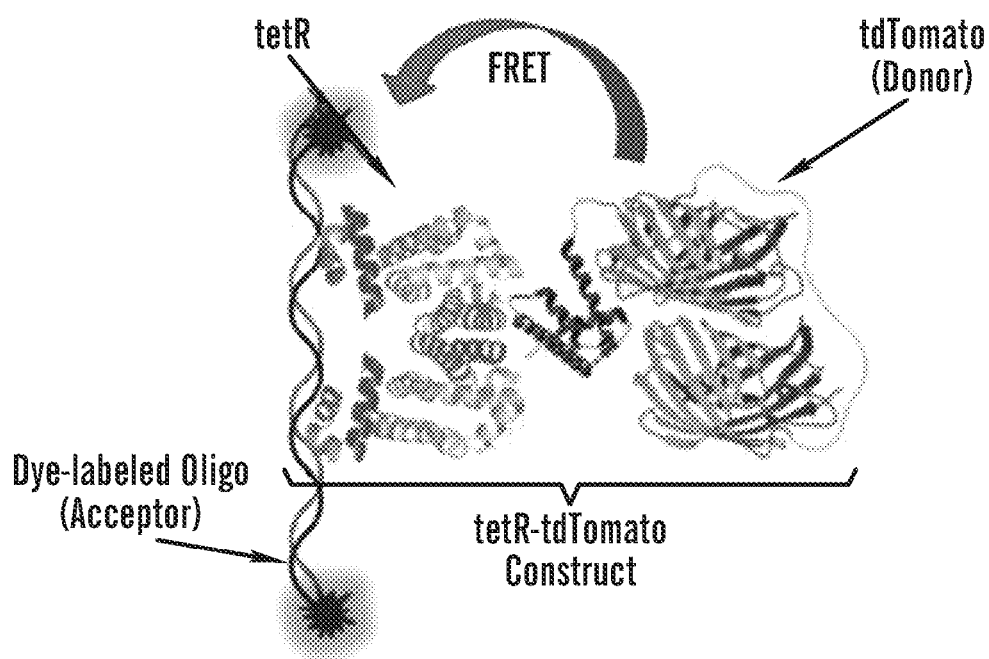
FIGS. 43A-43H show the design and the optimization of FRET-based biosensors.
Figure 43B:
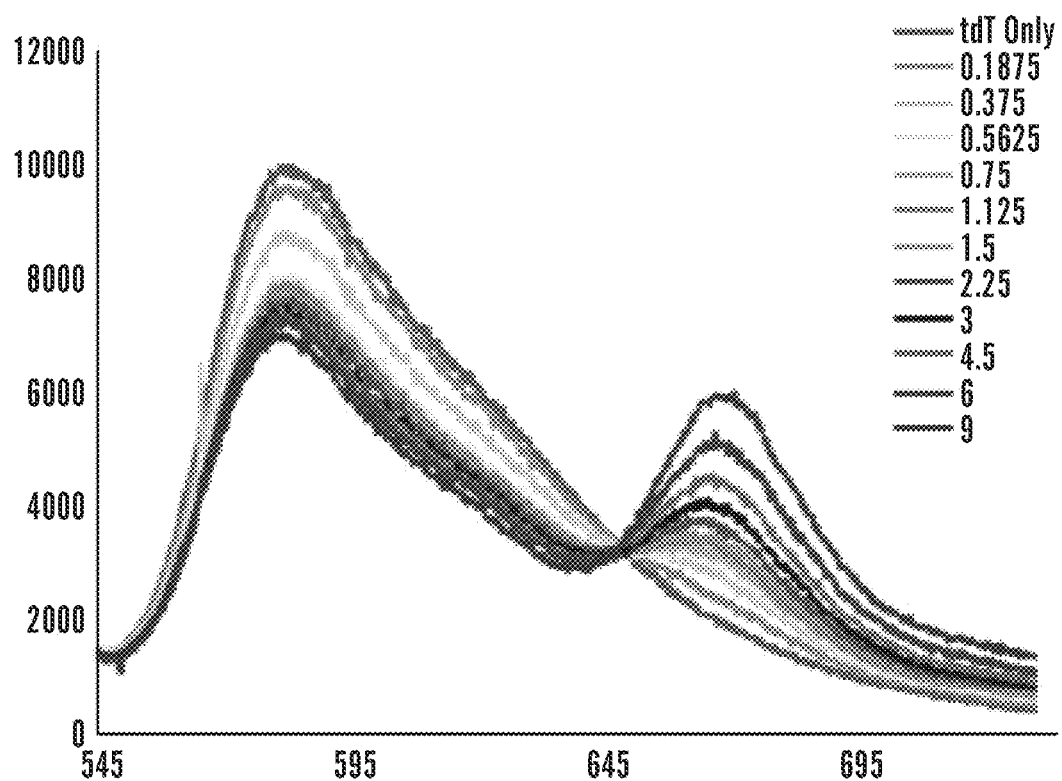
Figure 43C:
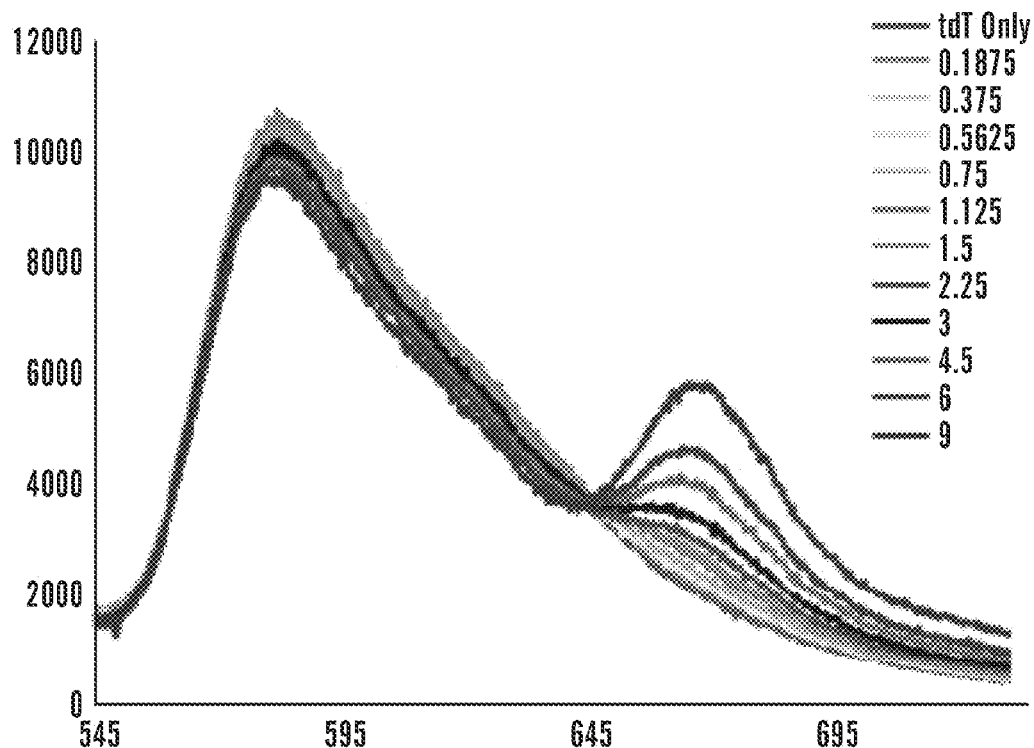
Figure 43D:
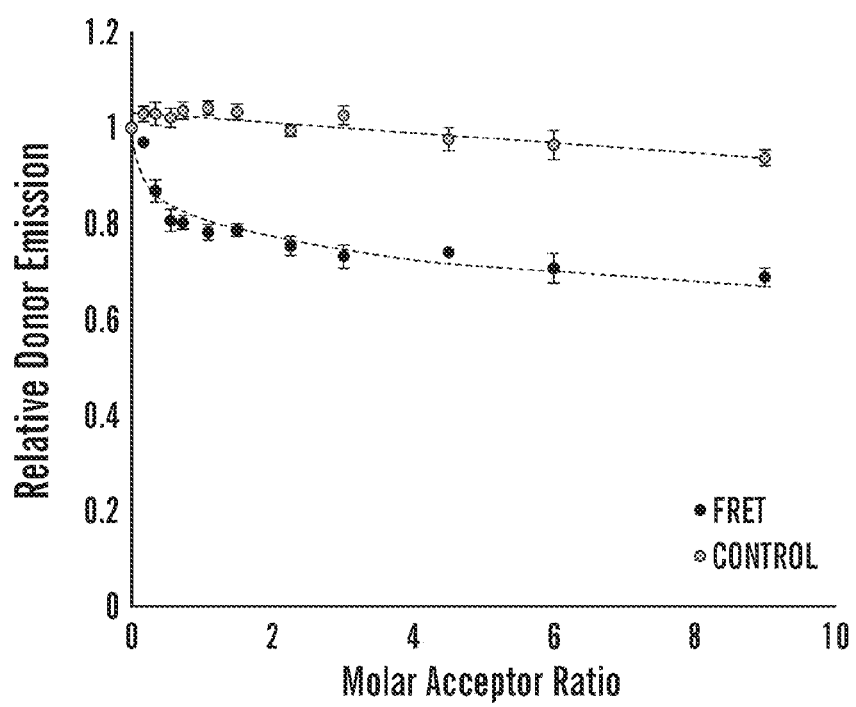
Figure 43E:
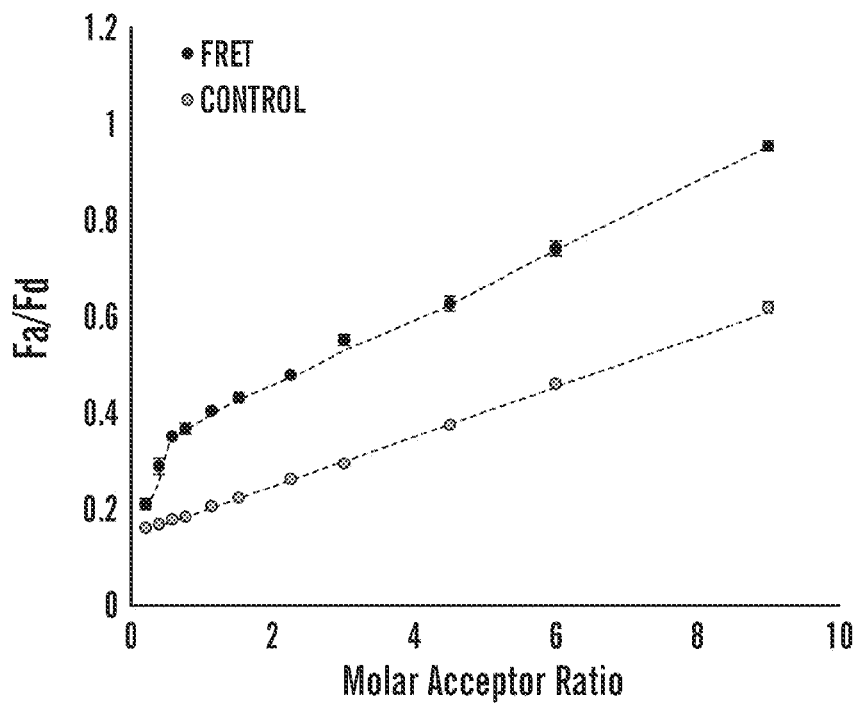
Figure 43F:
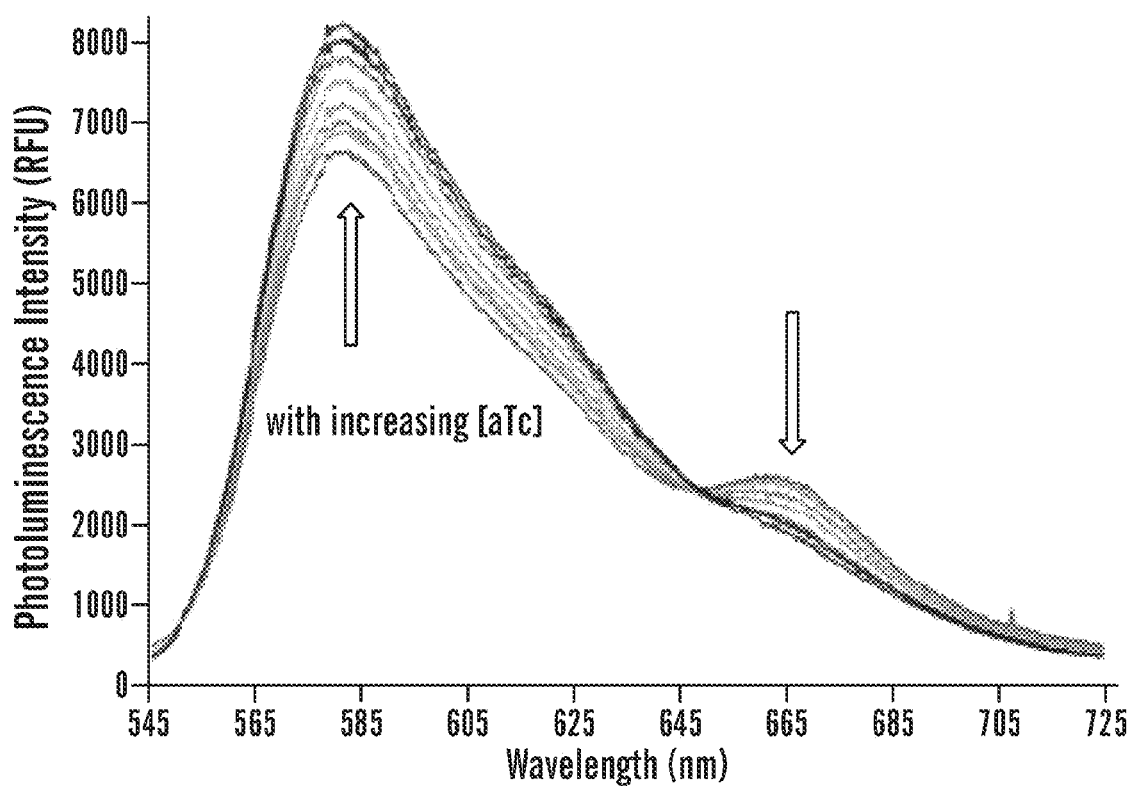
Figure 43G:
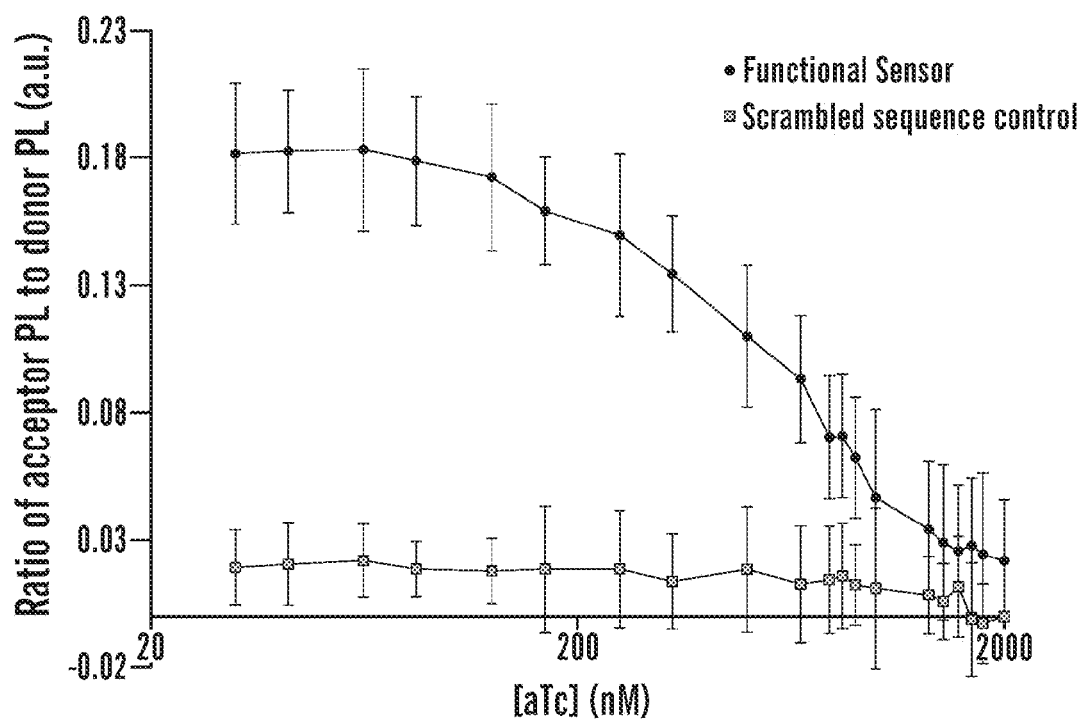
Figure 43H:
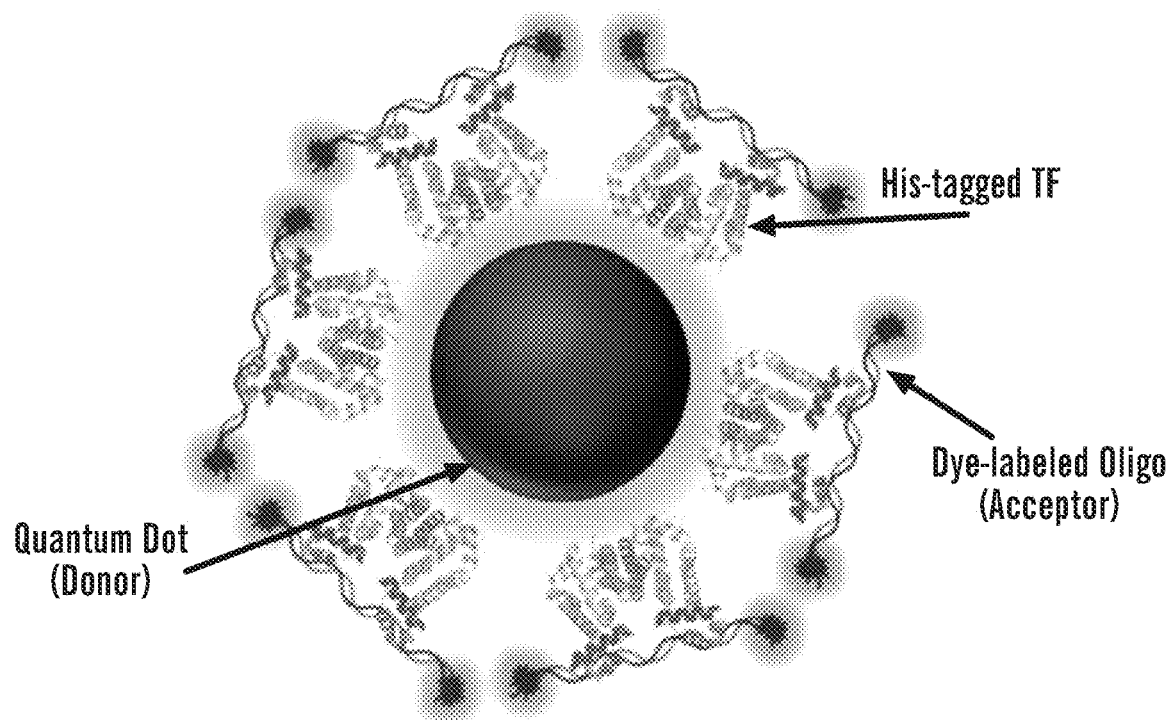
Figure 44A:
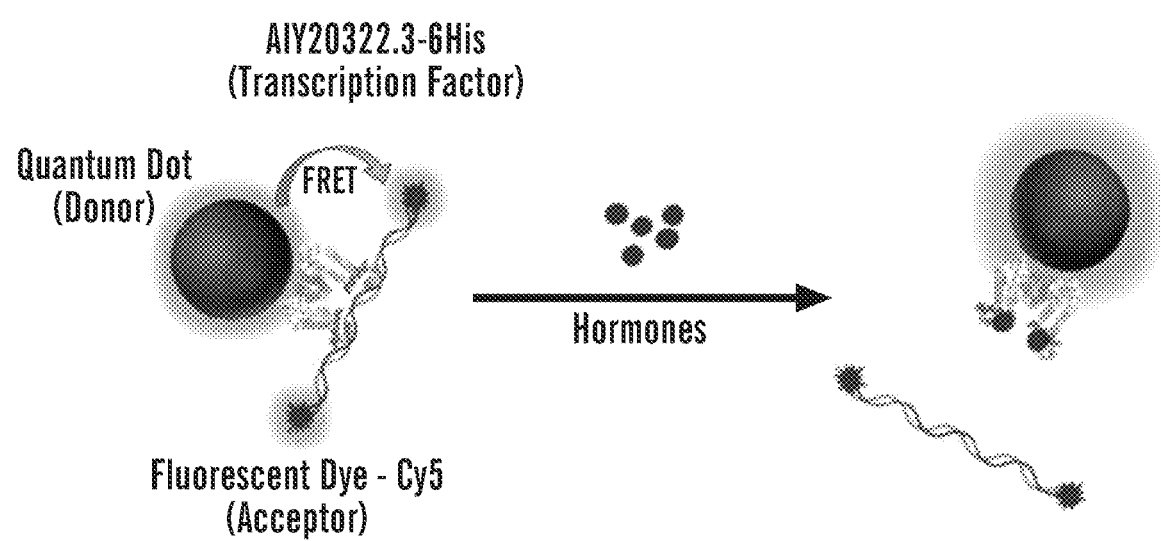
FIGS. 44A-44E show a schematic of the biosensor and emission plots.
Figure 44B:
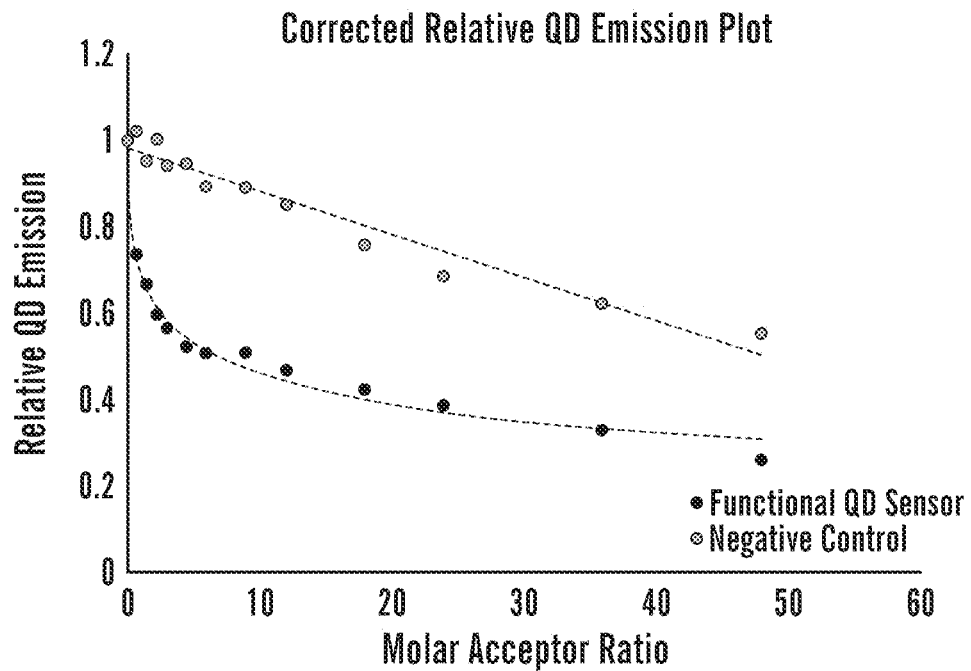
Figure 44C:
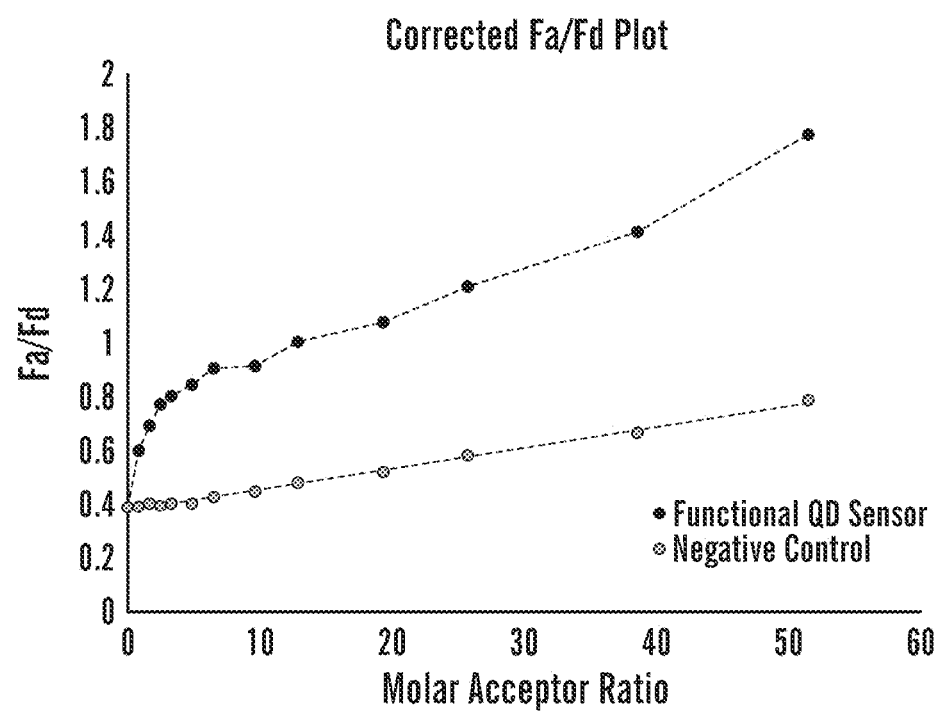
Figure 44D:
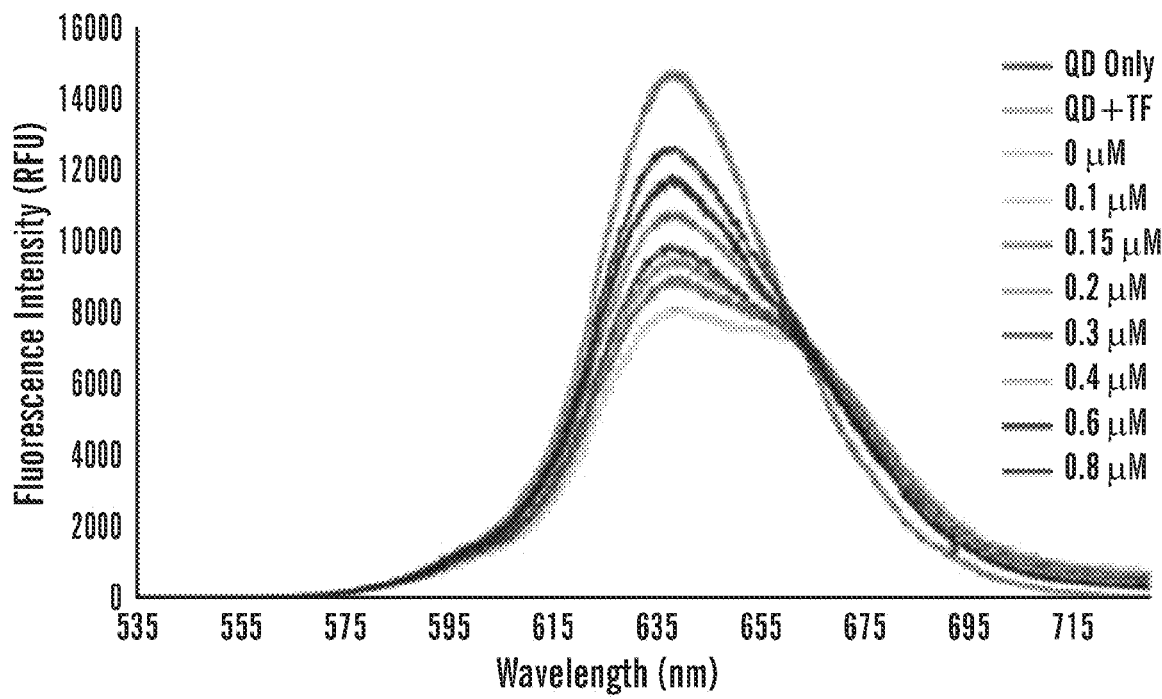
Figure 44E:
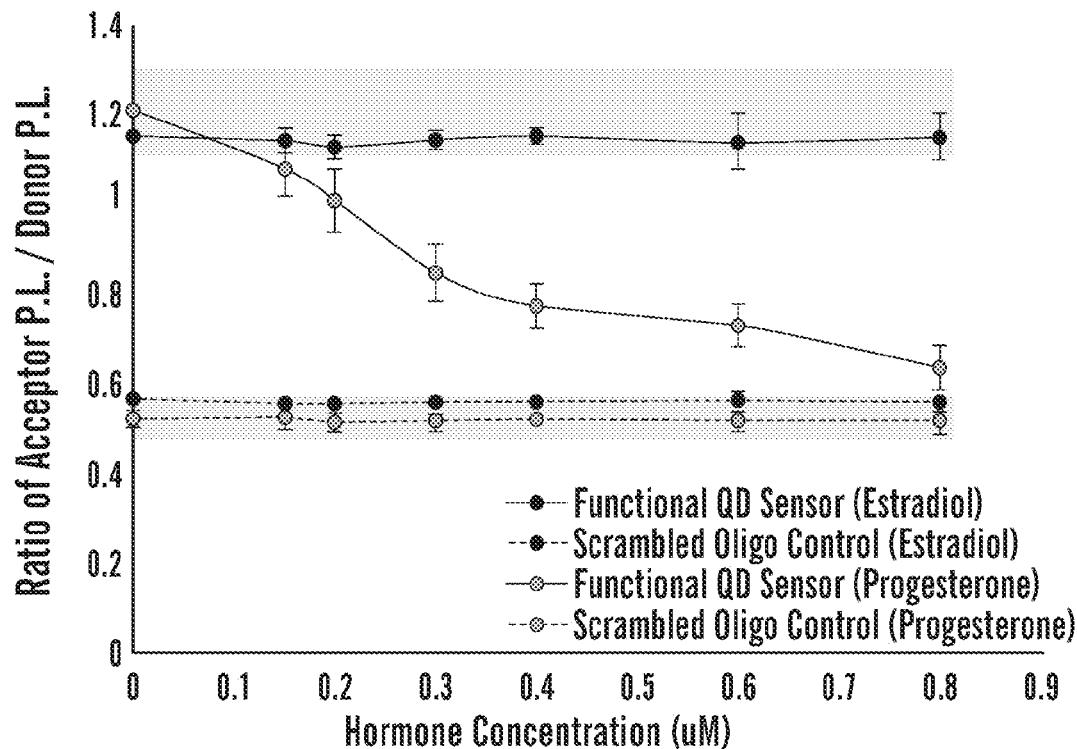
Figure 45A:
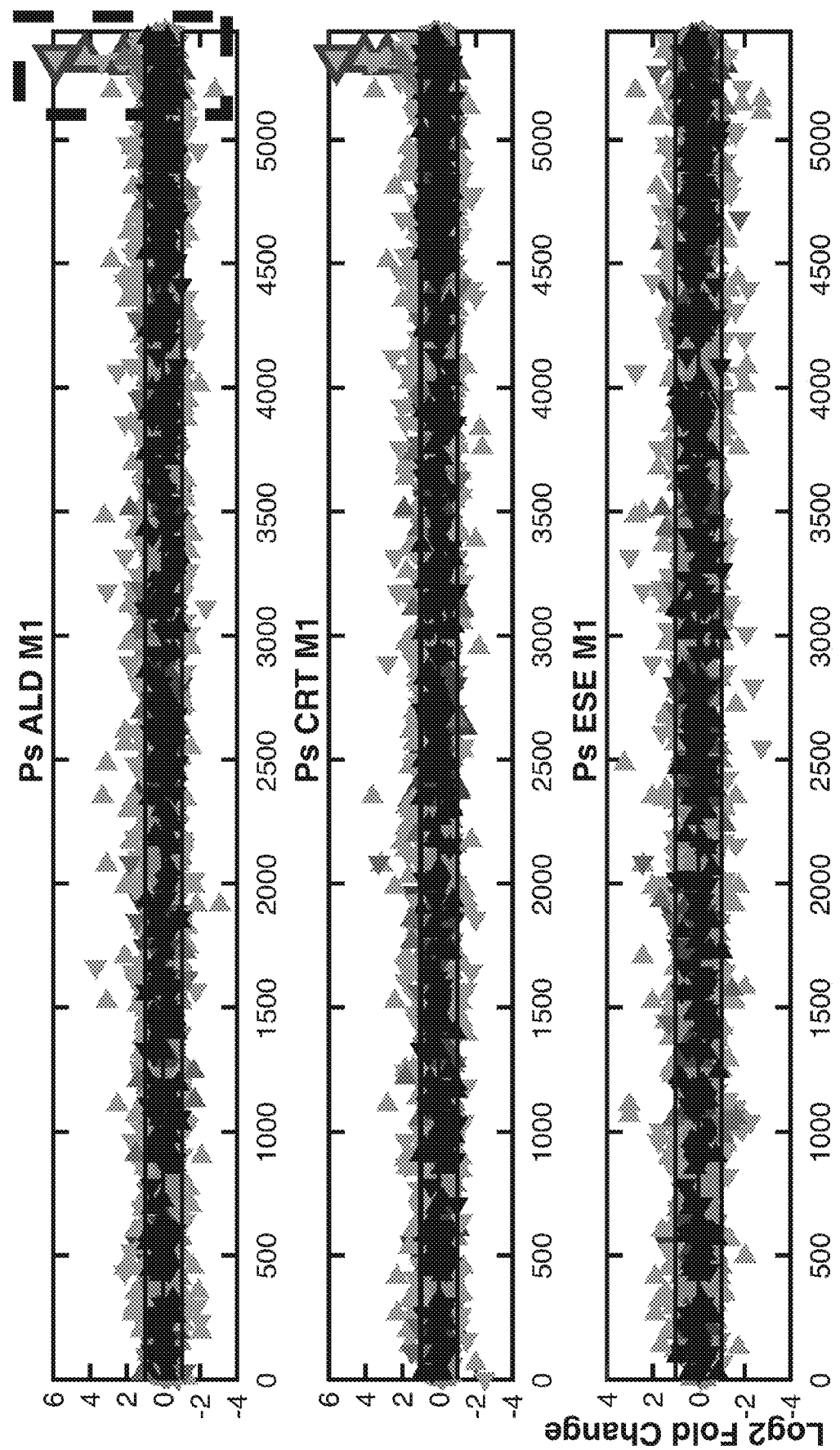
FIGS. 45A-45B show results of the screening approach to identify novel transcription factors.
Figure 45A:
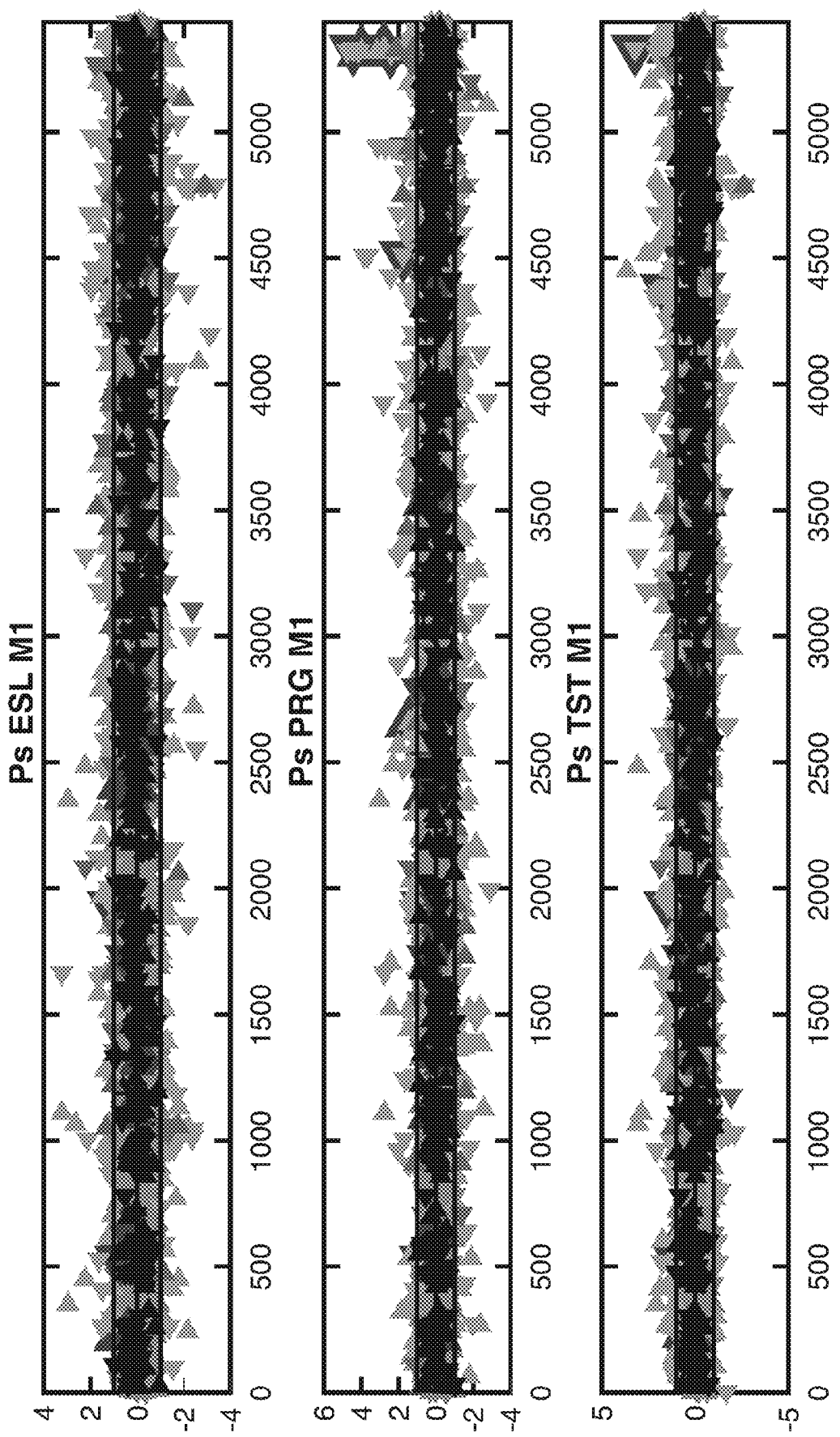
Figure 45B:
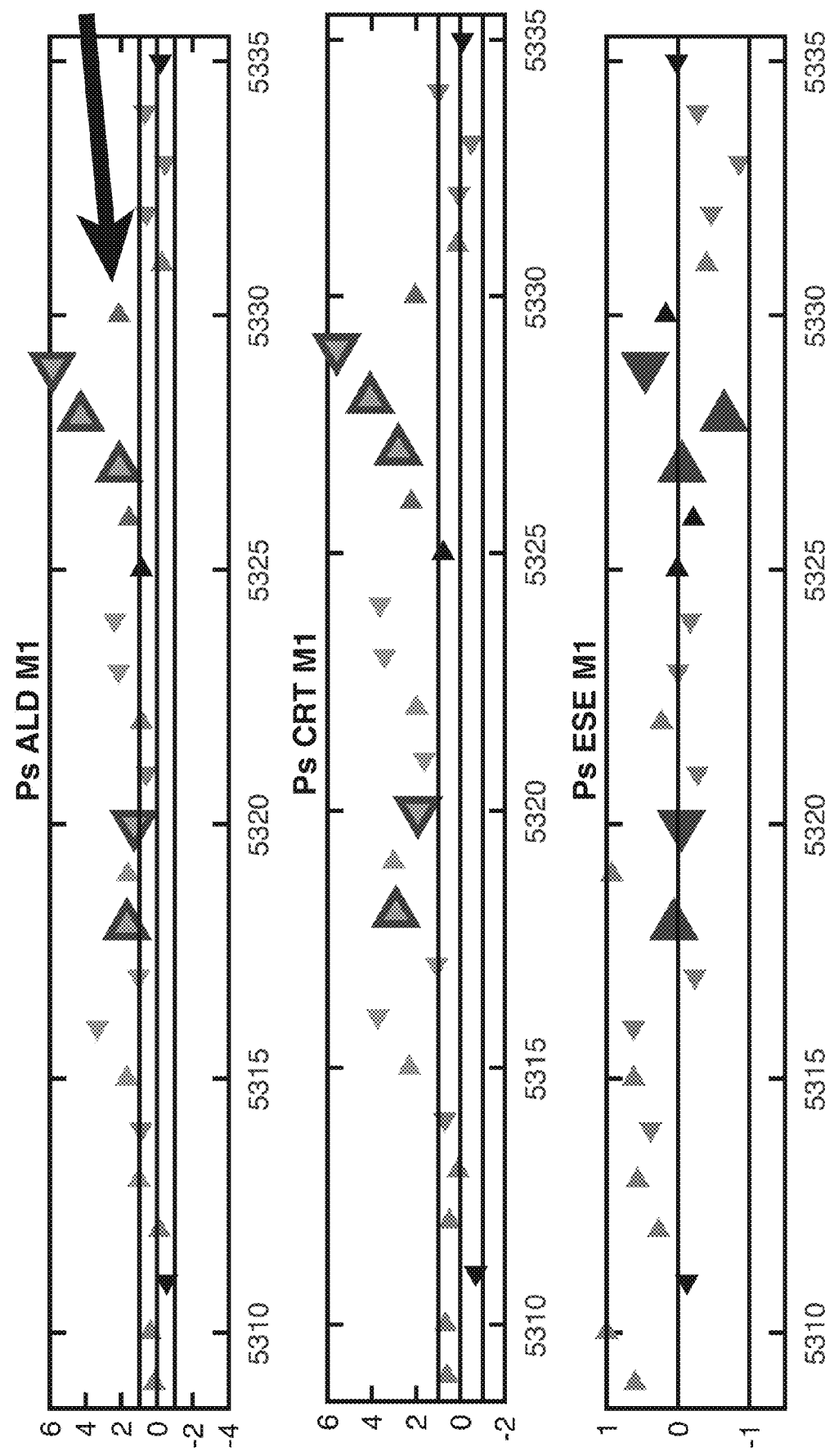
Figure 45B:
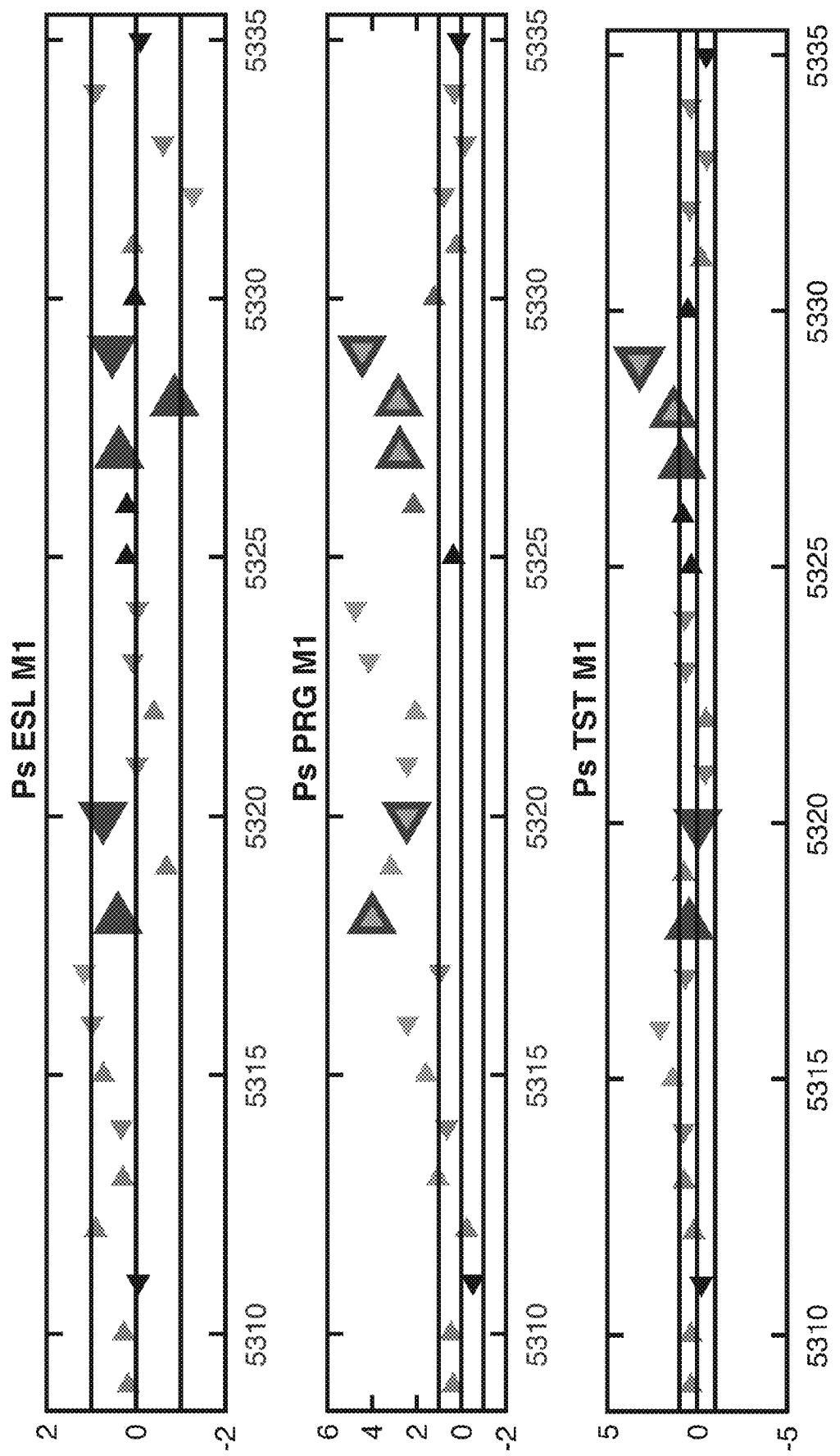
Figure 46A:
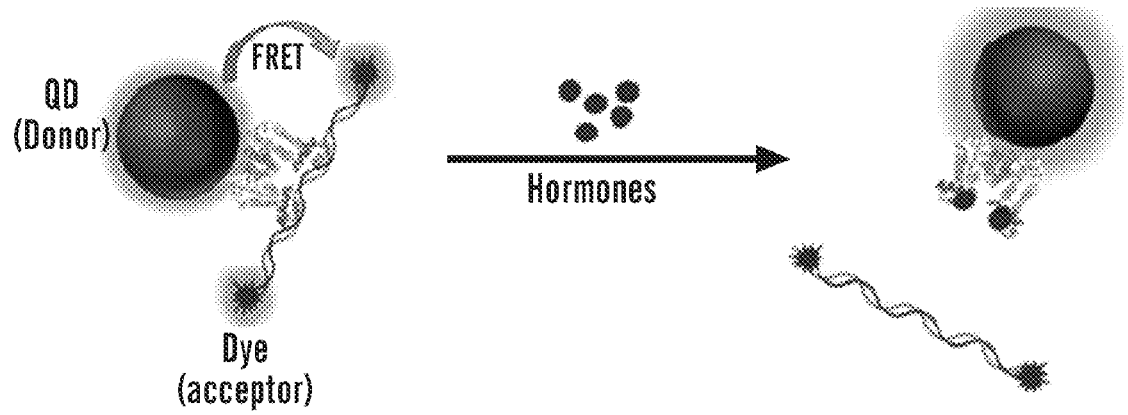
FIGS. 46A-46C show the general schematic for creating an optical sensor and the validation of the sensor.
Figure 46B:
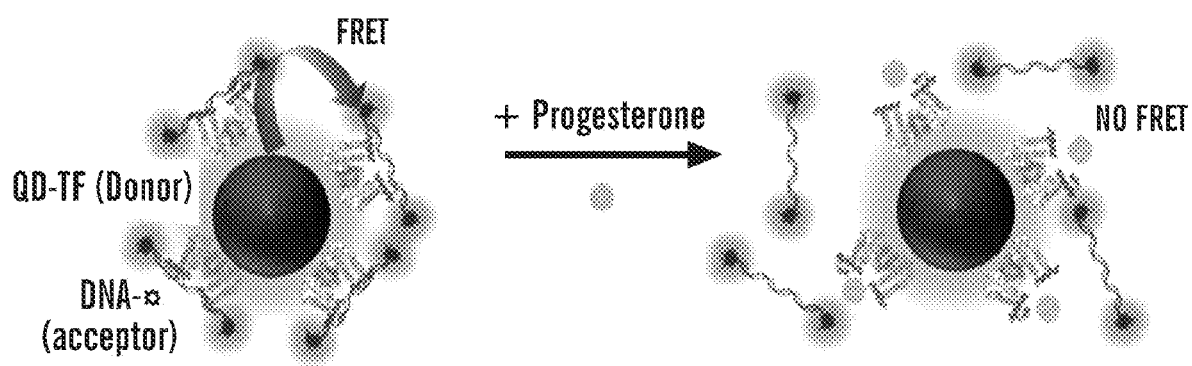
Figure 46C:
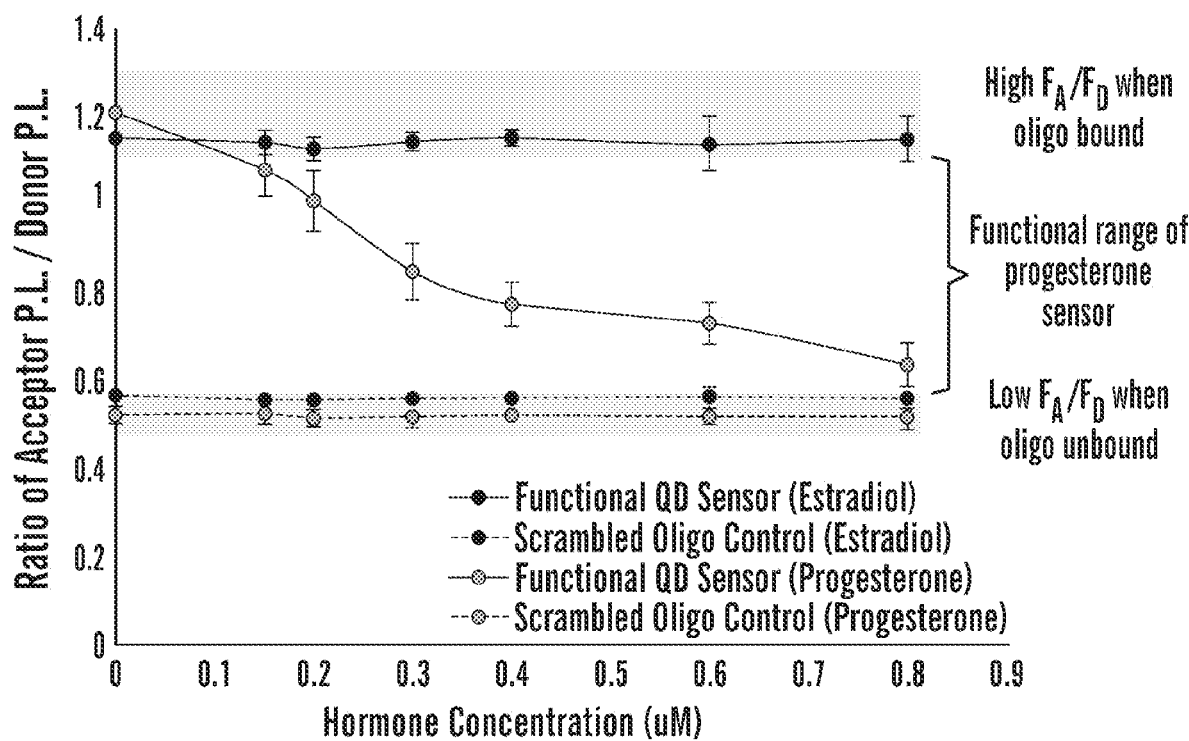
Figure 47:
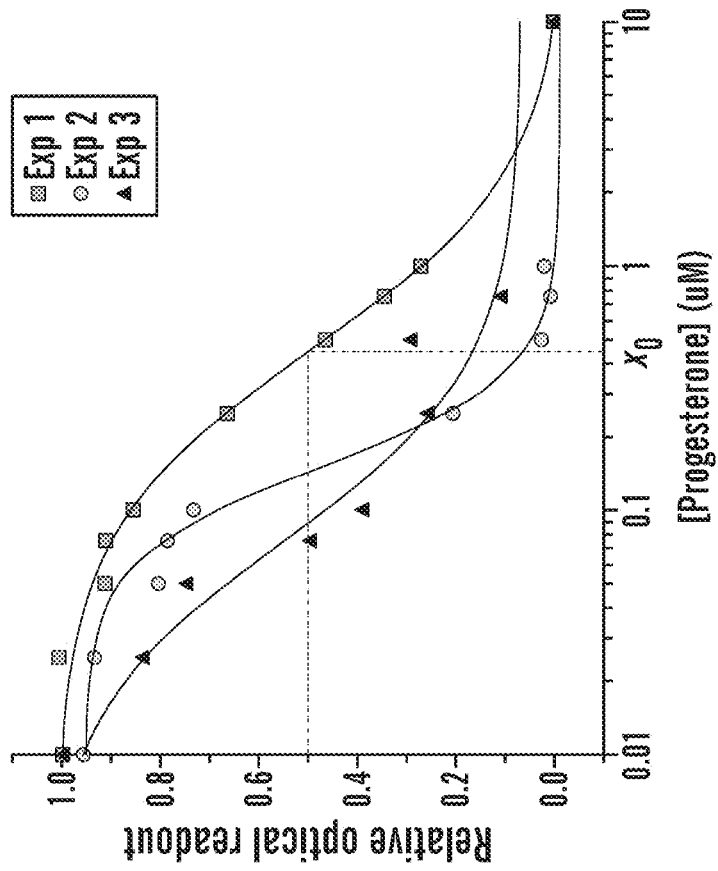
FIG. 47 shows the relative optical readout in relation to the progesterone concentration. Different sensor designs lead to different binding affinities.

In another embodiment, a conformational change TF-FRET biosensor system was used for the quantification of the target analyte with high sensitivity (e.g., see FIG. 17B). This mechanism depends on a TF, with two tethered fluorescent molecules such as CFP and YFP on the N and C terminus of the TF. The conformational change of the TF upon analyte induces binding of the two fluorescent molecules so that they are brought close enough together to induce FRET. This mechanism depends on a conformational change to occur with ligand binding and also does not depend on the DNA-binding domain.

II. Allosteric Transcription Factors (aTF)

As described herein, biosensors comprise an allostric transcription factor (aTF) conjugated to a first reporter molecule (e.g., fluorescent molecule or an electroactive molecule), such that when the aTF binds to the nucleic acid probe (also comprising a reporter molecule (e.g., fluorescent molecule or an electroactive molecule), a signal between the first and second reporter molecule occurs and can be detected. An exemplary allosteric transcription factor for use in a biosensor is PinR, which detects progesterone, and is discussed in more detail in the section entitled "Exemplary biosensor: progesterone biosensor" herein.

As disclosed herein, several FRET-based signal transduction mechanisms were developed to produce internally calibrated fluorescent signals from the binding and unbinding of an aTF to an oligomeric DNA sequence (e.g., the nucleic acid probe). By exploiting the difference in the binding affinity between the aTF and its specific binding sequence in the presence and absence of a small molecule or analyte, the aTF-DNA binding and unbinding becomes a sensor for the small molecule effector (e.g., see FIGS. 1, 9A and 10).

Some embodiments of the present disclosure are directed to a biosensor including a allosteric transcription factor conjugated to a first quantum dot of a FRET pair, the allosteric transcription factor comprising a ligand binding domain (LBD) and a DNA binding domain (DBD), and a nucleic acid probe conjugated to a second quantum dot of the FRET pair, the nucleic acid probe having a sequence comprising a transcription factor binding domain (TFBD) that is specific to the DBD of the transcription factor, wherein when the DNA binding domain (DBD) binds to the TFBD in a ligand-depended matter and the first quantum dot and the second quantum dot of the FRET pair emits a fluorescent signal. According to another aspect, the DNA binding domain (DBD) binds to the TFBD by a factor of about 2 fold or more. According to another aspect, the regulated DNA binding domain (DBD) binds to the TFBD by a factor of about 10 fold or more. According to another aspect, the regulated DNA binding domain (DBD) binds to the TFBD by a factor of about 50 fold or more. According to another aspect, the regulated DNA binding domain (DBD) binds to the TFBD by a factor of about 100 fold or more. According to another aspect, the regulated DNA binding domain (DBD) binds to the TFBD by a factor of about 250 fold or more. According to another aspect, the regulated DNA binding domain (DBD) binds to the TFBD by a factor of about 500 fold or more. According to another aspect, the regulated DNA binding domain (DBD) binds to the TFBD by a factor of about 1000 fold or more.

TetR: As exemplary example, the transcription factor TetR was used for this proof-of-concept sensing study because it is a well characterized allosteric TF that is used extensively for gene regulation and inducible protein expression in the laboratory setting. The TetR regulatory complex evolved in bacteria to turn on the production of TetA efflux pumps to protect the cells from the antibiotic tetracycline. In microbial systems, the biosynthetic precursor to tetracycline anhydrotetracycline (aTc) also binds to the repressor TF, TetR and induces production of the efflux pump shortly before the cell is exposed to the impending influx of tetracycline. As aTc itself is not an antimicrobial agent, its derepressor activity has been effectively harnessed to induce production of proteins encoded by downstream genes in synthetic biology. Many mutations of TetR are known to change its responsivity to the analyte, e.g., revTetR flips the mode of action causing TF-DNA binding in the presence of aTc rather than its absence, demonstrating the adapt-ability of the allosteric TF to a variety of sensing scenarios. In this study, two variants of TetR were used, TetRc and TetRd, to demonstrate that the sensor output can be tuned by subtly modifying the binding affinity of the TF to its DNA oligo. Both TetRc and TetRd bind to the TetO DNA sequence in the absence of the effector molecule aTc. The TetO cognate sequence comprises a 19 bp binding region. In the sensor de-sign, the 19 bp cognate sequence was flanked by 4-5 bp on each side to ensure binding, resulting in a 28 bp DNA oligo. One of the strands was labeled with the FRET acceptor Cy5 on both the 5' and 3' ends. A second 28 bp sequence with no affinity for TetR was similarly labeled to act as the negative control.

Figure 1B:
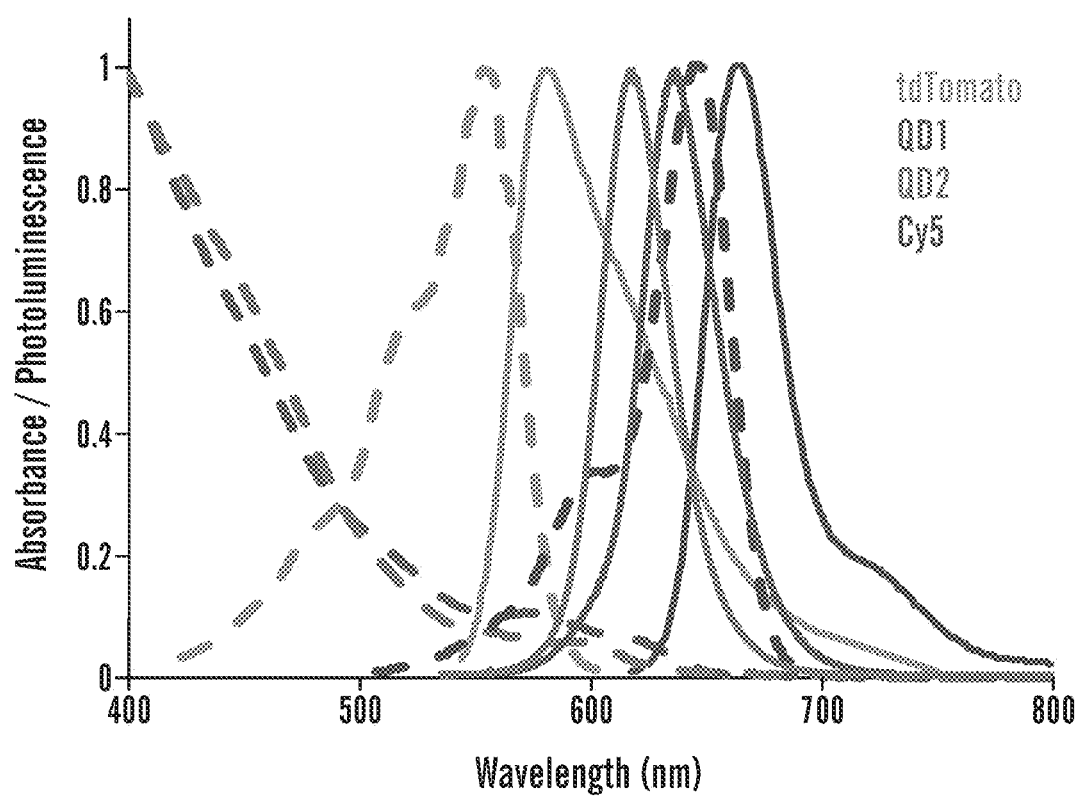

In some embodiments of any of the aspects, three FRET-based sensors utilizing the TF-DNA binding mechanism were developed and characterized for the sensing of the small molecule anhydrotetracycline, aTc. Each sensor consists of Cy5-modified DNA acting as the FRET acceptor with either a fluorescent protein-transcription factor (FP-TF) fusion protein (expressed in *E. coli*) or quantum dot-transcription factor (QD-TF) conjugate as the donor. The absorbance and emission spectra of the four fluorophores used in the study—the FP tdTomato, two different batches of QDs (QD1 and QD2), and the organic dye Cy5 are shown in FIG. 1. The QD-Cy5 FRET pairs exhibit increased spectral overlap between the respective emission peaks and the Cy5 absorption compared to tdTomato. The much higher quantum yield of tdTomato compared to the QDs, however, results in a larger calculated Förster distance, $R_0$, for the tdTomato-Cy5 FRET pair than the calculated $R_0$ for the QD1-Cy5 or QD2-Cy5 FRET pairs (Table 2). Thus, in a 1:1 donor: acceptor pairs with the same donor-acceptor distances, Sensor 1 would exhibit the most efficient energy transfer. This simplistic consideration ignores multiple possible confounders in the sensor geometry, however, including the likelihood of TetR dimerization, which would double the number of tdTomato donors per construct. On the other hand, the impact of multiple tdTomato donors is balanced by the double-labeling of the cognate DNA.

III. Fluorescence Based Biosensors for the Measurement of Analytes

In one embodiment, the technology herein relates to fluorescence based binding assays of analytes measured by the binding affinity of the aTF to its transcription factor binding domain (TFBD), such as assays utilizing fluorescence resonance energy transfer (FRET) as the mode of detection. In some embodiments, an in vitro biosensor system described herein is suitable for measuring concentration of an analyte in a fluid.

For example, the biosensor can comprise fluorescent reporter molecules. In some embodiments, the aTF can be conjugated to a first fluorescent molecule and the nucleic acid probe can be conjugated to one or more second fluorescent molecules, such that when the aTF is bound to the nucleic acid probe, the first and second fluorescent molecules are in close proximity to allow FRET to occur. That is, where the biosensor is an ON-biosensor, the presence of the analyte allows aTF binding to the nucleic acid probe, resulting in the first and second fluorescent molecules coming into close proximity and the emission of FRET. In alternative embodiments, where the biosensor is an OFF-biosensor, the presence of an analyte results in the aTF from dissociating from the nucleic acid probe, and the first and second fluorescent molecules are no longer in close proximity such that FRET signal is attested or stopped.

In one embodiment, the fluorescent molecule is selected from a group consisting of a semiconductor quantum dot (QD), a fluorescent dye, a fluorescent protein or a combination thereof. Semiconductor quantum dots (QDs) are well known in the art and are powerful fluorescent nanoparticles widely used in bioimaging and biosensing. Their high photostability, color tunability, and abundant particle surface area available for biofunctionalization make them attractive fluorophores for bright and stable FRET-based biosensors.

Additionally, while a fluorescent output with fluorescent reporter molecules is one method for detecting the presence of analytes, other detection system can be used, as disclosed herein, for example, in the section entitled "Electroconductive based-biosensors and Redox based biosensors for detecting analytes".

Also, for exemplary purposes only, the application and Examples describe an aTF conjugated to a QD and the nucleic acid probe conjugated to one or more fluorescent dyes. However, it is envisioned that modifications can be made. For example, aTF can be conjugated to one or more fluorescent dyes and the nucleic acid probe can be conjugated to a QD, or alternatively, both the aTF and the nucleic acid probe are conjugated to QDs, or both the aTF and the nucleic acid probe are conjugated to different fluorescence dyes. For example, FRET between QD is possible and envisioned for use in the biosensor herein, as described in US patent application 2010/0075361, which is incorporated in its entirety herein. Such modifications are easily determined by one of ordinary skill in the art, and can be assessed using the methods and assays described herein and in the Examples.

In one embodiment, the biosensor comprises an allosteric transcription factor (aTF) conjugated to a first fluorescent molecule of a Fluorescence Resonance Energy Transfer (FRET) pair, the aTF compromising a ligand binding domain (LBD) and a DNA binding domain (DBD), and a nucleic acid probe conjugated to a second fluorescent molecule of the FRET pair, the nucleic acid probe having a sequence compromising a TFBD that is specific to the DBD of the aTF.

IIIA. OFF Fluorescent Biosensors:

In one embodiment, in the presence of an analyte, the DNA binding domain (DBD) does not bind to the TFBD, and the first fluorescent reporter and the second fluorescent reporter of the FRET pair does not emit a fluorescent signal (e.g., an OFF biosensor). In such an embodiment, in the absence of an analyte, the DNA binding domain (DBD) of the aTF binds to the TFBD, the first fluorescent reporter and the second fluorescent reporter of the FRET pair emits a fluorescent signal.

Figure 9A:
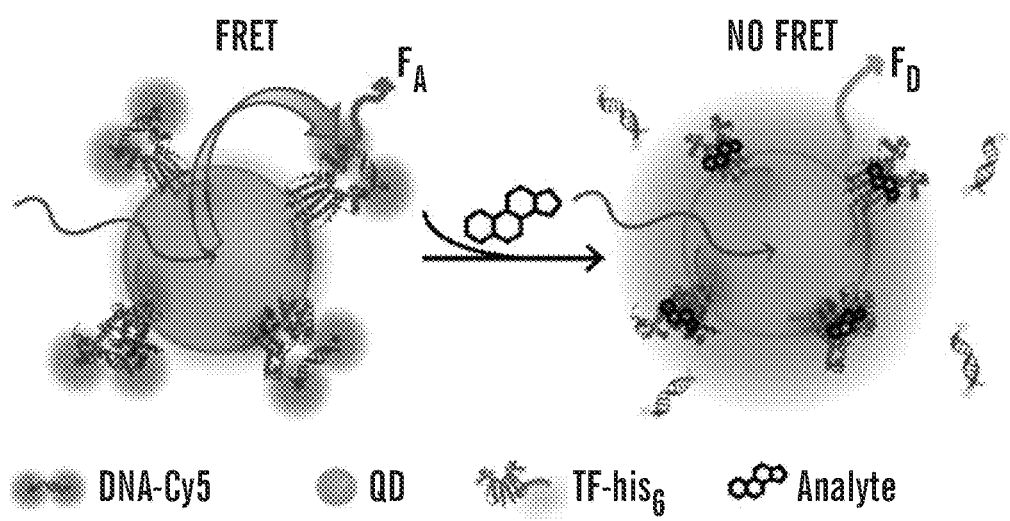
FIGS. 9A-9K show a schematic of the QD-based FRET sensor system.

In one embodiment, in the absence of an analyte in the media and upon UV-vis excitation and/or exposition, the excited fluorescent molecule conjugated to an aTF (donor) is able to emit fluorescence and transfer energy via FRET to the nucleic acid probe conjugated to a fluorescent molecule (acceptor) (FIG. 1 and FIG. 9A). Two fluorescent spectra are recorded, one from the fluorescent molecule conjugated to the aTF and one from the nucleic acid probe conjugated to a fluorescent molecule. By adding an analyte to the media, the fluorescence emission of the fluorescent molecule conjugated to the aTF (donor increases while the fluorescence emission of the nucleic acid probe conjugated to a fluorescent molecule (acceptor) decreases. When the aTF conjugated to a fluorescent molecule dissociates from the nucleic acid conjugated to a fluorescent molecule, the distance of the fluorescent probes is too far to be able to receive energy from the donor fluorescent molecule. As such no fluorescence is emitted. The analyte binding induces a ligand-induced folding of the aTF thereby increasing the affinity of the DBD to the TFBD. When the DBD binds to the TFB, the first fluorescent molecule and the second fluorescent molecule of the FRET pair emits a fluorescent signal. The fluorescent biosensor is designed to produce a two-color, radiometric signal output in response to different binding of the aTF and the nucleic acid probe.

IIIB: ON Fluorescent Biosensors:

In one embodiment, in the presence of an analyte, the DNA binding domain (DBD) of the aTF binds to the TFBD, the first fluorescent reporter and the second fluorescent reporter of the FRET pair emits a fluorescent signal (i.e., an ON biosensor). That is, in this embodiment, in the absence of an analyte, the DNA binding domain (DBD) does not bind to the TFBD, and the first fluorescent reporter and the second fluorescent reporter of the FRET pair does not emit a fluorescent signal.

In another embodiment, in the absence of an analyte in the media, the aTF conjugated to a fluorescent molecule dissociates from the nucleic acid conjugated to a fluorescent molecule, resulting in the distance of the fluorescent probes being too far to be able to receive energy from the donor fluorescent molecule, and upon UV-vis excitation and/or exposition, the aTF does not bind to the TFBD, and the first fluorescent molecule and the second fluorescent molecule of the FRET pair does not emit a fluorescent signal (see, e.g., FIG. 10). Accordingly, in such an embodiment, when the aTF conjugated to a fluorescent molecule is not bound to an analyte, is cannot bind to the nucleic acid probe conjugated to a fluorescent molecule, and therefore, the distance of the fluorescent probes is too far to be able to receive energy from the donor fluorescent molecule. As such no fluorescence is emitted. When the analyte binds to the aTF, it induces a ligand-induced folding or conformational change of the aTF to increase its affinity of the DBD to the TFBD. Therefore, when the DBD binds to the TFBD, the first fluorescent molecule and the second fluorescent molecule of the FRET pair emits a fluorescent signal. The fluorescent biosensor is designed to produce a two-color, ratiometric signal output in response to different binding of the aTF and the nucleic acid probe.

IIIC. Quantum Dots (QD) as a Reporter Fluorescent Molecule.

In one embodiment, a QD encompassed for use is a CdSe/CdS/ZnS QDs coated with a zwitterionic polymer bearing histamine anchoring function. Once the hydrophobix QDs are transferred into water using a biphasic ligand exchange, his-tagged TFs were self-assembled on the QD surface to produce the QD-TF. Addition of the double stranded, Cy5-labled TF binding sequence completed probe assembly as the oligo binds to the aTF in the absence of progesterone (FIG. 9A).

Methods to attach one or more aTF to a QD are well known in the art, and include, for example, attaching one or more histidine tags to the aTF and then self-assembly one or more aTF on the QD surface. The preparation of a QD bioconjugate for use in the biosensor described herein (e.g., a aTF-QD preparation or a nucleic acid probe-QD) uses a self-assembly method between nanocrystals (i.e., QDs) and protein/peptides appended with either a polyhistidine tract or a leucine zipper attachment domain in aqueous buffer. A small volume of water-soluble QD stock solution is added to a buffer containing the biomolecules (e.g., aTF or nucleic acid probe), e.g., as described in US2010/0075361, which is incorporated herein in its entirety by reference.

The term "quantum dot" or "QD" as used herein refers to an inorganic semiconductor crystallite of about 1 nm or more and about 1000 nm or less in diameter or any integer or fraction of an integer there between, preferably at least about 2 nm and about 50 nm or less in diameter or any integer or fraction of an integer there between, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). QDs are characterized by their substantially uniform nanometer size, frequently exhibiting approximately a 10% to 15% polydispersion or range in size. A QD is capable of emitting electromagnetic radiation upon excitation (i.e., the QD is photoluminescent) and includes a "core" of one or more first semiconductor materials, and may be surrounded by a "shell" of a second semiconductor material. A QD core surrounded by a semiconductor shell is referred to as a "core/shell" QD. The surrounding "shell" material will preferably have a bandgap energy that is larger than the bandgap energy of the core material and may be chosen to have an atomic spacing close to that of the "core" substrate.

Any QD can be used in the biosensor system as disclosed herein and are described in patent applications, 2002/0028457, 2008/0087843, US2010/0075361, US2010/0075361, US2013/0140518, WO2006/037226A1, US2010/0256918A1, each of which are incorporated herein in their entirety by reference.

In some embodiments, the core and/or the shell of the QD can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, PbS, PbSe, and an alloy or a mixture thereof. Preferred shell materials include ZnS.

A QD is optionally surrounded by a "coat" of an organic capping agent. The organic capping agent may be any number of materials, but has an affinity for the QD surface. In general, the capping agent can be an isolated organic molecule, a polymer (or a monomer for a polymerization reaction), an inorganic complex, or an extended crystalline or amorphous structure. The coat can be used to convey solubility, e.g., the ability to disperse a coated QD homogeneously into a chosen solvent, functionality, binding properties, or the like. In addition, the coat can be used to tailor the optical properties of the QD. Thus, the quantum dots herein include a those having a simple core with or without a coated, as well as optionally coated core/shell QDs.

As appreciated by one of ordinary skill in the art, "contacting" a quantum dot with a fluorescent dye effective to perform FRET does not necessarily require direct physical contact, as FRET is effective through space (albeit only over short distances). Likewise, one of ordinary skill in the art understands that "contacting" a quantum dot with a redox-active moiety effective to perform charge transfer can be done via a direct or indirect connection. In either case, contacting can include covalent bonding, ionic bonding, affinity binding (including polyhistidine/metal), and/or combinations thereof.

IIID. Fluorescent Dyes and Molecules:

Fluorescent molecules for use as a first fluorescent molecule or a second fluorescent molecule are known in the art, and include, but are not limited to, green fluorescent protein (GFP), enhanced green fluorescent protein (EGFP), green-fluorescent-like proteins; yellow fluorescent protein (YFP), enhanced yellow fluorescent protein (EYFP), blue fluorescent protein (BFP), enhanced blue fluorescent protein (EBFP), cyan fluorescent protein (CFP), enhanced cyan fluorescent protein (ECFP) or a red fluorescent protein (dsRED), and the like.

IIIE. Fluorescence Resonance Energy Transfer (FRET):

In one embodiment, the binding of the aTF to the nucleic acid probe is measured by Fluorescence Resonance Energy Transfer (FRET). FRET is a process that shifts energy from an electronically excited fluorescent molecule (donor) to a neighboring fluorescent molecule (donor). If the two fluorophores are close enough, then excitation of the first molecule (donor) results in fluorescence emission of the second fluorescent molecule (acceptor). In one embodiment, the first fluorescent molecule comprises a FRET acceptor, and the second fluorescent reporter each comprises a FRET donor. In another embodiment, the first fluorescent molecule comprises a FRET donor, and the second fluorescent reporter each comprises a FRET acceptor. FRET is a process that shifts energy from an electronically excited fluorescent molecule (donor) to a neighboring fluorescent molecule (donor). If the two fluorophores are close enough, then excitation of the first molecule (donor) results in fluorescence emission of the second fluorescent molecule (acceptor). In the process of FRET, initially a donor fluorophore absorbs the energy due to the excitation of incident light and transfer the excitation energy to a nearby fluorescent molecule the acceptor.

In one embodiment, energy transfer manifests itself through decrease or quenching of the donor fluorescence and a reduction of excited state lifetime accompanied also by an increase in acceptor fluorescence intensity. In presence of suitable acceptor, the donor fluorescent molecule can transfer its excited state energy directly to the acceptor without emitting a photon. There following criteria must be satisfied in order for FRET to occur. These are: (i) the fluorescence emission spectrum of the donor fluorescent molecule must overlap the absorption or excitation spectrum of the acceptor fluorescent molecule. The degree of overlap is referred to as spectral overlap integral (J). (ii) The two fluorescent molecules (donor and acceptor) must be in the close proximity to one another, the distance must be at least 10 Å, or at least 20 Å, or at least 30 Å, or at least 40 Å, or at least 50 Å, or at least 60 Å, or at least 70 Å, or at least 80 Å, or at least 90 Å, or 100 Å. (iii) The transition dipoles of the donor and acceptor must be approximately parallel to each other. (iv) The fluorescence lifetime of the fluorescent donor molecule must be of sufficient duration to allow the FRET to occur.

The efficiency of the FRET process ($E_{FRET}$) depends on the inverse sixth power of the distance between the donor and acceptor pair (r) and is given by:

$$E_{FRET} = R_0^6 / (R_0^6 + r^6)$$

$R_0$ is defined as the Förster radius at which half of the excitation energy of donor is transferred to the acceptor fluorescent molecule. Therefore, Förster radius ($R_0$) is referred to as the distance at which the efficiency of energy transfer is at least 10%, or at least 20%, or at least 30%, or at least 40%, or at least 40%, or at least 50%, or at least 60%, or at least 70%, or at least 80%, or at least 90%, or 100%.

$$R_0: R_0 = 9.78 \times 10^3 (\eta^{-4} * f_d * k^2 * J)^{1/6} \text{ Å}$$

The Förster radius ($R_0$) depends on the fluorescence quantum yield of the donor in the absence of acceptor ($f_d$), the refractive index of the solution (q), the dipole angular orientation of each molecule ($k^2$) and the spectral overlap integral of the donor-acceptor pair (J) and is given by Energy transfer manifests itself through decrease or quenching of the donor fluorescence and a reduction of excited state lifetime accompanied also by an increase in acceptor fluorescence intensity.

In presence of suitable acceptor, the donor fluorophore can transfer its excited state energy directly to the acceptor without emitting a photon. In summary, the rate of FRET depends upon the extent of spectral overlap between the donor acceptor pair, the quantum yield of the donor, the relative orientation of the donor-acceptor transition dipole moments and the distance separating the donor-acceptor chromophore. Any event or process that affects the distance between the donor-acceptor pair will affect the FRET rate, consequently allowing the phenomenon to be quantified, provided that the artifacts can be controlled or eliminated. As a result, FRET is often referred to as a ' spectroscopic/molecular ruler', for example to measure the distance between two active sites on a protein that have been labelled with suitable donor-acceptor fluorescent molecules, and therefore monitoring the conformational changes through the amount of FRET between the fluorophores.

Detection of Fluorescence Resonance Energy Transfer (FRET)

The detection and quantitation of FRET can be made in a number of different ways. The phenomenon can be observed by exciting a specimen containing both the donor and acceptor molecules with light emitted at wavelengths centered near the emission maximum of the acceptor. Because FRET can result in both a decrease in fluorescence of the donor molecule as well as an increase in fluorescence of the acceptor, a ratiometric determination of the two signals can be made. The advantage of this method is that a measure of interaction can be made that is independent of the absolute concentration of the sensor. Because not all acceptor moieties are fluorescent, they can be used as a means to quench fluorescence. In these instances, those interactions that result in a fluorescent donor molecule coming in close proximity to such a molecule would result in a loss of signal. Inversely, reactions that remove the proximity of a fluorescent donor and a quencher would result in an increase in fluorescence.

Fluorescent Molecules Used for the Detection of aTF-TFBD Binding.

In one embodiment, the fluorescent molecule is selected from a group consisting of a semiconductor quantum dot (QD), a fluorescent dye, a fluorescent protein or a combination thereof. Semiconductor quantum dots (QDs) are well known in the art and are powerful fluorescent nanoparticles widely used in bioimaging and biosensing. Their high photostability, color tunability, and abundant particle surface area available for biofunctionalization make them attractive fluorophores for bright and stable FRET-based biosensors.

As discussed herein, while a fluorescent output with fluorescent reporter molecules is one method for detecting the presence of analytes, other detection system can be used, as disclosed herein. Additionally, while in some embodiments, aTF is conjugated to a QD and the nucleic acid probe is conjugated to one or more fluorescent dyes and vice versa, it is envisioned that modifications can be made. For example, aTF can be conjugated to one or more fluorescent dyes and the nucleic acid probe can be conjugated to a QD, or alternatively, both the aTF and the nucleic acid probe are conjugated to QDs, or both the aTF and the nucleic acid probe are conjugated to different fluorescence dyes. For example, FRET between QD is possible and envisioned for use in the biosensor herein, as described in US patent application 2010/0075361, which is incorporated in its entirety herein. Such modifications are easily determined by one of ordinary skill in the art, and can be assessed using the methods and assays described herein and in the Examples.

IV. Electroconductive Based Biosensors and Redox Based Biosensors for the Measurement of Analytes.

One aspect of the technology relates to biosensors where the signal generated when the aTF binds to the nucleic acid probe is an electroconductive signal, that can be readily detected by a semiconductor circuit. For example, instead of fluorescent molecules conjugated to the aTF and the nucleic acid probe and a change in a FRET signal being detected in the presence of an analyte (i.e., increase in FRET signal in a biosensor ON system, or a decrease or attesting of a FRET signal in a biosensor OFF system), the aTF and/or nucleic acid probe can be conjugated to electroconductive molecules, such that when the aTF bind to the nucleic acid probe, a current is generated. In such embodiments, depending on the configuration of the electroconductive molecules to the aTF and/or nucleic acid probes, an increase in current can signal the presence of an analyte, or a decrease in current can signal the presence of an analyte.

For illustrative purposes only, the aTF can be conjugated to an electroactive molecule and the nucleic acid probe is attached or on the surface of a conducting surface of a semiconductor device, such that when the aTF is bound to the nucleic acid probe, the electroconductive molecule conjugated to the aTF and the nucleic acid are in close proximity to allow electron transfer, and the flow of electrons to the semiconductor device which is detected by an increase in current on the surface. That is, where the biosensor is an ON-biosensor, the presence of the analyte allows aTF binding to the nucleic acid probe, resulting in transfer of electrons from the electroconductive molecule to the surface of the semiconductor device, and an increase in current. In alternative embodiments, where the biosensor is an OFF-biosensor, the presence of an analyte results in the aTF from dissociating from the nucleic acid probe, and the electroconductive molecule and the conducting surface are no longer in close proximity such that electrons do not flow from the electroconductive molecule to the surface and a decrease in current, or stopping of current occurs.

In another embodiment, one aspect relates to the measurement of redox based binding assays of analytes measured by the binding affinity of the aTF to its transcription factor binding domain (TFBD), such as assays utilizing electrochemical redox reactions as the mode of detection. The accordingly, the technology described herein relates to an in vitro, and cell-free biosensor system for measuring concentration of an analyte in a fluid using electroconductive molecules and the change in current.

In one embodiment, the radiometric biosensor comprises an allosteric transcription factor (aTF) conjugated to an electroactive molecule, the allosteric transcription factor comprising a ligand binding domain (LBD) and a DNA binding domain (DBD), and a nucleic acid probe attached to a solid surface of a semiconductor circuit, the solid surface electroconductively connected a semiconductor circuit, whereby the sequence of the nucleic acid probe comprises a transcription factor binding domain (TFBD) that is specific to the DBD of the transcription factor.

In one embodiment, in the presence of an analyte, the DNA binding domain (DBD) of the aTFB binds to the TFBD and the electroactive molecule transfers electrons the nucleic acid, and is detected by an increase in current in the semiconductor device.

In another embodiment, in the presence of an analyte, the DNA binding domain (DBD) of the aTFB binds to the TFBD and the electroactive molecule transfers electrons the nucleic acid, and is detected by a decrease in current in the semiconductor device.

In one embodiment, in the absence of an analyte, the DNA binding domain (DBD) of the aTFB binds to the TFBD and the electroactive molecule transfers electrons the nucleic acid, and is detected by an increase in current in the semiconductor device.

In another embodiment, in the absence of an analyte, the DNA binding domain (DBD) of the aTFB binds to the TFBD and the electroactive molecule transfers electrons the nucleic acid, and is detected by a decrease in current in the semiconductor device.

Figures 5A, 5B:
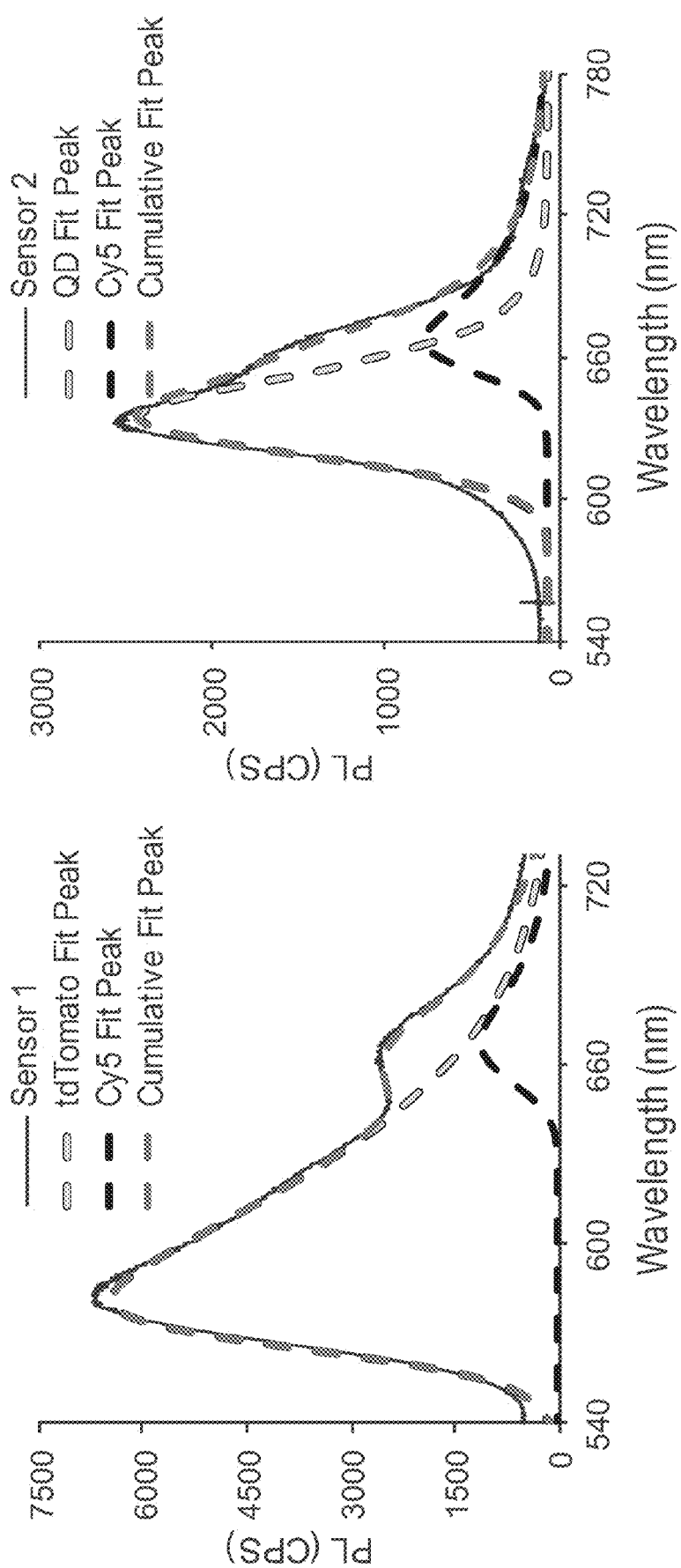
FIGS. 5A-5B show the Peak fitting results from Origin Pro.
Figures 6A, 6B, 6C:
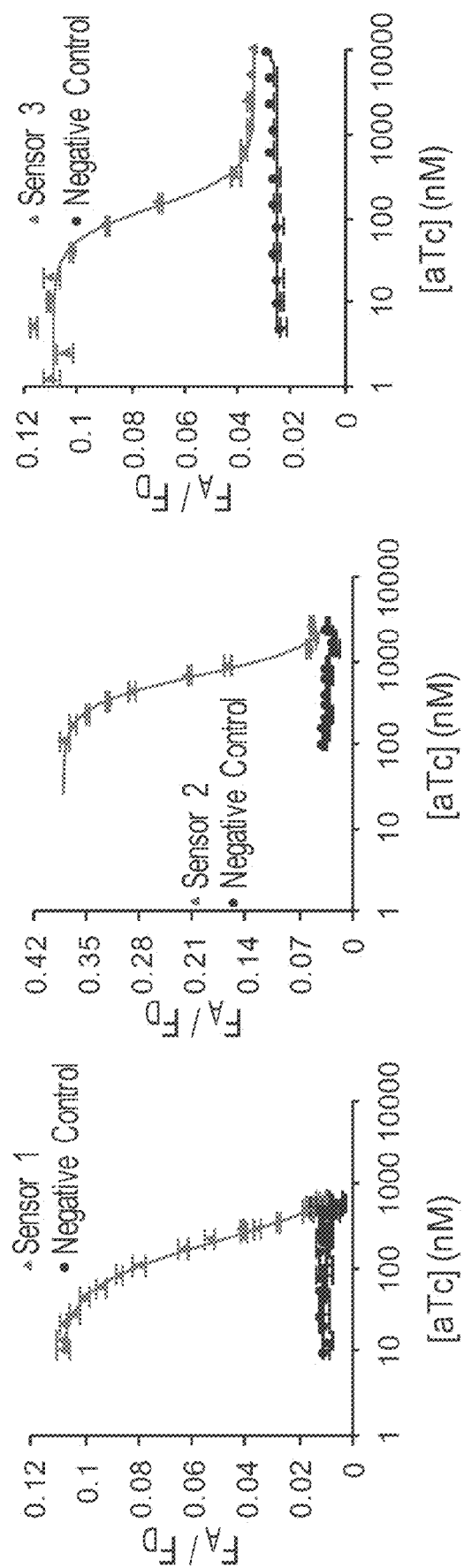
FIGS. 6A-6C show representative spectral data for sensor 1, 2 and 3.

The biosensors as disclosed herein can be modified by persons of ordinary skill in the art for analyte sensing. For example, in some embodiments, quantum dot (QD) gate field-effect transistors (FETs) can be used, e.g., as disclosed in US2013/0140518 (see, e.g., FIGS. 5, 6A and 6B therein), which is incorporated herein in its entirety by reference, where, for example, a QD is functionalized with the aTF, and when the nucleic acid probe binds to the aTF, there is a change in the gate charge of the QD and hence the current voltage characteristics of the QD in the FET channel. Similarly, in some embodiments, a QD is functionalized with a nucleic acid probe as described herein, and binding of the aTF to the nucleic acid probe results in a change in the gate charge of the QD and hence the current voltage characteristics of the QD. For example, in reference to FIG. 6A of US2013/0140518, the nucleic acid probe can be attached to the QD, and when in the presence of the analyte, the aTF binds to the nucleic acid probe and detection of the analyte is confirmed by a change in source-drain current of the quantum dot FET sensor 1. This system is different from conventional FET-based DNA detection where the nucleic acid probe is immobilized on gold plated p-channel FETs via gold-thiol interactions.

Other methods to modify the aTF and/or nucleic acid probes for electrochemical detection of the analyte and generating electroconductive biosensors for use herein are described in Electrochemical methods Fundamentals and applications, 2Ed., Allen Bard and Larry Faulkner, and Electrochemistry for biomedical researchers, Richie L C Chen, World Scientific Press, each of which are incorporated herein in their entiryt by reference. Other methods to modify the aTF and/or nucleic acid probes for electrochemical detection of the analyte and generating electroconductive biosensors for use herein are described in the section below:

IV.A Label Free Sensing

In one embodiment, electrochemical impedance spectroscopy can be used to measure the resistance of the system by using redox markers.

IV.B Labeling of aTF or Nucleic Acid Probe with a Redox Active Molecule

In another embodiment, an aTF that comprises a —SH bond can be conjugated with a redox molecule. The ssDNA with —SH bond is immobilized on a gold surface, followed by hybridization with the complementary strand. The aTF with redox initiator is attached to the dsDNA. Analyte presence causes DNA-TF dissociation increasing the proximity of ferrocene to the gold surface. Using cyclic voltammetry/square wave voltammetry, a change in current signal is observed depending on the proximity of ferrocene to the gold surface.

IV.C. Labeling of DNA with a Redox Molecule

In another embodiment, the nucleic acid probe (e.g., DNA) bearing—SH bond is conjugated with the redox molecule. Following the hybridization of DNA, the dsDNA is attached to the —SH moiety which has been immobilized on a gold electrode. The proximity of the redox molecule to the gold surface is captured by cyclic voltammetry/square wave voltammetry. DNA charge transport:

In another embodiment, the 5' end of one strand of DNA is used for the immobilization on a gold electrode using —SH. The complementary strand is modified with a redox molecule. Chronocoulometry is used for the measurement of charge transported due to the redox reaction of the probe. Presence of TF kinks the DNA and attenuates the charge transport.

IV. D. Fusion of Redox Enzyme and TF

In another embodiment, the immobilization of DNA to gold, followed by the attachment of TF fused with a redox enzyme catalyzing a particular reaction (e.g. lactate oxidase for lactate to pyruvate). The dissociation of DNA-TF in presence of analyte decreases the current generated due to this reaction.

V. Modifications to the Binding Affinity of the DNA Binding Domain (DBD) to the TFBD As discussed herein, the biosensors described herein a modular system. For example, the allosteric transcription factor (aTF) comprises an analyte binding domain (ABD), also referred to as a "ligand binding domain" or LBD that binds to the analyte or molecule, and a DNA binding domain (DBD) which has an affinity for a specific target nucleic acid sequence, referred to herein as a "transcription factor binding domain" or "TFBD" in the nucleic acid probe. It is envisioned that any DBD and TFBD pair known to an ordinary skilled artisan can be used, provided that their affinity for binding to each other is modified (i.e., increased in an ON-biosensor, or decreased on an OFF-biosensor) when an analyte binds to the LBD of the aTF. For example, a LBD of a microbial aTF can be fused to a known DBD that specifically binds to a known nucleic acid sequence of a TFBD.

In other embodiments, a LBD of a microbial aTF described herein can be modified to increase or decrease its affinity for the ligand (e.g., analyte).

In one embodiment, the DBD has been modified to increase or decrease is affinity for binding to the TFBD. Accordingly, in some embodiments, the binding affinity of a native aTF to a defined TFBD can be increased or by (i) the intranuclear aTF concentration, (ii) the concentration of specific DNA sites that are accessible for TF binding and (iii) the fraction of DNA sites bound by the TF.

In one embodiment, the binding affinity of a native aTF to a defined TFBD was increased by (i) the intranuclear aTF concentration, and/or (ii) the concentration of specific DNA sites that are accessible for TF binding. In one embodiment, the molar ratios of the QD, aTF, and a nucleic acid probe in the sensor were controlled through stoichiometric ratios of the mixed parts. The molar ratios of the QD, aTF, and a nucleic acid probe in the sensor were controlled through stoichiometric ratios of the mixed parts. A ratio of QD/aTF/Nucleic acid probe of at least 1 to 1 to 1, or of at least 2 to 1 to 1, or of at least 4 to 1 to 1, or of at least 5 to 1 to 1, or of at least 10 to 1 to 1, or of at least 20 to 1 to 1, or of at least 30 to 1 to 1, or of at least 40 to 1 to 1, or of at least 50 to 1 to 1, or of at least 60 to 1 to 1, or of at least 70 to 1 to 1, or of at least 80 to 1 to 1, or of at least 90 to 1 to 1, or of 100 to 1 to 1, or of at least 1 to 2 to 1, or of at least 1 to 4 to 1, of at least 1 to 5 to 1, or of at least 1 to 10 to 1, or of at least 1 to 20 to 1, or of at least 1 to 30 to 1, or of at least 1 to 40 to 1, or of at least 1 to 50 to 1, or of at least 1 to 60 to 1, or of at least 1 to 70 to 1, or of at least 1 to 80 to 1, or of at least 1 to 90 to 1, or of at least 1 to 100 to 1, or of at least 1 to 1 to 2, or of at least 1 to 1 to 4, or of at least 1 to 1 to 15, or of at least 1 to 1 to 10, or of at least 1 to 1 to 15, or of at least 1 to 1 to 18, or of at least 1 to 1 to 20, or of at least 1 to 1 to 30, or of at least 1 to 1 to 40, or of at least 1 to 1 to 50, or of at least 1 to 1 to 60, or of at least 1 to 1 to 70, or of at least 1 to 1 to 80, or of at least 1 to 1 to 90, or of at least 1 to 1 to 100, or any combinations thereof.

In one embodiment, the binding affinity of the DBD of the aTF has been modified to increase its affinity for binding of the DBD of the aTF to the TFBD by modifying the (iii) the fraction of TFBD bound by the TF (FIG. 10). Introducing mutations to the DNA sequence of the TFBDs can increase the strength of the interaction between aTF and their TFB. The binding of the DBD of the aTF to the TFB can be increased by at least 2, or by at least 4, or by at least 6, or by at least 8, or by at least 10, or by at least 15, or by at least 20, or by at least 30, or by at least 40, or by at least 50, or by at least 60, or by at least 70, or by at least 80, or by at least 90, or by at least 100, or by at least 500, or by at least 1000.

In one embodiment, the binding affinity of the DBD of the aTF has been modified to decrease its affinity for binding of the DBD of the aTF to the TFBD by modifying the (iii) the fraction of TFBD bound by the TF (FIG. 10). Introducing mutations to the DNA sequence of the TFBDs can decrease the strength of the interaction between aTF and their TFB without completely eliminating binding. The binding of the DBD of the aTF to the TFB can be decreased by at least 2, or by at least 4, or by at least 6, or by at least 8, or by at least 10, or by at least 15, or by at least 20, or by at least 30, or by at least 40, or by at least 50, or by at least 60, or by at least 70, or by at least 80, or by at least 90, or by at least 100, or by at least 500, or by at least 1000.

In another embodiment, when no progesterone is present in the media and upon UV-vis excitation and/or exposition, the excited QDs (donor) is able to emit fluorescence and transfer energy via FRET to the DANN-Cy5 (acceptor) (FIG. 1 or 9A). Two fluorescent spectra are recorded, one from the QDs and one from the Cy5. By adding progesterone to the media, the fluorescence emission of the QDs (donor increases while the fluorescence emission of the Cy5 (acceptor) decreases. When the DNA-Cy5 unbind the QD-TF, the Cy5 is too far from the QDs surface to be able to receive energy from the QDs. As such no fluorescence is emitted from the Cy5 molecule.

In one embodiment, the invention relates to a process for detecting an analyte in a sample, comprising contacting the sample with an allosteric transcription factor (aTF) conjugated to a QD of a Fluorescence Resonance Energy Transfer (FRET) pair, the aTF compromising a ligand binding domain (LBD) and a DNA binding domain (DBD), and a nucleic acid probe conjugated to a QD of the FRET pair, the nucleic acid probe having a sequence compromising a TFBD that is specific to the DBD of the aTF.

VI. Nucleic Acid Probe

As disclosed herein, the biosensor comprises an aTF that binds, via its DBD, to a target sequence, referred to as a TFBD, in a nucleic acid probe that is conjugated to a reporter molecule, e.g., a fluorescent molecule or an electroactive molecule, as described herein. In some embodiments, the reporter molecule is attached to the 5' or 3' of the nucleic acid probe, or both (i.e., both the 5' and 3' ends, see, e.g., FIG. 1, 9A). The nucleic acid can be single stranded or double stranded, and the reporter molecule can be attached to one or both strands of a double stranded nucleic acid probe. Importantly, the nucleic acid probe comprises a nucleic acid sequence that is a specific binding site for the DBD of the aTF, which is referred to as TFBD.

In some embodiments, the fluorescent molecule is a fluorescent dye, as disclosed herein, for example, see FIGS. 1, 9A and 10 herein, where the fluorescent dye will result in FRET when the DBD of the aTF is bound to the nucleic acid probe. In alternative embodiments, the fluorescent molecule is a QD. In such an embodiment, a plurality of nucleic acid probes can be conjugated to the QD, e.g., at least 2, 3, 4, 5, 6, 7 8, 9, 10, 11, 12, 13, 14, 15, 16, 17, 18, 19, 20, 21, 22, 23, 24, 25, 26, 27, 28, 29, 30 or more nucleotide probes conjugated to a single QD.

In some embodiments, e.g., for electrochemical signal generation, the nucleic acid probe is immobilized on a conducting surface of a semiconductor surface, which can be the surface of a semiconductor circuit or alternatively, a QD (e.g., a QD gate field-effect transistor (FETs) as disclosed in US2013/0140518).

In some embodiments, a nucleic acid probe can be single stranded (ss) or double stranded (ds) and can be DNA, RNA or a nucleic acid variant, e.g., modified RNA (modRNA, PNA, Locked nucleic acid (LNA) and the like.

In some embodiments, the nucleotide sequence of the TFBD is at least about 5, 6, 7 8, 9, 10, 11, 12, 13, 14, 15, 16, 17, 18, 19, 20, 21, 22, 23, 24, 25, 26, 27, 28, 29, 30 nucleotides in length. In some embodiments, the nucleotide sequence of the TFBD comprises between 10-15 nucleotides, 15-20 nucleotides, 20-25 nucleotides or 25-30 nucleotides.

In some embodiments, the nucleic acid probe comprises at least one TFBD, or at least 2, or at least 3, or at least 4, or at least 5 or at least 6 or more than 6 TFBD, where each TFBD can be the same nucleotide sequence that binds to the DBD of the aTF, or different nucleotide sequence that has a different affinity for the DBD of the aTF. That is, one can modify the nucleic acid probe to comprise multiple TFBDs that have different affinity for the aTF. For illustrative purposes only, a nucleic acid probe that comprises at least 2 TFBD can have one TFBD (TFBD1) that has a strong or high affinity for the DBD and a second TFBD (TFBD2) that has a lower affinity for the DBD. In such embodiments, in an ON biosensor, the presence of an analyte can induce a conformational change in the aTF such that the DBD binds rapidly to TFBD1 to induce a signal (i.e., increase FRET or increase in current or flow of electrons), and another aTF (with the bound analyte to the LBD) can bind to the TFBD2, resulting in a second signal (further increase in FRET or increase in current). In alternative embodiments of an OFF biosensor, the presence of an analyte can induce a conformational change in the aTF such that the DBD dissociates from TFBD2 to change the signal (i.e., decrease FRET or decrease current or flow of electrons), and if the level of analyte is high, then the DBD of a second aTF dissociates from TFBD1, resulting in a second signal (i.e., decrease in FRET or decrease in current/flow of electrons). Accordingly, it is envisioned that one can tailor the sensitivity of biosensor to the analyte by increasing both the number of TFBD in the nucleic acid probe, and/or altering the sequence of the TFBD such that they have different affinities for binding to the cognate DBD of the aTF in the presence or absence of analyte.

In some embodiments, where the nucleic acid probe comprises more than one TFBD nucleotide sequence, there may be between 1-10 or more than 10 nucleotides between each TFBD to ensure that binding of the DBD does not sterically hinder or block an adjacent TFBD sequence.

Exemplary nucleic acid probes are described in the section discussing the exemplary progesterone biosensor. For example, in some embodiments, a nucleic acid probe comprises a nucleic acid sequence of any of SEQ ID NO 13, SEQ ID NO: 14, SEQ ID NO: 15, or SEQ ID NO: 16 or SEQ ID NO: 17. In some embodiments, a nucleic acid probe comprises a nucleic acid sequence that has at least about 60%, or at least 70%, or at least 80%, or at least 85%, or at least 90%, or at least 95%, or at least 96%, or 97% or at least 98% or at least 99% sequence identity to any of SEQ ID NO 13, SEQ ID NO: 14, SEQ ID NO: 15, or SEQ ID NO: 16 or SEQ ID NO: 17.

VII: Analytes:

As disclosed herein, the analyte detected by the biosensor can be any small molecule, hormone, toxin and the like, as discussed herein. That is, the ligand binding domain of the aTF specifically binds to, or has high affinity, to a target small molecule, hormone, toxin and the like.

Non-limiting examples of analytes detected by a biosensor as described herein can be selected from any of non-limiting examples of analytes that can be detected by the biosensors described herein include, but are not limited to, Thyroid-stimulating hormone (TSH), Follicle-stimulating hormone (FSH), Luteinizing hormone (LH), Prolactin (PRL), Growth hormone (GH), Adrenocorticotropic hormone (ACTH), Vasopressin, Oxytocin, Thyrotropin-releasing hormone (TRH), Gonadotropin-releasing hormone (GnRH), Growth hormone-releasing hormone (GHRH), Corticotropin-releasing hormone (CRH), Somatostatin, Calcitonin, Parathyroid hormone (PTH), FGF-23 (phosphatonin), Osteocalcin, Erythropoietin (EPO), Human chorionic gonadotropin (HCG), Insulin, Glucagon, Somatostatin, Amylin, Atrial-natriuretic peptide (ANP), Gastrin, Secretin, Cholecystokinin (CCK), Fibroblast Growth Factor 19 (FGF19), Incretins, Somatostatin, Neuropeptide Y, Ghrelin, PYY3-36, Insulin-like growth factor-1 (IGF-1), Angiotensinogen, Thrombopoietin, Hepcidin, Betatrophin, Leptin, Retinol Binding Protein 4, Adiponectin, Irisin. Non-limiting examples of steroid hormones that can be detected by the current invention include progesterone, aldosterone, testosterone, estradiol, and Cortisol. In particular embodiments, the analyte is progesterone. In some embodiments, the progesterone is human progesterone.

In some embodiments the analyte is a drug or drug metabolite, for example, opioid drug (including natural alkaloids, and synthetic and semi-synthetic opioids) or opioid metabolite (e.g., oxymorphone, noroxycodone, morphine, hydrocodone, norcodeine, oxymorphone, 6-hydroxyoxymorphone, hydromorphine, norhydrocodone, dihydrocodeine, hydromorphol, codeine-6-glucuronide and norcodeine, morphine-6-glucuronide (M6G)), cocaine, cocaine metabolites, *cannabis* or cannoboid-based drug or metabolite, marijuana, benzodiazepine, barbiturate, amphetamine, methtamphetamine, alcohol. In some embodiments, the analyte is selected from an of: cannabidiol (terahydrocannabinol) and other marijuana metabolite: a metabolite of cocaine, opiates metabolites, phencyclidine (the PCP, angel dust), amphetamines, barbiturates, benzene, dinitrogen classes, methaqualone, and propoxyphene. Such biosensors that detect such analytes are useful for caregivers and enforcement officials (e.g., police officers, sports testing, prison officers etc.) as well as clinical practitioners for drug screening purposes and/or to assess if a subject has taken a drug or other regulated substance, and also to quantify the drug dose.

In some embodiments, the analyte is of mammalian origin, e.g., human origin and in some embodiments, the analyte is non-mammalian origin. Additional examples of small molecules and hormones that can be measured according to the current invention are well known to a person of ordinary skill in the art and such embodiments are within the purview of the current invention.

In all aspects herein, the sample can be a biological sample obtained from the subject. Exemplary samples include, but are not limited to serum, plasma, cell lysate, milk, saliva, vitrous fluid, and other secretions, synovial fluid, peritoneal cavity fluid, lacrimal fluid, and tissue homogenate. In some embodiments, the sample is a bodily fluid, including sweat, blood, cerebrospinal fluid (CSF), plasma, whole blood, serum, semen, synovial fluid, saliva, vaginal lubrication, breast milk, amniotic fluid, urine, human feces, phlegm tears, saliva, lymph, peritoneal intracellular fluid, or an original tissue from fetuses, newborn babies, children, teenagers or adults. In some embodiments, the sample may be from a subject who has been treated with a drug, or may be from an untreated or drug naïve subject. In some embodiments, the biological sample may be from an animal, including economically useful animals such as goats, cows, sheep, chicken. In some embodiments, the biological samples may be from milk-producing animals. Moreover, the sample can be in various forms including but not limited to a liquid, frozen, chilled, lyophilized sample. The sample may be subjected to additional purification or treatment steps prior to and/or following the biosensor measurement described herein. In some embodiments, the sample is a non-biological fluid, such as a number of ecological environments such as river or lake water, ocean, drinking water supply or lab solution.

VIII. Exemplary Biosensor: Progesterone Biosensor for Progesterone Detection.

One aspect of the present invention is directed at a progesterone biosensor, for example a microbial aTF that specifically binds to, and has affinity for progesterone. As disclosed herein, the biosensor can be a progesterone ON biosensor—i.e., where, in the presence of progesterone, aTF binds to the nucleic acid probe and a signal is produced. In some embodiments, the progesterone biosensor is a fluorescent ON biosensor, e.g., a FRET is turned ON, or an increase in FRET signal is detected if the aTF and nucleic acid are conjugated to fluorescent molecules, e.g., QD and dyes as disclosed herein which can be detected by an optical sensor.

In some embodiments, the biosensor is a progesterone OFF biosensor,—i.e., where, in the absence of progesterone, the aTF is bound to a nucleic acid probe and a signal is generated, and in presence of progesterone, the aTF changes confirmation and decreases its affinity for the nucleic acid probe and a signal is turned off. In some embodiments, the progesterone biosensor is a fluorescent OFF biosensor, e.g., a FRET is turned OFF, or there is a decrease in FRET signal if the aTF and nucleic acid probes are conjugated to fluorescent molecules, e.g., QD and dyes as disclosed herein which can be detected by an optical sensor.

In some embodiments, the progesterone biosensor is an electroconductive biosensor, e.g., an electron is transferred from the aTF-electroconductive conjugate to a nucleic acid probe on a conductible surface to increase or decrease electron flow or increase or decrease current, which can be detected by one of ordinary skill in the art, where the aTF and/or the nucleic acid probe are conjugated to electroconductive molecules as disclosed herein.

In alternative embodiments, the progesterone biosensor is an electroconductive OFF biosensor, e.g., an electron is transferred from the aTF-electroconductive conjugate to a nucleic acid probe on a conductible surface to increase in electron flow or increase current, which can be detected by one of ordinary skill in the art, where the aTF and/or the nucleic acid probe are conjugated to electroconductive molecules as disclosed herein.

In some embodiments, the progesterone biosensor is described in the Examples, e.g., the sensitivity and dynamic range of the sensor is assessed based on modifications to the DBD and its binding to the TFBD of the nucleic acid probe, as well as ratio of QD/TF/DNA for optimal biosensor detection of progesterone. As disclosed in the Examples, a progesterone biosensor as described herein is extremely sensitive and can detect progesterone in the range of from at least 0.001 ng/ml to 0.005 ng/ml; or from at least 0.001 ng/ml to 0.01 ng/ml; or from at least 0.001 ng/ml to 0.05 ng/ml; or from at least 0.001 ng/ml to 0.1 ng/ml; from at least 0.001 ng/ml to 0.5 ng/ml; or from at least 0.01 ng/ml to 1 ng/ml; or from at least 0.001 ng/ml to 10 ng/ml; or from at least 0.05 ng/ml to 0.5 ng/ml; from at least 0.05 ng/ml to 5 ng/ml; or from at least 0.05 ng/ml to 50 ng/ml.

VIII (A) Progesterone Sensing aTF

Progesterone is a key hormone in the female reproductive cycle; monitoring progesterone levels is critical to human health and fertility as well as the dairy industry. The vast majority of biosensors for progesterone are based on antibody binding, including commercially available enzyme-linked immunosorbent assays used in clinical blood tests and home urine tests for the progesterone metabolite pregnanediol glucuronide (PdG). These assays are effective, but suffer from classic limitations of antibody sandwich assays including the hook, or prozone, effect and the expense of antibody reagents. Furthermore, the antibodies used for these tests cannot distinguish between progesterone and PdG.

In one embodiment, the aTF is a progesterone transcription factor, referred to herein as "PinR", and is, for example, an aTF comprising a protein comprising SEQ ID NO: 1, SEQ ID NO: 2 and/or SEQ ID NO: 3, encoded by the sequence of SEQ ID NO: 4-6, with predicted DNA binding domains comprising SEQ ID NO: 7-12.

For clarification, the amino acid sequence of the progesterone aTF PinR that binds to progesterone is as follows:

(SEQ ID NO: 1)
MSSTAERIRPGRSG<u>ILAAATRLFATHGVSGTSLQQIADATGITKAAVYHH</u>

<u>FPTKEEVVVAVL</u>APALEAIQGIVRTAGAHEDPRAATEAAIIGLADQAVTH

RQRWAVLLQDAAVEEYVRNNPDHDELFTRLRLLLTGPDPTPGTRLQVSLF

LSGLLGPAQDPSCADIDDDALRAGIVRAGRRLLLADDDA, where the underlined amino acids in SEQ ID NO: 1 identify the DBD (i.e., 15-61 of SEQ ID NO:1) and the bold amino acid residues identify to the LBD (i.e., 62-189 of SEQ ID NO: 1).

Accordingly, a progesterone aTF for use in a biosensor as described herein comprises SEQ ID NO: 1 or a modified version thereof, e.g., SEQ ID NO: 2 or SEQ ID NO: 3, where a tag (e.g., GSHHHHHH (SEQ ID NO: 22)) has been added to the C-terminus for ease of attaching to a QD and/or the PinR has been codon optimized. In some embodiments, a progesterone aTF for use in a biosensor as described herein comprises at least amino acids 15-189 of SEQ ID NO: 1, or a fragment of at least 170, 160, 150, 140, 130, 120, 110, 100 of amino acids 15-189 of SEQ ID NO: 1, where the fragment is a C-terminal or N-terminal, or C- and N-terminal truncated variants of amino acid residues of 15-189 of SEQ ID NO: 1

In some embodiments, a progesterone aTF for use in a biosensor as described herein comprises SEQ ID NO: 1, SEQ ID NO: 2 or SEQ ID NO: 3 or a polypeptide comprising at least 50%, or at least 60%, or at least 70%, or at least 80%, or at least 85%, or at least 90%, or at least 95%, or at least 96%, or 97% or at least 98% or at least 99% sequence identity to SEQ ID NO: 1, SEQ ID NO: 2 or SEQ ID NO: 3, or amino acid residues 15-189 of SEQ ID NO: 1.

PinR comprises a DNA binding domain (DBD) comprising amino acids residues of SEQ ID NO: 7. Accordingly, an aTF for a progesterone biosensor comprises a DBD comprising a protein sequence that has at least 50%, or at least 60%, or at least 70%, or at least 80%, or at least 85%, or at least 90%, or at least 95%, or at least 96%, or 97% or at least 98% or at least 99% sequence identity to SEQ ID NO: 7. In some embodiments, a progesterone aTF comprises a DBD of a fragment of SEQ ID NO: 7, e.g., at least 5, or at least 6, or at least 7, or at least 8, or at least 10 of amino acid sequences of SEQ ID NO: 7. The DBD of SEQ ID NO: 7 is encoded by nucleotide sequence SEQ ID NO: 8.

PinR comprises a ligand binding domain (LBD) that binds to progesterone (e.g., human progesterone), comprising the amino acid sequence of SEQ ID NO: 18, or a modified version thereof, e.g., SEQ ID NO: 19 or SEQ ID NO: 20, where a tag (e.g., GSH HHRH (SEQ ID NO: 22) or 6xHis-tag (SEQ ID NO: 23)) has been added to the C-terminus for ease of attaching to a QD and/or the LBD of PinR has been codon optimized. Accordingly, a progesterone aTF for a progesterone biosensor comprises a LBD comprising a proteins sequence that has at least 50%, or at least 60%, or at least 70%, or at least 80%, or at least 85%, or at least 90%, or at least 95%, or at least 96%, or 97% or at least 98% or at least 99% sequence identity to SEQ ID NO: 18, 19 or 20. In some embodiments, a progesterone aTF comprises a DBD of a fragment of SEQ ID NO: 18-20, e.g., at least 125, or at least 120, or at least 115, or at least 110, or at least 100, 95, 90, 85, 80, 75, 70, 65, 60, 55, 50, 45 amino acid residues sequences of SEQ ID NO: 18, where the fragment is a C-terminal or N-terminal, or C- and N-terminal truncated variants of amino acid residues of SEQ ID NO: 18.

PinR comprises a DNA binding domain (DBD) comprising SEQ ID NO: 7. Accordingly, a progesterone aTF for a progesterone biosensor comprises a DBD comprising a polypeptide sequence that has at least 50%, or at least 60%, or at least 70%, or at least 80%, or at least 85%, or at least 90%, or at least 95%, or at least 96%, or 97% or at least 98% or at least 99% sequence identity to SEQ ID NO: 7. In some embodiments, a progesterone aTF comprises a DBD of a fragment of SEQ ID NO: 7, e.g., at least 5, or at least 6, or at least 7, or at least 8, or at least 10 of amino acid sequences of SEQ ID NO: 7.

Accordingly, exemplary DNA binding domain sequences comprise at least 4, or at least 5, or at least 6, or at least 7, or at least 8, or at least 10 of amino acid sequences of SEQ ID NO: 7-12 or at least 50%, or at least 60%, or at least 70%, or at least 80%, or at least 85%, or at least 90%, or at least 95% of SEQ ID NO: 7-12 (Table 1).

In some embodiments, a PinR for use in a biosensor comprises a His Tag (e.g., 6xHis-tag) (SEQ ID NO: 23) as disclosed herein attached to the C-terminal or N-terminal to facilitate conjugation of PinR to the QD. Other tags or epitope tags for attaching proteins to surfaces of QDs are envisioned for use herein.

PinR sequences and predicted DNA binding domains (DBD)

TABLE 1

Sequences of the Transcription Factor PinR and the predicted DNA binding domains (DBD) and Ligand Binding Domains (LBDs).

| Name | Sequence |
|---|---|
| AIY20223.2/PinR | MSSTAERIRPGRSG<u>ILAAATRLFATHGVSGTSLQQIADATGITKAAVY</u> <u>HHFPTKEEVVVAVL</u>APALEAIQGIVRTAGAHEDPRAATEAAIIGLADQ AVTHRQRWAVLLQDAAVEEYVRNNPDHDELFTRLRLLLTGPDPTPGT RLQVSLFLSGLLGPAQDPSCADIDDDALRAGIVRAGRRLLLADDDA (SEQ ID NO: 1) |
| PinR-Chis Tag | MSSTAERIRPGRSGILAAATRLFATHGVSGTSLQQIADATGITKAAVY HHFPTKEEVVVAVLAPALEAIQGIVRTAGAHEDPRAATEAAIIGLADQ AVTHRQRWAVLLQDAAVEEYVRNNPDHDELFTRLRLLLTGPDPTPGT RLQVSLFLSGLLGPAQDPSCADIDDDALRAGIVRAGRRLLLADDDAGS HHHHHH (SEQ ID NO: 2) |
| PinR-CHis_A65V_Q70H | MSSTAERIRPGRSGILAAATRLFATHGVSGTSLQQIADATGITKAAVY HHFPTKEEVVVAVLAPVLEAIHGIVRTAGAHEDPRAATEAAIIGLADQ |

TABLE 1-continued

Sequences of the Transcription Factor PinR and the predicted DNA binding domains (DBD) and Ligand Binding Domains (LBDs).

| Name | Sequence |
|---|---|
| | AVTHRQRWAVLLQDAAVEEYVRNNPDHDELFTRLRLLLTGPDPTPGT RLQVSLFLSGLLGPAQDPSCADIDDDALRAGIVRAGRRLLLADDDAGS HHHHHH (SEQ ID NO: 3) |
| Wild Type PinR Coding Sequence | ATGAGCAGCACCGCCGAACGCATCCGCCCGGGCCGCAGCGGCATCCTCGC CGCCGCGACCCGGCTCTTCGCCACGCACGGCGTCTCCGGCACCTCGCTGC AGCAGATCGCGGACGCCACCGGGATCACCAAGGCCGCCGTCTACCACCAC TTCCCCACCAAGGAGGAGGTCGTCGTCGCCGTCCTGGCGCCCGCGCTCGA GGCGATCCAGGGCATCGTCCGCACCGCCGGCGCCCACGAGGACCCGCGG GCCGCGACCGAGGCCGCCATCATCGGCCTCGCCGACCAGGCCGTCACCCA CCGCCAGCGCTGGGCCGTGCTCCTCCAGGACGCCGCCGTCGAGGAGTACG TCCGCAACAACCCCGACCACGACGAGCTCTTCACCCGGCTGCGCCTGCTC CTCACCGGCCCGGATCCCACCCCGGGCACCCGGCTCCAGGTCTCCCTCTTC CTCTCCGGCCTGCTCGGGCCCGCGCAGGACCCCAGCTGCGCCGACATCGA CGACGACGCGCTGCGCGGGCATCGTCCGGGCCGGACGCCGGCTCCTGC TGGCCGACGACGACGCC (SEQ ID NO 4) |
| Codon Optimized PinR Coding Sequence | ATGTCGTCAACGGCTGAACGCATCCGTCCTGGACGTTCTGGGATTCTTGCT GCAGCAACGCGCTTATTCGCAACCCACGGCGTAAGCGGAACCTCACTGCA GCAAATTGCAGACGCAACGGGTATCACTAAGGCGGCGGTATATCACCATT TCCCTACAAAGGAAGAAGTTGTAGTGGCCGTGTTAGCACCTGCGTTAGAG GCCATTCAAGGTATTGTGCGCACAGCCGGAGCGCATGAGGACCCACGTGC AGCAACAGAGGCCGCCATTATTGGATTAGCGGATCAGGCGGTTACTCACC GTCAACGCTGGGCGGTACTGTTGCAAGACGCTGCCGTCGAAGAGTATGTT CGCAATAACCCAGATCACGATGAGCTTTTCACACGTTTACGCCTGTTATTG ACGGGTCCAGACCCAACACCAGGCACTCGTTTACAAGTGTCGTTGTTCTTG TCGGGATTGCTGGGTCCAGCTCAAGATCCGTCATGTGCTGACATCGATGA CGACGCCCTTCGTGCCGGGATCGTCCGTGCCGGACGTCGTTTATTACTTGC GGACGACGACGCCGGGTCACATCATCACCACCATCAC (SEQ ID NO: 5) |
| PinR_A65V_Q70H Coding Sequence | ATGTCGTCAACGGCTGAACGCATCCGTCCTGGACGTTCTGGGATTCTTGCT GCAGCAACGCGCTTATTCGCAACCCACGGCGTAAGCGGAACCTCACTGCA GCAAATTGCAGACGCAACGGGTATCACTAAGGCGGCGGTATATCACCATT TCCCTACAAAGGAAGAAGTTGTAGTGGCCGTGTTAGCACCTGTGTTAGAG GCCATTCATGGTATTGTGCGCACAGCCGGAGCGCATGAGGACCCACGTGC AGCAACAGAGGCCGCCATTATTGGATTAGCGGATCAGGCGGTTACTCACC GTCAACGCTGGGCGGTACTGTTGCAAGACGCTGCCGTCGAAGAGTATGTT CGCAATAACCCAGATCACGATGAGCTTTTCACACGTTTACGCCTGTTATTG ACGGGTCCAGACCCAACACCAGGCACTCGTTTACAAGTGTCGTTGTTCTTG TCGGGATTGCTGGGTCCAGCTCAAGATCCGTCATGTGCTGACATCGATGA CGACGCCCTTCGTGCCGGGATCGTCCGTGCCGGACGTCGTTTATTACTTGC GGACGACGACGCCGGGTCACATCATCACCACCATCAC (SEQ ID NO: 6) |
| PinR DBD | ILAAATRLFATHGVSGTSLQQIADATGITKAAVYHHFPTKEEVVVAV (SEQ ID NO: 7) |
| Wild Type PinR Putative pfam00440 (TetR_N) DNA Binding Domain Coding Sequence | ATCCTCGCCGCCGCGACCCGGCTCTTCGCCACGCACGGCGTCTCCGGCAC CTCGCTGCAGCAGATCGCGGACGCCACCGGGATCACCAAGGCCGCCGTCT ACCACCACTTCCCCACCAAGGAGGAGGTCGTCGTCGCCGTC (SEQ ID NO: 8) |
| Wild type PinR ligand binding domain (LBD) | LAPALEAIQGIVRTAGAHEDPRAATEAAIIGLADQAVTHRQRWAVLLQDAAV EEYVRNNPDHDELFTRLRLLLTGPDPTPGTRLQVSLFLSGLLGPAQDPSCADI DDDALRAGIVRAGRRLLLADDDA (SEQ ID NO: 18) |
| Modified LBD (PinR-Chis Tag LBD | LAPALEAIQGIVRTAGAHEDPRAATEAAIIGLADQAVTHRQRWAVLLQDAAV EEYVRNNPDHDELFTRLRLLLTGPDPTPGTRLQVSLFLSGLLGPAQDPSCADI DDDALRAGIVRAGRRLLLADDDA (SEQ ID NO: 19) |
| Modified LBD (PinR-CHis_A65V_Q70H LBD) | LAPVLEAIHGIVRTAGAHEDPRAATEAAIIGLADQAVTHRQRWAVLLQDAAV EEYVRNNPDHDELFTRLRLLLTGPDPTPGTRLQVSLFLSGLLGPAQDPSCADI DDDALRAGIVRAGRRLLLADDDA (SEQ ID NO: 20) |
| Wild Type PinR Putative Ligand Binding Domain | CTGGCGCCCGCGCTCGAGGCGATCCAGGGCATCGTCCGCACCGCCGGCGC CCACGAGGACCCGCGGGCCGCGACCGAGGCCGCCATCATCGGCCTCGCCG ACCAGGCCGTCACCCACCGCCAGCGCTGGGCCGTGCTCCTCCAGGACGCC GCCGTCGAGGAGTACGTCCGCAACAACCCCGACCACGACGAGCTCTTCAC CCGGCTGCGCCTGCTCCTCACCGGCCCGGATCCCACCCCGGGCACCCGGC |

TABLE 1-continued

Sequences of the Transcription Factor PinR and the predicted DNA binding domains (DBD) and Ligand Binding Domains (LBDs).

| Name | Sequence |
|---|---|
| | TCCAGGTCTCCCTCTTCCTCTCCGGCCTGCTCGGGCCCGCGCAGGACCCCA<br>GCTGCGCCGACATCGACGACGACGCGCTGCGCGCGGGCATCGTCCGGGCC<br>GGACGCCGGCTCCTGCTGGCCGACGACGACGCC<br>(SEQ ID NO: 9) |
| Codon Optimized PinR and PinR_A65V_Q70H Putative pfam00440 (TetR_N) DNA Binding Domain Coding Sequence | ATTCTTGCTGCAGCAACGCGCTTATTCGCAACCCACGGCGTAAGCGGAAC<br>CTCACTGCAGCAAATTGCAGACGCAACGGGTATCACTAAGGCGGCGGTAT<br>ATCACCATTTCCCTACAAAGGAAGAAGTTGTAGTGGCCGTG<br>(SEQ ID NO: 10) |
| Codon Optimized PinR Putative Ligand Binding Domain with C-terminal 6His Tag Coding Sequence | TTAGCACCTGCGTTAGAGGCCATTCAAGGTATTGTGCGCACAGCCGGAGC<br>GCATGAGGACCCACGTGCAGCAACAGAGGCCGCCATTATTGGATTAGCGG<br>ATCAGGCGGTTACTCACCGTCAACGCTGGGCGGTACTGTTGCAAGACGCT<br>GCCGTCGAAGAGTATGTTCGCAATAACCCAGATCACGATGAGCTTTTCAC<br>ACGTTTACGCCTGTTATTGACGGGTCCAGACCCAACACCAGGCACTCGTTT<br>ACAAGTGTCGTTGTTCTTGTCGGGATTGCTGGGTCCAGCTCAAGATCCGTC<br>ATGTGCTGACATCGATGACGACGCCCTTCGTGCCGGGATCGTCCGTGCCG<br>GACGTCGTTTATTACTTGCGGACGACGACGCCGGGTCACATCATCACCAC<br>CATCAC<br>(SEQ ID NO: 11) |
| PinR_A65V_Q70H Putative Ligand Binding Domain with C-terminal 6His Tag Coding Sequence | TTAGCACCTGTGTTAGAGGCCATTCATGGTATTGTGCGCACAGCCGGAGC<br>GCATGAGGACCCACGTGCAGCAACAGAGGCCGCCATTATTGGATTAGCGG<br>ATCAGGCGGTTACTCACCGTCAACGCTGGGCGGTACTGTTGCAAGACGCT<br>GCCGTCGAAGAGTATGTTCGCAATAACCCAGATCACGATGAGCTTTTCAC<br>ACGTTTACGCCTGTTATTGACGGGTCCAGACCCAACACCAGGCACTCGTTT<br>ACAAGTGTCGTTGTTCTTGTCGGGATTGCTGGGTCCAGCTCAAGATCCGTC<br>ATGTGCTGACATCGATGACGACGCCCTTCGTGCCGGGATCGTCCGTGCCG<br>GACGTCGTTTATTACTTGCGGACGACGACGCCGGGTCACATCATCACCAC<br>CATCAC<br>(SEQ ID NO: 12) |

VIII (B) Nucleic Acid Probe for Binding to DBD of Progesterone aTF

As disclosed herein, the PinR aTF comprises a DBD and a LBD. The DBD of PinR binds with specific affinity to the transcription factor binding domain (TFBD) nucleic acid sequences of any of: IG.AIY20222.2 (SEQ ID NO: 13), IG.AIY20223.2 (SEQ ID NO: 14), 13,15-T,T (SEQ ID N: 15), M. absc (SEQ ID NO: 16) or IG.AIY19519.1 (SEQ ID NO: 17).

Accordingly, exemplary nucleic probes for a progesterone biosensor comprises at least one TFBD comprising least 3, or at least 4, or at least 5, or at least 6, or at least 7, or at least 8, or at least 10 of nucleic acid sequence of SEQ ID NO: 13-17 or at least 50%, or at least 60%, or at least 70%, or at least 80%, or at least 85%, or at least 90%, or at least 95% of SEQ ID NO: 13-17 (Table 2). In some embodiments, a nucleic acid probe for a progesterone biosensor comprises at least 1 TFBD, or at least 2, or at least 3, or at least 4, or at least 5 or at least 6 or more than 6 TFBD selected from any of SEQ ID NO: 13-17. In some embodiments, each TFBD can be the same nucleotide sequence (e.g., they can all be SEQ ID NO: 13), or different nucleotide sequence (e.g., any selected from SEQ ID NO: 13-17) such that the nucleic acid probe of the progesterone biosensor comprises multiple TFBDs that have different affinity for the DBD of PinR.

TABLE 2

Sequences of the Transcription Factor binding domains (TFBDs) of PinR. The use of these in a progesterone biosensor is described in Examples 2 and 3.

| Name | Sequence |
|---|---|
| IG.AIY20222.2 (DNA3) | AACTAGCCGTTCGGCAAGTA<br>(SEQ ID NO: 13) |
| IG.AIY20223.2 (DNA1) | AACTAGCCGTTCGGCTAGTT<br>(SEQ ID NO: 14) |
| 13,15-T,T (DNA4) | AACTAGCCGTTCTGTTAGTT<br>(SEQ ID NO: 15) |
| M. absc | TACTTAACGATAGGTAAGTA<br>(SEQ ID NO: 16) |
| IG.AIY19519.1 (DNA2) | GACTAGCCGATCGGCTAGTT<br>(SEQ ID NO: 17) |

IX. Detection and Optical Sensors

In one embodiment, fluorescent molecule detection can be achieved using a number of detection systems. The choice of a proper detection system for a particular application is well within the abilities of one skilled in the art. Exemplary optical detection system capable of detecting the fluorescence means include, but are not limited to, detection by unaided eye, Fluorescence activated cell sorting (FACS), light microscopy using the eye or an optical sensor as the detector, confocal microscopy, laser scanning confocal microscopy, imaging using quantum dot color, fluorescence spectrum or other quantum dot property and wide-field imaging with a 2 D CCD camera and a high numerical aperture microscope objective. An exemplary laser based microscope system capable of detecting and spectrally resolving the fluorescence from single semiconductor nanocrystals is known in the art.

In another preferred embodiment, the assay is probed with an optical detection system capable of detecting the fluorescence from single semiconductor nanocrystals (or other labels) with a spatial resolution of about 10 µm or less, preferably about 1 µm or less. In an exemplary embodiment, the optical system includes a wide-field imaging system with a 2D CCD camera and a high numerical aperture microscope objective. An exemplary laser based microscope system capable of detecting and spectrally resolving the fluorescence from single semiconductor nanocrystals is known in the art.

In some embodiments, an optical detector useful for measuring FRET is a light detector and may comprise a plurality of optical sensors. An optical sensor can include any one or more of, e.g., a photodiode, an avalanche photodiode (APD), a phototransistor, a photogate, a quantum-well infrared photodetector (QWIP), a thin-film on ASIC (TFA), a metal-semiconductor-metal (MSM) photodetector, or a combination thereof. In one embodiment, the optical sensor may be a photodiode.

In some embodiments, the optical detection system may or may not comprise at least one source of excitatory light, such as at least one laser. A source of excitatory light is not needed to detect objects which luminesce independently of light absorption, such as can be generated via bioluminescence or chemiluminsescence, for example. In some embodiments, an optical detection system useful herein to measure FRET may comprise a light detector detecting light emitted from the object. The light detector is capable of at least partially absorbing light incident thereon and generating output signals in response to the light. The light detector may comprise a control circuit for controlling the operation of the light detector. The control circuit may comprise a circuit of signal amplifier, A/D convertor, integrator, comparator, logic circuit, readout circuit, memory, microprocessor, clock, and/or address.

In some embodiments, the detecting apparatus may comprise a computer for processing output signals from the light detector and generating a determination result. The detecting apparatus may further comprise a blind sheet with a pinhole. The apparatus may further comprise an excitation light source. The object may absorb light emitted from the excitation light source and then emit another light to be detected by the detecting apparatus. The light emitted from the object may have different wavelength than the light emitted from the excitation light source.

Portable FRET detection devices are known to one of ordinary skill in the art and are disclosed in US application US2015/0346097, and U.S. Pat. No. 9,895,692 which are incorporated herein in its entirety by reference. Such devices can be miniaturized for analysis of cartridges, including consumable cartridges for point of care quantitative testing of analytes and analyte levels.

Detection Using an Optical Reader or Semiconductor Device

Figure 11A:
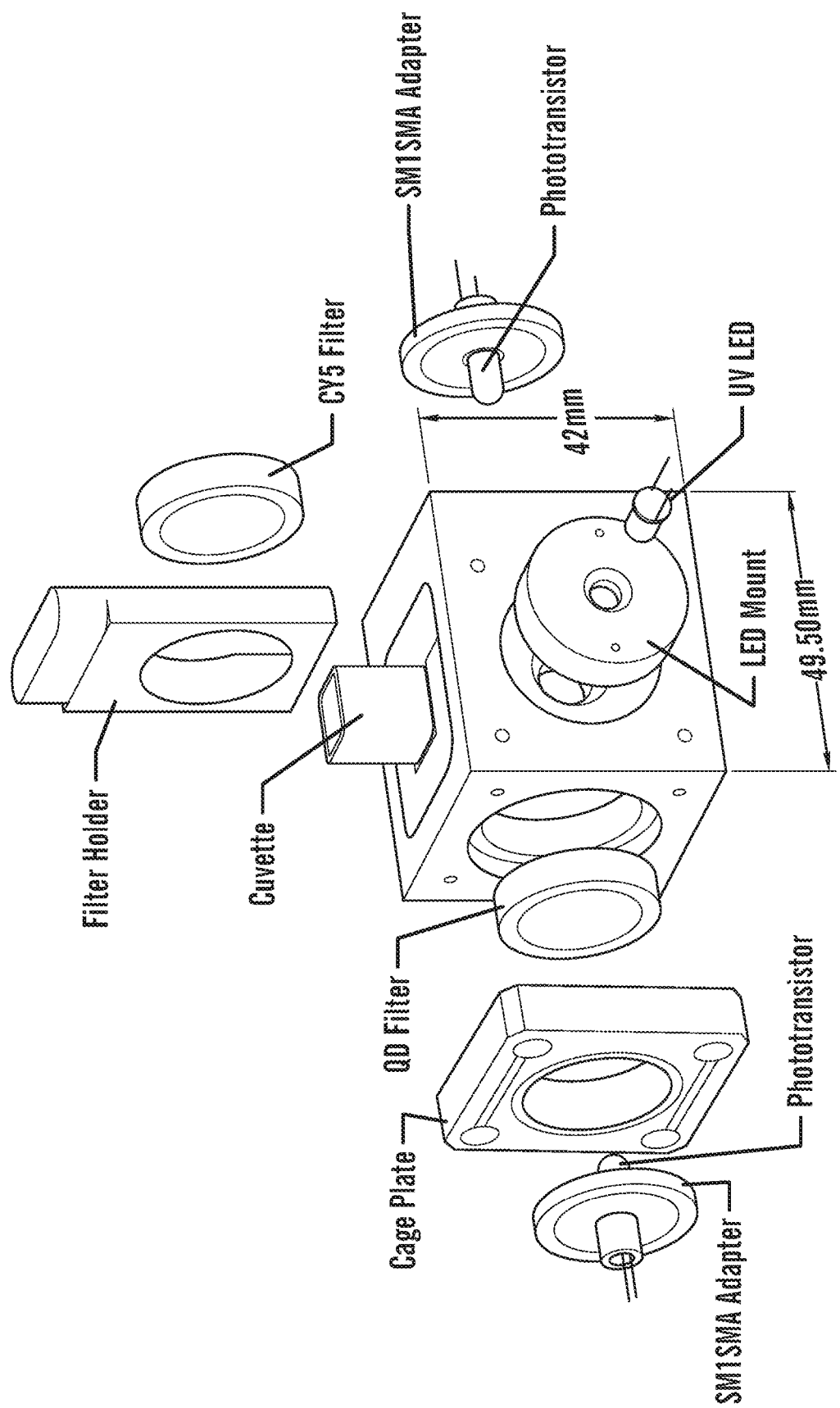
FIGS. 11A-11B show a schematic of the device and the optical setup diagram for the measurement of analytes.
Figure 11B:
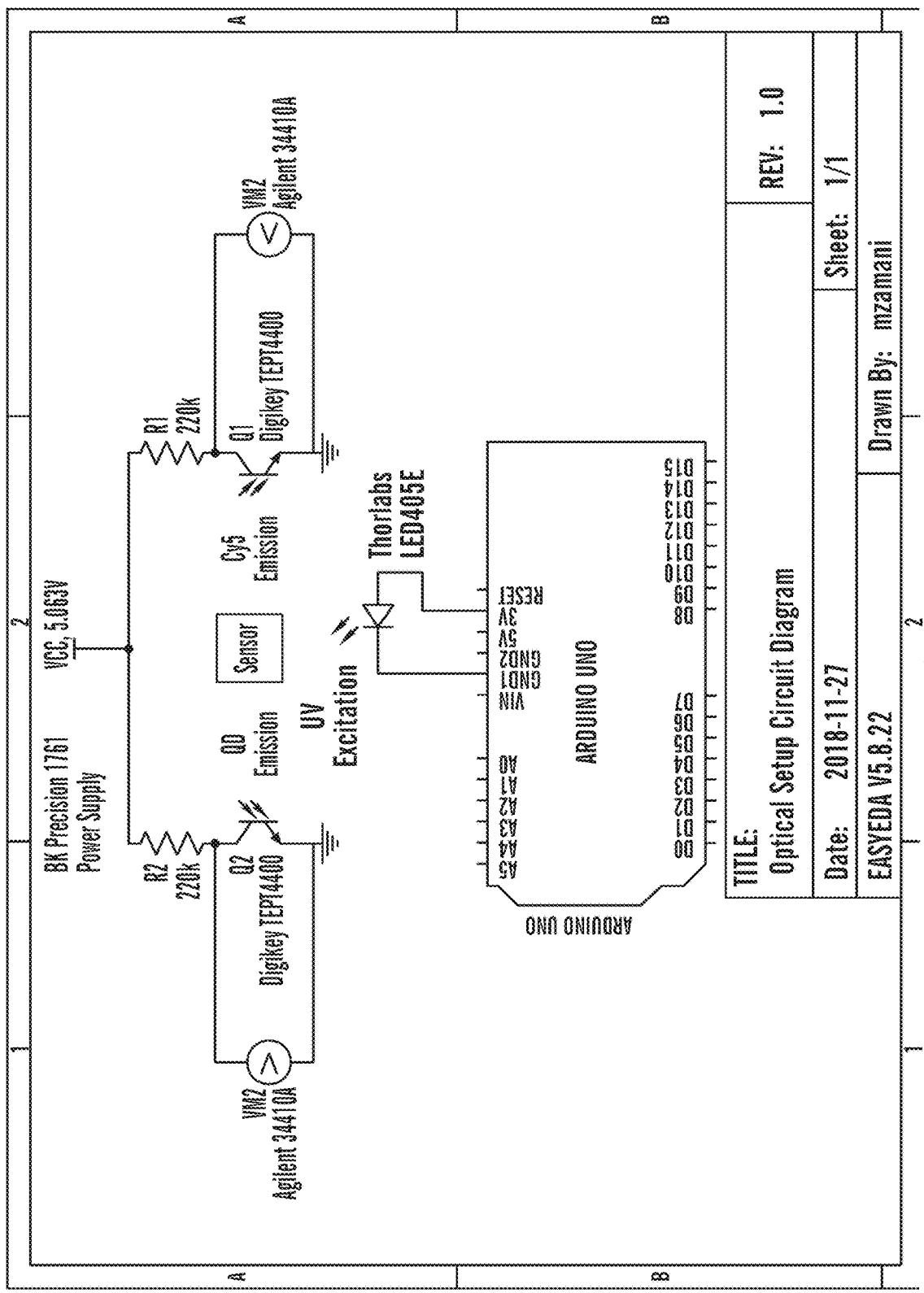
Figure 11C:
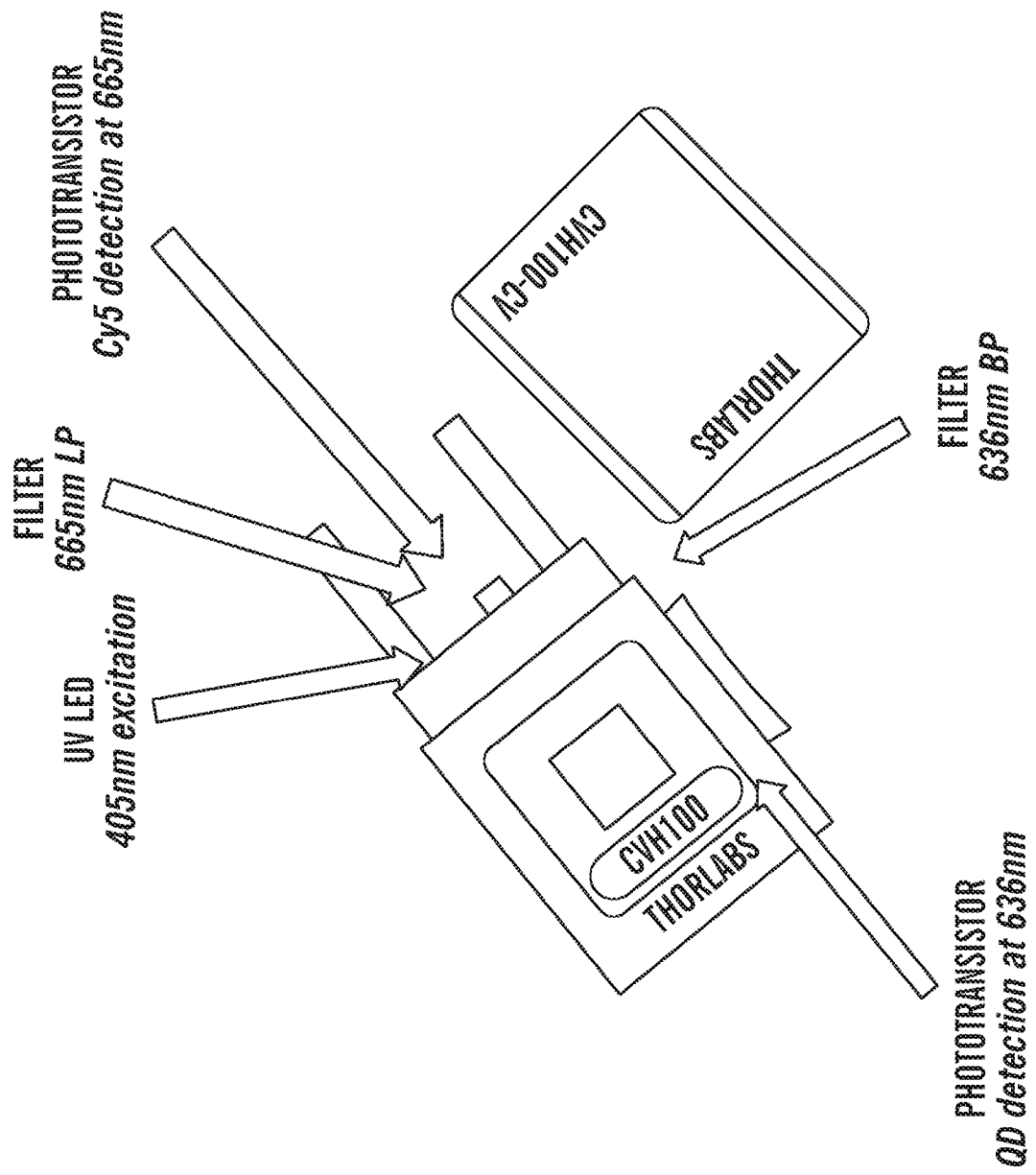
FIGS. 11C-E show a low-cost detector based on off-the-shelf electronics that is capable of detecting progesterone using our QD-FRET sensor.
Figure 11D:
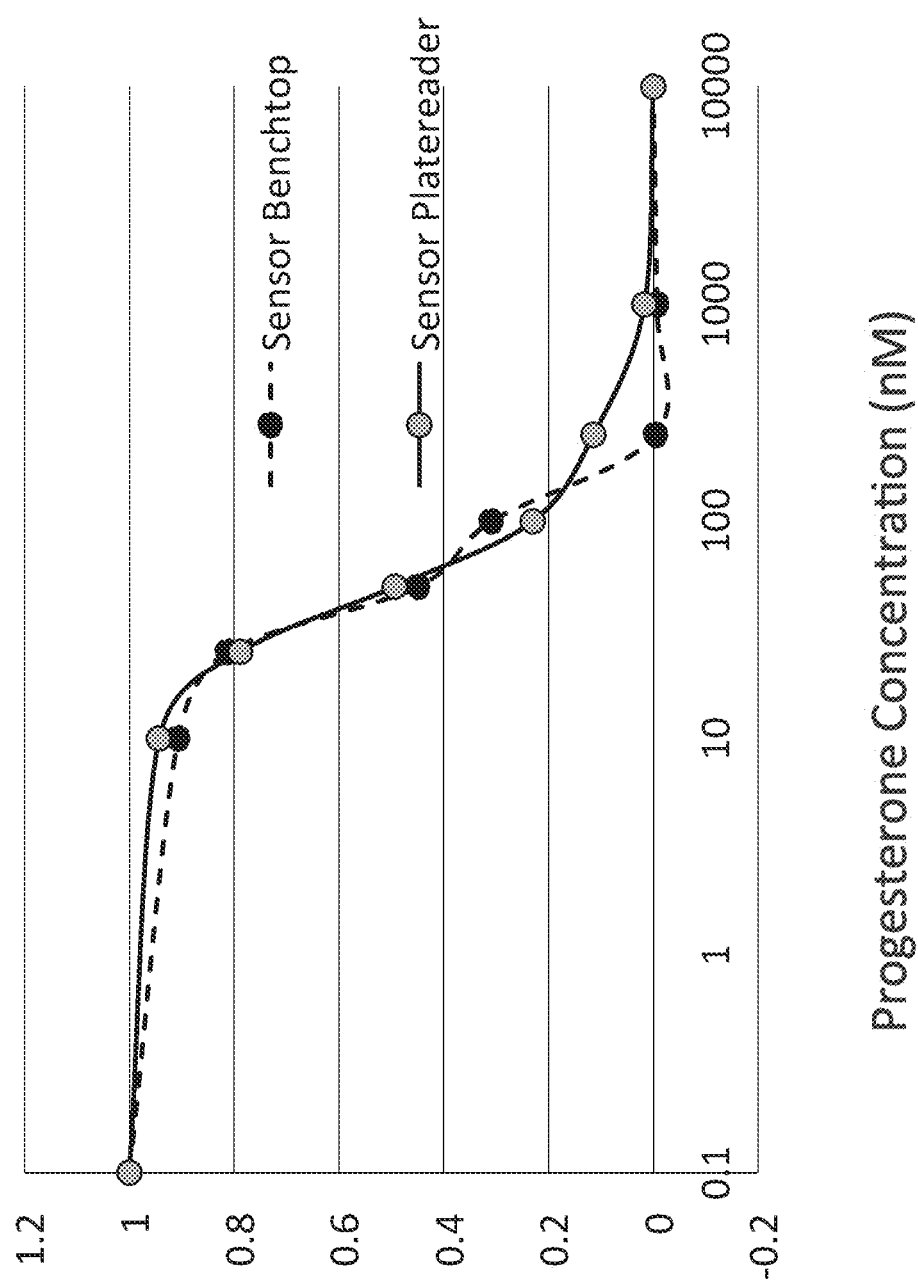

An exemplary optical or other sensor useful herein is can be used to read the microfluidic chip (also referred to herein as a microfluidic cartridge) using low cost optical parts, see, e.g., FIGS. 11A-11C and 12 which are used for illustrative purposes only. An optical reader for the measurement of the FRET emission and/or the semiconductor device for the measurement of an alteration (e.g., increase or decrease) in current is based on a prototype system built with off the shelf parts (FIG. 11C). The reader can be modified and miniaturized as necessary for a point of care (POC) device. In some embodiments, an optical reader is powered by wall power or battery (including rechargeable battery) or solar power, or a mobile device (e.g., phone or tablet or computer battery) and can be designed to be small enough to be used as a wristband watch, or can be configured to sit on a bathroom counter (and/or to take up minimal space in a physician's office). After a cartridge is read by the reader, the reader will store the quantitative data in its memory or an associated laptop computer. The reader can be connected via Bluetooth for mobile phone use, and can store data locally and in the cloud, and/or can be sent to the subject's clinical practitioner. In this manner, analyte levels, (e.g., hormone levels, such as progesterone or other levels) for a subject can be measured over time. Changes in hormone levels are indicated on a readout that can be later connected to web based applications. The design of the reader is modular, such that at any time filter sets can be easily be exchanged. The results thus provide proof-of-concept for a novel class of hormone biosensors adaptable for usage as inexpensive, real-time, point-of-care (POC) or consumer health devices.

In some embodiments, the detection device, e.g., optical sensor or semiconductive device allows point of care testing (POCT), that is, the subject can perform all the relevant step in analyte detection, including obtaining the sample, applying the sample to the cassette/cartridge, placement in the reader device (e.g., optical sensor or semiconductive device), which will transmit the results to a mobile device (e.g., a mobile phone or smartphone, ipad, tablet, smartwatch), or other interface, e.g., cloud to be accessed by the subjects clinical practitioner.

Figure 11E:
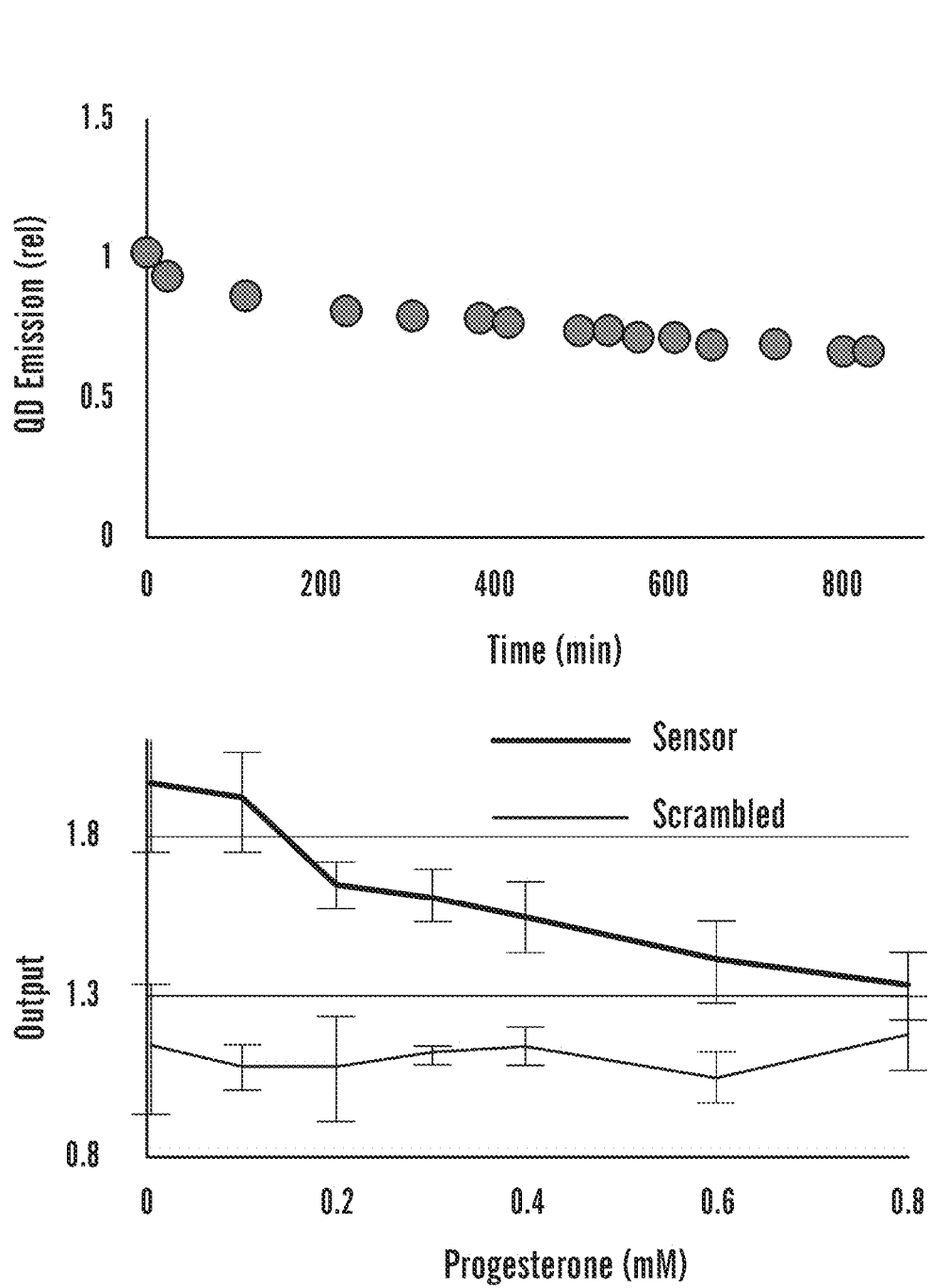
Figure 13A:
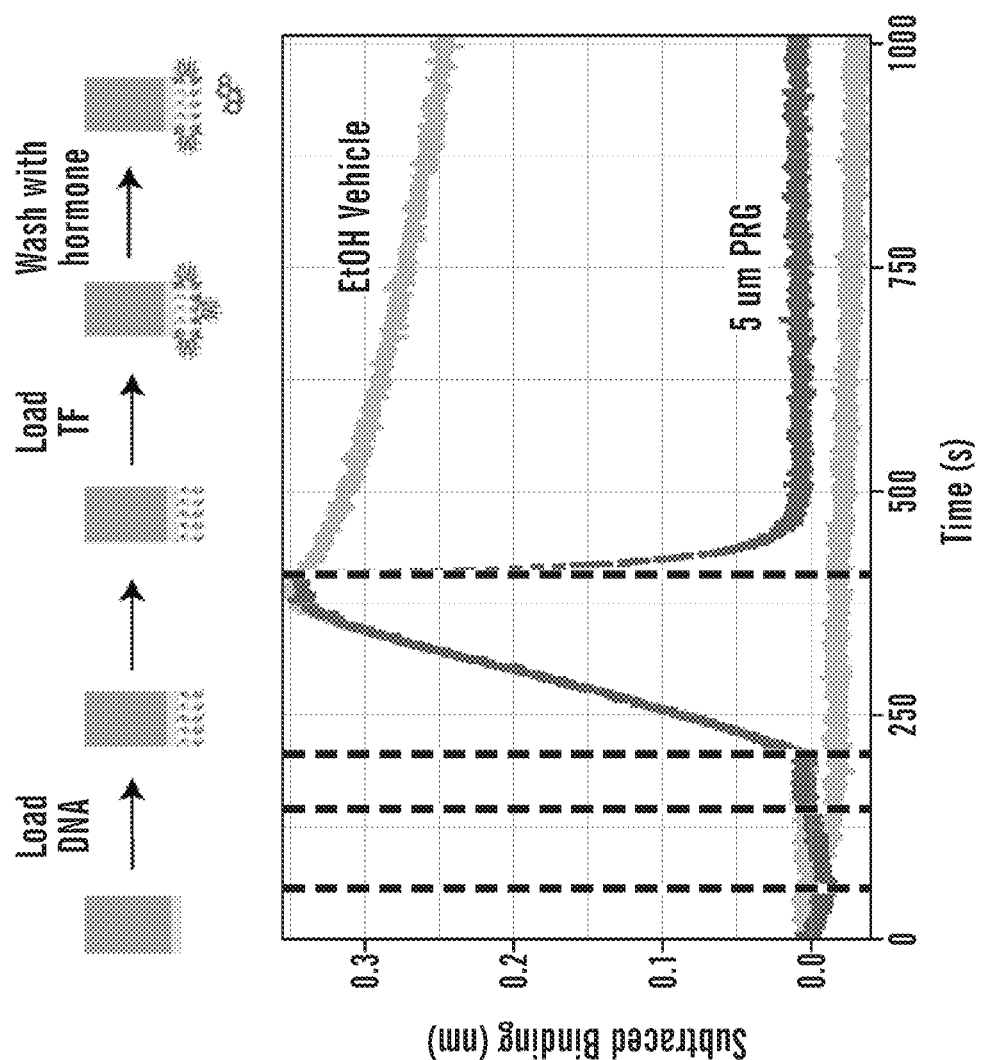
FIGS. 13A-13C show a schematic of a BioLayer Interferometry procedure.
Figure 13B:
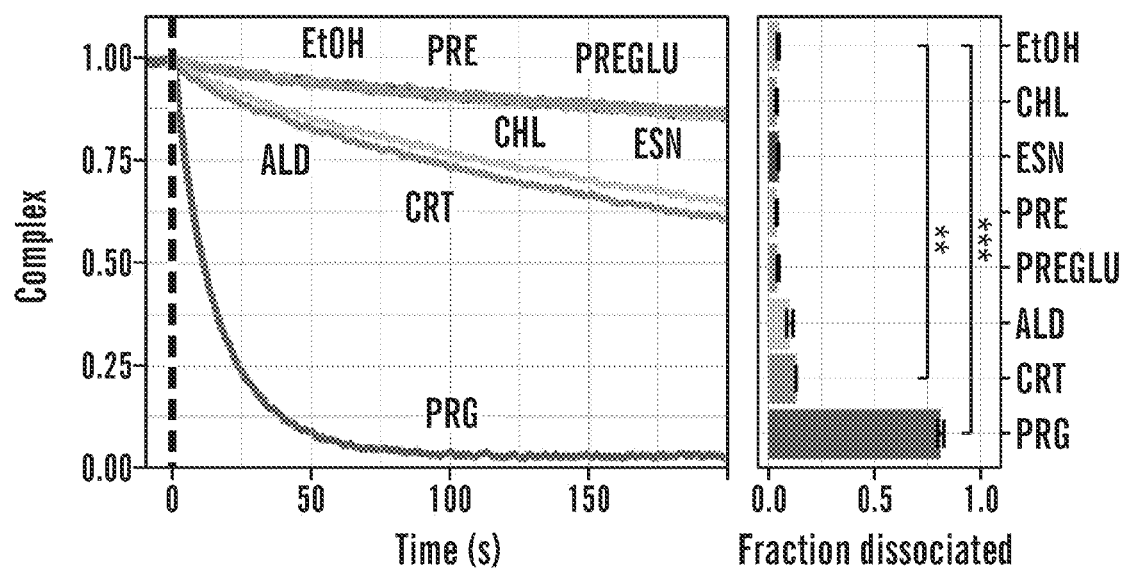
Figure 13C:
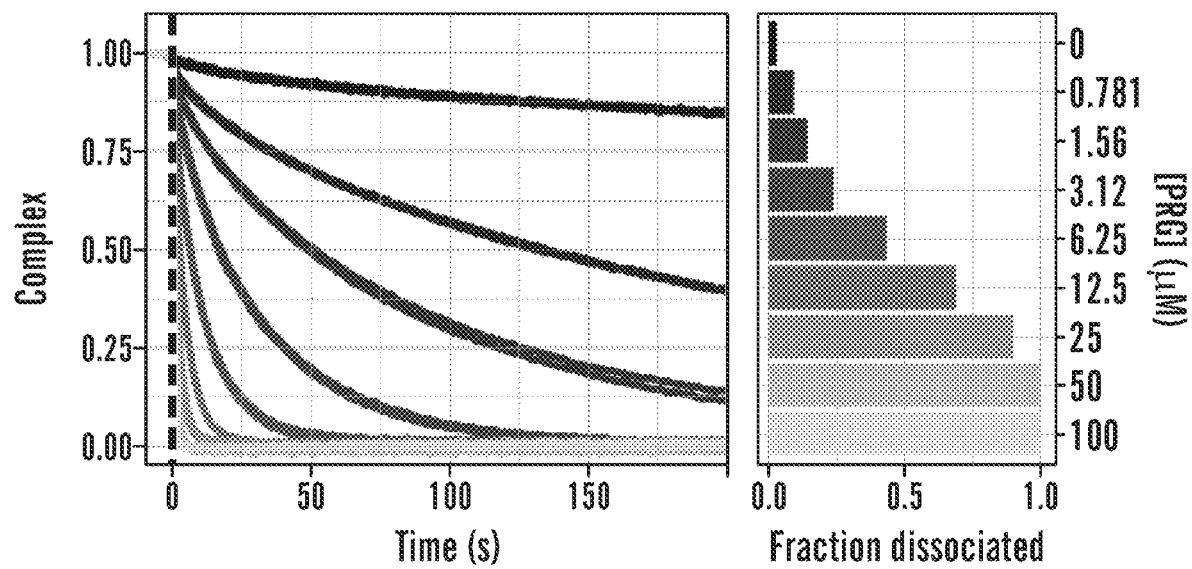

In some embodiments, an exemplary point-of-care (POC) optical device is shown in FIG. 11C, which was built to detect the transcription-factor based sensors with inexpensive, off-the-shelf parts for use in a point-of-care (POC) setting. Using such a POC device, the sample is excited at the appropriate wavelength; the resulting QD and Cy5 emissions are simultaneously and independently detected. A UV LED is used to excite the sample and phototransistors are used to detect QD and Cy5 emissions. As shown in FIG. 11E, detection of the emitted light takes place in two separate channels that are orthogonal to the light source. One channel has a 600 nm bandpass filter in between the sample and the phototransistor; this is used to detect emission from the QDs. The other channel has a 665 nm longpass filter in between the sample and the phototransistor; this is used to detected emission from the Cy5 dye.

The exemplary POC device shown in FIG. 11C can be modified by persons of ordinary skill in the art and demonstrates the ability to use inexpensive, off-the-shelf components to measure fluorescence in the sample contacted with the biosensor. Such a POC device can be miniaturized and provided to a practitioner or subject who will routinely be assessing samples for an analyte. Such miniaturized devices can be cost-saving, time-efficient and more convenient for the subject, by allowing a subject to measure analytes in a sample at their convenience and at their preferred location (e.g., home), thereby reducing costs, time and necessary arrangements required normally associated with the subject having to go to a testing facility and/or send a sample to a testing facility to determine the analyte concentration in the sample. In some embodiments, miniaturization can be done by persons of ordinary skill in the art and reducing the size and/or cost of the device, for example, by using 3D printing and/or cartridges or cassettes (e.g., disposable or consumable cassettes), and fabricating PCB boards to replace the multimeters and power supply used in the setup as disclosed herein.

X. Genomic Screening for the Identification and Isolation of Allosteric TFs that Recognize a Target Analyte.

Bacteria have evolved over 3 billion years to detect and respond to virtually all classes of stimuli relevant to our own biology, including steroid hormones. Steroid utilizing bacteria have been isolated from diverse sources including activated sludge from wastewater, soil, composts, aquifers, sea waters, and the human microbiome. One mechanism by which bacteria sense stimuli is via allosteric transcription factors (aTFs). Allosteric TFs are used as biosensors in whole cell applications, but in this setting are limited by slow response times, biosafety concerns, and the practical limitations of using a cellular host.

Figure 8A:
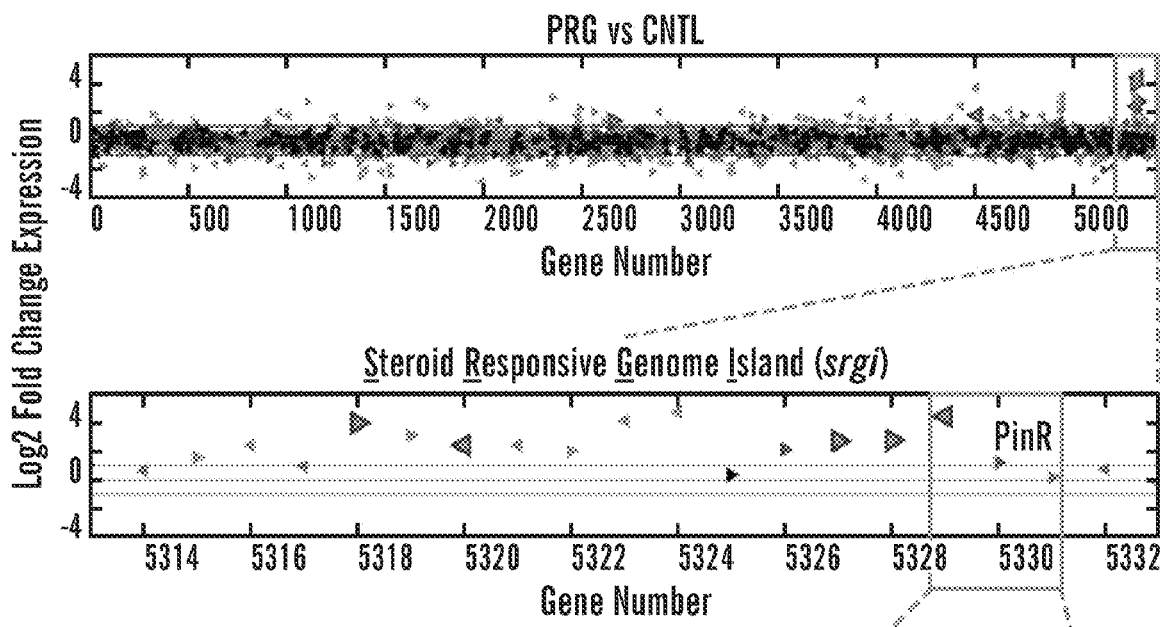
FIGS. 8A-8C show whole genome views of the upregulation of *P. simplex* gene in the presence of with progesterone (PRG), aldosterone (ALD), hydrocortisone (CRT), 17β-estradiol (ESL), estrone (ESE), and testosterone (TST) exposure vs a control.
Figure 8B:
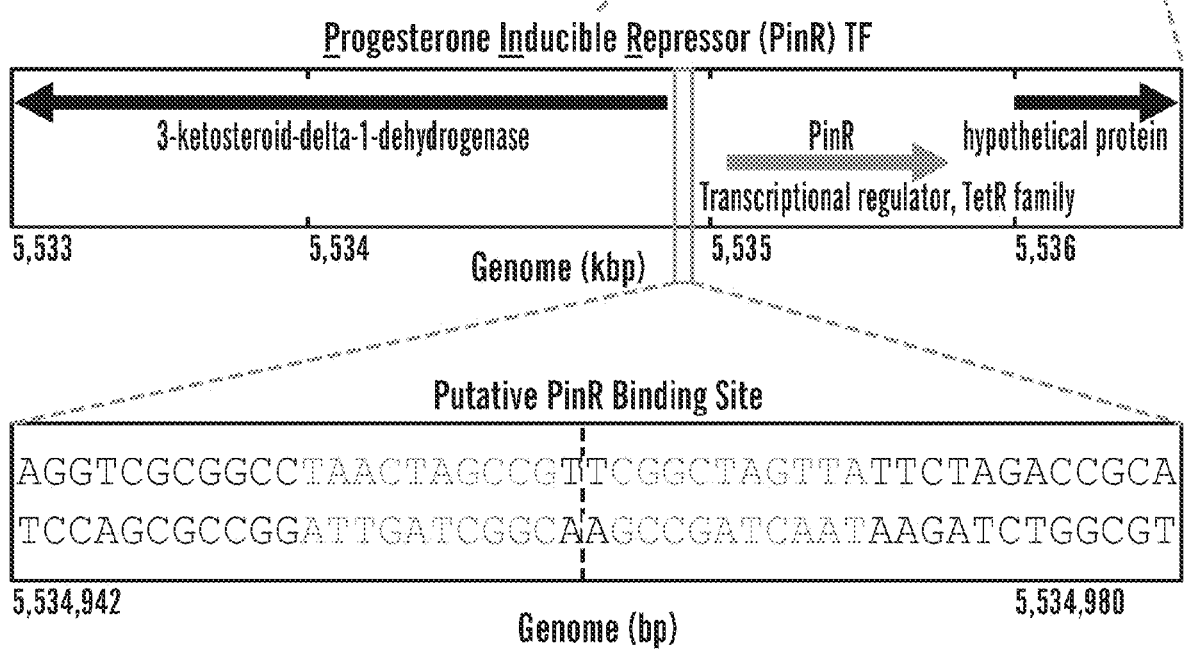
Figure 8C:
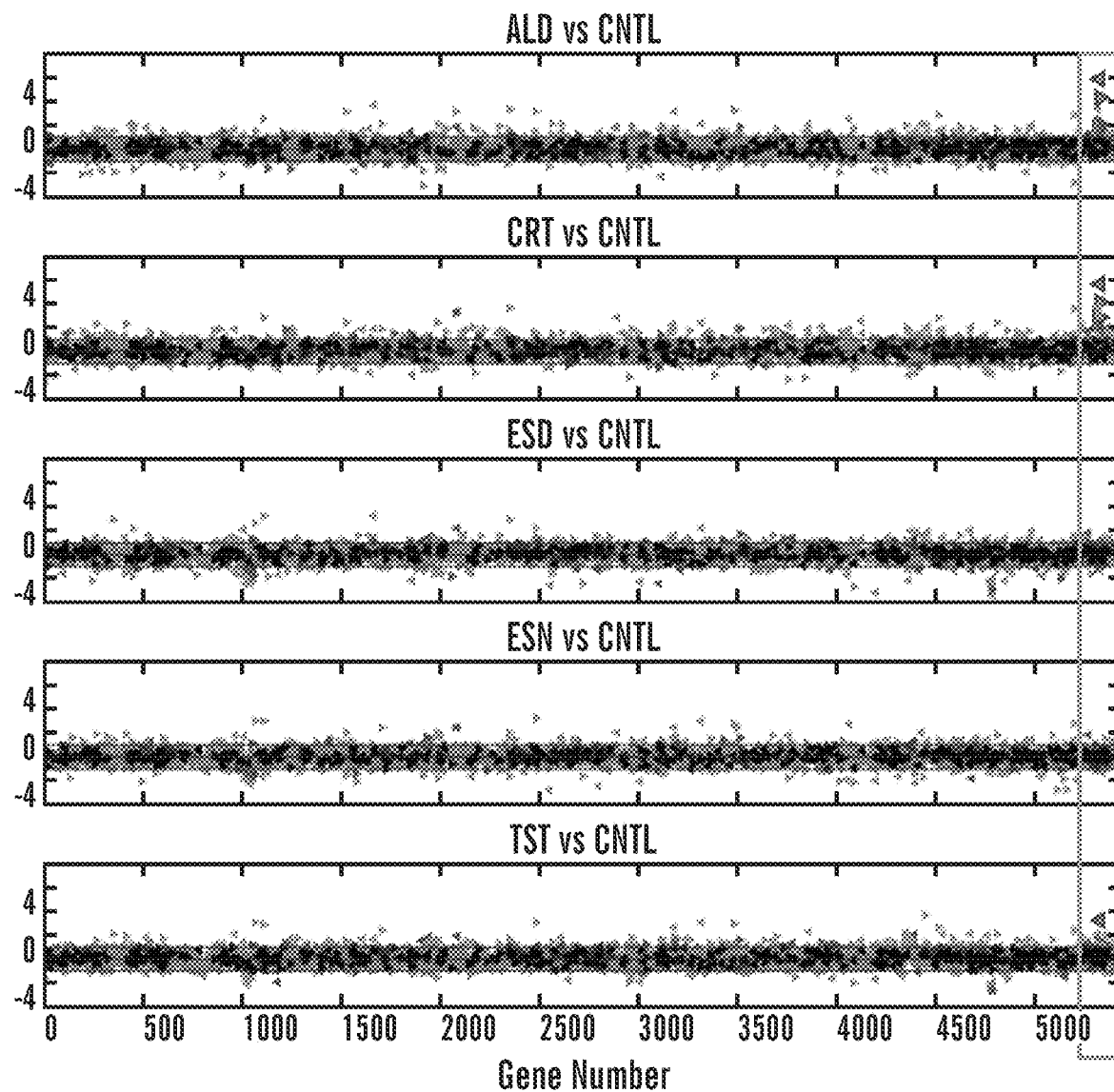
Figure 16:
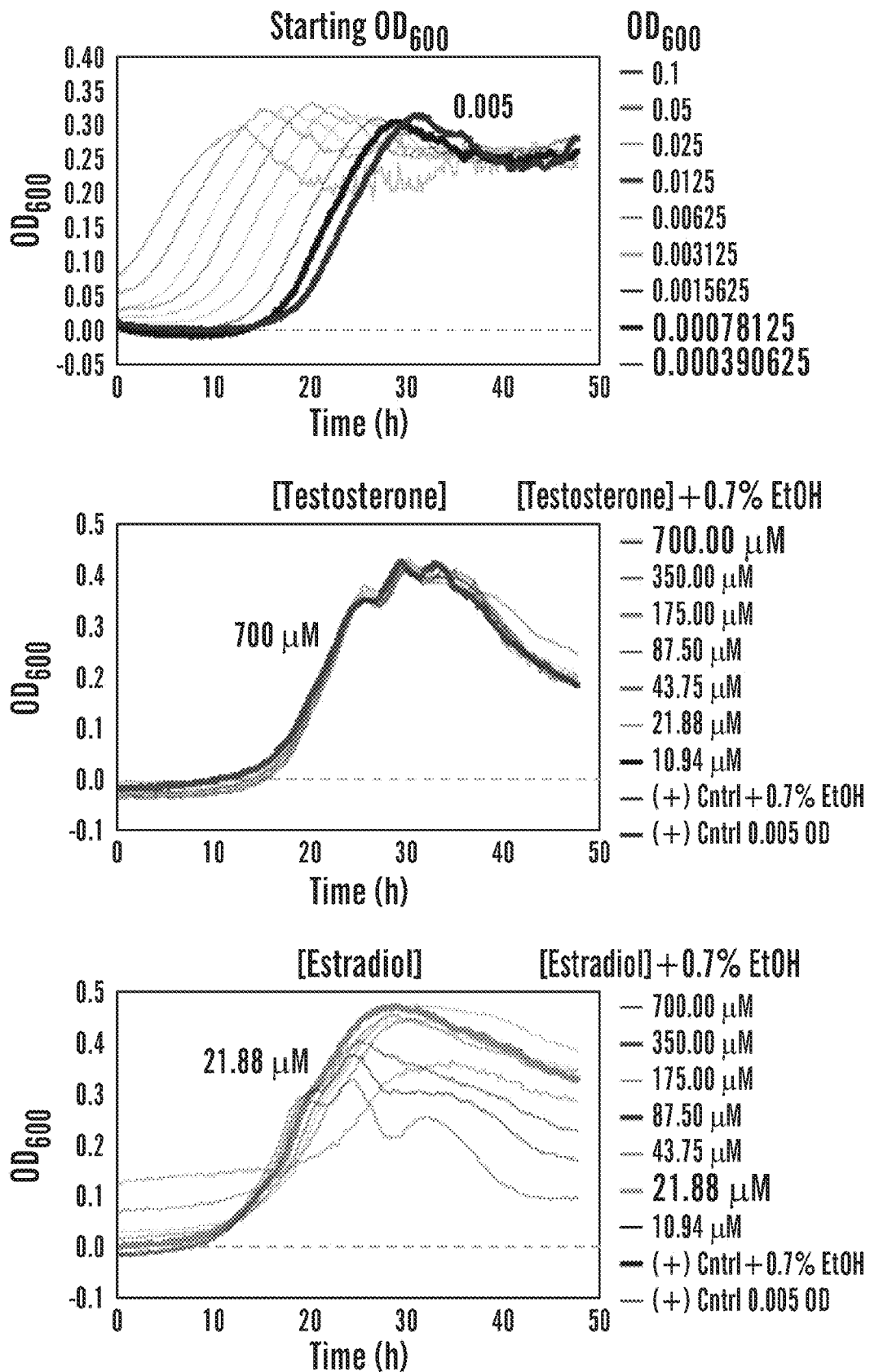
FIG. 16 shows the growth curves of *P. simplex* with respect to the starting inoculation density, solvent toxicity and the addition of steroids. To prevent overexpression of genes related to the stress response pathway against toxic molecules, *P. simplex* was screened against the steroid solvents ethanol (EtOH) and dimethylsulfoxide (DMSO). The highest solvent concentration that did not produce physiological change in growth compared to a solvent-free control was chosen. Subsequent experiments were performed using 0.70% and 0.35% by volume EtOH or DMSO concentrations, respectively.
Figure 16:
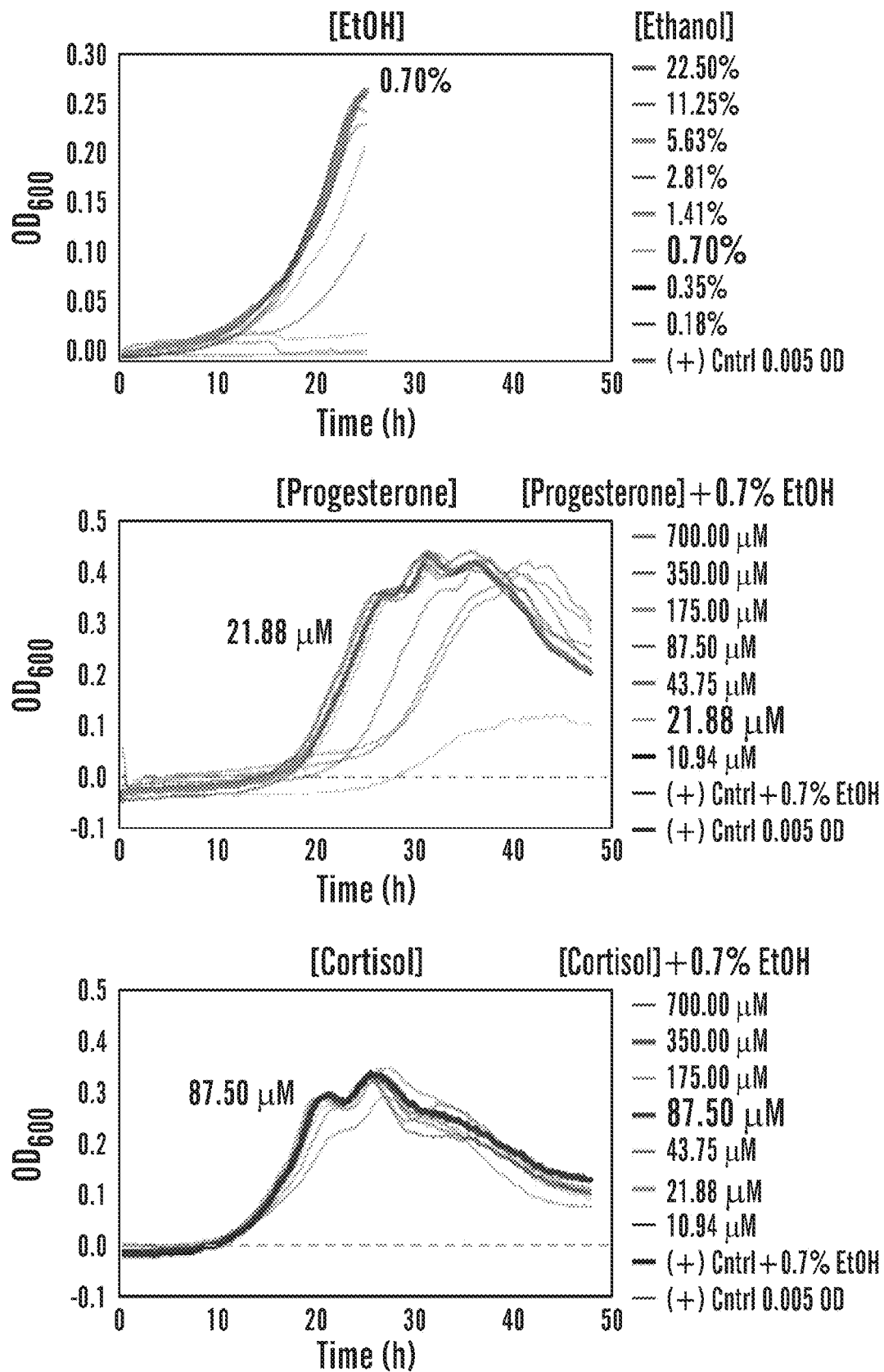
Figure 16:
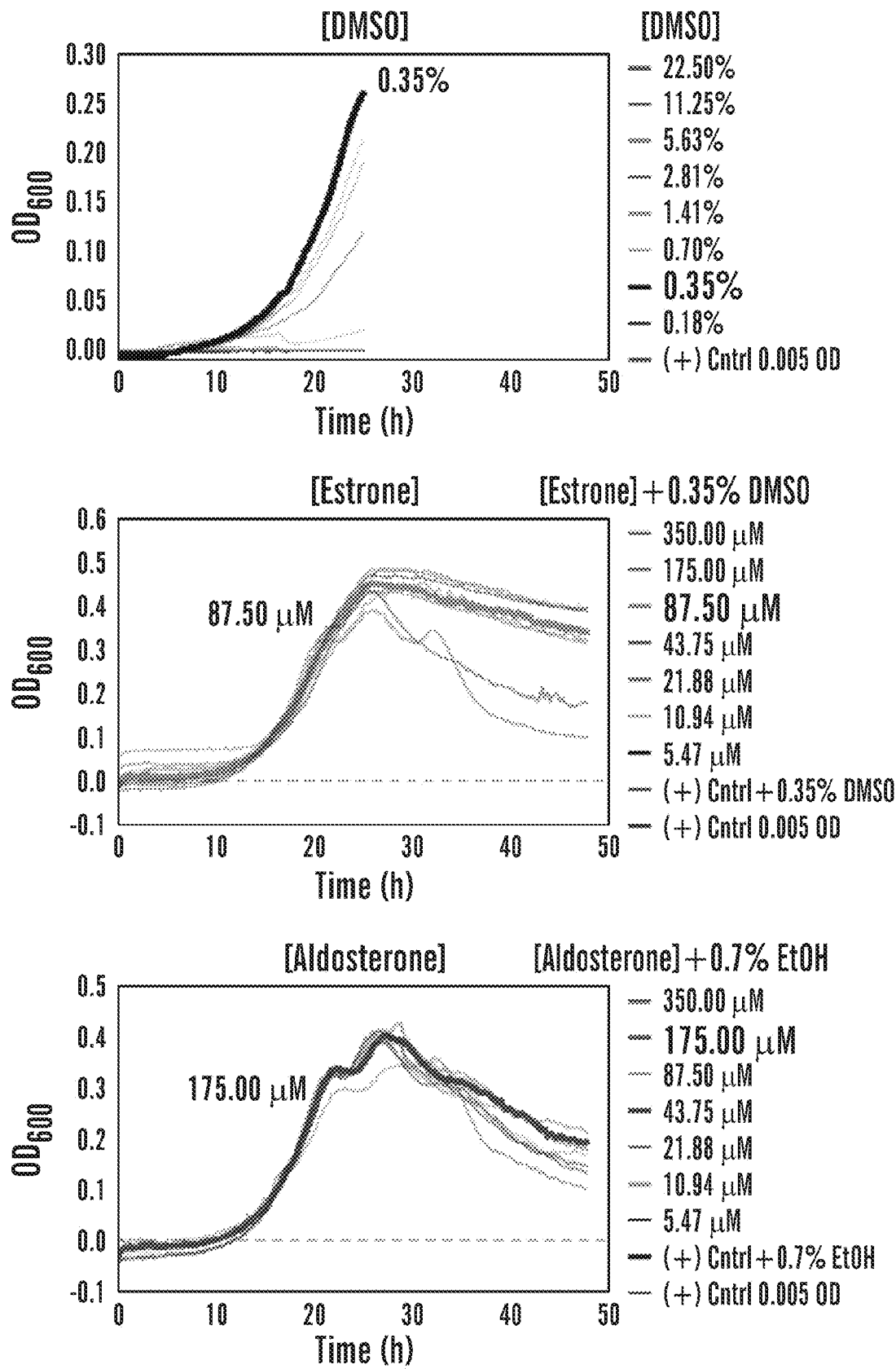

Another aspect of the technology described herein is a method to identify and isolate bacterial TFs or aTFs that recognize a target analyte. In particular, the method utilizes a combination of genomics and functional screens to identify and isolate biosensing TFs and a novel quantum-dot fluorescence resonance energy transfer (QD-FRET) strategy for transducing analyte recognition into real-time quantitative measurements in vitro (FIG. 7). This approach was used to develop a novel hormone sensor for progesterone based on a previously uncharacterized TF (FIG. 8). Importantly, demonstrated herein is a method to identify an aTF that binds to a specific nucleic acid sequence (i.e., TFBD) for the generation of a biosensor useful for real-time hormone measurements using an inexpensive and portable electronic reader consistent with requirements for a point-of-care device (FIG. 11C).

medium with solvents used to dissolve each steroid, and medium with each steroid at a range of concentrations (FIG. 16). Bacteria were exposed to each hormone, and control media, at concentrations determined from growth curves, and RNA harvested at lag, log, and stationary phase (FIG. 16). RNA was extracted using standard procedures, and barcoded RNA-Seq libraries produced using Illumina ScriptSeq Library Kits, and multiplexed sequencing performed on an Illumina NextSeq Sequencer using 75 bp single-end reads. Reads were aligned to a reference sequence. Differentially regulated aTFs were prioritized based on their proximity to genes, and clusters of genes, with computationally predicted roles in sterol metabolism. Identified aTF genes were cloned and/or synthesized with a Strep-tag, codon adapted as necessary, inserted into standard expression vectors, and transformed into *E. coli*. aTFs were then expressed and purified. Identify binding sites for cloned aTFs for QD-FRET sensing, was performed by in vitro ChIP-Seq on the tagged aTFs using genomic DNA from the host organism. In vitro ChIP-Seq analysis was performed on a progesterone sensor (FIG. 7). The binding site used and two additional potential genomic binding sites were identified. All three sites occur in the sterol degradation cluster that contains a novel progesterone sensing aTF (FIG. 8).

It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for

TABLE 3

Target organisms for screening. All strains have experimental evidence for general steroid metabolism (S) or the specific metabolism of estrogens (E), testosterone (T), or cholesterol (C). Most have either been sequenced or are phylogenetically close to a sequenced reference strain.

| Strain | Source | Genome | Reference |
|---|---|---|---|
| Shewanella paelena | ATCC | CP000851.1 | Bergstrand |
| Cupriavidas necator N-1 | ATCC | GCF_00021922 | Bergstrand |
| Thermomonospora curvata | ATCC | CP001738.1 | Bergstrand |
| Actinoplanes missouriensis 431 | ATCC | AP012319.1 | Bergstrand |
| Salinispora arenicola CNS-205 | ATCC | CP000850.1 | Bergstrand |
| Amycolatopsis sp. strain | ATCC | AFWY0200000 | Bergstrand |
| Steroidobacter denitrificans FS | DSM | CP011971.1 | Fahrbach et al. |
| Novosphingobium tardaugens | ATCC | NZ_BASZ0000 | Fuji (2003) |
| Sphingobium estrogenivorans | ATCC | None | Unpublished |
| Rhodococcus equi | ATCC | Ref Strain | Yu (2013) |
| Rhodococcus erythropolis | ATCC | Ref Strain | Yu (2013) |
| Rhodococcus rhodochrous | ATCC | Ref Strain | Yu (2013) |
| Mycoplasma yeatsii GIH [NCTC | ATCC | Ref Strain | DaMassa (1994) |
| Mycoplasma cottewii VIS [NCTC | ATCC | None | DaMassa (1994) |
| Mycoplasma auris UIA [NCTC | ATCC | Ref Strain | DaMassa (1994) |
| Entomoplasma luminosum PIMN- | ATCC | NZ_JAGW000 | Williamson |
| Entomoplasma somnilux PYAN-1 | ATCC | NZ_JAGV0000 | Williamson |
| Entomoplasma melaleucae M1 | ATCC | NZ_JMKX000 | Williamson |
| Clostridium scindens VPI 13733 | ATCC | NZ_ABFY0200 | Morris (1985) |

Methods to Identify Novel Allosteric TFs from Bacteria

Figure 14:
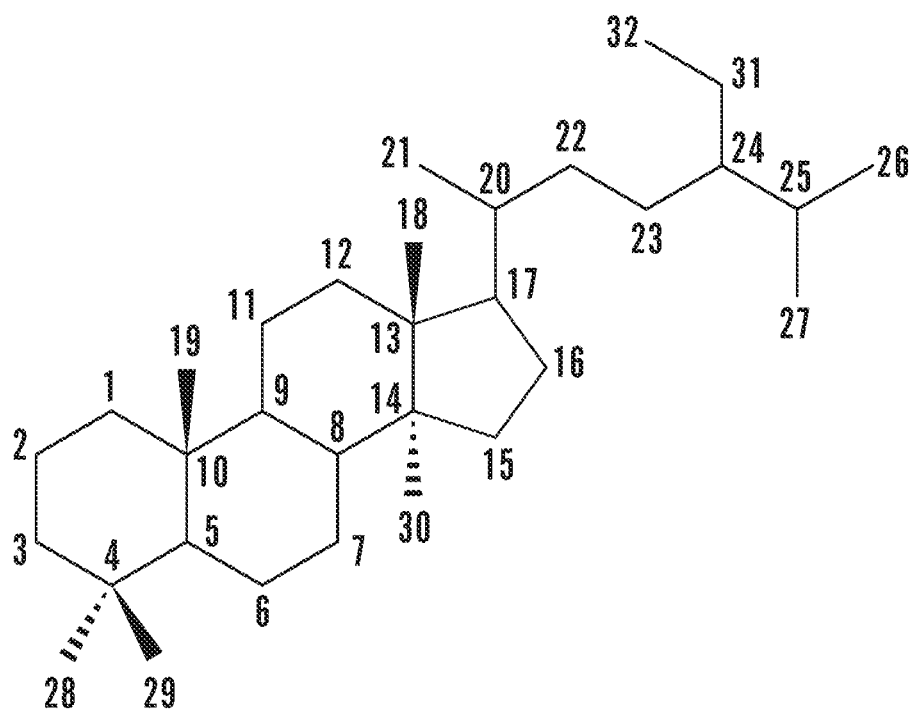
FIG. 14 shows the chemical structure of the steroid skeleton hormones, including Progesterone (PRG), Aldosterone (ALD), 5β-Pregnane-3α,20α-diol glucuronide (PRE-Glu), Hydrocortisone (CRT), Testosterone (TST), 5β-Pregnane-3α,20α-diol (PRE), 17β-Estradiol (ESD), Estrone (ESN) and Cholesterol (CHL).

In one embodiment bacteria were used to identify novel aTFs. RNA-seq was used to identify aTFs that are differentially regulated on exposure to the following target steroids: estradiol, estrone, estriol, progesterone, testosterone, aldosterone, prednisolone, androstadienone, cortisol, and cholesterol (FIGS. 7, 14 and 15). Growth curves were generated for each bacterium listed in Table 3 to determine doubling times in the corresponding growth medium, example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. A biosensor comprising:
(a) an allosteric transcription factor polypeptide conjugated to one or more first fluorescent molecules of a Fluorescence Resonance Energy Transfer (FRET) pair, the allosteric transcription factor comprising one or more ligand binding domains (LBDs) and one or more DNA binding domains (DBDs),
(b) a nucleic acid probe conjugated to one or more second fluorescent molecules of the FRET pair, the nucleic acid probe having a sequence comprising one or more transcription factor binding domains (TFBDs) that is specific to the DBD of the transcription factor,
wherein in the absence of an analyte of interest, the DBD of the transcription factor is bound to the TFBD of the nucleic acid probe, and the first fluorescent molecule and the second fluorescent molecule of the FRET pair emits a fluorescent signal, and in the presence of the analyte of interest, the analyte binds to the ligand binding domain (LBD) resulting in a conformational change that decreases the affinity of the DBD for the TFBD such that the DBD dissociates from the TFBD, resulting in the first fluorescent molecule and the second fluorescent molecule of the FRET pair no longer emitting a fluorescent signal (OFF biosensor); or
wherein in the absence of an analyte of interest, the DBD of the transcription factor is not bound to the TFBD of the nucleic acid probe, and the first fluorescent molecule and the second fluorescent molecule of the FRET pair does not emit a fluorescent signal, and in the presence of the analyte of interest, the analyte binds to the ligand binding domain (LBD) resulting in a conformational change that increases the affinity of the DBD for the TFBD such that the DBD binds to the TFBD, resulting in the first fluorescent molecule and the second fluorescent molecule of the FRET pair emitting a fluorescent signal (ON biosensor),
wherein the first fluorescent molecule or second fluorescent molecule, or both is a quantum dot (QD).
2. The biosensor of paragraph 1, wherein the first fluorescent molecule comprises a FRET acceptor, and the second fluorescent reporter each comprises a FRET donor.
3. The biosensor of paragraph 1, wherein the first fluorescent molecule is a quantum dot (QD) and the second fluorescent reporter is a fluorescent dye.
4. The biosensor of paragraph 1, wherein the first fluorescent molecule comprises a FRET donor, and the second fluorescent reporter each comprises a FRET acceptor.

5. The biosensor of paragraph 1, wherein the fluorescent molecule is selected from the group consisting of a quantum dot, a fluorescent dye, a fluorescent protein, and combinations thereof.
6. A biosensor comprising:
(a) an allosteric transcription factor polypeptide conjugated to one or more electroactive molecules, the allosteric transcription factor comprising one or more ligand binding domains (LBDs) and one or more DNA binding domains (DBDs),
(b) a nucleic acid probe attached to a conducting surface, the nucleic acid probe having a sequence comprising one or more transcription factor binding domains (TFBDs) that is specific to the DBD of the transcription factor,
wherein in the absence of an analyte of interest, the DBD of the transcription factor is bound to the TFBD of the nucleic acid probe, resulting in an increase in flow of electrons from the electroactive molecule to the conductive surface which is detected by the presence of, or an increase in a current across the surface, and in the presence of the analyte of interest, the analyte binds to the ligand binding domain (LBD) resulting in a conformational change that decreases the affinity of the DBD for the TFBD such that the DBD dissociates from the TFBD, resulting a decrease in the flow of electrons from the electroconductive molecule to the conductive surface which is detected by a decrease in current across the surface (OFF biosensor); or
wherein in the absence of an analyte of interest, the DBD of the transcription factor is not bound to the TFBD of the nucleic acid probe, and no flow of electrons from the electroactive molecule to the conductive surface which is detected by absence of a current across the surface, and in the presence of the analyte of interest, the analyte binds to the ligand binding domain (LBD) resulting in a conformational change that increases the affinity of the DBD for the TFBD such that the DBD binds to the TFBD, resulting in an increase in flow of electrons from the electroactive molecule to the conductive surface which is detected by the presence of, or increase in a current across the surface (ON biosensor).
7. The biosensor of any of paragraphs 1-6, wherein the ligand binding domain (LBD) that binds to an analyte of interest.
8. The biosensor of any of paragraphs 1-7 wherein the analyte of interest is selected from any of a small molecule, toxin, neurotransmitter, steroid, immunomodulator, metabolite, hormone.
9. The biosensor of any of paragraphs 1-8, wherein the hormone is selected from any of the group of: progesterone, estradiol, estrone, estriol, progesterone, testosterone, aldosterone, prednisolone, androstadienone, cortisol, cholesterol.
10. The biosensor of any of paragraphs 1-9, wherein the DNA binding domain (DBD) has been modified to increase or decrease its affinity for binding to the TFBD in the presence of the analyte.
11. The biosensor of any of paragraphs 1-10, wherein the TFBD has been modified to increase or decrease its affinity for binding to the DBD in the presence of the analyte.
12. The biosensor of any of paragraphs 1-11, wherein the allosteric transcription factor undergoes a confirmation change upon binding of the ligand to the LBD, thereby allowing the DBD to bind to the transcription factor binding domain.
13. The biosensor of any of paragraphs 1-12, wherein the allosteric transcription factor polypeptide is a microbial transcription factor.

14. The biosensor of any of paragraphs 1-13, wherein the allosteric transcription factor polypeptide is a microbial transcription factor to a hormone and the biosensor is a hormone biosensor.

15. The biosensor of any of paragraphs 1-14, wherein the analyte of interest is progesterone and the allosteric transcription factor is PinR comprising a polypeptide of at least 15-189 of SEQ ID NO: 1 or a variant of at least 85% sequence identity to the amino acids 15-189 of SEQ ID NO: 1.

16. The biosensor of paragraph 15, wherein PinR comprises a DBD comprising amino acids SEQ ID NO: 7 or a variant having at least 85% sequence identity to SEQ ID NO: 7, and wherein the nucleic acid probe comprises at least one TFBD comprising a nucleic acid sequence selected from any of SEQ ID NO: 13-17, or a nucleic acid sequence at least 85% homologous to any of SEQ ID NO: 13-17.

17. The biosensor of any of paragraphs 15-16, wherein PinR comprises a histidine tag at the C-terminus or N-terminus, or both.

18. The biosensor of any of paragraphs 15-16, wherein PinR is conjugated to a quantum dot (QD), and the nucleic acid probe is conjugated to a fluorescent dye or a fluorescent protein.

19. A hormone biosensor comprising:
(a) a microbial allosteric transcription factor polypeptide conjugated to one or more first fluorescent molecules of a Fluorescence Resonance Energy Transfer (FRET) pair, the allosteric transcription factor comprising one or more ligand binding domains (LBDs) and one or more DNA binding domains (DBDs),
(b) a nucleic acid probe conjugated to one or more second fluorescent molecules of the FRET pair, the nucleic acid probe having a sequence comprising one or more transcription factor binding domains (TFBDs) that is specific to the DBD of the transcription factor,
wherein in the absence of a hormone of interest, the DBD of the microbial allosteric transcription factor is bound to the TFBD of the nucleic acid probe, and the first fluorescent molecule and the second fluorescent molecule of the FRET pair emits a fluorescent signal, and in the presence of the hormone of interest, the hormone binds to the ligand binding domain (LBD) resulting in a conformational change that decreases the affinity of the DBD for the TFBD such that the DBD dissociates from the TFBD, resulting in the first fluorescent molecule and the second fluorescent molecule of the FRET pair no longer emitting a fluorescent signal (OFF biosensor); or
wherein in the absence of the hormone of interest, the DBD of the microbial allosteric transcription factor is not bound to the TFBD of the nucleic acid probe, and the first fluorescent molecule and the second fluorescent molecule of the FRET pair does not emit a fluorescent signal, and in the presence of the hormone of interest, the hormone binds to the ligand binding domain (LBD) resulting in a conformational change that increases the affinity of the DBD for the TFBD such that the DBD binds to the TFBD, resulting in the first fluorescent molecule and the second fluorescent molecule of the FRET pair emitting a fluorescent signal (ON biosensor), and
wherein the first fluorescent molecule or second fluorescent molecule, or both is a quantum dot (QD).

20. The hormone biosensor of paragraph 19, wherein the hormone biosensor is a progesterone biosensor.

21. The hormone biosensor of paragraph 20, wherein the progesterone biosensor comprises:

(a) a progesterone detecting polypeptide comprising a progesterone binding domain and a DNA binding domain (DBD) conjugated to a first fluorescent molecule of a FRET pair, the progesterone binding domain comprising amino acids of any of SEQ ID NO: 18, SEQ ID NO: 19 or SEQ ID NO: 10, or a variant thereof having an amino acid sequence at least 85% sequence identity to SEQ ID NO: 18-20, and the DNA binding domain comprising amino acids of SEQ ID NO: 7 or a variant thereof having an amino acid sequence at least 85% sequence identity to amino acids of SEQ ID NO:7, and
(b) a nucleic acid probe comprising at least one transcription factor binding domain (TFBD) comprising the nucleic acid sequence selected from any of: SEQ ID NO: 13-17, wherein the nucleic acid probe is conjugated to a second fluorescent molecule of a FRET pair,
wherein in the absence of progesterone, the DBD of the progesterone detecting polypeptide is bound to the TFBD of the nucleic acid probe, and the first fluorescent molecule and the second fluorescent molecule of the FRET pair emits a fluorescent signal, and in the presence of progesterone, progesterone binds to the ligand binding domain (LBD) resulting in a conformational change that decreases the affinity of the DBD for the TFBD such that the DBD dissociates from the TFBD, resulting in the first fluorescent molecule and the second fluorescent molecule of the FRET pair no longer emitting a fluorescent signal (OFF progesterone biosensor); or
wherein in the absence of progesterone, the DBD of the progesterone detecting polypeptide is not bound to the TFBD of the nucleic acid probe, and the first fluorescent molecule and the second fluorescent molecule of the FRET pair does not emit a fluorescent signal, and in the presence of progesterone, progesterone binds to the ligand binding domain (LBD) resulting in a conformational change that increases the affinity of the DBD for the TFBD such that the DBD binds to the TFBD, resulting in the first fluorescent molecule and the second fluorescent molecule of the FRET pair emitting a fluorescent signal (ON progesterone biosensor), and
wherein the first fluorescent molecule or second fluorescent molecule, or both is a quantum dot (QD).

22. The hormone biosensor of paragraph 21, wherein the progesterone detecting polypeptide comprises at least amino acids 15-189 of SEQ ID NO: 1 or a variant of at least 85% sequence identity to SEQ ID NO: 1.

23. The progesterone biosensor of paragraph 21, wherein the first fluorescent molecule of the FRET pair is a quantum dot (QD) and the second fluorescent molecule of the FRET pair is a fluorescent dye or fluorescent protein.

24. The hormone biosensor of any of paragraphs 21-23, wherein the ratio of quantum dot (QD) to progesterone detecting polypeptide to nucleic acid probe (i.e., QD/TF/DNA ratio) is selected from any of: (a) 1-10 of QD; to any of, (b) 1-20 of TF; to any of (c) 5-30 of DNA.

25. The hormone biosensor of any of paragraphs 21-24, where the progesterone biosensor can detect progesterone in a sample in range of: (a) from at least 0.001 ng/ml to 0.1 ng/ml; or (b) from at least 0.01 ng/ml to 10 ng/ml; or (c) from at least 0.05 ng/ml to 50 ng/ml.

26. A hormone biosensor comprising:
(a) a microbial allosteric transcription factor polypeptide conjugated to one or more electroactive molecules, the allosteric transcription factor comprising one or more ligand binding domains (LBDs) and one or more DNA binding domains (DBDs), (b) a nucleic acid probe attached to a conducting surface, the nucleic acid probe having a sequence comprising one or more transcription factor binding domains (TFBDs) that is specific to the DBD of the microbial allosteric transcription factor polypeptide wherein in the absence of a hormone of interest, the DBD of the microbial allosteric transcription factor is bound to the TFBD of the nucleic acid probe, resulting in an increase in flow of electrons from the electroactive molecule to the conductive surface which is detected by the presence of, or an increase in a current across the surface, and in the presence of the hormone of interest, the hormone binds to the ligand binding domain (LBD) resulting in a conformational change in the microbial allosteric transcription factor that decreases the affinity of the DBD for the TFBD such that the DBD dissociates from the TFBD, resulting a decrease in the flow of electrons from the electroconductive molecule to the conductive surface which is detected by a decrease in current across the surface (OFF biosensor); or wherein in the absence of a hormone of interest, the DBD of the microbial allosteric transcription factor is not bound to the TFBD of the nucleic acid probe, and no flow of electrons from the electroactive molecule to the conductive surface which is detected by absence of a current across the surface, and in the presence of the hormone of interest, the hormone binds to the ligand binding domain (LBD) resulting in a conformational change in the microbial allosteric transcription factor that increases the affinity of the DBD for the TFBD such that the DBD binds to the TFBD, resulting in an increase in flow of electrons from the electroactive molecule to the conductive surface which is detected by the presence of, or increase in a current across the surface (ON biosensor).

27. The hormone biosensor of paragraph 26, wherein the hormone biosensor is a progesterone biosensor.

28. The hormone biosensor of paragraph 27, wherein the progesterone biosensor comprises:

(a) a progesterone detecting polypeptide comprising a progesterone binding domain and a DNA binding domain (DBD) conjugated to at least one or more electroactive molecules, the progesterone binding domain comprising amino acids of any of SEQ ID NO: 18, SEQ ID NO: 19 or SEQ ID NO: 10, or a variant thereof having an amino acid sequence at least 85% sequence identity to SEQ ID NO: 18-20, and the DNA binding domain comprising amino acids of SEQ ID NO: 7 or a variant thereof having an amino acid sequence at least 85% sequence identity to amino acids of SEQ ID NO:7, and (b) a nucleic acid probe comprising at least one transcription factor binding domain (TFBD) comprising the nucleic acid sequence selected from any of: SEQ ID NO: 13-17, wherein the nucleic acid probe is immobilized or attached to a conducting surface, wherein in the absence of progesterone, the DBD of the progesterone detecting polypeptide is bound to the TFBD of the nucleic acid probe, resulting in an increase in flow of electrons from the electroactive molecule to the conductive surface which is detected by the presence of, or an increase in a current across the surface, and in the presence of progesterone, progesterone binds to the ligand binding domain (LBD) resulting in a conformational change in the progesterone detecting polypeptide that decreases the affinity of the DBD for the TFBD such that the DBD dissociates from the TFBD, resulting a decrease in the flow of electrons from the electroconductive molecule to the conductive surface which is detected by a decrease in current across the surface (OFF biosensor); or wherein in the absence of progesterone, the DBD of the progesterone detecting polypeptide is not bound to the TFBD of the nucleic acid probe, and no flow of electrons from the electroactive molecule to the conductive surface which is detected by absence of a current across the surface, and in the presence of progesterone, progesterone binds to the ligand binding domain (LBD) resulting in a conformational change in the progesterone detecting polypeptide that increases the affinity of the DBD for the TFBD such that the DBD binds to the TFBD, resulting in an increase in flow of electrons from the electroactive molecule to the conductive surface which is detected by the presence of, or increase, in a current across the surface (ON biosensor).

29. The progesterone biosensor of paragraph 28, wherein the progesterone detecting polypeptide comprises at least amino acids 15-189 of SEQ ID NO: 1 or a variant of at least 85% sequence identity to SEQ ID NO: 1.

30. A method of detecting an analyte of interest comprising using the biosensor of any of paragraphs 1-29.

31. The method of paragraph 30, wherein the biosensor is detected on a point-of care device (POC) device.

32. The method of paragraph 31, wherein the point-of-care device can electronically communicate with any one or more of: a smart device, a smartphone or mobile device, tablet, or clinical practitioner.

33. A system for detecting an analyte of interest in a sample;
(a) contacting the sample with a biosensor comprising:
  i. allosteric transcription factor polypeptide conjugated to one or more first fluorescent molecules of a Fluorescence Resonance Energy Transfer (FRET) pair, the allosteric transcription factor comprising one or more ligand binding domains (LBDs) and one or more DNA binding domains (DBDs), and
  ii. a nucleic acid probe conjugated to one or more second fluorescent molecules of the FRET pair, the nucleic acid probe having a sequence comprising one or more transcription factor binding domains (TFBDs) that is specific to the DBD of the transcription factor, wherein the biosensor is an OFF biosensor such that in the absence of an analyte of interest, the DBD of the transcription factor is bound to the TFBD of the nucleic acid probe, and the first fluorescent molecule and the second fluorescent molecule of the FRET pair emits a fluorescent signal, and in the presence of the analyte of interest, the analyte binds to the ligand binding domain (LBD) resulting in a conformational change in the allosteric transcription factor polypeptide that decreases the affinity of the DBD for the TFBD such that the DBD dissociates from the TFBD, resulting in the first fluorescent molecule and the second fluorescent molecule of the FRET pair no longer emitting a fluorescent signal (OFF biosensor); or wherein the biosensor is an ON biosensor such that in the absence of an analyte of interest, the DBD of the transcription factor is not bound to the TFBD of the nucleic acid probe, and the first fluorescent molecule and the second fluorescent molecule of the FRET pair does not emit a fluorescent signal, and in the presence of the analyte of interest, the analyte binds to the ligand binding domain (LBD) resulting in a conformational change in the allosteric transcription factor polypeptide that increases the affinity of the DBD for the TFBD such that the DBD binds to the TFBD, resulting in the first fluorescent molecule and the second fluorescent molecule of the FRET pair emitting a fluorescent signal (ON biosensor), and wherein the first fluorescent molecule or second fluorescent molecule, or both is a quantum dot (QD);

(b) measuring the fluorescence in the sample, and identifying the presence of the analyte of interest when one of the following occurs: (i) a decrease in FRET signal is detected when the biosensor is an OFF biosensor; or (ii) an increase in FRET signal is detected when the biosensor is an ON biosensor.

34. The system of paragraph 33, wherein the first fluorescent molecule comprises a FRET acceptor, and the second fluorescent reporter comprises a FRET donor.

35. The system of paragraph 33, wherein the first fluorescent molecule is a quantum dot (QD) and the second fluorescent reporter is a fluorescent dye.

36. The system of paragraph 33, wherein the first fluorescent molecule comprises a FRET donor, and the second fluorescent reporter each comprises a FRET acceptor.

37. The system of any of paragraphs 33-36, wherein the fluorescent molecule is selected from the group consisting of a quantum dot, a fluorescent dye, a fluorescent protein, and combinations thereof.

38. The system of any of paragraphs 33-37, wherein contacting the sample with a biosensor comprises placing the sample on, or in a sample well of a cassette or cartridge, wherein the cassette or cartridge comprises the biosensor, and wherein the sample well is in fluid communication with the biosensor, and the fluorescence from the biosensor can be measured.

39. The system of any of paragraphs 33-38, wherein the measuring the fluorescence is performed with a point-of-care device.

40. The system of paragraph 39, wherein the point-of-care device can electronically communicate with any one or more of: a smart device, a smartphone or mobile device, tablet, or clinical practitioner.

41. A system for detecting an analyte in a sample comprising:
(a) contacting the sample with a biosensor comprising:
    i. an allosteric transcription factor polypeptide conjugated to one or more electroactive molecules, the allosteric transcription factor comprising one or more ligand binding domains (LBDs) and one or more DNA binding domains (DBDs), and
    ii. a nucleic acid probe immobilized to a conducting surface, the nucleic acid probe having a sequence comprising one or more transcription factor binding domains (TFBDs) that is specific to the DBD of the transcription factor,
    wherein the biosensor is an OFF biosensor such that in the absence of an analyte of interest, the DBD of the transcription factor is bound to the TFBD of the nucleic acid probe, resulting in an increase in flow of electrons from the electroactive molecule to the conductive surface which is detected by the presence of, or an increase in a current across the surface, and in the presence of the analyte of interest, the analyte binds to the ligand binding domain (LBD) resulting in a conformational change in the allosteric transcription factor polypeptide that decreases the affinity of the DBD for the TFBD such that the DBD dissociates from the TFBD, resulting a decrease in the flow of electrons from the electroconductive molecule to the conductive surface which is detected by a decrease in current across the surface (OFF biosensor); or
    wherein the biosensor is an ON biosensor such that in the absence of an analyte of interest, the DBD of the transcription factor is not bound to the TFBD of the nucleic acid probe, and no flow of electrons from the electroactive molecule to the conductive surface which is detected by absence of a current across the surface, and in the presence of the analyte of interest, the analyte binds to the ligand binding domain (LBD) resulting in a conformational change in the allosteric transcription factor polypeptide that increases the affinity of the DBD for the TFBD such that the DBD binds to the TFBD, resulting in an increase in flow of electrons from the electroactive molecule to the conductive surface which is detected by the presence of, or increase in a current across the surface (ON biosensor), and
(b) measuring the current across the conducting surface, and identifying the presence of an analyte when one of the following occurs: (i) a decrease in current flow is detected when the biosensor is an OFF biosensor; or (ii) an increase in current flow is detected when the biosensor is an ON biosensor.

42. The system of any of paragraphs 33-41, wherein the ligand binding domain (LBD) that binds to an analyte of interest.

43. The system of any of paragraphs 33-42, wherein the analyte of interest is selected from any of a small molecule, toxin, neurotransmitter, immunomodulator, steroid, metabolite, hormone.

44. The system of any of paragraphs 33-43, wherein the hormone is selected from any of the group of: progesterone, estradiol, estrone, estriol, progesterone, testosterone, aldosterone, prednisolone, androstadienone, cortisol, cholesterol.

45. The system of any of paragraphs 33-44, wherein the DNA binding domain (DBD) has been modified to increase or decrease its affinity for binding to the TFBD in the presence of an analyte of interest.

46. The system of any of paragraphs 33-45, wherein the TFBD has been modified to increase or decrease its affinity for binding to the DBD in the presence of an analyte of interest.

47. The system of any of paragraphs 33-46, wherein the allosteric transcription factor is a microbial transcription factor.

48. The system of any of paragraphs 33-47, wherein the analyte of interest is progesterone and the allosteric transcription factor polypeptide is PinR comprising a polypeptide of at least 15-189 of SEQ ID NO: 1 or a variant of at least 85% sequence identity to the amino acids 15-189 of SEQ ID NO: 1.

49. The system of paragraphs 48, wherein PinR comprises a DBD comprising amino acids SEQ ID NO: 7 or a variant having at least 85% sequence identity to SEQ ID NO: 7, and wherein the nucleic acid probe comprises at least one TFBD comprising a nucleic acid sequence selected from any of SEQ ID NO: 13-17, or a nucleic acid sequence at least 85% homologous to any of SEQ ID NO: 13-17.

50. The system of any of paragraphs 48 or 49, wherein PinR comprises a histidine tag at the C-terminus or N-terminus, or both.

51. The system of any of paragraphs 48-50, wherein PinR is conjugated to a quantum dot (QD), and the nucleic acid probe is conjugated to a fluorescent dye or a fluorescent protein.

52. The system of any of paragraphs 33-51, wherein the sample is selected from a group of body fluids comprising sweat, blood, cerebrospinal fluid (CSF), plasma, whole blood, serum, semen, synovial fluid, saliva, vaginal lubrication, breast milk, amniotic fluid, urine, human feces, phlegm tears or saliva.

53. The system of any of paragraphs 33-52, wherein the sample is not a blood sample or a plasma sample.

54. The system of any of paragraphs 33-52, wherein the sample is not a biological sample.

55. The system of any of paragraphs 41-54, wherein contacting the sample with a biosensor comprises placing the sample into or on a sample well of a cassette or cartridge, wherein the cassette or cartridge comprises the biosensor, and wherein the sample well is in fluid communication with the biosensor, wherein the nucleic acid is immobilized to the surface of the conductible surface and the current across the conductible surface can be measured.

56. The system of any of paragraphs 41-55, wherein the measuring the current is performed with a point-of-care (POC) device.

57. The system of paragraph 49, wherein the point-of-care (POC) device can electronically communicate with any one or more of: a smart device, a smartphone or mobile device, tablet, or clinical practitioner.

58. A system for detecting a hormone of interest in a sample, comprising:
(a) contacting the sample with a hormone biosensor comprising:
  i. microbial allosteric transcription factor polypeptide conjugated to one or more first fluorescent molecules of a Fluorescence Resonance Energy Transfer (FRET) pair, the allosteric transcription factor comprising one or more ligand binding domains (LBDs) and one or more DNA binding domains (DBDs), and
  ii. a nucleic acid probe conjugated to one or more second fluorescent molecules of the FRET pair, the nucleic acid probe having a sequence comprising one or more transcription factor binding domains (TFBDs) that is specific to the DBD of the transcription factor,
  wherein the biosensor is an OFF biosensor such that in the absence of hormone of interest, the DBD of the microbial allosteric transcription factor is bound to the TFBD of the nucleic acid probe, and the first fluorescent molecule and the second fluorescent molecule of the FRET pair emits a fluorescent signal, and in the presence of the hormone of interest, the analyte binds to the ligand binding domain (LBD) resulting in a conformational change in the microbial allosteric transcription polypeptide that decreases the affinity of the DBD for the TFBD such that the DBD dissociates from the TFBD, resulting in the first fluorescent molecule and the second fluorescent molecule of the FRET pair no longer emitting a fluorescent signal (OFF biosensor); or
  wherein the biosensor is an ON biosensor such that in the absence of a hormone of interest, the DBD of the transcription factor is not bound to the TFBD of the nucleic acid probe, and the first fluorescent molecule and the second fluorescent molecule of the FRET pair does not emit a fluorescent signal, and in the presence of the hormone of interest, the analyte binds to the ligand binding domain (LBD) resulting in a conformational change in the microbial allosteric transcription polypeptide that increases the affinity of the DBD for the TFBD such that the DBD binds to the TFBD, resulting in the first fluorescent molecule and the second fluorescent molecule of the FRET pair emitting a fluorescent signal (ON biosensor), and
  wherein the first fluorescent molecule or second fluorescent molecule, or both is a quantum dot (QD);
(b) measuring the fluorescence in the sample, and identifying the presence of the hormone of interest when one of the following occurs: (i) a decrease in FRET signal is detected when the biosensor is an OFF biosensor; (ii) an increase in FRET signal is detected when the biosensor is an ON biosensor.

59. The system of paragraph 58, wherein the hormone of interest is progesterone.

60. The system of paragraph 59 for detecting progesterone in a sample, comprising:
(a) contacting the sample with a progesterone biosensor comprising:
  i. a progesterone detecting polypeptide comprising a progesterone binding domain and a DNA binding domain (DBD) conjugated to a first fluorescent molecule of a FRET pair, the progesterone binding domain comprising amino acids of any of SEQ ID NO: 18, SEQ ID NO: 19 or SEQ ID NO: 10, or a variant thereof having an amino acid sequence at least 85% sequence identity to SEQ ID NO: 18-20, and the DNA binding domain comprising amino acids of SEQ ID NO: 7 or a variant thereof having an amino acid sequence at least 85% sequence identity to amino acids of SEQ ID NO:7, and
  ii. a nucleic acid probe comprising at least one transcription factor binding domain (TFBD) comprising the nucleic acid sequence selected from any of: SEQ ID NO: 13-17, wherein the nucleic acid probe is conjugated to a second fluorescent molecule of a FRET pair,
  wherein the biosensor is an OFF progesterone biosensor such that in the absence of progesterone, the DBD of the progesterone detecting polypeptide is bound to the TFBD of the nucleic acid probe, and the first fluorescent molecule and the second fluorescent molecule of the FRET pair emits a fluorescent signal, and in the presence of progesterone, progesterone binds to the ligand binding domain (LBD) resulting in a conformational change that decreases the affinity of the DBD for the TFBD such that the DBD dissociates from the TFBD, resulting in the first fluorescent molecule and the second fluorescent molecule of the FRET pair no longer emitting a fluorescent signal (OFF progesterone biosensor); or
  wherein the biosensor is an ON progesterone biosensor such that in the absence of progesterone, the DBD of the progesterone detecting polypeptide is not bound to the TFBD of the nucleic acid probe, and the first fluorescent molecule and the second fluorescent molecule of the FRET pair does not emit a fluorescent signal, and in the presence of progesterone, progesterone binds to the ligand binding domain (LBD) resulting in a conformational change that increases the affinity of the DBD for the TFBD such that the DBD binds to the TFBD, resulting in the first fluorescent molecule and the second fluorescent molecule of the FRET pair emitting a fluorescent signal (ON progesterone biosensor), and
  wherein the first fluorescent molecule or second fluorescent molecule, or both is a quantum dot (QD).
(b) measuring the fluorescence in the sample, and identifying the presence of progesterone when one of the following occurs: (i) a decrease in FRET signal is detected when the biosensor is an OFF biosensor; (ii) an increase in FRET signal is detected when the biosensor is an ON biosensor.

61. The system of paragraph 60, wherein the progesterone detecting polypeptide comprises at least amino acids 15-189 of SEQ ID NO: 1 or a variant of at least 85% sequence identity to SEQ ID NO: 1.

62. The system of paragraph 60, wherein the first fluorescent molecule of the FRET pair is a quantum dot (QD) and the second fluorescent molecule of the FRET pair is a fluorescent dye or fluorescent protein.

63. The system of paragraph 60, wherein the ratio of fluorescent molecule to transcription factor, to Nucleic acid probe (i.e., QD/TF/DNA ratio) is selected from any of: (a) 1-10 of QD; to any of (b) 1-20 of TF; to any of (c) 5-30 of DNA.

64. The system of any of paragraphs 60-63, wherein contacting the sample with a biosensor comprises placing the sample into or on a sample well of a cassette or cartridge, wherein the cassette or cartridge comprises the biosensor, and wherein the sample well is in fluid communication with the biosensor, and the fluorescence from the biosensor can be measured.

65. The system of any of paragraphs 60-34, wherein the measuring the fluorescence is performed with a point-of-care device.

66. The system of paragraph 65, wherein the point-of-care device can electronically communicate with any one or more of: a smart device, a smartphone or mobile device, tablet, or clinical practitioner.

67. A system for detecting a hormone of interest in a sample, comprising:
(a) contacting the sample with a microbial biosensor comprising:
  i. a microbial allosteric transcription factor polypeptide conjugated to one or more electroactive molecules, the allosteric transcription factor comprising one or more ligand binding domains (LBDs) and one or more DNA binding domains (DBDs), and
  ii. a nucleic acid probe immobilized to a conducting surface, the nucleic acid probe having a sequence comprising one or more transcription factor binding domains (TFBDs) that is specific to the DBD of the transcription factor,
  wherein the biosensor is an OFF biosensor such that in the absence of a hormone of interest, the DBD of the transcription factor is bound to the TFBD of the nucleic acid probe, resulting in an increase in flow of electrons from the electroactive molecule to the conductive surface which is detected by the presence of, or an increase in a current across the surface, and in the presence of the hormone of interest, the hormone binds to the ligand binding domain (LBD) resulting in a conformational change in the microbial allosteric transcription factor polypeptide to decreases the affinity of the DBD for the TFBD such that the DBD dissociates from the TFBD, resulting a decrease in the flow of electrons from the electroconductive molecule to the conductive surface which is detected by a decrease in current across the surface (OFF biosensor); or
  wherein the biosensor is an ON biosensor such that in the absence of a hormone of interest, the DBD of the transcription factor is not bound to the TFBD of the nucleic acid probe, and no flow of electrons from the electroactive molecule to the conductive surface which is detected by absence of a current across the surface, and in the presence of hormone of interest, the hormone binds to the ligand binding domain (LBD) resulting in a conformational change in the microbial allosteric transcription factor polypeptide to increase the affinity of the DBD for the TFBD such that the DBD binds to the TFBD, resulting in an increase in flow of electrons from the electroactive molecule to the conductive surface which is detected by the presence of, or increase in a current across the surface (ON biosensor), and
(b) measuring the current across the conducting surface, and identifying the presence of the hormone of interest when one of the following occurs: (i) a decrease in current flow is detected when the biosensor is an OFF biosensor; (ii) an increase in current flow is detected when the biosensor is an ON biosensor;

68. The system of paragraph 67, wherein the hormone of interest is progesterone and the microbial biosensor is a progesterone microbial biosensor.

69. The system of paragraph 68, comprising a progesterone biosensor.

70. The system of paragraph 68, for detecting progesterone in a sample, comprising:
(a) contacting the sample with a progesterone biosensor comprising:
  i. a progesterone detecting polypeptide comprising a progesterone binding domain and a DNA binding domain (DBD) conjugated to at least one or more electroactive molecules, the progesterone binding domain comprising amino acids of any of SEQ ID NO: 18, SEQ ID NO: 19 or SEQ ID NO: 10, or a variant thereof having an amino acid sequence at least 85% sequence identity to SEQ ID NO: 18-20, and the DNA binding domain comprising amino acids of SEQ ID NO: 7 or a variant thereof having an amino acid sequence at least 85% sequence identity to amino acids of SEQ ID NO:7, and
  ii. a nucleic acid probe comprising at least one transcription factor binding domain (TFBD) comprising the nucleic acid sequence selected from any of: SEQ ID NO: 13-17, wherein the nucleic acid probe is immobilized or attached to a conducting surface,
  wherein the biosensor is an OFF progesterone biosensor such that in the absence of progesterone, the DBD of the progesterone detecting polypeptide is bound to the TFBD of the nucleic acid probe, resulting in an increase in flow of electrons from the electroactive molecule to the conductive surface which is detected by the presence of, or an increase in a current across the surface, and in the presence of progesterone, progesterone binds to the ligand binding domain (LBD) resulting in a conformational change in the progesterone detecting polypeptide that decreases the affinity of the DBD for the TFBD such that the DBD dissociates from the TFBD, resulting a decrease in the flow of electrons from the electroconductive molecule to the conductive surface which is detected by a decrease in current across the surface (OFF biosensor); or
  wherein the biosensor is an ON progesterone biosensor such that in the absence of progesterone, the DBD of the progesterone detecting polypeptide is not bound to the TFBD of the nucleic acid probe, and no flow of electrons from the electroactive molecule to the conductive surface which is detected by absence of a current across the surface, and in the presence of progesterone, progesterone binds to the ligand binding domain (LBD) resulting in a conformational change in the progesterone detecting polypeptide that increases the affinity of the DBD for the TFBD such that the DBD binds to the TFBD, resulting in an increase in flow of electrons from the electroactive molecule to the conductive surface which is detected by the presence of, or increase, in a current across the surface (ON biosensor).
(b) measuring the current across the conducting surface, and identifying the presence of progesterone when one of the following occurs: (i) a decrease in current flow is detected when the biosensor is an OFF biosensor; or (ii) an increase in current flow is detected when the biosensor is an ON biosensor 71. The system of paragraph 70, wherein the progesterone detecting polypeptide comprises at least amino acids 15-189 of SEQ ID NO: 1 or a variant of at least 85% sequence identity to SEQ ID NO: 1.

72. The system of any of paragraphs 67-71, where the system can detect progesterone in a sample in range of: (a) from at least 0.001 ng/ml to 0.1 ng/ml; or (b) from at least 0.01 ng/ml to 10 ng/ml; or (c) from at least 0.05 ng/ml to 50 ng/ml.

73. The system of any of paragraphs 67-72, where the system can detect progesterone in a sample in the range of: (a) from at least 0.01 nM to 1 µM; or (b) from at least 1 nM to 10 µM; or (c) from at least 5 nM to 50 µM.
74. The system of any of paragraphs 67-73, wherein the sample is is selected from a group of body fluids comprising sweat, blood, cerebrospinal fluid (CSF), plasma, whole blood, serum, semen, synovial fluid, saliva, vaginal lubrication, breast milk, amniotic fluid, urine, human feces, phlegm tears or salivablood, plasma, whole blood, serum, urine, stool, tear drop or saliva.
75. The system of any of paragraphs 67-74, wherein the sample is not a blood sample or a plasma sample.
76. The system of any of paragraphs 67-75, wherein the sample is a urine sample.
77. The system of any of paragraphs 67-76, wherein the sample is not a biological sample.
78. The system of any of paragraphs 67-77, wherein contacting the sample with a biosensor comprises placing the sample into or on a sample well of a cassette or cartridge, wherein the cassette or cartridge comprises the biosensor, and wherein the sample well is in fluid communication with the biosensor, wherein the nucleic acid is immobilized to the surface of the conductible surface and the current across the conductible surface can be measured.
79. The system of any of paragraphs 67-77, wherein the measuring the current is performed with a point-of-care (POC) device.
80. The system of paragraph 65, wherein the point-of-care device can electronically communicate with any one or more of: a smart device, a smartphone or mobile device, tablet, or clinical practitioner.

EXAMPLES

The following examples are provided by way of illustration not limitation.

Example 1

Development of a fluorescence biosensing system mediated by Transcription Factor-DNA Binding.

Transcription factors (TFs) are regulatory proteins that contain a DNA-binding domain as well as a ligand-binding domain able to recognize small molecules with high specificity and selectivity. In the presence of the target analyte, TF affinity for its DNA binding sequence is modulated, facilitating the repressor or derepressor regulation of downstream gene expression. Thus, both affinity-based target recognition and modulation capacity are inherent in the single protein.

Several FRET-based signal transduction mechanisms were developed to produce internally calibrated fluorescent signals from the binding and unbinding of a transcription factor to an oligomeric DNA sequence. By exploiting the difference in the binding affinity between the TF and its specific binding sequence in the presence and absence of a small molecule analyte, the TF-DNA binding and unbinding becomes a sensor for the small molecule effector (FIG. 1).

The transcription factor TetR was used because it is a well characterized allosteric TF that is used extensively for gene regulation and inducible protein expression in the laboratory setting. The TetR regulatory complex evolved in bacteria to turn on the production of TetA efflux pumps to protect the cells from the antibiotic tetracycline. In microbial systems, the biosynthetic precursor to tetracycline anhydrotetracycline (aTc) also binds to the repressor TF, TetR and induces production of the efflux pump shortly before the cell is exposed to the impending influx of tetracycline (McCormick J et al., 1968). As aTc itself is not an antimicrobial agent, its derepressor activity has been effectively harnessed to induce production of proteins encoded by downstream genes in synthetic biology.

Many mutations of TetR are known to change its responsivity to the analyte, e.g., revTetR flips the mode of action causing TF-DNA binding in the presence of aTc rather than its absence (Kamionka A et al., 2004), demonstrating the adaptability of the allosteric TF to a variety of sensing scenarios. Two variants of TetR were used, TetRc and TetRd, to demonstrate that the sensor output can be tuned by subtly modifying the binding affinity of the TF to its DNA oligo. Both TetRc and TetRd bound to the TetO DNA sequence in the absence of the effector molecule aTc. The TetO cognate sequence comprises a 19 bp binding region. The 19 bp cognate sequence was flanked by 4-5 bp on each side to ensure binding, resulting in a 28 bp DNA oligo. One of the strands was labeled with the FRET acceptor Cy5 on both the 5' and 3' ends. A second 28 bp sequence with no affinity for TetR was similarly labeled to act as the negative control (Table 4).

TABLE 4

Synthetic DNA oligonucleotides for TetR binding.
The TetO binding sequence is the center region shown in bold;
nucleotides labeled with Cy5 dye are underlined.

| Name | Sequence | |
|---|---|---|
| TetO (forward) | 5'-GTCA TCCCTATCATTGATAGAGA TACTG-3' | (SEQ ID NO: 18) |
| TetO (reverse) | 3'-<u>C</u>AGT AGGGATAGTAACTATCTCT ATGA<u>C</u>-5' | (SEQ ID NO: 19) |
| Scrambled (forward) | 5'-TCGT GAAACCGAGCGAGGGACAC GCACA-3' | (SEQ ID NO: 20) |
| Scrambled (reverse) | 3'-<u>A</u>GCA CTTTGGCTCGCTCCCTGTG CGTG<u>T</u>-5' | (SEQ ID NO: 21) |

Three FRET-based sensors utilizing the TF-DNA binding mechanism were developed and characterized for the sensing of the small molecule anhydrotetracycline, aTc. Each sensor consists of Cy5-modified DNA acting as the FRET acceptor with either a fluorescent protein-transcription factor (FP-TF) fusion protein (expressed in E. coli) or quantum dot-transcription factor (QD-TF) conjugate as the donor. The absorbance and emission spectra of the four fluorophores (FP tdTomato, two different batches of QDs (QD1 and QD2), and the organic dye Cy5) used are shown in FIG.

1. The QD-Cy5 FRET pairs exhibit increased spectral overlap between the respective emission peaks and the Cy5 absorption compared to tdTomato (Table 5). The much higher quantum yield of tdTomato compared to the QDs, however, results in a larger calculated Förster distance, R0, for the tdTomato-Cy5 FRET pair than the calculated R0 for the QD1-Cy5 or QD2-Cy5 FRET pairs (Table 5).

TABLE 5

The FRET parameters of sensors 1-3.

| Sensor | Donor | QY (%) | J (×10$^{16}$ M$^{-1}$ cm$^{-1}$ nm$^4$) | R$_0$ (nm) |
|---|---|---|---|---|
| 1 | tetR-tdTomato | 69.0 | 1.34 | 7.43 |
| 2 | QD1 CdSe/4CdS/2ZnS | 23.4 | 2.69 | 6.96 |
| 3 | QD2 CdSe/6CdS/2ZnS | 17.0 | 2.02 | 6.29 |

$^a$ All three sensors utilized Cy5 as the acceptor dye; the Cy5 molar extinction coefficient of 250,000 M$^{-1}$ cm$^{-1}$ was used for each of the overlap integral calculations.

While as synthesized QDs can exhibit near unity Quantum yields (QYs), the thiolate-based ligands that produce the smallest possible organic coating on the semiconductor surface for water solubility are widely known to significantly quench the QD photoluminescence due to the introduction of surface trap states. The thin organic coating is desirable both to reduce donor-acceptor distance and to facilitate histidine-tag-mediated self-assembly of the proteins to the QD surface. A moderately thick shelled core/shell QD heterostructure can be used to improve the QD QY following ligand exchange while moderating the distance added between the donor and acceptor molecules for efficient energy transfer (Chern et al. 2017).

A core/shell/shell QDs comprising CdSe/4CdS/2ZnS and CdSe/6CdS/2ZnS as QD1 and QD2 donors was used, respectively, where the number before the shell composition indicates the number of atomic monolayers that were deposited on the core. The diameter of the semiconductor QD1 based on TEM imaging was 7.6±1.1 nm while DLS of the water-soluble particles indicated a hydrodynamic diameter of 10±1.9 nm, showing the minimal increase in size from the CL4 ligand coating.

Figures 2A, 2B, 2C:
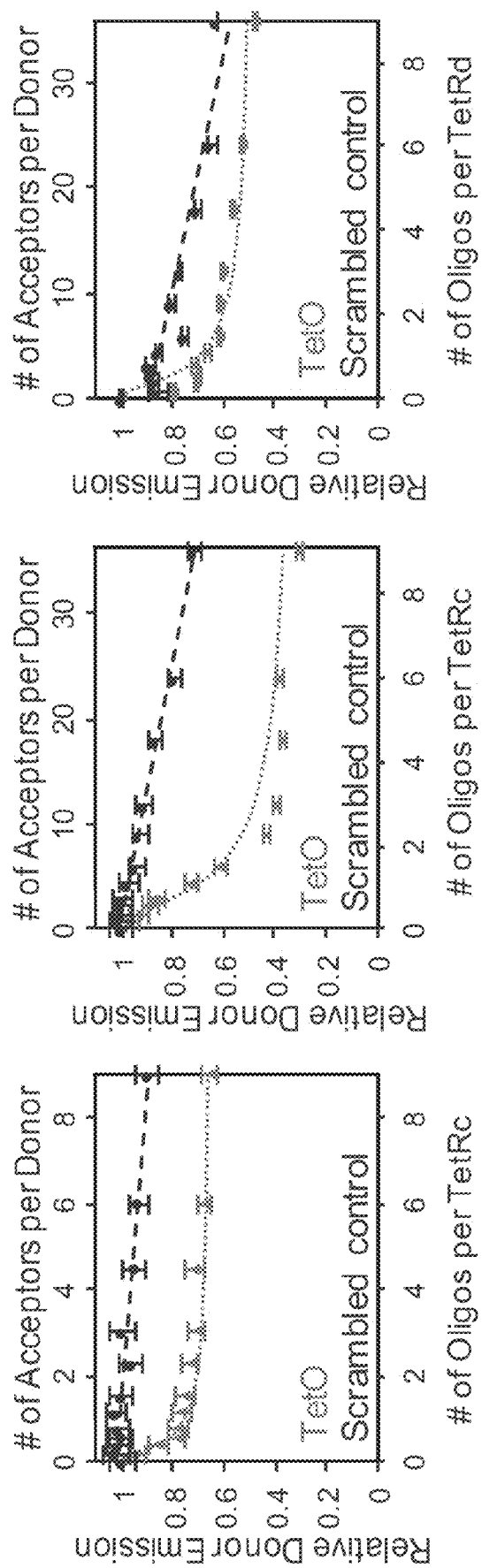
FIGS. 2A-2C show the relative donor emission as a function of the amount of Cy5-labeled DNA acceptor. The bottom axis indicates the ratio of Cy5-DNA to TF (TetRc or TetRd), while the top axis indicates the ratio of Cy5-DNA to the donor fluorophore (tdTomato, QD1, or QD2) to account for the difference in the stoichiometry of sensor 1 compared to sensors 2 and sensor 3.
Figures 3A, 3B, 3C:
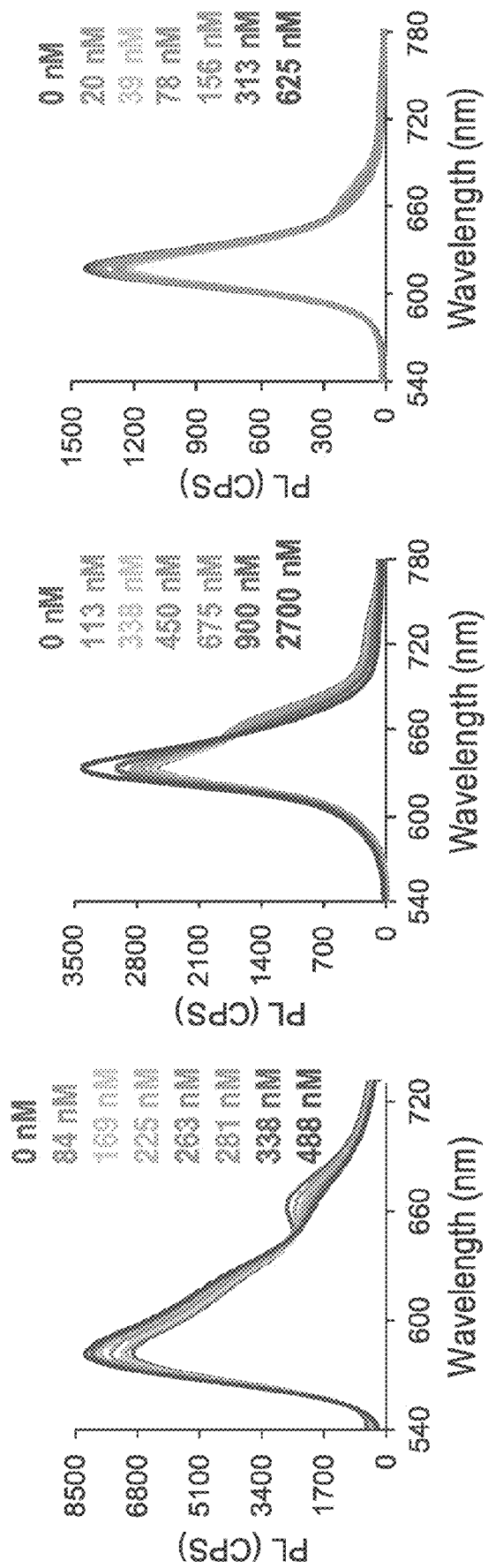
FIGS. 3A-3F show representative spectral data for sensor 1, senor 2 and sensor 3.
Figures 3D, 3E, 3F:
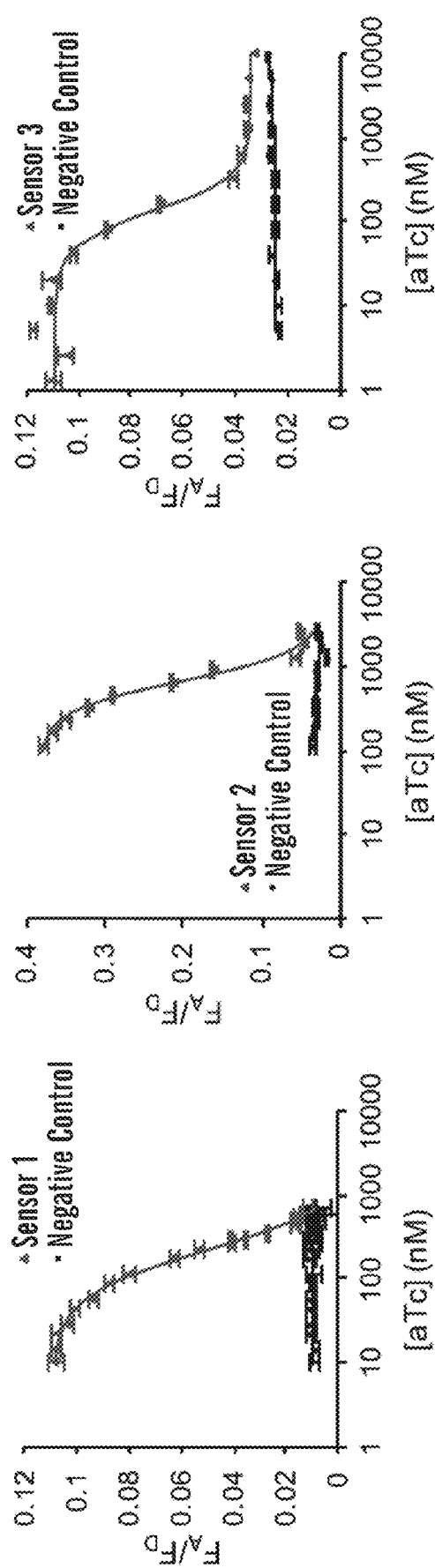

For QD-based nanoconstructs, the his-tagged proteins self-assemble to the QD surface stoichiometrically according to the mixture ratio with a Poissonian distribution of proteins on the QD surface was used. Stoichiometric ratios of protein to QD (i.e., 1, 2, 4, or 6 His6-TFs per QD) showed that the largest response to the Cy5-DNA titration was seen when a sufficient number of TFs were used (i.e., >2) for all QDs to be labeled. Four his6-TetR monomers were used per QD for the titrations of Sensors 2 and 3 (FIG. 2A-C). Binding of the Cy5-modified DNA to the TetR-modified donors was demonstrated by titrating increasing concentrations of the DNA; the donor concentration was adjusted to keep overall TF concentration constant at 200 nM. Upon increasing DNA concentration, there is increased donor quenching in all three cases. There was much less donor quenching when titrating a non-binding DNA sequence at the same concentrations, demonstrating specific binding and donor quenching (FIG. 2A-C).

A TF to DNA ratio was chosen for each sensor (1:3 for Sensor 1, 1:4.5 for Sensors 2 and 3) and kept constant for subsequent experiments testing sensor sensitivity to aTc. Photoluminescence spectra were measured from sensors with increasing concentrations of aTc yielded changes in the ratio between the acceptor emission and donor emission ($F_A/F_D$). With increasing concentrations of aTc, $F_A/F_D$ values decreased indicating unbinding of the DNA from the TF resulting in an increase in donor emission and decrease in acceptor emission (FIG. 3A-F). No changes were observed when aTc was titrated into a solution of non-binding donor-acceptor pairs (scrambled controls). This shows the specific recovery of donor emission (and reduction in acceptor emission) due to TF-DNA unbinding.

Sensor 2 exhibited the highest FRET efficiency (50%) compared to Sensor 1 (30%) and Sensor 3 (14%). Sensor 3 also demonstrates the lowest FRET efficiency of the three sensors. To compare the three sensors, the sensor outputs were fit to a modified Hill equation written as:

$$S(c) = S_1 + \frac{(S_0 - S_1)}{1 + \left(\frac{c}{EC_{50}}\right)^h},$$

where $S_0$ is the intensity of the sensor signal with no analyte present, $S_1$ is the intensity of the sensor signal at saturating analyte concentration, c is the analyte concentration, $EC_{50}$ is the concentration at which there is 50% signal (aka the effective concentration, or EC50), and h is the Hill coefficient, which indicates cooperative binding. For visual comparison, the sensor outputs were normalized and plotted together (FIGS. 4A and B).

TABLE 6

Summary of Logistic Fit Coefficients and Limit of detection (LOD) Analysis.

| Sensor | Esensor | EC50 (nM) | h | LOD* (nM) | Signal-to-Noise Ratio |
|---|---|---|---|---|---|
| 1 | 0.300 | 218 ± 9.18 | 1.57 ± 0.0802 | 15.8-26.7 | 6.20 |
| 2 | 0.500 | 699 ± 26.4 | 2.37 ± 0.191 | 0-164 | 13.9 |
| 3 | 0.140 | 133 ± 6.15 | 2.14 ± 0.185 | 0-30.3 | 3.90 |

*Reported LOD range is the 95% confidence interval around the calculated LOD based on n = 3 replicates.

Comparisons of the sensor outputs of Sensor 1-3 during the titration of aTc revealed a hierarchy of sensitivity where Sensor 3>Sensor 1>Sensor 2. These results indicated an inverse relationship between FRET efficiency and sensor sensitivity. Sensor 1 exhibited a higher sensitivity compared to Sensor 2. The inherent 1:1 donor: acceptor ratio of Sensor 1 allowed for the sensor components to exist only in two states at equilibrium when aTc is present: (1) tetR-tdTomato bound to Cy5-DNA and (2) tetR-tdTomato unbound to Cy5-DNA. This allows for a much greater change in signal intensity between the two states. The multivalency of Sensor 2 allowed for four different binding states from Cy5-DNA and QD-TetR being completely unbound to Cy5-DNA occupying all four binding sites of the QD-tetR conjugate. The ability for Sensor 2 to exist in multiple bound states hinders its sensitivity (i.e. multiple (un)binding events requiring multiple aTc molecules are required to transition between the maximum and minimum FRET states).

The comparison between Sensor 2 and 3 further showed that binding (and unbinding) of the TF and DNA primarily determined the sensor sensitivity. Sensor 2 and 3 used very similar FRET schemes, but exhibited higher sensitivity to aTc compared to Sensor 2 when comparable sensor components are used and only the binding affinity of the TF is changed. The lower affinity for TetRd for the DNA results in weaker binding, and therefore requires a lower concentration of aTc present to induce unbinding. Sensors 1 and 3 show a more pronounced response to the analyte compared to Sensor 2 (FIG. 4B).

Materials and Methods for the development of a fluorescence biosensing system mediated by Transcription Factor-DNA Binding.

Materials

Quantum Dot Synthesis. Cadmium oxide (CdO; 99.95%, Alfa Aesar), sulfur (99.95%, ACROS Organics), and 1-octadecene (ODE; 90%, ACROS Organics) were used as purchased from Fisher Scientific. Zinc acetate (99.99%), selenium (99.99%; pellets), oleic acid (OA; 90%), oleylamine (80%-90%), trioctylphosphine (TOP; 97%), and trioctylphosphine oxide (TOPO; ReagentPlus®, 99%) were used as purchased from Sigma-Aldrich. HPLC-grade solvents including hexanes (Fisher Scientific), methanol (Honeywell), chloroform (J. T. Baker), and ethanol (Sigma-Aldrich) were bought and used without further purification.

CL4 Ligand Synthesis. DL-Thioctic acid (≥98%; ACROS Organics), 1,1'-carbonyldiimidazole (CDI; 97%, ACROS Organics), methyl acrylate (≥99%, ACROS Organics), sodium borohydride (NaBr4), and silica gel sorbent (230-400 mesh, grade 60) were purchased from Fisher Scientific. Ethylenediamine (≥99%), lithium hydroxide (LiOH; ≥98%), hydrochloric acid (HCl; 37%), and sodium hydroxide (NaOH; 50% in H2O) were purchased from Sigma-Aldrich.

Protein Expression and Purification. NEB® 5-alpha (Cat #C2987I) and BL21(DE3) (Cat #C2527I) competent *Escherichia coli* cells were purchased from New England Biolabs and used to replicate and express plasmids, respectively. LB broth (Lennox; powder), kanamycin sulfate (mixture of Kanamycin A (main component) and Kanamycin B and C; powder), isopropyl b-D-thiogalactopyranoside (IPTG; ≥99%), phosphate buffered saline, pH 7.4 (PBS; packets), and lysozyme from chicken egg white (~7000 U/mg; powder (crystalline)) were purchased from Sigma-Aldrich. Dextrose (granules (crystalline)), Halt™ protease inhibitor cocktails (100×) were purchased from Fisher Scientific. 1,4-Dithiothreitol (DTT; >99% (protease-free)) was bought and used as is from Gold Biotechnology (St. Louis, Mo.). Nickel-nitrilotriacetic acid (Ni-NTA) agarose resin and Strep-tactin® Superflow Plus resin were purchased from Qiagen (Germantown, Md.) for affinity-tag chromatography purification of proteins. Strep-tactin® Purification Buffer Set was purchased from IBA (Gottingen, Germany). Sodium phosphate (NaH$_2$PO$_4$; ≥98%, monobasic monohydrate), sodium chloride (NaCl; BioXtra, ≥99.5%), and imidazole (≥99%) were purchased from Sigma for buffer preparation used with Ni-NTA agarose resin. Acrylamide/Bis-Acrylamide (37.5:1) 40% (w/v) solution (BioBasic, ON, Canada), glycine (≥99%, Sigma-Aldrich), N,N,N',N'-tetramethylethylenediamine (TEMED; ~99%, Sigma-Aldrich), ammonium persulfate (APS; ≥98%, Sigma-Aldrich), SDS-PAGE protein standards, broad range (unstained, Bio-Rad), tris(hydroxymethyl) aminomethane (ultra pure, Research Products International (RPI)), sodium dodecylsulfate (SDS; powder, RPI), bromophenol blue (Sigma-Aldrich), 2-mercaptoethanol (BME; ≥99%, Sigma-Aldrich), glycerol (≥99.5%, Fisher Scientific), Coomassie Brillant Blue G (250, Sigma-Aldrich), and acetic acid (glacial, J. T. Baker) were purchased for SDS-PAGE protein molecular weight verification. Protein assay kit II (Bradford reagent) was purchased from Bio-Rad for protein quantification.

FRET assays. Bovine serum albumin (BSA; DNase- and protease-free, Fisher Scientific), tris-hydrochloride (Tris-HCl; ≥99%, Promega), magnesium chloride hexahydrate (MgCl$_2$; ≥99%, Sigma-Aldrich), salmon sperm DNA solution (UtraPure™, Invitrogen), and anhydrotetracycline hydrochloride (aTc; Alfa Aesar) were used as purchased.

Methods

Dose-Response Curves Analysis

Fluorescent spectra were analyzed using MATLAB (Mathworks) and were fitted with a sum of 2 Gaussians (D=QD: FWHM=27 nm, $\lambda_{max}$=607 nm; A=DNA-Cy5: FWHM=40 nm, $\lambda_{max}$=669 nm). The area of each Gaussian was extracted and $F_D$ and $F_A$ are obtained respectively for the fluorescence of QD (donor) and Cy5 (acceptor).

Raw dose-response curves were obtained by plotting $F_A/F_D$ as a function of the steroid concentration. Sensor output is the normalization of the fluorescent spectra of the donor and acceptor according to the following equation:

$$\text{Sensor output} = \frac{Fi - Fmax}{(Fmin - Fmax)}$$

Where $F=F_A/F_D$, Fi is for [PRG]=i, $F_{min}$ stands for the average on 3 experiments of F for [PRG]=0 nM and Fmax stands for the average on 3 experiments of F for [PRG]=10 uM.

Non-normalized dose-response were fitted with Origin Pro 8 software with the non-linear equation:

$$y = A_2 + \frac{A_1 - A_2}{1 + \left(\frac{x}{IC50}\right)^p}$$

Cross Reactivity

The cross-reactivity of progesterone regarding the different steroids was calculated with the following equation:

$$\% \text{ Cross reactivity} = \frac{IC50 \text{ of analyte}}{IC50 \text{ of cross} - \text{reactant}}$$

Cross-reactivity assays were performed using sensor 3 in HEPES 1×.

No cross-reactivity was observed with PRE, PRE-glu, CHL and ESN from 0 to 10 uM of steroids and the dose-response curves could not be fitted with the non-linear equation.

TABLE 7

The crossreactivity of progesterone in regard of different steroids.

| Steroid | $X_0$/nM | P | % cross-reactivity |
|---|---|---|---|
| ALD | 289 ± 36 | 1.65 ± 0.28 | 20 ± 2 |
| CRT | 180 ± 19 | 1.23 ± 0.13 | 33 ± 3 |
| PRG | 59 ± 4 | 1.31 ± 0.10 | — |

Limit of Detection

The detection limit (according to IUPAC) is the smallest concentration or absolute amount of analyte that has a signal significantly larger than the signal arising from a reagent blank. Mathematically, the limit of detection in the signal domain ($L_D$) is given by: $L_D = \text{mean}_{blank} - 3.3 \times \sigma_{test}$ $$L_D = \text{mean}_{blank} - 3.3 \times \sigma_{test}$$

where $\text{mean}_{blank}$ is the mean signal for a reagent blank and $\sigma_{test}$ is the pool standard deviation for all test samples in the dilution series, calculated as[9]:

$$\sigma_{test} = \sqrt{\frac{\sum_{i=1}^{m} \sigma_i^2}{m}}$$

where $\sigma_i$ is the standard deviation in signal intensities for n replicates of the ith test concentration, with a total of m different test concentrations.

Then the Limit of detection (LOD) is calculated using the parameters of the fit with the non-linear equation (XX) for y=$L_D$:

$$LOD = IC_{50} \times \sqrt[p]{\frac{A_1 - A_2}{L_D - A_2} - 1}$$

The 95% Confidence Interval was calculated using Origin Pro Software. Thus the 95% interval on LOD was calculated using $L_D$ on those confidence intervals.

Quantum Dot Preparation. CdSe cores were nucleated using a modification of a previously described protocol[18]. Briefly, 1 g TOPO, 8 ml ODE, and 1.9 ml 0.2 M Cd(OA)$_2$ (1:4) were added to a 100 ml round bottom flask and degassed at room temperature for 30 mins. The flask was heated to 80° C. and degassed for another 30 mins. The temperature was raised to 300° C. under argon atmosphere and a pre-mixed solution of 0.4 ml 1 M TOP:Se, 3 ml oleylamine, and 1 ml ODE was immediately injected into the flask. After 3 mins, the flask was removed from the heating mantle and cooled to room temperature on a cork ring. Once cooled, the raw QD core solution was transferred into an argon atmosphere glovebox and precipitated using a mixture of methanol and ethanol. After centrifugation, CdSe cores were resuspended in hexanes and stored at 4° C. under air-free conditions for future use.

Four or six atomic layers of a CdS shell were deposited on top of the CdSe cores using a previously described modified successive ion layer adsorption and reaction (SILAR) method (Li et al., 2003; Ghsosh et al., 2012; Chern et al., 2017) to produce QD1 and QD2, respectively. For this, 5 ml ODE and 5 ml oleylamine were added to a 100 ml round bottom flask and degassed for 30 mins at room temperature and 30 mins at 80° C. before two hundred nmols of CdSe cores in hexanes were injected into the reaction flask and degassed for another 30 mins at 80° C. The core solution was heated to 160° C. and enough cadmium oleate to coat the CdSe cores with a single atomic monolayer of material was added in the form of 0.2 M Cd(OA)$_2$ (1:4 Cd:OA) in ODE. The reaction was maintained at 160° C. for 1 hour before the temperature was raised to 240° C., where it was held for 1.5 hr. The same amount of sulfur was added in the form of 0.2 M sulfur dissolved in ODE and the reaction annealed for 1 hour. All subsequent injections and anneals were performed at 240° C. with Cd and S anneals of 2.5 and 1 hours, respectively. An additional 2 layers of ZnS was added on top of the QDs to passivate the surface in preparation of water solubilizition. The same SILAR method was used as above, but with 0.2 M Zn(OA)$_2$ (1:4 Zn: OA) as the cation precursor and 1 hour anneal times for both Zn and S additions.

QDs were precipitated using a mixture of methanol and ethanol and resuspended in chloroform. TEM images were taken on a JOEL 2100 and images analyzed to determine size distribution. QDs were transferred to water in a biphasic ligand exchange reaction using a zwitterionic ligand CL4 as previously described. Quantum yield measurements were taken using the six-inch Quanti-phi integrating sphere attachment on the Horiba Nanolog.

Protein Expression and Purification. *Escherichia coli* BL21(DE3) were transformed with plasmids. Cells were grown at 37° C. in LB broth supplemented with a final concentration of 0.4% glucose and 33 µg/ml kanamycin. Protein expression was induced at an OD600 between 0.5-1 by adding IPTG to a final concentration of 1 mM followed by expression at 30° C. for 4-16 hours. Cells were harvested by centrifugation, redispersed in 10 mM PBS, 1 mM DTT, 1× Halt protease inhibitor cocktail, and stored at −80° C. until purification. For purification, 1 mg of lysozyme was added for every ml of thawed whole cell lysate and allowed to incubate for 1 hour at 4° C.

Soluble proteins were obtained by centrifugation at 4° C. for 30 mins at 18,000 rpm. Cleared cell lysates were purified using a Strep-tactin column for the tetR-tdTomato (FP-TF) fusion protein and a Ni-NTA column for tetR-6His. Fractions were collected and analyzed using a 12% SDS-PAGE gel and fractions containing FP-TF were pooled. The pooled fractions were concentrated and buffer exchanged into tris-buffered saline (TBS) via 10 kDa centrifugal filters (Amicon). Concentrations were determined using a Bradford assay as well as UV spectroscopy using the molar extinction coefficient of tdTomato (138,000 $M^{-1}$ $cm^{-1}$).

DNA Hybridization. The synthetic 28 bp tetO-containing oligonucleotide and its complement with modified 5'- and 3'-Cy5 were purchased from Integrated DNA Technologies (IDT) and hybridized to generate double-stranded fluorescent oligos. Equimolar amounts of each oligonucleotide were mixed with 1× nuclease-free duplex buffer (30 mM Hepes pH 7.5, 100 mM KAc, IDT), heated to 95° C. for 2 mins, and cooled to room temperature wrapped in aluminum foil to prevent photooxidation of the Cy5 dye.

FRET assays. The FRET response of each sensor as a function of the donor-acceptor ratio was tested by titration of the acceptor while the concentration of the donor was kept constant. Briefly, the sensors were prepared in a solution of TBS+0.2% (w/v) BSA and 1× binding buffer (20 mM Tris-HCl, 5 mM $MgCl_2$, 5% glycerol, 50 ng/µl salmon sperm DNA). For Sensor 1, the final concentration of tetR-tdTomato was kept constant at 200 nM, while Cy5-modified DNA were titrated to yield donor-acceptor ratios ranging from 0-9. The sensor solution was pipetted into wells of a black, non-binding 384-well plate (Corning) with a final volume of 60 µl. For triplicate measurements, each of the above solutions were prepared with a final volume of 180 µl in microcentrifuge tubes and pipetted into 3 separate wells of 60 µl each.

For Sensors 2 and 3, QDs and tetR-6His were mixed at a 1:4 ratio with a final QD concentration of 50 nM for self-assembly of the tetR-6His to the surface of the QDs[21]. The QD-tetR conjugates were then incubated with varying concentrations of the Cy5-modified DNA to yield donor-acceptor ratios ranging from 0-9.

Emission spectra were taken with the MicroMax plate reader attachment on a Horiba Nanolog fluorimeter with tetR-tdTomato excitation set at 500 nm and QD excitation set at 400 nm with a slit width of 2 nm and 3 s integration time per well. Negative controls were prepared as described above using a Cy5-modified scrambled DNA sequence as the acceptor to account for collisional quenching of the donor.

The analyte response curves of each sensor were obtained as described above, but with the titration of aTc. For Sensor 1, the ratio of tetR-tdTomato and Cy5-modified DNA were kept constant at 1:3. aTc was added such that the final concentrations of the components were 200 nM TetR-tdTomato, 600 nM Cy5-modified DNA, and 0-675 nM aTc. For Sensors 2 and 3, a 1:4:18 ratio of QDs, TetR-6His, and Cy5-modified DNA was kept constant respectively, and aTc was added with final concentrations of 50 nM QDs, 200 nM TetR-6His, 900 nM Cy5-modified SNA, and 0-2700 nM aTc.

Calculating FRET parameters. The overlap integral, J, describes the spectral overlap of the donor emission and acceptor absorbance according to the following equation[14]:

$$J = \int \overline{F_D}(\lambda) \varepsilon_A(\lambda) \lambda^4 d\lambda,$$

where $\overline{F_D}(\lambda)$ is the normalized donor emission spectrum and $\varepsilon_A(\lambda)$ is the molar extinction coefficient of the acceptor as a function of wavelength $\lambda$. The Förster distance $R_0$ is defined as the donor-acceptor distance at which 50% FRET efficiency is observed as described by[14]:

$$R_0^6 = (0.02108) \kappa^2 Q_D \frac{1}{\eta^4},$$

where $\kappa^2$ is the dipole orientation factor, which is set to 2/3 under the assumption of random dipole orientation, $Q_D$ is the donor quantum yield, and $\eta$ is the solvent refractive index.

Raw spectral data were smoothed using a Pearson model to remove any instrument noise, background subtracted for direct acceptor excitation and the donor and acceptor emission peak-fitted using OriginPro. The sensor output, defined as the ratio of the areas of acceptor emission over donor emission ($F_A/F_D$), was calculated using the integrals of the peak emissions and plotted to determine the linear and dynamic range of the sensors. Where normalized data is presented, errors were propagated mathematically with an assumption of no covariance.

Calculating Sensor Limit of Detection. The limit of detection of each sensor was calculated using method previously described[22] by first determining its limit of detection in the signal domain defined as:

$$L_D = \text{mean}_{blank} - 3.3 \sigma_{test},$$

where $\text{mean}_{blank}$ is the average signal of the sensor with no analyte present and $\sigma_{test}$ is the pool standard deviation for all test samples in the dilution series, calculated as follows:

$$\sigma_{test} = \sqrt{\frac{\sum_{i=1}^{m} \sigma_i^2}{m}},$$

where $\sigma_i$ is the standard deviation in signal intensities for n replicates of the ith test concentration, with a total of m different test concentrations.

The limit of detection (LOD) is calculated using the fit coefficients (Table 6) and modified Hill equation (Eq.3) with $S(c) = L_D$ to yield:

$$LOD = EC_{50} \times \sqrt[p]{\frac{S_0 - S_1}{L_D - S_1} - 1}$$

The linear ranges of the sensors were calculated using the inflection points of the sigmoidal fits, as previously described.

Example 2

Development of a whole transcriptome RNA sequencing screen for steroid binding Transcription Factors.

Genes for the bacterial utilization of steroids are often found as islands in the genome. These islands are typically induced by their substrates under the control of steroid binding Transcription Factors often found in close genomic proximity. Bacterial Transcription Factors also commonly bind their own promoters.

In order to identify steroid binding Transcription Factors, a whole transcriptome RNA sequencing (RNA-Seq) screen was developed (FIG. 7). The growth of *Pimelobacter simplex* bacteria was profiled with respect to the starting inoculation density, solvent toxicity, and the addition of steroids (FIG. 16). A starting OD of 0.005 produced an optimal growth curve with a clear lag phase, linear log phase, and steady stationary phase. *P. simplex* bacteria were screened against the steroid solvents ethanol (EtOH) and dimethyl sulfoxide (DMSO). Selecting the highest solvent concentration that did not produce a physiological change in growth compared to a solvent-free control, subsequent experiments included 0.70% and 0.35% by volume EtOH or DMSO, respectively. Steroid growth curves were similarly performed using a starting OD of 0.005 and constant solvent dosing with titrations of steroids. To elicit the largest possible steroid-specific change in gene regulation while avoiding a stress response, the highest steroid concentrations exhibiting normal growth profiles was used in subsequent cultures for RNA extraction and RNA-Seq. *P. simplex* bacteria were grown in the presence of 700 μM testosterone, 21.88 μM progesterone, 87.50 μM estrone, 21.88 μM 17β-estradiol, 21.88 μM hydrocortisone, or 175.00 μM aldosterone concentrations were selected for comparison.

Analysis of RNA-Seq libraries by a Log2 fold change expression comparison of steroid treated *P. simplex* bacteria against solvent controls identified a steroid responsive genome island (SRGI) denoted by a red box in the whole genome view in FIG. 8. The upregulation of genes inside the SRGI were observed in *P. simplex* bacteria when exposed to progesterone, aldosterone, hydrocortisone, and testosterone, but not when exposed to 17β-estradiol and estrone.

The RNA-Seq analysis identified genes with significant changes in their gene expression, defined as more than a 1× Log2 fold change. Using accession gene tags, genes were annotated for steroid relevant enzymes or transcription factors. Analysis of the SRGI revealed a variety of genes responsible for steroid recognition and degradation. The list of genes in the SRGI include a 3-ketosteroid-9-α-hydroxylase, 3-ketosteroid-δ-dehydrogenases, and a steroid 6-isomerase. Zooming into the TF coded for by gene 5330, a TetR family TF, revealed an upstream 22 bp imperfect palindrome sequence immediately before the ketosteroid dehydrogenase. Allosteric TF binding sequences are often palindromes and typically located near the start of its gene location in an intergenic space. With such a design, the allosteric TF can regulate itself or the open reading frame (ORF) near it in response to its effector molecule. Within the SRGI two TF candidates were identified, both next to a ketosteroid dehydrogenase. Once identified, the TFs were cloned and recombinantly expressed for thorough characterization.

Materials and Methods for the development of a whole transcriptome RNA sequencing screen for steroid binding Transcription Factors.

Materials

All DNA oligonucleotides were purchased from IDT Technologies. Progesterone, Cholesterol, Cortisol, Estrone, 5β-Pregnane-3α,20-α-diol and 5β-Pregnane-3α,20-α-diol glucuronide were bought from Sigma Aldrich. Artificial urine DIN EN1616:199 was bought from Pickering laboratories.

Cadmium oxide (CdO; 99.95%, Alfa Aesar), Sulfur (99.95%, ACROS Organics), 1-octadecene (ODE; 90% ACROS Organics), and oleylamine (80%-90%) were bought from Fisher Scientific and used as purchased. Zinc acetate (99.99%), Selenium pellets (99.99%), Trioctylphosphine (TOP, 97%), and oleic acid (OA, 90%), Poly(isobutylene-alt-maleic anhydride)-6000 g/mol, (2-aminoethyl)trimethylammonium chloride, Histamine, Trimethylamine, HEPES (4-(2-hydroxyethyl)-1-piperazineethanesulfonic acid) were obtained from Sigma-Aldrich. HPLC-grade solvents including hexanes (Fisher Scientific), methanol (Honeywell), anhydrous dimethyl sulfoxide (Sigma Aldrich) and chloroform (J. T. Baker) were bought and used without further purification. HEPES 1× is a solution of 25 mM of HEPES and 150 mM of NaCl, adjusted to pH 7.6.

TABLE 8

Abbreviations

| Abbreviation | Name |
| --- | --- |
| ALD | Aldosterone |
| CHL | Cholesterol |
| CRT | Hydrocortisone |
| ESN | Estrone |
| ESD | 17β-Estradiol |
| FWHM | Full Width Half Maximum |
| IC50 | Half maximal inhibitory concentration |
| LOD | Limit of detection |

TABLE 8-continued

Abbreviations

| Abbreviation | Name |
| --- | --- |
| PRE | 5β-Pregnane-3α,20-α-diol |
| PRE-glu | 5β-Pregnane-3α,20-α-diol glucuronide |
| PRG | Progesterone |
| QD | Quantum Dot |
| TF (aTF) | Transcription Factor (allosteric transcription factor) |

TABLE 9

DNA-Cy5 sequences.

| Name | Abb. | Sequence 5'→3' |
| --- | --- | --- |
| AIY20223.2 | DNA1 | 5Cy5-GCCTAACTAGCCGTTCGGCTAGTTATTC-3Cy5 (SEQ ID NO: 24) |
| ccAIY20223.2 | CcDNA1 | 5'-GAATAACTAGCCGAACGGCTAGTTAGGC-3' (SEQ ID NO: 25) |
| IG.AIY19519.15 | DNA2 | 5Cy5-GCCTAACTAGCCGATCGGCTAGTCATTC-3Cy5 (SEQ ID NO: 26) |
| ccIG.AIY19519.15 | ccDNA2 | 5'-GAATGACTAGCCGATCGGCTAGTTAGGC-3' (SEQ ID NO: 27) |
| AIY20222.2 | DNA3 | 5Cy5-GCCTAACTAGCCGTTCGGCAAGTAATTC-3Cy5 (SEQ ID NO: 28) |
| ccAIY20222.2 | CcDNA3 | 5'-GAATTACTTGCCGAACGGCTAGTTAGGC-3' (SEQ ID NO: 29) |
| 13,15-T,T | DNA4 | 5Cy5-CCTTAACTAGCCGTTCTGTTAGTTATT C-3Cy5 (SEQ ID NO: 30) |
| cc13,15-T,T | ccDNA4 | 5'-GAATAACTAACAGAACGGCTAGTTAAGG-3' (SEQ ID NO: 31) |
| scrambled | scbd | 5Cy5-TGTGCGTGTCCCTCGCTCGGTTTCA GA-3Cy5 (SEQ ID NO: 32) |
| ccscrambled | ccscbd | 5'-TCGTGAAACCGAGCGAGGGACACGCACA-3' (SEQ ID NO: 33) |

TABLE 10

Effect of DNA sequence on sensitivity and dynamic range of the sensor.

| DNA | X0/uM | P | [Pro]min/uM |
| --- | --- | --- | --- |
| DNA1 | 0.46 ± 0.02 | 1.16 | 0.073 |
| DNA2 | 0.37 ± 0.01 | 1.13 | 0.051 |
| DNA3 | 0.29 ± 0.02 | 1.17 | 0.040 |
| DNA4 | 0.15 ± 0.01 | 2.29 | 0.044 |

TABLE 11

Effect of different ratio of QD/TF/DNA for DNA 3 on sensitivity and dynamic range of the sensor.

| QD/TF/DNA | X0/uM | P | [Pro]min/uM |
| --- | --- | --- | --- |
| 1/1/2 | 0.21 | 1.45 | 0.040 |
| 1/2/2 | 0.27 | 1.43 | 0.053 |
| 1/4/2 | 0.20 | 1.69 | 0.050 |
| 1/1/18 | 0.35 | 1.30 | 0.072 |
| 1/2/18 | 0.41 | 1.26 | 0.070 |
| 1/4/18 | 0.29 | 1.17 | 0.040 |
| 1/10/18 | 0.39 | 1.20 | 0.065 |
| 1/16/18 | 0.44 | 1.20 | 0.075 |

TABLE 12

Effect of different ratio of QD/TF/DNA for DNA 4 on sensitivity and dynamic range of the sensor.

| QD/TF/DNA | X0/uM | P | [Pro]$_{min}$/uM |
|---|---|---|---|
| 1/1/18 | 0.074 ± 0.018 | 1.21 | 0.017 |
| 1/4/9 | 0.14 ± 0.014 | 3.19 | 0.066 |
| 1/4/18 | 0.15 ± 0.012 | 2.29 | 0.044 |
| 1/16/8 | 0.38 ± 0.016 | 3.83 | 0.190 |
| 1/1/4 | 0.049 ± 0.012 | 2.88 | 0.024 |

Strain Selection

*Pimelobacter simplex* (nee *Corynebacterium*) has been selected due to literature reports suggesting steroid sensitivity. The strain was purchased from the American Type Culture Collection (ATCC) (#6946) and referenced with a corresponding GenBank accession number (CP009896.1). The strain is an obligate aerobe and was propagated and grown in media and conditions as recommended by ATCC.

Strain Characterization

In order to properly determine the doubling time of the strain, growth curves were performed. All growth curves were done in 100 μL per well volumes in 96 well flat clear bottom black polystyrene TC-treated microplates which were individually wrapped with a lid and sterile (Corning #3603). Measurements were done by an Infinite M200 Pro (TECAN) spectrophotometer at the temperature suited for *P. simplex*. Readings were performed over 96 cycles of 15 minutes each at 600 nm absorbance with 25 flashes in a 3×3 (XY-Line) type reads per well. In between reads there was orbital shaking at 150 rpm frequency for a total of 10 minutes. In order to characterize the growth alone, a ½ serial dilution of 9 concentrations from 0.5-0.0020 OD600 nm were prepared in the respective media. Then each concentration was measured as previously described using a microplate reader (TECAN) and normalized against a media background control in technical triplicate. Afterward, an appropriate starting concentration of cells was chosen with a substantially long lag-phase, linear log phase, and a plateau of stationary-phase.

Solvent Exposure

Once an appropriate starting cell concentration was chosen, a secondary growth curve was performed to test the toxicity levels of the solvents used to dissolve steroids of interest. Since the steroids used are heavily hydrophobic, they often need to be dissolved in organic solvents such as DMSO or ethanol which are toxic to bacteria at high concentrations. *P. simplex* was incubated under microplate reader conditions previously mentioned at a starting OD determined by the first growth curve with DMSO, ethanol, or H$_2$O at ½ serial dilutions for a total of eight concentrations (50-0.39%) tested in technical triplicate. Two controls were included per solvent; a positive control without solvent and a media control which allowed for appropriate normalization. Solvent exposure growth curves allowed for choosing the maximum amount of solvent concentration that strains would sustain while maintaining relative viability in order to determine a range of steroid concentrations which could be used.

Steroid Exposure

A tertiary growth curve was performed to test the toxicity levels of steroid specific to *P. simplex*. The strain was incubated under microplate reader conditions previously mentioned at a starting OD determined by the first growth curve and the highest solvent concentration corresponding to the steroid of interest with steroid at ½ serial dilutions for a total of seven concentrations tested in singlet. Testosterone, progesterone, 17β-estradiol, hydrocortisone, and aldosterone were all dissolved in ethanol while estrone was dissolved in DMSO. Three controls were included for each steroid; a positive control with the highest tolerable solvent concentration (%), a positive control with media, and a media control which allowed for normalization. Steroid exposure growth curves allowed for choosing the maximum amount of steroid concentration that *P. simplex* would sustain while maintaining relative viability.

RNA Extraction

Cells were grown in 6 mL volumes of media at the OD, solvent, and steroid concentrations found from the growth curves in 14 mL polypropylene round-bottom tubes (Corning #352059) in technical duplicate. The same controls as in the steroid exposure growth curve were used for setting up RNA extraction samples. The cells were incubated at their corresponding temperature with continuous orbital shaking at 150 rpm until the end of lag-phase, mid-log phase, or stationary phase from the start of inoculation. Afterward, samples were removed and a 1:1 ratio of RNAprotect Bacteria Reagent (Qiagen #76506) was added followed by spinning down at 4° C. for 10 minutes at 4000 g. Supernatant was removed and the pellet re-suspended in 300 μL of RNAprotect and transferred into 2.0 mL Safe-Lock Tubes (Eppendorf #3101). The samples were then spun down once again at 4° C. for 10 minutes at 10000 g. Once the supernatant has been removed the samples were placed on ice and ready for RNA extraction. RNA extraction was done by Qiacube (Qiagen #9001292) set to the RNeasy Protect Bacteria Mini Kit protocol of bacterial cell pellet with enzymatic lysis. Tube A was prepared as described except with the addition of 150 mg/mL lysozyme (Sigma-Aldrich #L6876) and 20 mg/mL proteinase K (Roche #03115879001) all diluted in 1xTE buffer. RNA samples were subsequently quantified using Qubit RNA HS Assay Kit (Thermo Fisher Scientific #Q32852) and analyzed using a RNA 6000 Pico Kit (Agilent 5067-1513) in a 2100 Bioanalyzer (Agilent G2939A). RNA samples were either immediately used for RNA-Seq library preparation or stored long-term at −80° C.

RNA-Seq Library Preparation

After RNA samples have been quantified and analyzed they were DNase treated using a TURBO DNase 2 U/μL (Thermo Fisher Scientific #AM2238) and cleaned using Agencourt RNAClean XP SPRI beads (Beckman Coulter #A63987). RNA-Seq libraries were then produced from these samples using a slightly modified ScriptSeq v2 RNA-Seq Library Preparation Kit (Illumina 455A/22124) ensuring use of unique index primers through ScriptSeq Index PCR Primers (Sets 1-4) 48 rxns/set (Illumina #SSIP1234). Libraries were quantified by both a Qubit dsDNA HS Assay Kit (Thermo Fisher Scientific #Q32851) and by High Sensitivity DNA Kit (Agilent #5067-4626). The resulting molarity was then used to determine at what concentration samples should be pooled to (either 1, 2, or 4 nM). After a desired pooling concentration was chosen, the samples were diluted to that particular molarity and 2 μL of each sample dilution was added into a single tube and submitted to the Boston University Microarray and Sequencing Resource Core Facility. Whole transcriptome RNA sequencing was performed by a NextSeq 500 (Illumina) at high output (400 M reads) with 75 bp paired end sequencing read length.

Example 3

Development of a Biosensor Optical Readout

A fluorescent biosensor was designed to produce a two-color, ratiometric signal output in response to differential binding of the TF and the DNA oligonucleotide. FRET (Förster resonance energy transfer) is a non-radiative energy transfer process that is highly dependent on the distance between the donor and acceptor fluorophores, making it an effective signal transduction mechanism to indicate molecular binding. Semiconductor quantum dots (QDs) are powerful fluorescent nanoparticles widely used in bioimaging and biosensing. Their high photostability, color tunability, and abundant particle surface area available for biofunctionalization make them attractive fluorophores for bright and stable FRET-based biosensors.

CdSe/CdS/ZnS QDs were coated with a zwitterionic polymer bearing histamine anchoring functions (P1, SI). Once the hydrophobic QDs were transferred into H2O using a biphasic ligand exchange, his-tagged TFs were self-assembled on the QD surface to produce the QD-TF. Addition of the double stranded, Cy5-labeled TF-binding sequence completed probe assembly as the oligo binds to the TF in the absence of progesterone (PRG). The molar ratios of the QD, TF, and DNA in the sensor were controlled through the stoichiometric ratios of the mixed parts. His-tag binding to QDs is exhibits a Poissonian distribution of biomolecules per QD centered around the stoichiometric ratio, and the binding of the DNA to the TF is dictated by their binding affinity.

When no PRG is present in the media and upon UV-vis axcitation and/or exposition, the excited QDs (donor) was able to emit fluorescence and transfer energy via FRET to the DNA-Cy5 (acceptor) (FIG. 9A). Two fluorescent spectra were recorded, one from the QDs and one from the Cy5 due to the FRET. By adding PRG to the media, the fluorescence emission of the QDs (donor) increase while the fluorescence emission of the Cy5 (acceptor) decrease. Indeed, when the DNA-Cy5 unbind the QD-TF, the Cy5 is too far from the QDs surface to be able to receive energy from the QDs. As such, no fluorescence is emitted anymore from the Cy5.

Figure 9B:
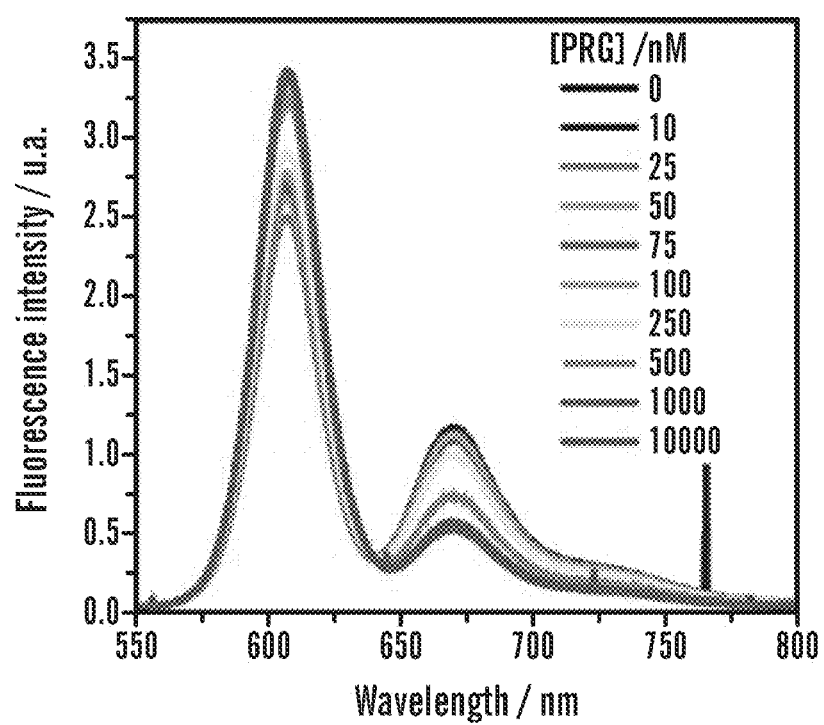
Figures 9C, 9D:
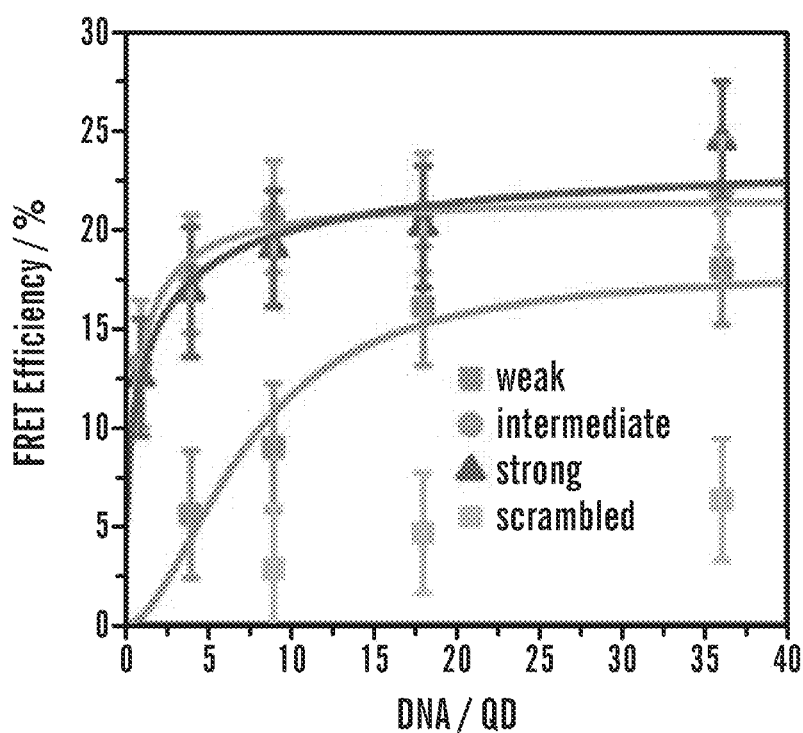
Figure 9E:
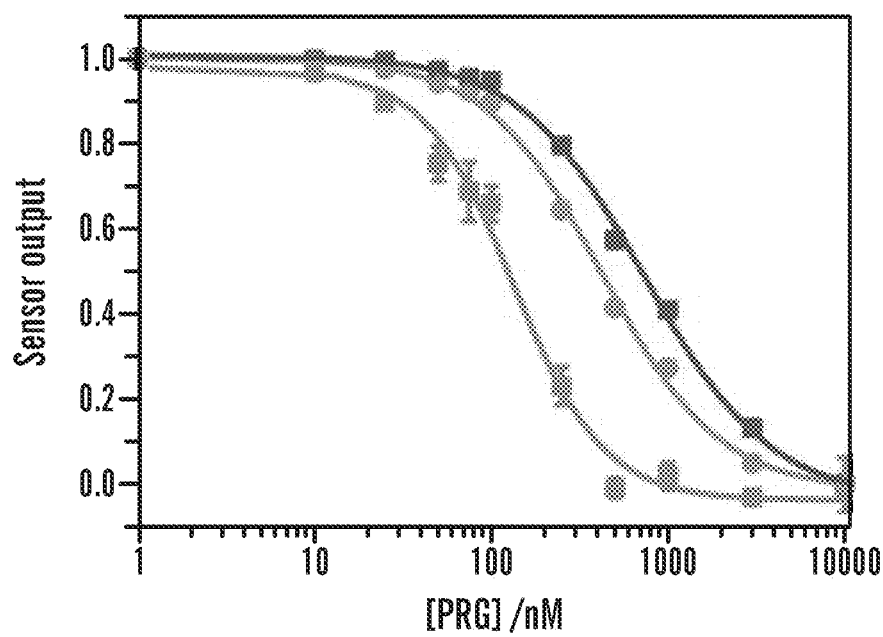
Figure 9F:
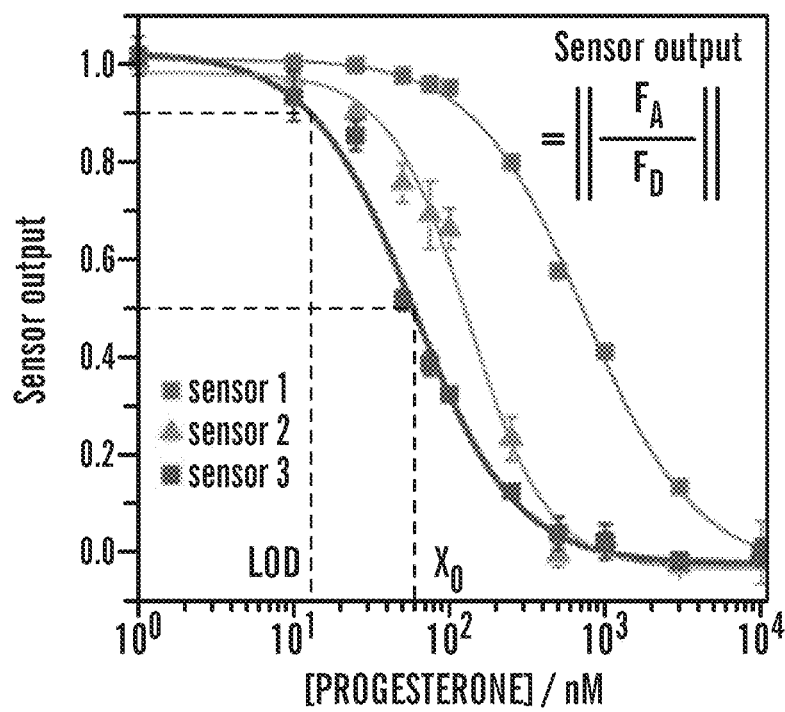
Figure 9G:
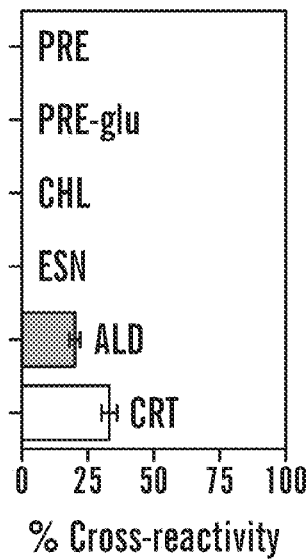

First, the DNA1 (most binding sequence) has been used to build the first biosensor, named sensor 1. For this sensor, a ratio of QD/TF/DNA of 1/4/18 was chosen. There was a significant decrease of the fluorescence of Cy5 (FA), and an increase of the fluorescence of QDs (FD) when the PRG concentration varies from 0 to 10 uM (FIG. 9B). As such, over this concentration range, the $F_A/F_D$ ratio plotted against PRG concentration (FIG. 9C) significantly decrease (from 0.267 to 0.086). In order to homogenize the fluorescent signals in between batches and different sensor variations, $F_A/F_D$ was normalized to give the signal output. Signal output is then plotted against PRG concentration to give a dose-response curve (FIG. 9C) This curve was fitted with the non-linear equation XX to obtain the half-maximal inhibitory concentration (IC50) (Table 13). For sensor 1, the IC50 was 738±46 nM of PRG. For sensor 2, the IC50 was 133±9 nM of PRG. The IC50 was further lowered and the number of TF/QD was decreased from 4 (sensors 1 and 2) to 1 (sensor 3). For sensor 3, the IC50 was 57±3 nM of PRG. For this sensor, the limit of detection (LOD) was a low as 15.30 nM of PRG.

TABLE 13

IC50 and LOD values obtained for each sensor.

| Sensor | IC50 nM | LOD nM | LOD 95% CI nM |
|---|---|---|---|
| 1 | 738 ± 27 | 52.58 | [49.62; 56.65] |
| 2 | 133 ± 9 | 35.66 | [29.10; 42.47] |
| 3 | 57 ± 3 | 15.30 | [12.50; 17.90] |

In order to test the reversibility of the sensor, sensor 3 was exposed to PRG and dialyzed on a 10k membrane (FIG. 9D-H). After the first round of dialysis, sensor 3 recovered the original signal output. This sensor was then exposed to PRG at 5 concentrations and a significant decrease of the sensor output was observed, matching the results obtained after the first excitation and/or exposition. The sensor was dialyzed and exposed to PRG one more round and similar results were obtained.

The stability of sensor 3 was tested under different conditions (FIG. 9F): before PRG addition, the sensor was either stored in the fridge or at RT up to 7 days or was lyophilized and recovered in $H_2O$. The sensor was then exposed to PRG at 4 different concentrations. In all the conditions tested, no significant changed was observed between the freshly made sensor (JO) or the stored one. More interestingly, the sensor could be lyophilized and stored dried without affecting its performance. The TF, QD, and DNA assembly is then highly stable under harsh conditions which is critical for the potential manufacturing and distribution of this new type of TF-based biosensor.

The sensor was highly reproducible from one batch to the other (FIG. 9G): when changing the batch of QDs-P1 and the batch of TF, no change was observed.

Figure 9H:
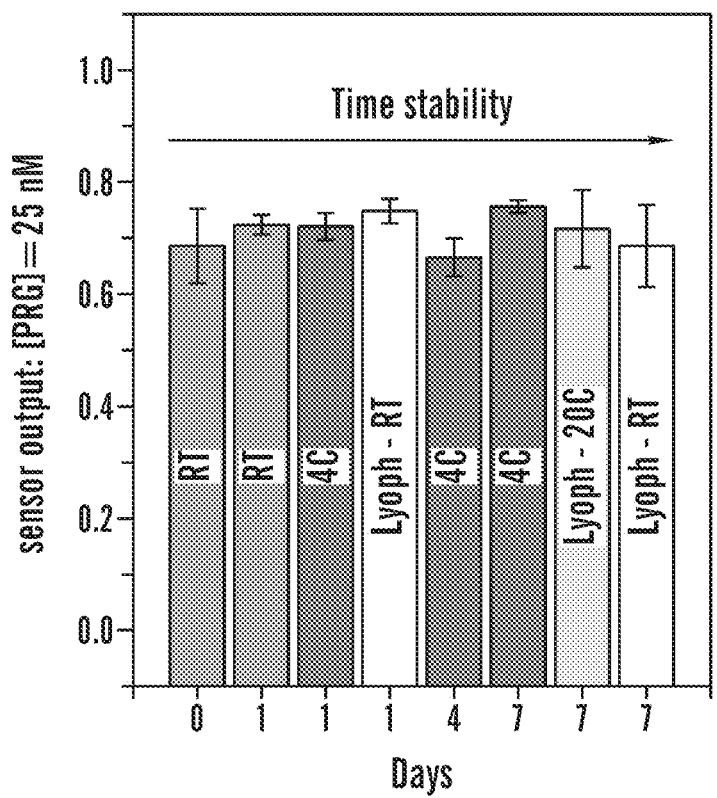
Figures 9I, 9J, 9K:
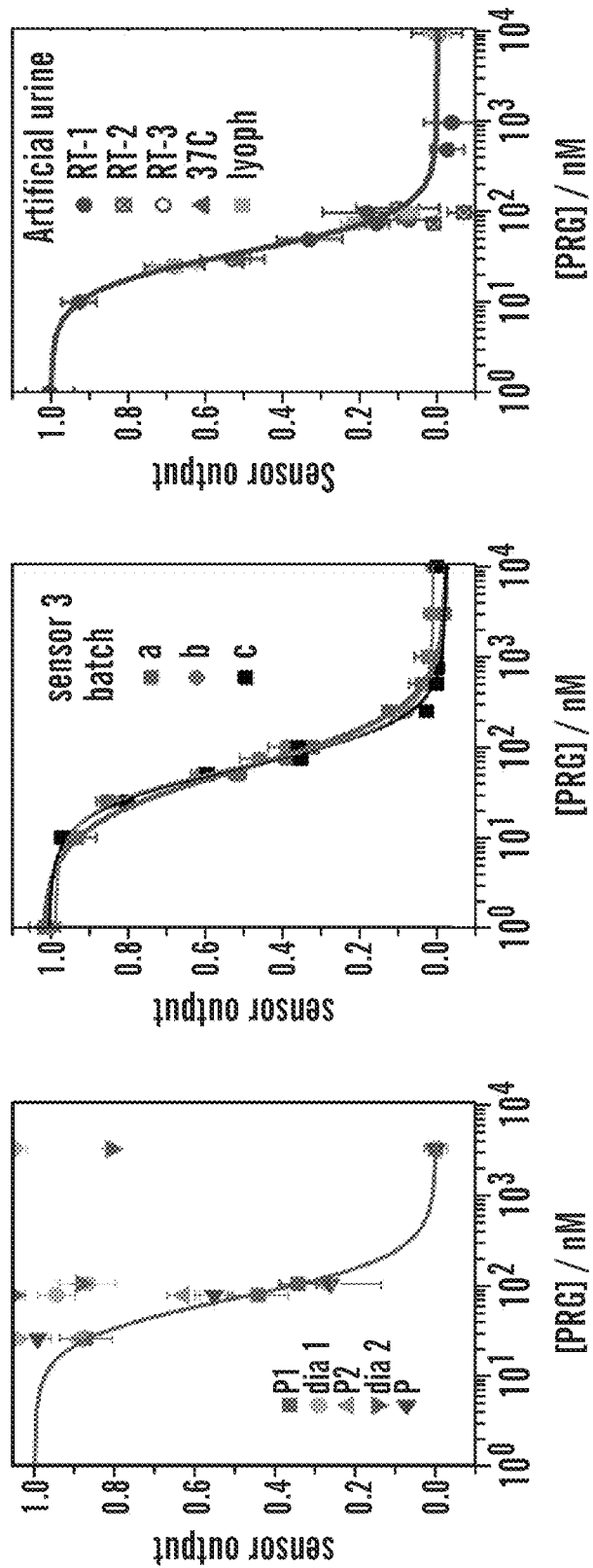

Sensor 3 was also tested for the detection of artificial urine (FIG. 9H). Sensor 3 showed a good dose-response in artificial urine. Sensor 3 was also tested in artificial urine warmed at 37C, lyophilized and recovered in urine with similar results.

Materials and Methods for the Development of a Biosensor Optical Readout

Quantum Dot Synthesis

Core/shell/shell quantum dots were made using a slightly modified version of a previously reported procedure. The precursors used for this synthesis included: 0.2 M Cd(OA)2, 0.2 M Zn(OA)2, 0.2M Sulfur in ODE, and 1M TOP:Se. For the sulfur and selenium precursors, the appropriate amount of anion was weighed and dissolved into either ODE or TOP at the desired concentration by heating. Once the solutions were fully dissolved, the precursors were heated under vacuum at 120 C for at least 1 hr before use. For Cd(OA)2 and Zn(OA)2, CdO or ZnAc were weighed and added to oleic acid at a 1:4 molar ratios. The solutions were then heated under vacuum at 120 C until fully dissolved and then diluted to a final concentration of 0.2 M with ODE. All precursors were stored under argon at room temperature. Both Cd(OA)2 and Zn(OA)2 are solids at room temperature and were therefore heated to 120 C when using for QD synthesis.

For nucleation of CdSe cores, an air-free hot injection method was done. 1 g of TOPO, 8 mL of ODE, and 1.9 mL of 0.2M Cd(OA)2 were loaded into a 100 mL round bottom flask (rbf) and put under vacuum at room temperature for 30 min. The flask was then heated to 80 C and degassed by backfilling with argon and switching back to vacuum 3× over the course of 1 hr. Once the solution had been sufficiently degassed, the flask was put under active argon flow and heated to 300 C. 4 mL of 1M TOP:Se, 3 mL of oleylamine, and 1 mL of ODE were pre-mixed in air-free conditions and injected into the Cd solution at 300 C. The reaction temperature was then set to 270C. After 3 mins, the flask was taken off of the heating element and allowed to cool to room temperature. The CdSe cores were precipitated from solution under air-free conditions using ethanol and methanol and re-dispersed in hexanes.

For shelling, a successive ion layer adsorption reaction (SILAR) was used (Ghosh et al.; 2012). 5 mL of ODE and 5 mL of oleylamine were added to a 100 mL rbf and heated under vacuum at 120 C for 1 hr. 200 nmol of CdSe cores in hexanes were then added to the flask and the hexanes evaporated off. For each shell material, a single monolayer, defined by the lattice constant of each material, was added at a time. The amount of precursor needed to add each monolayer was calculated on a volume basis using the density and lattice constants for wurtzite CdS and ZnS. For the CdS shell, 1 monolayer of CdS was added. The first Cd addition was added dropwise at 160 C to the core solution under argon and annealed for 2.5 hrs. The temperature was then increased to 240 C and the corresponding amount of S precursor was added dropwise and annealed for 1 hr. All additional monolayers were reacted at 240 C. After CdS shelling, 2 monolayers of ZnS were added in a similar fashion. After 2 full monolayers of ZnS were added an additional layer of Zn was added to ensure that the QD surface was Zn rich.

Different ratios of QD/TF/DNA have been performed with different oligos.

TABLE 14

Experiments conducted using different oligonucleotides sequences and different molar ratios of TF and DNA regarding the QDs with a final concentration of QDs of 25 nM.

| DNA sequence | QF/TF | QD/DNA |
|---|---|---|
| DNA1 | 4 | 18 |
| DNA2 | 4 | 18 |
| DNA3 | 4 | 18 |
| DNA4 | 4 | 18 |
| scrambled | 4 | 18 |
| DNA3 | 1 | 2 |
| DNA3 | 2 | 2 |
| DNA3 | 4 | 2 |
| DNA3 | 1 | 8 |
| DNA3 | 2 | 8 |
| DNA3 | 4 | 8 |
| DNA3 | 1 | 18 |
| DNA3 | 2 | 18 |
| DNA3 | 10 | 18 |
| DNA3 | 16 | 18 |
| DNA4 | 1 | 18 |
| DNA4 | 4 | 9 |
| DNA4 | 4 | 18 |
| DNA4 | 16 | 8 |
| DNA4 | 1 | 4 |

Polymer Synthesis

The polymer capping the QDs (P1) was synthesized using a slightly modified version of a previously reported procedure. In a typical experiment, 180 mg of PIMA (poly (isobutylene-alt-maleic anhydride), 6000 g/mol, 0.03 mmol, 1 equ.) was dissolved in 3 mL of anhydrous dimethyl sulfoxide at 45C. In parallel, 116 mg of (2-aminoethyl) trimethylammonium chloride (0.66 mmol, 22 equ.), 73 mg of histamine (0.66 mmol, 22 equ.) and 193 uL of trimethylamine (1.39 mmol, 46 equ.) were dissolved in 1.5 mL of anhydrous dimethyl sulfoxide at 50C. After complete dissolution of both solution, the solution containing the amines was added with a syringue to the PIMA solution. The reaction was kept overnight at 45C. The polymer was purified by two several precipitation in ethyl acetate. A white powder was obtained with 67% yield.

Ligand Exchange

QDs were transferred in water by capping their surface with the polymer P1. In a typical experiment, 475 uL of QDs ([QD]=3.0 uM, n=1.4 nmol) were dissolved in 600 uL of chloroform. In parallel, 560 uL of P1 at 10 mg/mL in DMSO was dissolved in 560 uL of chloroform. The solution of P1 was added to the QDs dispersion and the reaction was left overnight under fast stirring. The next day, 0.5 mL of NaOH at 0.1M was added and the dispersion was quickly shaken by hand. The QDs nicely transferred to the upper water phase. The water phase was extracted and centrifuged at 3000 rpm for 1 min. Then the supernatant was filtered on 100 nm PVDF filtered and washed 3 times with $NaHCO_3$ 0.1M on 100k ultra-centrifugal filters. QDs were recovered in $NaHCO_3$ 0.1M at a concentration around 5uM.

Assembly of the Sensor and Progesterone Titration

Description for a typical experiment, using a molar ratio of QD/TF/DNA=1/4/18. QDs in (275 uL, 0.15 uM in HEPES 1×, pH 7.6 with 1% BSA) were mixed with AIY-his6 (275 uL, 0.6 uM in HEPES 1× pH 7.6) at room temperature for 45 min. Then, the double-stranded DNA labelled with a Cy5 fluorescent probe at the 3' and 5' ends (275 uL, 2.7 uM in HEPES 1× pH 7.6) was added to the mixture. After 30 min, 220 uL of HEPES 1× pH 7.5 and 330 uL of 5× binding buffer (25 mM $MgCl_2$, 25% glycerol, and 250 mg/L Invitrogen™ UltraPure™ Salmon Sperm DNA in Tris-HCl 0.1M) were added and the mixture is left 15 more min at RT.

50 uL of the sensor (QD/TF/DNA) was then splitted in 3×9 centrifuge tubes to which 10 uL of progesterone at the desired concentration is added. As such, the final concentration of QD/TF/DNA for the measurements is 25 nM/100 nM/450 nM. A 384 well plate was filled with 60 uL of each solution. The fluorescence intensity was monitored on a spectrofluorimeter from 535 nm to 800 nm exciting at 400 nm, equipped with a 450 nm long-pass filter in emission.

Stability Assays

For all the stability assays, the sensor was not fully assembled, only QDs, TF and DNA were mixed together and the sensor was stored as it. HEPES 1× and 5× binding buffer were added before starting the progesterone titration. The lyophilized sensor was first recovered in ultra-pure water (same volume as sublimated during lyophilization process), then HEPES 1+ and 5× binding buffer were added before the progesterone titration.

Artificial Urine Assays

Artificial urine composition: pH 6.6±0.1, urea 25.0 g/L, Sodium Chloride 9.0 g/L, Disodium Hydrogen Orthophosphate anhydrous 2.5 g/L, Potassium Dihydrogen Orthophosphate 2.5 g/L, Ammonium Chloride 3.0 g/L, Creatinine 2.0 g/L, Sodium Sulfite hydrated 3.0 g/L.

For the artificial urine assays, only QDs, TF and DNA were mixed together in HEPES 1×. Then, artificial urine and artificial urine+PRG was added to reach a final volume of urine=50% of the sensor volume.

Artificial urine at 37C: the sensor was assembled at RT then artificial urine and artificial urine+PRG were added at 37C.

Artificial urine lyophilized: QDs, TF and DNA were assembled only in 1% BSA for QDs and MQ (no salts) and lyophilized. The sensor was recovered in artificial urine (same volume as sublimated during lyophlization process). Then, artificial urine+PRG was added to the sensor.

Instrumentation

Fluorescence measurements were recorded on a Horiba Nanolog spectrofluorometer equipped with a plate reader. Absorption spectra were recorded using a Nanodrop 2000c.

REFERENCES

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference. Accordingly, the references are each incorporated herein in their entirety by reference.

Ghosh, Y., et al., New Insights into the Complexities of Shell Growth and the Strong Influence of Particle Volume in Nonblinking "Giant" Core/Shell Nanocrystal Quantum Dots. Journal of the American Chemical Society, 2012. 134(23): p. 9634-9643.

McCormick J R D, Jensen E R, Johnson S J, Sjolander N O. Biosynthesis of the tetracyclines. IX. 4-Aminodedimethylaminoanhydrodemethylchlortetracycline from a mutant of *Streptomyces aureofaciens*. J Am Chem Soc. 1968; 90(8):2201-2202.

Kamionka A, Bogdanska-Urbaniak J, Scholz O, Hillen W. Two mutations in the tetracycline repressor change the inducer anhydrotetracycline to a corepressor. Nucleic Acids Res. 2004; 32(2):842-847.

Chern M, Nguyen T T H, Mahler A H, Dennis A. Shell Thickness Effects on Quantum Dot Brightness and Energy Transfer. Nanoscale. 2017:16446-16458.

Li J J, Wang Y A, Guo W, et al. Large-scale synthesis of nearly monodisperse CdSe/CdS core/shell nanocrystals using air-stable reagents via successive ion layer adsorption and reaction. *J Am Chem Soc.* 2003; 125(41):12567-12575.

Saenger W, Orth P, Kisker C, Hillen W, Hinrichs W The tetracycline repressor: A paradigm for a biological switch. *Angew Chem Int Ed Engl* 2000; 39:2042-2052.

References for Example 1

1. Leung K H, He B, Yang C, Leung C H, Wang H M D, Ma D L. Development of an Aptamer-Based Sensing Platform for Metal Ions, Proteins, and Small Molecules through Terminal Deoxynucleotidyl Transferase Induced G-Quadruplex Formation. *ACS Appl Mater Interfaces*. 2015. doi:10.1021/acsami.5b08314
2. Liu J, Liu Y, Yang X, et al. Exciton energy transfer-based fluorescent sensing through aptamer-programmed self-assembly of quantum dots. *Anal Chem*. 2013. doi: 10.1021/ac403023p
3. Diaz-González M, González-García M B, Costa-García A. Recent advances in electrochemical enzyme immunoassays. *Electroanalysis*. 2005; 17(21):1901-1918. doi: 10.1002/elan.200503357
4. Fernandez-López R, Ruiz R, de la Cruz F, Moncalián G. Transcription factor-based biosensors enlightened by the analyte. *Front Microbiol*. 2015. doi:10.3389/ fmicb.2015.00648
5. Lee M H, Kim J S, Sessler J L. Small molecule-based ratiometric fluorescence probes for cations, anions, and biomolecules. *Chem Soc Rev*. 2015; 44(13):4185-4191. doi:10.1039/c4cs00280f
6. McCormick J R D, Jensen E R, Johnson S J, Sjolander N O. Biosynthesis of the tetracyclines. IX. 4-Aminodedimethylaminoanhydrodemethylchlortetracycline from a mutant of *Streptomyces aureofaciens*. J Am Chem Soc. 1968; 90(8):2201-2202. doi:10.1021/ja01010a063
7. Kamionka A, Bogdanska-Urbaniak J, Scholz O, Hillen W. Two mutations in the tetracycline repressor change the inducer anhydrotetracycline to a corepressor. *Nucleic Acids Res*. 2004; 32(2):842-847. doi:10.1093/nar/gkh200
8. Bolintineanu D S, Volzing K, Vivcharuk V, Sayyed-Ahmad A, Srivastava P, Kaznessis Y N. Investigation of changes in tetracycline repressor binding upon mutations in the tetracycline operator. *J Chem Eng Data*. 2014; 59(10):3167-3176. doi:10.1021/je500225x
9. Shaner N C, Campbell R E, Steinbach P A, Giepmans B N G, Palmer A E, Tsien R Y. Improved monomeric red, orange and yellow fluorescent proteins derived from Discosoma sp. red fluorescent protein. *Nat Biotechnol*. 2004; 22(12):1567-1572. doi:10.1038/nbt1037
10. Gao Y, Peng X. Photogenerated excitons in plain core CdSe nanocrystals with unity radiative decay in single channel: the effects of surface and ligands. *J Am Chem Soc*. 2015; 137(12):4230. doi:10.1021/jacs.5b01314
11. Dennis A M, Sotto D C, Mei B C, Medintz I L, Mattoussi H, Bao G. Surface ligand effects on metal-affinity coordination to quantum dots: Implications for nanoprobe self-assembly. *Bioconjug Chem*. 2010; 21(7):1160-1170. doi:10.1021/bc900500m
12. Medintz I L, Uyeda H T, Goldman E R, Mattoussi H. Quantum dot bioconjugates for imaging, labelling and sensing. *Nat Mater*. 2005; 4(6):435. doi:10.1038/ nmat1390
13. Chern M, Nguyen T T H, Mahler A H, Dennis A. Shell Thickness Effects on Quantum Dot Brightness and Energy Transfer. *Nanoscale*. 2017:16446-16458. doi: 10.1039/C7NR04296E
14. Chou K, Dennis A. Förster Resonance Energy Transfer between Quantum Dot Donors and Quantum Dot Acceptors. *Sensors*. 2015; 15(6):13288-13325. doi:10.3390/ s150613288
15. Dennis A M, Bao G. Quantum Dot—Fluorescent Protein Pairs as Novel Fluorescence Resonance Energy Transfer Probes 2008. *Nano Lett*. 2008; 8:1439-1445. doi:10.1021/ n1080358
16. Lakowicz J R. *Principles of Fluorescence Spectroscopy;* 2006. doi:10.1007/978-0-387-46312-4
17. Pons T, Medintz I L, Wang X, English D S, Mattoussi H. Solution-phase single quantum dot fluorescence resonance energy transfer. *J Am Chem Soc*. 2006; 128(47): 15324-15331. doi:10.1021/ja0657253
18. Ghosh Y, Mangum B D, Casson J L, Williams D J, Htoon H, Hollingsworth J A. New insights into the complexities of shell growth and the strong influence of particle volume in nonblinking "giant" core/shell nanocrystal quantum dots. *J Am Chem Soc.* 2012; 134(23):9634-9643. doi:10.1021/ja212032q
19. Li J J, Wang Y A, Guo W, et al. Large-scale synthesis of nearly monodisperse CdSe/CdS core/shell nanocrystals using air-stable reagents via successive ion layer adsorption and reaction. *J Am Chem Soc.* 2003; 125(41):12567-12575. doi:10.1021/ja0363563
20. Susumu K, Oh E, Delehanty J B, et al. Multifunctional compact zwitterionic ligands for preparing robust biocompatible semiconductor quantum dots and gold nanoparticles. *J Am Chem Soc.* 2011; 133(24):9480-9496. doi:10.1021/ja201919s
21. Clapp A R, Goldman E R, Mattoussi H. Capping of CdSe-ZnS quantum dots with DHLA and subsequent conjugation with proteins. *Nat Protoc.* 2006; 1(3):1258-1266. doi:10.1038/nprot.2006.184
22. Holstein C A, Griffin M, Hong J, Sampson P D. Statistical Method for Determining and Comparing Limits of Detection of Bioassays. *Anal Chem.* 2015; 87(19):9795-9801. doi:10.1021/acs.analchem.5b02082
23. Sebaugh J L, McCray P D. Defining the linear portion of a sigmoid-shaped curve: bend points. *Pharm Stat.* 2003; 2(3):167-174. doi:10.1002/pst.62

References Referred to in Examples 2 and 3

1. Posthuma-Trumpie, G. A., et al., *Perspectives for on-site monitoring of progesterone.* Trends in Biotechnology, 2009. 27(11): p. 652-660.
2. Alvarez, M. M., et al., *Emerging Trends in Micro- and Nanoscale Technologies in Medicine: From Basic Discoveries to Translation.* ACS Nano, 2017. 11(6): p. 5195-5214.
3. Du, G., et al., *Colorimetric aptasensor for progesterone detection based on surfactant-induced aggregation of gold nanoparticles.* Analytical Biochemistry, 2016. 514 (Supplement C): p. 2-7.
4. Alhadrami, H. A., et al., *High affinity truncated DNA aptamers for the development of fluorescence based progesterone biosensors.* Analytical Biochemistry, 2017. 525 (Supplement C): p. 78-84.
5. Oh, S.-D., H. D. Duong, and J. I. Rhee, *Simple and sensitive progesterone detection in human serum using a CdSe/ZnS quantum dot-based direct binding assay.* Analytical Biochemistry, 2015. 483 (Supplement C): p. 54-61.
6. Trapiella-Alfonso, L., et al., *Development of a quantum dot-based fluorescent immunoassay for progesterone determination in bovine milk.* Biosensors and Bioelectronics, 2011. 26(12): p. 4753-4759.
7. Libis, V., B. Delépine, and J.-L. Faulon, *Sensing new chemicals with bacterial transcription factors.* Current Opinion in Microbiology, 2016. 33 (Supplement C): p. 105-112.
8. Fernandez-López, R., et al., *Transcription factor-based biosensors enlightened by the analyte.* Frontiers in Microbiology, 2015. 6(648).
9. Feng, J., et al., *A general strategy to construct small molecule biosensors in eukaryotes.* eLife, 2015. 4: p. e10606.
10. Li, S., et al., *A platform for the development of novel biosensors by configuring allosteric transcription factor recognition with amplified luminescent proximity homogeneous assays.* Chemical Communications, 2017. 53(1): p. 99-102.
11. Eglen, R. M., et al., *The Use of AlphaScreen Technology in HTS: Current Status.* Current Chemical Genomics, 2008. 1: p. 2-10.
12. French, C. E., K. de Mora, and N. Joshi, *A5 SYNTHETIC BIOLOGY AND THE ART OF BIOSENSOR DESIGN,* in ncbi.nlm.nih.gov.
13. Pardee, K., et al., *Paper-based synthetic gene networks.* Cell, 2014. 159(4): p. 940-54.
14. Charney, W. and H. L. Herzog, *Microbial Transformations of Steroids: A Handbook* 2014: Academic Press.
15. Yu, C. P., R. A. Deeb, and K. H. Chu, *Microbial degradation of steroidal estrogens.* Chemosphere, 2013. 91(9): p. 1225-35.
16. Galagan, J., *Genomic Insights into Tuberculosis.* Nature Reviews Genetics, 2014.
17. Neuman, H., et al., *Microbial endocrinology: the interplay between the microbiota and the endocrine system.* FEMS Microbiol Rev, 2015. 39(4): p. 509-21.
18. Kendall, M. M. and V. Sperandio, *What a Dinner Party! Mechanisms and Functions of Interkingdom Signaling in Host-Pathogen Associations.* MBio, 2016. 7(2).
19. Garcia, J. L., I. Uhia, and B. Galan, *Catabolism and biotechnological applications of cholesterol degrading bacteria.* Microb Biotechnol, 2012. 5(6): p. 679-99.
20. Bergstrand, L. H., et al., *Erratum for Bergstrand et al., Delineation of Steroid-Degrading Microorganisms through Comparative Genomic Analysis.* MBio, 2016. 7(4).
21. Garcia-Fernandez, E., et al., *Deciphering the transcriptional regulation of cholesterol catabolic pathway in mycobacteria: identification of the inducer of KstR repressor.* J Biol Chem, 2014. 289(25): p. 17576-88.
22. Kendall, S. L., et al., *Cholesterol utilization in mycobacteria is controlled by two TetR-type transcriptional regulators: kstR and kstR2.* Microbiology, 2010. 156(Pt 5): p. 1362-71.
23. Uhia, I., et al., *Characterization of the KstR-dependent promoter of the first step of cholesterol degradative pathway in Mycobacterium smegmatis.* Microbiology, 2011.
24. McGuire, A. M., et al., *Comparative analysis of Mycobacterium and related Actinomycetes yields insight into the evolution of Mycobacterium tuberculosis pathogenesis.* BMC Genomics, 2012. 13(1): p. 120.
25. Galagan, J., A. Lyubetskaya, and A. Gomes, *ChIP-Seq and the complexity of bacterial transcriptional regulation.* Curr Top Microbiol Immunol, 2013. 363: p. 43-68.
26. Jaini, S., et al., *Transcription Factor Binding Site Mapping Using ChIP-Seq,* in *Molecular Genetics of Mycobacteria, 2nd Edition,* G. Hatfull and W. R. Jacobs, Jr., Editors. 2014, ASM Press.
27. Alon, U., *Network motifs: theory and experimental approaches.* Nat Rev Genet, 2007. 8(6): p. 450-61.
28. Rosenfeld, N., M. B. Elowitz, and U. Alon, *Negative autoregulation speeds the response times of transcription networks.* J Mol Biol, 2002. 323(5): p. 785-93.
29. Kashtan, N., et al., *Topological generalizations of network motifs.* Phys Rev E Stat Nonlin Soft Matter Phys, 2004. 70(3 Pt 1): p. 031909.
30. Constantinides, A., *Steroid transformation at high substrate concentrations using immobilized Corynebacterium simplex cells.* Biotechnol Bioeng, 1980. 22(1): p. 119-36.
31. Medintz, I. L., et al., *Quantum dot bioconjugates for imaging, labelling and sensing.* Nature Materials, 2005. 4: p. 435.
32. Hildebrandt, N., et al., *Energy Transfer with Semiconductor Quantum Dot Bioconjugates: A Versatile Platform* for Biosensing, Energy Harvesting, and Other Developing Applications. Chemical Reviews, 2017. 117(2): p. 536-711.
33. Zhang, Y. and T.-H. Wang, *Quantum Dot Enabled Molecular Sensing and Diagnostics.* Theranostics, 2012. 2(7): p. 631-654.
34. Ghosh, Y., et al., New Insights into the Complexities of Shell Growth and the Strong Influence of Particle Volume in Nonblinking "Giant" Core/Shell Nanocrystal Quantum Dots. Journal of the American Chemical Society, 2012. 134(23): p. 9634-9643.
35. Wang, W., et al., Photoligation of an Amphiphilic Polymer with Mixed Coordination Provides Compact and Reactive Quantum Dots. Journal of the American Chemical Society, 2015. 137(16): p. 5438-5451.

---

What is claimed herein is:

1. A biosensor comprising:
a) at least one allosteric transcription factor polypeptide conjugated to a first fluorescent molecule of a fluorescence Resonance Energy Transfer (FRET) pair, the allosteric transcription factor polypeptide comprising one or more ligand binding domains (LBDs) and one or more DNA binding domains (DBDs), and
b) a nucleic add probe conjugated to one or more second fluorescent molecules of the FRET pair, the nucleic add probe having a sequence comprising one or more transcription factor binding domains (TFBDs) that is specific to the DBD of the transcription factor,
wherein in the absence of an analyte of interest, the DBD of the transcription factor is bound to the TFBD of the nucleic acid probe, and the first fluorescent molecule and the second fluorescent molecule of the FRET pair emits a fluorescent signal, and in the presence of the analyte of interest, the analyte binds to the ligand binding domain (LBD) resulting in a conformational change in allosteric transcription factor polypeptide that decreases the affinity of the DBD for the TFBD such that the DBD dissociates from the TFBD, resulting in the first fluorescent molecule and the second fluorescent molecule of the FRET pair no longer emitting a fluorescent signal (OFF biosensor); or
wherein in the absence of an analyte of interest, the DBD of the transcription factor is not bound to the TFBD of the nucleic acid probe, and the first fluorescent molecule and the second fluorescent molecule of the FRET pair does not emit a fluorescent signal, and in the presence of the analyte of interest, the analyte binds to the ligand binding domain (LBD) resulting in a conformational change in the allosteric transcription factor polypeptide that increases the affinity of the DBD for the TFBD such that the DBD binds to the TFBD, resulting in the first fluorescent molecule and the second fluorescent molecule of the FRET pair emitting a fluorescent signal (ON biosensor), wherein the first fluorescent molecule or second fluorescent molecule, or both is a quantum dot (QD), wherein the ratio of first fluorescence molecule to the second fluorescent molecule 1-10 of the amount of first fluorescent molecule to 5-30 of the amount of the second fluorescent molecule, and wherein the biosensor is capable of detecting the analyte of interest at a concentration in range of between 0.0001 ng/ml and 50 ng/ml.

2. The biosensor of claim 1, wherein the first fluorescent molecule is a quantum dot (QD) and the second fluorescent molecule is a fluorescent dye.

3. The biosensor of claim 1, wherein the analyte of interest is selected from the group consisting of a small molecule, toxin, neurotransmitter, steroid, immunomodulator, metabolite and hormone.

4. The biosensor of claim 1, wherein the analyte of interest is a hormone.

5. The biosensor of claim 4, wherein the hormone is selected from the group consisting of: progesterone, estradiol, estrone, estriol, testosterone, aldosterone, prednisolone, androstadienone, cortisol and cholesterol.

6. The biosensor of claim 1, wherein the allosteric transcription factor polypeptide is a microbial transcription factor.

7. The biosensor of claim 1, wherein the analyte of interest is progesterone and the allosteric transcription factor is PinR comprising a polypeptide of at least 15-189 of SEQ ID NO: 1 or a protein having at least 95% sequence identity to the amino acids 15-189 of SEQ ID NO: 1 and can bind to progesterone and to a nucleic acid sequence selected from any of SEQ ID NO: 13-17.

8. The biosensor of claim 7, wherein PinR comprises a DBD comprising amino acids SEQ ID NO: 7 or a protein having at least 95% sequence identity to SEQ ID NO: 7 and can bind to a nucleic acid sequence selected from any of SEQ ID NO: 13-17, and wherein the nucleic acid probe comprises at least one TFBD comprising a nucleic acid sequence selected from any of SEQ ID NO: 13-17, or a nucleic acid sequence having at least 95% sequence identity to any of SEQ ID NO: 13-17.

9. The biosensor of claim 8, wherein PinR comprises a histidine tag at the C-terminus or N-terminus, or both.

10. The biosensor of claim 7, wherein PinR is conjugated to a quantum dot (QD), and the nucleic acid probe is conjugated to a fluorescent dye or a fluorescent protein.

11. A hormone biosensor comprising:
a) a microbial allosteric transcription factor polypeptide conjugated to one or more first fluorescent molecules of a fluorescence Resonance Energy Transfer (FRET) pair, the allosteric transcription factor polypeptide comprising one or more ligand binding domains (LBDs) and one or more DNA binding domains (DBDs), and
b) a nucleic add probe conjugated to one or more second fluorescent molecules of the FRET pair, the nucleic add probe having a sequence comprising one or more transcription factor binding domains (TFBDs) that is specific to the DBD of the transcription factor, wherein in the absence of a hormone of interest, the DBD of the microbial allosteric transcription factor is bound to the TFBD of the nucleic add probe, and the first fluorescent molecule and the second fluorescent molecule of the FRET pair emits a fluorescent signal, and in the presence of the hormone of interest, the hormone hinds to the ligand binding domain (LBD) resulting in a conformational change that decreases the affinity of the DBD for the TFBD such that the DBD dissociates from the TFBD, resulting in the first fluorescent molecule and the second fluorescent molecule of the FRET pair no longer emitting a fluorescent signal (OFF biosensor); or wherein in the absence of the hormone of interest, the DBD of the microbial allosteric transcription factor is not bound to the TFBD of the nucleic add probe, and the first fluorescent molecule and the second fluorescent molecule of the FRET pair does not emit a fluorescent signal, and in the presence of the hormone of interest, the hormone binds to the ligand binding domain (LBD) resulting in a conformational change that increases the affinity of the DBD for the TFBD such that the DBD binds to the TFBD, resulting in the first fluorescent molecule and the second fluorescent molecule of the FRET pair emitting a fluorescent signal (ON biosensor), wherein the first fluorescent molecule or second fluorescent molecule, or both is a quantum dot (QD) and wherein the progesterone biosensor is capable of detecting progesterone at a concentration range of from at least 0.001 ng/ml to 0.1 ng/ml; or from at least 0.01 ng/ml to 10 ng/ml; or from at least 0.05 ng/ml to 50 ng/ml.

12. The hormone biosensor of claim 11, wherein the hormone biosensor is a progesterone biosensor, wherein the progesterone biosensor comprises:
(a) a progesterone detecting polypeptide comprising a progesterone binding domain and a DNA binding domain (DBD) conjugated to a first fluorescent molecule of a FRET pair, the progesterone binding domain comprising amino acids of any of SEQ ID NO: 18, SEQ ID NO: 19 or SEQ ID NO: 20, or a variant thereof having an amino acid sequence at least 95% sequence identity to SEQ ID NO: 18-20 that can bind to progesterone, and the DNA binding domain comprising amino acids of SEQ ID NO: 7 or a variant thereof having an amino acid sequence at least 95% sequence identity to amino acids of SEQ ID NO:7 that can bind to a nucleic acid sequence selected from any one of SEQ ID NO: 13-17, and
(b) a nucleic acid probe comprising at least one transcription factor binding domain (TFBD) comprising the nucleic acid sequence selected from any of: SEQ ID NO: 13-17, wherein the nucleic acid probe is conjugated to a second fluorescent molecule of a FRET pair, wherein in the absence of progesterone, the DBD of the progesterone detecting polypeptide is bound to the TFBD of the nucleic acid probe, and the first fluorescent molecule and the second fluorescent molecule of the FRET pair emits a fluorescent signal, and in the presence of progesterone, progesterone binds to the ligand binding domain (LBD) resulting in a conformational change that decreases the affinity of the DBD for the TFBD such that the DBD dissociates from the TFBD, resulting in the first fluorescent molecule and the second fluorescent molecule of the FRET pair no longer emitting a fluorescent signal (OFF progesterone biosensor); or wherein in the absence of progesterone, the DBD of the progesterone detecting polypeptide is not bound to the TFBD of the nucleic acid probe, and the first fluorescent molecule and the second fluorescent molecule of the FRET pair does not emit a fluorescent signal, and in the presence of progesterone, progesterone binds to the ligand binding domain (LBD) resulting in a conformational change that increases the affinity of the DBD for the TFBD such that the DBD binds to the TFBD, resulting in the first fluorescent molecule and the second fluorescent molecule of the FRET pair emitting a fluorescent signal (ON progesterone biosensor), wherein the first fluorescent molecule or second fluorescent molecule, or both is a quantum dot (QD).

13. The hormone biosensor of claim 12, wherein the progesterone detecting polypeptide comprises at least amino acids 15-189 of SEQ ID NO: 1 or a protein having at least 95% sequence identity to SEQ ID NO: 1 and can bind progesterone and to a nucleic acid selected from any of SEQ ID NO: 13-17.

14. The progesterone biosensor of claim 12, wherein the first fluorescent molecule of the FRET pair is a quantum dot (QD) and the second fluorescent molecule of the FRET pair is a fluorescent dye or fluorescent protein.

15. The hormone biosensor of claim 12, wherein the ratio of the amount of quantum dot (QD) to the amount of progesterone detecting polypeptide (TF) to the amount of nucleic acid probe (i.e., QD:TF:DNA ratio) is 1-10 of the QD, to 1-20 of the amount of the TF to the amount of 5-30 nucleic acid probe.

16. A hormone biosensor comprising:
a) a microbial allosteric transcription factor polypeptide conjugated to one or more electroactive molecules, the allosteric transcription factor comprising one or more ligand binding domains (LBDs) and one or more DNA binding domains (DBDs),
b) a nucleic acid probe attached to a conducting surface, the nucleic acid probe having a sequence comprising one or more transcription factor binding domains (TFBDs) that is specific to the DBD of the microbial allosteric transcription factor polypeptide wherein in the absence of a hormone of interest, the DBD of the microbial allosteric transcription factor is bound to the TFBD of the nucleic acid probe, resulting in an increase in flow of electrons from the electroactive molecule to the conductive surface which is detected by the presence of, or an increase in a current across the surface, and in the presence of the hormone of interest, the hormone binds to the ligand binding domain (LBD) resulting in a conformational change in the microbial allosteric transcription factor that decreases the affinity of the DBD for the TFBD such that the DBD dissociates from the TFBD, resulting a decrease in the flow of electrons from the electroconductive molecule to the conductive surface which is detected by a decrease in current across the surface (OFF biosensor); or wherein in the absence of a hormone of interest, the DBD of the microbial allosteric transcription factor is not bound to the TFBD of the nucleic acid probe, and no flow of electrons from the electroactive molecule to the conductive surface which is detected by absence of a current across the surface, and in the presence of the hormone of interest, the hormone binds to the ligand binding domain (LBD) resulting in a conformational change in the microbial allosteric transcription factor that increases the affinity of the DBD for the TFBD such that the DBD binds to the TFBD, resulting in an increase in flow of electrons from the electroactive molecule to the conductive surface which is detected by the presence of, or increase in a current across the surface (ON biosensor), and wherein the hormone biosensor is capable of detecting the hormone of interest at a concentration in range of between 0.0001 ng/ml and 50 ng/ml.

17. The hormone biosensor of claim 16 is a progesterone biosensor,
wherein the progesterone biosensor comprises:
a) a progesterone detecting polypeptide comprising a progesterone binding domain and a DNA binding domain (DBD) conjugated to at least one or more electroactive molecules, the progesterone binding domain comprising amino acids of any of SEQ ID NO: 18, SEQ ID NO: 19 or SEQ ID NO: 20, or a variant thereof having an amino acid sequence at least 95% sequence identity to SEQ ID NO: 18-20, and the DNA binding domain comprising amino acids of SEQ ID NO: 7 or a variant thereof having an amino acid sequence at least 95% sequence identity to amino acids of SEQ ID NO:7, and
b) a nucleic acid probe comprising at least one transcription factor binding domain (TFBD) comprising the nucleic acid sequence selected from any of: SEQ ID NO: 13-17, wherein the nucleic acid probe is immobilized or attached to a conducting surface, wherein in the absence of progesterone, the DBD of the progesterone detecting polypeptide is bound to the TFBD of the nucleic acid probe, resulting in an increase in flow of electrons from the electroactive molecule to the conductive surface which is detected by the presence of, or an increase in a current across the surface, and in the presence of progesterone, progesterone binds to the ligand binding domain (LBD) resulting in a conformational change in the progesterone detecting polypeptide that decreases the affinity of the DBD for the TFBD such that the DBD dissociates from the TFBD, resulting a decrease in the flow of electrons from the electroconductive molecule to the conductive surface which is detected by a decrease in current across the surface (OFF biosensor); or wherein in the absence of progesterone, the DBD of the progesterone detecting polypeptide is not bound to the TFBD of the nucleic acid probe, and no flow of electrons from the electroactive molecule to the conductive surface which is detected by absence of a current across the surface, and in the presence of progesterone, progesterone binds to the ligand binding domain (LBD) resulting in a conformational change in the progesterone detecting polypeptide that increases the affinity of the DBD for the TFBD such that the DBD binds to the TFBD, resulting in an increase in flow of electrons from the electroactive molecule to the conductive surface which is detected by the presence of, or increase, in a current across the surface (ON biosensor).

18. The progesterone biosensor of claim 17, wherein the progesterone detecting polypeptide comprises at least amino acids 15-189 of SEQ ID NO: 1 or a variant of at least 95% sequence identity to SEQ ID NO: 1.

19. A method for detecting an analyte of interest in a sample comprising;
a) contacting the sample with a biosensor comprising:
i. allosteric transcription factor polypeptide conjugated to one or more first fluorescent molecules of a Fluorescence Resonance Energy Transfer (FRET) pair, the allosteric transcription factor polypeptide comprising one or more ligand binding domains (LBDs) and one or more DNA binding domains (DBDs), and
ii. a nucleic acid probe conjugated to one or more second fluorescent molecules of the FRET pair, the nucleic acid probe having a sequence comprising one or more transcription factor binding domains (TFBDs) that is specific to the DBD of the transcription factor,
wherein the biosensor is an OFF biosensor such that in the absence of an analyte of interest, the DBD of the transcription factor is bound to the TFBD of the nucleic acid probe, and the first fluorescent molecule and the second fluorescent molecule of the FRET pair emits a fluorescent signal, and in the presence of the analyte of interest, the analyte binds to the ligand binding domain (LBD) resulting in a conformational change in the allosteric transcription factor polypeptide that decreases the affinity of the DBD for the TFBD such that the DBD dissociates from the TFBD, resulting in the first fluorescent molecule and the second fluorescent molecule of the FRET pair no longer emitting a fluorescent signal (OFF biosensor); or
wherein the biosensor is an ON biosensor such that in the absence of an analyte of interest, the DBD of the transcription factor is not bound to the TFBD of the nucleic acid probe; and the first fluorescent molecule and the second fluorescent molecule of the FRET pair does not emit a fluorescent signal, and in the presence of the analyte of interest, the analyte binds to the ligand binding domain (LBD) resulting in a conformational change in the allosteric transcription factor polypeptide that increases the affinity of the DBD for the TFBD such that the DBD binds to the TFBD; resulting in the first fluorescent molecule and the second fluorescent molecule of the FRET pair emitting a fluorescent signal (ON biosensor), and
wherein the first fluorescent molecule or second fluorescent molecule, or both is a quantum dot (OD);
and
b) measuring the fluorescence in the sample, and identifying the presence of the analyte of interest when one of the following occurs:
A) a decrease in FRET signal is detected when the biosensor is an OFF biosensor; or
B) an increase in FRET signal is detected when the biosensor is an ON biosensor,
wherein the biosensor is capable of detecting the analyte of interest in a range of between 0.0001 ng/m and 50 ng/ml.

20. The method of claim 19, wherein contacting the sample with a biosensor comprises placing the sample on, or in a sample well of a cassette or cartridge, wherein the cassette or cartridge comprises the biosensor, and wherein the sample well is in fluid communication with the biosensor, and the fluorescence from the biosensor can be measured.

21. The method of claim 19, wherein the measuring the fluorescence is performed with a point-of-care (POC) device, wherein the POC device can electronically communicate with any one or more of: a smart device, a smartphone or mobile device, tablet, or clinical practitioner.

22. The method of claim 19, wherein the analyte of interest is selected from the group consisting of: small molecule, toxin, neurotransmitter, immunomodulator, steroid, metabolite and hormone.

23. The method of claim 22, wherein the hormone is selected from the group consisting of: progesterone, estradiol, estrone, estriol, progesterone, testosterone, aldosterone, prednisolone, androstadienone, cortisol and cholesterol.

24. The method of claim 19, wherein the analyte of interest is progesterone and the allosteric transcription factor polypeptide is PinR comprising a polypeptide of at least 15-189 of SEQ ID NO: 1 or a protein having at least 95% sequence identity to the amino acids 15-189 of SEQ ID NO: 1 and can bind progesterone and bind to a nucleic acid selected from any of SEQ ID NO: 13-17.

25. The method of claim 24, wherein PinR comprises a DBD comprising amino acids SEQ ID NO: 7 or a variant having at least 95% sequence identity to SEQ ID NO: 7 and can bind to a nucleic acid sequence selected from any of SEQ ID NO: 13-17, and wherein the nucleic acid probe comprises at least one TFBD comprising a nucleic acid sequence selected from any of SEQ ID NO: 13-17, or a nucleic acid sequence at least 95% homologous to any of SEQ ID NO: 13-17.

26. The method of claim 19, wherein the sample is a body fluid selected from the group consisting of: sweat, blood, cerebrospinal fluid (CSF), plasma, whole blood, serum, semen, synovial fluid, saliva, vaginal lubrication, breast milk, amniotic fluid, urine, human feces, phlegm tears and saliva.

27. The method of claim 19, wherein contacting the sample with a biosensor comprises placing the sample into or on a sample well of a cassette or cartridge, wherein the cassette or cartridge comprises the biosensor, and wherein the sample well is in fluid communication with the biosensor, wherein the nucleic acid is immobilized to the surface of the conductible surface and the current across the conductible surface can be measured.

28. The method of claim 27, wherein the measuring the current across a conductible surface is performed with a point-of-care (POC) device, where the POC device can electronically communicate with any one or more of: a smart device, a smartphone or mobile device, tablet, or clinical practitioner.

29. The method of claim 19, where the analyte is progesterone, and the method can detect progesterone in a sample in range of
a) from at least 0.001 ng/ml to 0.1 ng/ml; or
b) from at least 0.01 ng/ml to 10 ng/ml; or
c) from at least 0.05 ng/ml to 50 ng/ml.

* * * * *